United States Patent
Sambursky et al.

(10) Patent No.: US 10,808,287 B2
(45) Date of Patent: *Oct. 20, 2020

(54) METHODS AND DEVICES FOR ACCURATE DIAGNOSIS OF INFECTIONS

(71) Applicant: Rapid Pathogen Screening, Inc., Sarasota, FL (US)

(72) Inventors: Robert P. Sambursky, Bradenton, FL (US); Robert W. VanDine, Montoursville, PA (US); Uma Mahesh Babu, Bradenton, FL (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 780 days.

This patent is subject to a terminal disclaimer.

(21) Appl. No.: 15/012,897

(22) Filed: Feb. 2, 2016

(65) Prior Publication Data
US 2017/0114392 A1   Apr. 27, 2017

Related U.S. Application Data

(60) Provisional application No. 62/245,431, filed on Oct. 23, 2015.

(51) Int. Cl.
  *C12Q 1/689*  (2018.01)
  *C12Q 1/70*  (2006.01)
  *G01N 33/569*  (2006.01)

(52) U.S. Cl.
  CPC ............ *C12Q 1/689* (2013.01); *C12Q 1/70* (2013.01); *G01N 33/56911* (2013.01);
  (Continued)

(58) Field of Classification Search
  None
  See application file for complete search history.

(56) References Cited

U.S. PATENT DOCUMENTS 4,299,916 A   11/1981   Litman et al.
4,405,711 A   9/1983   Masuda et al.
(Continued)

FOREIGN PATENT DOCUMENTS

DE   4439429 C2   2/1996
DE   19622503 C2   7/1998
(Continued)

OTHER PUBLICATIONS

Halminen et al., Expression of MxA Protein in Blood Lymphocytes Discriminates between Viral and Bacterial Infections in Febrile Children, 1997, Pediatric Research, vol. 41, pp. 647-650 (Year: 1997).*

(Continued)

*Primary Examiner* — Rebecca M Giere
(74) *Attorney, Agent, or Firm* — Brown & Michaels, PC

(57) ABSTRACT

Diagnostic devices test markers for viral infection and markers for bacterial infection to effectively assist in the rapid differentiation of viral and bacterial infections, to differentiate between colonization and active infection, and to better diagnose microbiologically unconfirmed patients. In other embodiments, detecting a presence of MxA in combination with either the bacterial biomarker C-reactive protein or the bacterial biomarker procalcitonin increases the specificity of the bacterial biomarker with a concurrent improvement in sensitivity.

26 Claims, 41 Drawing Sheets

(52) U.S. Cl.
CPC ... *G01N 33/56983* (2013.01); *G01N 2333/47* (2013.01); *G01N 2333/4737* (2013.01); *G01N 2333/585* (2013.01)

(56) References Cited

U.S. PATENT DOCUMENTS

| | | | |
|---|---|---|---|
| 4,429,050 A | 1/1984 | Yasuda et al. |
| 4,473,652 A | 9/1984 | Okazaki et al. |
| 4,508,820 A | 4/1985 | Merril et al. |
| 4,554,254 A | 11/1985 | Krystal |
| 4,703,016 A | 10/1987 | Merril |
| 4,861,711 A | 8/1989 | Friesen et al. |
| 4,920,046 A | 4/1990 | McFarland et al. |
| 4,956,302 A | 9/1990 | Gordon et al. |
| 4,960,691 A | 10/1990 | Gordon et al. |
| 4,960,692 A | 10/1990 | Lentrichia et al. |
| 4,963,325 A | 10/1990 | Lennon et al. |
| 4,981,786 A | 1/1991 | Dafforn et al. |
| 5,026,653 A | 6/1991 | Lee et al. |
| 5,120,643 A | 6/1992 | Ching et al. |
| 5,221,678 A | 6/1993 | Atkinson et al. |
| 5,312,921 A | 5/1994 | Glazer et al. |
| 5,348,891 A | 9/1994 | van Es et al. |
| 5,405,430 A | 4/1995 | Groves et al. |
| 5,415,994 A | 5/1995 | Imrich et al. |
| 5,436,134 A | 7/1995 | Haugland et al. |
| 5,496,562 A | 3/1996 | Burgoyne |
| 5,559,041 A | 9/1996 | Kang et al. |
| 5,569,608 A | 10/1996 | Sommer |
| 5,607,863 A | 3/1997 | Chandler |
| 5,637,469 A | 6/1997 | Wilding et al. |
| 5,638,828 A | 6/1997 | Lauks et al. |
| 5,653,243 A | 8/1997 | Lauks et al. |
| 5,658,751 A | 8/1997 | Yue et al. |
| 5,666,967 A | 9/1997 | Lauks et al. |
| 5,695,949 A | 12/1997 | Galen et al. |
| 5,705,353 A | 1/1998 | Oh et al. |
| 5,714,341 A | 2/1998 | Thieme et al. |
| 5,756,126 A | 5/1998 | Burgoyne |
| 5,763,162 A | 6/1998 | Glazer et al. |
| 5,779,650 A | 7/1998 | Lauks et al. |
| 5,783,687 A | 7/1998 | Glazer et al. |
| 5,807,527 A | 9/1998 | Burgoyne |
| 5,824,268 A | 10/1998 | Bernstein et al. |
| 5,863,740 A | 1/1999 | Kientsch-Engel et al. |
| 5,869,345 A | 2/1999 | Chandler |
| 5,877,028 A | 3/1999 | Chandler et al. |
| 5,888,778 A | 3/1999 | Shuber |
| 5,939,252 A | 8/1999 | Lennon et al. |
| 5,945,345 A | 8/1999 | Blatt et al. |
| 5,972,386 A | 10/1999 | Burgoyne |
| 5,985,327 A | 11/1999 | Burgoyne |
| 5,985,675 A | 11/1999 | Charm et al. |
| 5,989,813 A | 11/1999 | Gerdes |
| 5,998,220 A | 12/1999 | Chandler |
| 6,002,734 A | 12/1999 | Steinman |
| 6,010,463 A | 1/2000 | Lauks et al. |
| 6,017,767 A | 1/2000 | Chandler |
| 6,037,127 A | 3/2000 | Ebersole et al. |
| 6,046,058 A | 4/2000 | Sun |
| 6,054,272 A | 4/2000 | Glazer et al. |
| 6,060,237 A | 5/2000 | Nygren et al. |
| 6,087,184 A | 7/2000 | Magginetti et al. |
| 6,106,779 A | 8/2000 | Buechler et al. |
| 6,136,610 A | 10/2000 | Polito et al. |
| 6,146,589 A | 11/2000 | Chandler |
| 6,200,559 B1 | 3/2001 | von Wussow |
| 6,225,046 B1 | 5/2001 | Vesey et al. |
| 6,235,539 B1 | 5/2001 | Carpenter |
| 6,284,550 B1 | 9/2001 | Carroll et al. |
| 6,335,205 B1 | 1/2002 | Bausback |
| 6,350,578 B1 | 2/2002 | Stark et al. |
| 6,355,429 B1 | 3/2002 | Nygren et al. |
| 6,358,752 B1 | 3/2002 | Durst et al. |
| 6,514,773 B1 | 2/2003 | Klein et al. |
| 6,548,309 B1 | 4/2003 | Moore et al. |
| 6,555,390 B2 | 4/2003 | Chandler |
| 6,565,808 B2 | 5/2003 | Hudak et al. |
| 6,566,101 B1 | 5/2003 | Shuber et al. |
| 6,569,627 B2 | 5/2003 | Wittwer et al. |
| 6,602,669 B2 | 8/2003 | Letsinger et al. |
| 6,727,073 B1 | 4/2004 | Moore et al. |
| 6,783,938 B2 | 8/2004 | Nygren et al. |
| 6,818,452 B2 | 11/2004 | Wong |
| 6,845,327 B2 | 1/2005 | Lauks et al. |
| 6,875,619 B2 | 4/2005 | Blackburn |
| 6,893,880 B2 | 5/2005 | Carpenter |
| 6,896,778 B2 | 5/2005 | Lauks et al. |
| 6,902,900 B2 | 6/2005 | Davies et al. |
| 7,125,728 B2 | 10/2006 | Ott |
| 7,189,522 B2 | 3/2007 | Esfandiari |
| 7,267,992 B2 | 9/2007 | Goerlach-Graw et al. |
| 7,309,611 B2 | 12/2007 | DiNello et al. |
| 7,314,763 B2 | 1/2008 | Song et al. |
| 7,341,837 B2 | 3/2008 | Lawton |
| 7,354,614 B2 | 4/2008 | Quinlan et al. |
| 7,371,582 B2 | 5/2008 | Nahm et al. |
| 7,374,950 B2 | 5/2008 | Kang et al. |
| 7,379,167 B2 | 5/2008 | Mawhirt et al. |
| 7,384,598 B2 | 6/2008 | Quirk et al. |
| 7,393,697 B2 | 7/2008 | Charlton |
| 7,419,796 B2 | 9/2008 | Durst et al. |
| 7,419,821 B2 | 9/2008 | Davis et al. |
| 7,425,302 B2 | 9/2008 | Piasio et al. |
| 7,459,314 B2 | 12/2008 | Guo et al. |
| 7,583,379 B2 | 9/2009 | Zhao et al. |
| 7,629,116 B2 | 12/2009 | Ott |
| 7,704,729 B2 | 4/2010 | Chandler |
| 7,723,124 B2 | 5/2010 | Aberl et al. |
| 7,732,132 B2 | 6/2010 | Huang et al. |
| 7,736,890 B2 | 6/2010 | Sia et al. |
| 7,741,103 B2 | 6/2010 | Guirguis |
| 7,910,381 B2 | 3/2011 | Ford et al. |
| 8,017,382 B2 | 9/2011 | Davis et al. |
| 8,383,422 B2 | 2/2013 | Katada et al. |
| 8,603,835 B2 | 12/2013 | Esfandiari |
| 8,609,433 B2 | 12/2013 | Sambursky et al. |
| 8,658,431 B2 | 2/2014 | Ott |
| 8,815,609 B2 | 8/2014 | Babu et al. |
| 8,821,876 B2 | 9/2014 | Ginsburg et al. |
| 8,962,260 B2 * | 2/2015 | Sambursky ......... G01N 33/569 435/5 |
| 9,372,192 B2 | 6/2016 | Sambursky et al. |
| 9,910,036 B2 * | 3/2018 | Sambursky ............ B82Y 30/00 |
| 9,933,423 B2 * | 4/2018 | Sambursky ............ B82Y 30/00 |
| 2003/0027866 A1 | 2/2003 | Johnson et al. |
| 2003/0049658 A1 | 3/2003 | Smart et al. |
| 2003/0073121 A1 | 4/2003 | Mendel-Hartvig et al. |
| 2003/0104506 A1 | 6/2003 | Durst et al. |
| 2003/0108940 A1 | 6/2003 | Inoko et al. |
| 2003/0119209 A1 | 6/2003 | Kaylor et al. |
| 2003/0186463 A1 | 10/2003 | Hudak et al. |
| 2003/0190681 A1 | 10/2003 | Shai |
| 2004/0101889 A1 | 5/2004 | Letsinger et al. |
| 2004/0110167 A1 | 6/2004 | Gerdes et al. |
| 2004/0152142 A1 | 8/2004 | Klepp et al. |
| 2004/0156037 A1 | 8/2004 | Mawhirt et al. |
| 2004/0203086 A1 | 10/2004 | Piasio et al. |
| 2004/0241779 A1 | 12/2004 | Piasio et al. |
| 2005/0019814 A1 | 1/2005 | Laugham, Jr. et al. |
| 2005/0032244 A1 | 2/2005 | Nie et al. |
| 2005/0130120 A1 | 6/2005 | Lambotte et al. |
| 2005/0164305 A1 | 7/2005 | Golz et al. |
| 2005/0175992 A1 | 8/2005 | Abed et al. |
| 2005/0181517 A1 | 8/2005 | Chandler et al. |
| 2005/0221386 A1 | 10/2005 | Turner et al. |
| 2005/0227223 A1 | 10/2005 | Miyawaki |
| 2005/0227275 A1 | 10/2005 | Jung et al. |
| 2005/0239056 A1 | 10/2005 | Piasio et al. |
| 2005/0272106 A1 | 12/2005 | Moore et al. |
| 2006/0003390 A1 | 1/2006 | Schaffler et al. |
| 2006/0019406 A1 | 1/2006 | Wei et al. |
| 2006/0024843 A1 | 2/2006 | Lee et al. |
| 2006/0057608 A1 | 3/2006 | Kaufman |

(56) References Cited

U.S. PATENT DOCUMENTS

| | | |
|---|---|---|
| 2006/0110285 A1 | 5/2006 | Piasio et al. |
| 2006/0121626 A1 | 6/2006 | Imrich |
| 2006/0147927 A1 | 7/2006 | Geddes et al. |
| 2006/0148097 A1 | 7/2006 | Yamaguchi et al. |
| 2006/0160078 A1 | 7/2006 | Cardy et al. |
| 2006/0172434 A1 | 8/2006 | Rowell |
| 2006/0199278 A1 | 9/2006 | Leclipteux et al. |
| 2006/0216704 A1 | 9/2006 | Newton et al. |
| 2006/0223192 A1 | 10/2006 | Smith et al. |
| 2006/0240569 A1 | 10/2006 | Goldenbaum et al. |
| 2006/0263907 A1 | 11/2006 | Zweig |
| 2007/0003992 A1 | 1/2007 | Pentyala |
| 2007/0015290 A1 | 1/2007 | Raj |
| 2007/0059682 A1 | 3/2007 | Aberl et al. |
| 2007/0141564 A1 | 6/2007 | Aberl et al. |
| 2007/0184506 A1 | 8/2007 | Klepp |
| 2007/0202497 A1 | 8/2007 | Renuart et al. |
| 2007/0224701 A1 | 9/2007 | Rosenstein |
| 2007/0264629 A1 | 11/2007 | Holmes et al. |
| 2008/0003141 A1 | 1/2008 | Iketani |
| 2008/0032319 A1 | 2/2008 | Nam |
| 2008/0057493 A1 | 3/2008 | Gao et al. |
| 2008/0085525 A1 | 4/2008 | Van Herwijnen |
| 2008/0102473 A1 | 5/2008 | Fouquet et al. |
| 2008/0145843 A1 | 6/2008 | Song |
| 2008/0194041 A1 | 8/2008 | Guirguis |
| 2008/0199851 A1 | 8/2008 | Egan et al. |
| 2008/0310998 A1 | 12/2008 | Lamotte |
| 2008/0318341 A1 | 12/2008 | Esfandiari |
| 2009/0011436 A1 | 1/2009 | Piasio et al. |
| 2009/0047673 A1 | 2/2009 | Cary |
| 2009/0155811 A1 | 6/2009 | Natan et al. |
| 2009/0203059 A1 | 8/2009 | Davis et al. |
| 2009/0232702 A1 | 9/2009 | Wu et al. |
| 2009/0289201 A1 | 11/2009 | Babu et al. |
| 2009/0291508 A1 | 11/2009 | Babu et al. |
| 2009/0305231 A1 | 12/2009 | Weidemaier et al. |
| 2009/0305290 A1 | 12/2009 | Sambursky et al. |
| 2009/0311247 A1 | 12/2009 | Priest et al. |
| 2010/0015634 A1 | 1/2010 | VanDine et al. |
| 2010/0112725 A1 | 5/2010 | Babu et al. |
| 2010/0143891 A1 | 6/2010 | Aberl et al. |
| 2010/0143941 A1 | 6/2010 | Wu et al. |
| 2010/0173423 A1 | 7/2010 | Zuaretz et al. |
| 2010/0209297 A1 | 8/2010 | Raj et al. |
| 2010/0279310 A1 | 11/2010 | Sia et al. |
| 2010/0291536 A1 | 11/2010 | Viljoen et al. |
| 2010/0297611 A1 | 11/2010 | Sambursky et al. |
| 2011/0136258 A1 | 6/2011 | Sambursky et al. |
| 2011/0151584 A1 | 6/2011 | Esfandiari |
| 2011/0275542 A1 | 11/2011 | Eden et al. |
| 2012/0331576 A1 | 12/2012 | Brass et al. |
| 2013/0130367 A1 | 5/2013 | Sambursky et al. |
| 2013/0196310 A1* | 8/2013 | Sambursky .......... G01N 33/569 435/5 |
| 2013/0196311 A1 | 8/2013 | Sambursky et al. |
| 2014/0128286 A1 | 5/2014 | Khabar et al. |
| 2014/0206754 A1 | 7/2014 | Rodriguez et al. |
| 2015/0099666 A1 | 4/2015 | Sambursky et al. |
| 2016/0084832 A1 | 3/2016 | Sambursky et al. |

FOREIGN PATENT DOCUMENTS

| | | |
|---|---|---|
| DE | 10054093 A1 | 5/2005 |
| EP | 0306772 A1 | 3/1989 |
| EP | 0582231 A1 | 2/1994 |
| EP | 1489416 A1 | 12/2004 |
| EP | 1686378 A2 | 8/2006 |
| JP | 2006189317 A1 | 7/2006 |
| JP | 2007322310 A1 | 12/2007 |
| JP | 2008537145 A1 | 9/2008 |
| RU | 244017 C1 | 2/2012 |
| WO | 9628715 | 9/1996 |
| WO | 9638720 | 12/1996 |
| WO | 9742341 | 11/1997 |
| WO | 9960402 A1 | 11/1999 |
| WO | 0136975 A1 | 5/2001 |
| WO | 03073817 A2 | 9/2003 |
| WO | 2006115866 A1 | 11/2006 |
| WO | 2007063326 A2 | 6/2007 |
| WO | 2007070117 A1 | 6/2007 |
| WO | 2007081330 A1 | 7/2007 |
| WO | 2007110779 A2 | 10/2007 |
| WO | 2007123507 A1 | 11/2007 |
| WO | 2008014709 A1 | 2/2008 |
| WO | 2009044167 A1 | 4/2009 |
| WO | 2009108224 A1 | 9/2009 |
| WO | 20090152209 A1 | 12/2009 |
| WO | 2010009206 A2 | 1/2010 |
| WO | 2014137858 A1 | 9/2014 |

OTHER PUBLICATIONS

Vazquez et al., C-reactive protein levels in community-acquired pneumonia, 2003, European Respiratory Journal, 21: 702-705. (Year: 2003).*

Engelmann et al., Diagnosis of Viral Infections Using Myxovirus Resistance Protein A (MxA), Apr. 2015, Pediatrics, 134(4): e985-993 (Year: 2015).*

Lee, Procalcitonin as a biomarker of infectious diseases, Korean J Intern Med., 2013, 28(3): 285-291 (Year: 2013).*

Jennifer Weglowski, An Evidence-Based Approach To The Evaluation And Treatment Of Pharyngitis In Children, 2011, Pediatric Emergency Medicine Practice, vol. 8, No. 12, 28 pages (Year: 2011).*

Gill, et al., "Counterregulation between the FcepsilonRI pathway and antiviral responses in human plasmacytoid dendritic cells," J Immunol. 2010; 184:5999-6006.

Gonzales, et al., "Principles of appropriate antibiotic use for treatment of nonspecific upper respiratory tract infections in adults: Background, specific aims, and methods," Ann Emerg Med., 2001; 37(6):690-697.

Gorse, et al., "Human coronavirus and acute respiratory illness in older adults with chronic obstructive pulmonary disease," J Infect Dis., Mar. 15, 2009; 199(6):847-57.

Gowardman, et al., "Severe community-acquired pneumonia: a one-year analysis in a tertiary referral intensive care unit," NZ Med J, 2000, 113:161-164.

Graat, et al., "A prospective, community-based study on virologic assessment among elderly people with and without symptoms of acute respiratory infection," J Clin Epidemiol, 2003; 56:1218-23.

Green, et al., "Synergism between allergens and viruses and risk of hospital admission with asthma: case-control study," BMJ, 2002; 324:763.

Gulich, "Improving diagnostic accuracy of bacterial pharyngitis by near patient measurement of C-reactive protein (CRP)," British Journal of General Practice, 1999, 49, 119-121.

Holm, et al., "Procalcitonin versus C-reactive protein for predicting pneumonia in adults with lower respiratory tract infection in primary care," British Journal of General Practice, 2007; 57: 555-560.

Hopstaken, et al., "Contributions of symptoms, signs, erythrocyte sedimentation rate, and C-reactive protein to a diagnosis of pneumonia in acute lower respiratory tract infection," Br J Gen Pract. 2003; 53(490):358-364.

Horby, et al., "A boarding school outbreak of pertussis in adolescents: value of laboratory diagnostic methods," Epidemiol. Infect. (2005), 133, 229-236.

Huang, et al., "Association between point-of-care CRP testing and antibiotic prescribing in respiratory tract infections: a systematic review and meta-analysis of primary care studies," Br J Gen Pract 2013.

Huijskens, et al., "The value of signs and symptoms in differentiating between bacterial, viral and mixed aetiology in patients with community-acquired pneumonia," J Med Microbiol, 2014; 63:441-52.

(56) References Cited

OTHER PUBLICATIONS

Huijskens, et al., "Viral and bacterial aetiology of community-acquired pneumonia in adults," Influenza Other Respi Viruses, 2013; 7:567-73.
Huovinen, et al., "Pharyngitis in Adults: The Presence and Coexistence of Viruses and Bacterial Organisms," Ann Intern Med, 1989; 110(8):612-616.
Hyman, et al., "Prevalence of Asymptomatic Nasopharyngeal Carriage of Chlamydia pneumoniae in Subjectively Healthy Adults: Assessment by Polymerase Chain Reaction-Enzyme Immunoassay and Culture," Clinical Infectious Diseases, 1995; 20:1174-8.
Ingram, et al., "Procalcitonin and C-reactive protein in severe H1N1 influenza infection," Intensive Care Med, 2010, 36:528-532.
International Search Report and Written Opinion dated Jan. 19, 2017, International Application No. PCT/US2016/058025.
International Search Report and Written Opinion dated Feb. 2, 2017, International Application No. PCT/058031.
Ip, et al., "Value of serum procalcitonin, neopterin, and C-reactive protein in differentiating bacterial from viral etiologies in patients presenting with lower respiratory tract infections," Diagnostic Microbiology and Infectious Disease 59 (2007) 131-136.
Irwin, et al., "Diagnosis and management of cough executive summary: ACCP evidence-based clinical practice guidelines," Chest, 2006; 129(1 Suppl):1S-23S.
Jansen, et al., "Frequent Detection of Respiratory Viruses without Symptoms: Toward Defining Clinically Relevant Cutoff Values," J Clin Microbiol, 2011, 49: 2631-2636.
Jartti, et al., "Identification of Respiratory Viruses in Asymptomatic Subjects," Pediatr Infect Dis J 2008; 27(12): 1103-1107.
Jartti, et al., "Persistence of rhinovirus and enterovirus RNA after acute respiratory illness in children," J Med Virol 2004; 72:695-9.
Jartti, et al., "Serial viral infections in infants with recurrent respiratory illnesses," Eur Respir J 2008; 32:314-20.
Johansson, et al., "Etiology of community-acquired pneumonia: increased microbiological yield with new diagnostic methods," Clin Infect Dis, 2010; 50:202-9.
Johnson, et al., "The Human Immune Response to Streptococcal Extracellular Antigens: Clinical, Diagnostic, and Potential Pathogenetic Implications," Clin Infect Dis, 2010; 50:481-90.
Johnston, et al., "Community study of role of viral infections in exacerbations of asthma in 9-11 year old children," Br. Med. J., 1995, 310:1225-1229.
Johnston, et al., "The relationship between upper respiratory infections and hospital admissions for asthma: a time trend analysis," Am. J. Respir. Grit. Care Med., 1996, 154:654-660.
Johnston, et al., "Use of polymerase chain reaction for diagnosis of picornavirus infection in subjects with and without respiratory symptoms," J Clin Microbiol, 1993; 31(1):111-117.
Kaplan, et al., "Antistreptolysin O and Anti-Deoxyribonuclease B Titers: Normal Values for Children Ages 2 to 12 in the United States," Pediatrics, 1998, 101:86-88.
Kaplan, et al., "Diagnosis of streptococcal pharyngitis: differentiation of active infection from the carrier state in the symptomatic child," J Infect Dis, 1971, 123:490-501.
Kaplan, et al., "Significance of Quantitative Salivary Cultures for Group A and Non-group a B-Hemolytic Streptococci in Patients with Pharyngitis and in their Family Contacts," Pediatrics, vol. 64, 1979, pp. 904-912.
Kavanagh, et al., "A pilot study of the use of near-patient C-Reactive Protein testing in the treatment of adult respiratory tract infections in one Irish general practice," BMC Fam Pract, Aug. 31, 2011; 12:93.
Kellogg, et al., "Detection of group A streptococci in the laboratory of physician's office. Culture vs. antibody methods," J. Am. Med. Assoc., 1986, 255:2638-2642.
Kendrick, "A gene's mRNA level does not usually predict its protein level," Sep. 25, 2014, Kendrick labs.
Kennedy, et al., "Comparison of viral load in individuals with and without asthma during infections with rhinovirus," Am J Respir Crit Care Med, Mar. 1, 2014; 189(5):532-9.
Kim, et al., "Utility of procalcitonin as an early diagnostic marker of bacteremia in patients with acute fever," Yonsei Med J, Mar. 2011; 52(2):276-81.
Klein, et al., "Upper limits of normal antistreptolysin O and antideoxyribonuclease B titers," Appl Microbiol, 1971, 21:999-1001.
Kling, et al., "Persistence of rhinovirus RNA after asthma exacerbation in children," Clin Exp Allergy, 2005; 35:672-8.
Komaroff, et al., "The Prediction of Streptococcal Pharyngitis in Adults," J Gen Intern Med, 1986; 1:1-7.
Koo, et al., "Towards evidence-based emergency medicine: Best BETs from the Manchester Royal Infirmary," Emerg Med J Aug. 2011 vol. 28 No. 8.
Korppi, "Non-specific host response markers in the differentiation between pneumococcal and viral pneumonia: What is the most accurate combination?" Pediatrics International (2004) 46, 545-550.
Korppi, et al., "C-Reactive Protein in Viral and Bacterial Respiratory Infection in Children," Scand J Infect Dis J, 1992; 207-213.
Korppi, et al., "White blood cells, C-reactive protein and erythrocyte sedimentation rate in pneumococcal pneumonia in children," Eur Respir J, 1997; 10(5):1125-1129.
Koskenvuo, et al., "Expression of MxA protein in blood lymphocytes of children receiving anticancer chemotherapy," Pediatric Hematology and Oncology, 23:649-660, 2006.
Kristoffersen, et al., "Antibiotic treatment interruption of suspected lower respiratory tract infections based on a single procalcitonin measurement at hospital admission—a randomized trial," Clin Microbiol Infect, 2009, 15:481-487.
Lände, et al., "HRCT findings in the lungs of primary care patients with lower respiratory tract infection," Acta Radiol, 2002; 43(2):159-163.
Laing, et al., "Community-acquired pneumonia in Christchurch and Waikato 1999-2000: microbiology and epidemiology," N Z Med J, Nov. 9, 2001; 114(1143):488-92.
Lala, et al., "The discriminative value of C-reactive protein levels in distinguishing between community-aquired bacteraemic and respiratory virus-associated lower respiratory tract infections in HIV-1-infected and -uninfected children," Ann Trop Pediatr, 2002; 22:271-279.
Le, et al., "Alterations of the oropharyngeal microbial flora after adenotonsillectomy in children: a randomized controlled trial," Arch Otolaryngol Head Neck Surg, Oct. 2007; 133(10):969-72.
Aouifi, et al. Usefulness of Procalcitonin for Diagnosis of Infection in Cardia Surgical Patents, Crit Care Med. 2000, vol. 28, No. 9, pp. 3171-3176.
Baigent SJ, et al. Inhibition of beta interferon transcription by noncytopathogenic bovine viral diarrhea virus is though an interferon regulatory factor 3-dependent mechanism, J Vir. 2002; 76(18):8979-8988.
Baker MD, et al., Outpatient management without antibiotics of fever in selected infants. N Engl J Med 1993;329:1437-1441.
Barden LS, Dowell SF, Schwartz B, Lackey C. Current attitudes regarding use of antimicrobial agents, Clin Pediatr. 1998; 37:665-672.
Barnard, et al., Development of an Oligonucleotide-Based SNP Detection Method on Lateral Flow Strips Using Hexapet Tags, Point of Care, vol. 4, No. 3, pp. 108-118 (Sep. 2005).
Baskin MN, et al., Outpatient treatment of febrile infants 28 to 89 days of age with intramuscular administration of ceftriaxone. J Pediatr 1992;120:22-27.
Berezovski, et al., Cell lysis inside the capillary facilitated by transverse diffusion of laminar flow profiles (TDLFP), Anal Bioanal Chem (2007) 387:91-96.
Bruning et al., A rapid chromatographic strip test for the pen-side diagnosis of rinderpest virus, Journal of Virological Methods 81 (1999) 143-154.
Bulletin of the World Health Organization (WHO), 1998, 76(1): 101-103.
Calandra T, et al. Prognostic values of tumor necrosis factor/cachectin, interleukin-1, interferon-alpha, and interferon-gamma in the serum of patients with septic shock. J Infect Dis 1990;161:982-987.

(56) References Cited

OTHER PUBLICATIONS

Cals JWL, et al. Effect of point of care testing for C reactive protein and training in communication skills on antibiotic use in lower respiratory tract infections: cluster randomised trial, BMJ 2009; 338:b1374.

Charleston B and Stewart HJ. An interferon-induced Mx protein: cDNA sequence and high-level expression in the endometrium of pregnant sheep, Gene 1993; 137:327-331.

Chi H, Chin NC, Li WC, Huang FY, Etiology of acute pharyngitis in children: is antibiotic therapy needed?, J Microbial Immunol Infect 2003;36(1): 26-30.

Chieux V, et al. MxA protein in capillary blood of children with viral infections. J Med Virol. 1999;59:547-51.

Chieux V, et al. The MxA protein levels in whole blood lysates of patients with various viral infections. J Virol Methods. 1998;70:183-91.

Choi, et al., A rapid, simple measurement of human albumin in whole blood using a fluorescence immunoassay (I), Clinica Chimica Acta 339 (2004) 147-156.

Dahler Eriksen BS, et al. Near-patient test for C-reactive protein in general practice: assessment of clinical, organizational, and economic outcomes, Clin Chem 1999, 45(4):478-485.

Diederichsen HZ, et al. Randomised controlled trial of CRP rapid test as a guide to treatment of respiratory infections in general practice, Scand J Prim Health Care 2000, 18(1):39-43.

Dineva et al., Simultaneous Visual Detection of Multiple Viral Amplicons by Dipstick Assay, Journal of Clinical Microbiology, Aug. 2005, p. 4015-4021.

Djavani et al., Early Blood Profiles of Virus Infection in a Monkey Model for Lassa Fever, Journal of Virology, Aug. 2007, p. 7960-7973, vol. 81, No. 15.

Envitec SmartClip Brochure, Rapid Detection of Drugs of Abuse in Saliva or Sweat; ENVITEC-Wismar GmbH, Wismar, Germany, www.envitec.com, 2004.

Ewig, S., and A. Torres. Severe community-acquired pneumonia Curr. Opin. Crit. Care. 2002; 8:453-460.

Extended European Search Report dated Apr. 17, 2013. European Application No. 10835165.1 (PCT/US2010058827).

Falk G, Fahey T. C-reactive protein and community-acquired pneumonia in ambulatory care: systematic review of diagnostic accuracy studies. Family Practice 2009;26(1): 10-21.

Flood RG, et al. The utility of serum C-reative protein in differentiating bacterial from nonbacterial pneumonia in children, Ped Infec Dis J 2008; 27(2):95-99.

Forster J, et al. MxA protein in infants and children with respiratory tract infection. Acta Paediatr 1996;85:163-167.

FTA Nucleic Acid Collection, Storage and Purification, http://whatman.com/products.aspx?PID=108, 2007.

Girardin E, et al. Tumor necrosis factor and interleukin-1 in the serum of children with severe infectious purpura. N Engl J Med 1988;319:397-400.

Goetschy JF, et al. Regulation of the interferon-inducible IFI-78K gene, the human equivalent of the murine Mx gene, by interferons, double-stranded RNA, certain cytokines, and viruses. J Virol 1989; 63(6):2616-22.

Gonzales R, et al. Excessive Antibiotic Use for Acute Respiratory Infections in the United States. Clin Infect Dis 2001;33:757-62.

Haller O, Kochs G, Interferon induced Mx proteins: Dynamin like GTPases with antiviral activity, Traffic. 2002; 3:710-717.

Halminen M, et al. Expression of MxA protein in blood lymphocytes discriminates between viral and bacterial infections in febrile children. Pediatr Res 1997;41:647-650.

Hansson LO, Carlsson I, Hansson E, Hovelius B, Svensson P, Tryding N, Measurement of C-reactive protein and the erythrocyte sedimentation rate in general practice, Scand J Prim Health Care 1995;13:39-45.

Hatherill et al. Diagnostic Markers of Infection: Comparison of Procalcitonin with C Reative Protein and Leucocyte Count; Arch Dis Child 1999: 81: 417-21.

Hedlund J, Hansson LO. Procalcitonin and C-reactive protein levels in community-acquired pneumonia: correlation with etiology and prognosis. Infection 2000;28:68-73.

Hjortdahl P, Melbye H, Does near-to-patient testing contribute to the diagnosis of streptococcal haryngitis in adults?, Scand J Prim Health Care 1994;12:70-6.

Nicholson, et al., "Acute viral infections of upper respiratory tract in elderly people living in the community: comparative, prospective, population based study of disease burden," BMJ, 1997; 315:1060-4.

Nicholson, et al., Respiratory viruses and exacerbations of asthma in adults, Br Med J, 1993, 307:982-986.

Nilsson, et al., "*Staphylococcus aureus* Throat Colonization is More Frequent than Colonization in the Anterior Nares," J Clin Microbiol, 2006; 44:3334-9.

Nobre, et al., "Use of procalcitonin to shorten antibiotic treatment duration in septic patients: a randomized trial," Am J Respir Crit Care Med, 2008; 177:498-505.

O'Brien, et al., "The WHO Pneumococcal Vaccine Trials Carriage Working Group Report from a WHO working group: Standard method for detecting upper respiratory carriage of *Streptococcus pneumoniae*," Pediatr Infect Dis J, 2003; 22:133-40.

Okamura, et al., "Potential clinical applications of C-reactive protein," J Clin Lab Anal 1990; 4:231-235.

O'Mahony, et al., "Integration of Bacteria Capture via Filtration and in Situ Lysis for Recovery of Plasmid DNA under Industry-Compatible Conditions," Biotechnol. Prog. 2007, 23, pp. 895-903.

Oosterheert, et al., "Impact of rapid detection of viral and atypical bacterial pathogens by real-time polymerase chain reaction for patients with lower respiratory tract infection," Clin Infect Dis, Nov. 15, 2005; 41(10):1438-44.

Oppong, et al., "Cost-effectiveness of point-of-care C-reactive protein testing to inform antibiotic prescribing decisions," Br J Gen Pract, Jul. 2013; 63(612):e465-71.

Oshita, et al., Semi-quantitative procalcitonin test for the diagnosis of bacterial infection: Clinical use and experience in Japan, J Microbiol Immunol Infect. 2010; 43(3):222-227.

Paran, et al., "C-reactive protein velocity to distinguish febrile bacterial infections from non-bacterial febrile illnesses in the emergency department," Critical Care, 2009, 13:R50.

Parida, "Rapid and real-time detection technologies for emerging viruses of biomedical importance," J. Biosci. 33 (4), Nov. 2008, 617-728.

Pavlovic, et al., "Human and mouse Mx proteins inhibit different steps of the influenza virus multiplication cycle," J Vir. 1992; 66(4):2564-2569.

Peltola, et al., "Rhinovirus transmission within families with children: incidence of symptomatic and asymptomatic infections," J Infect Dis 2008; 197:382-9.

Penel, et al., "Fever and Solid Tumor: Diagnostic Utility of Procalcitonin and C-reactive Protein," Rev Med Interne 2001;22:706-714.

Peter, et al., "Group A streptococcal infections of the skin and pharynx, part 2," N Engl J Med 1977; 297(7): 365-370.

Pitossi, et al., "A Functional GTP-Binding Motif Is Necessary for Antiviral Activity of Mx Proteins," Journal of Virology, Nov. 1993, vol. 67(11), pp. 6726-6732.

Powell, et al., "Criteria for exclusion of serious bacterial infections in young infants," Journal of Pediatrics, Nov. 1992, pp. 831-832.

Prehaud, et al., "Virus Infection Switches TLR-3-Positive Human Neurons To Become Strong Producers of Beta Interferon," Journal of Virology, Oct. 2005, p. 12893-12904.

Putto, et al., "C-reactive protein in the evaluation of febrile illness," Arch Dis Child, 1986; 61(1):24-29.

Rattinger, et al., "A sustainable strategy to prevent misuse of antibiotics for acute respiratory infections," PLoS One, 2012; 7(12):e51147.

Restrepo, et al., "Severe community-acquired pneumonia: current outcomes, epidemiology, etiology, and therapy," Curr. Opin. Infect. Dis. 2001; 14:703-709.

Rhedin, et al., "Clinical Utility of PCR for Common Viruses in Acute Respiratory Illness," Pediatrics, Mar. 2014; 133(3): e538-45.

(56) References Cited

OTHER PUBLICATIONS

Riedel, et al., "Procalcitonin as a Marker for the Detection of Bacteremia and Sepsis in the Emergency Department," Am J Clin Pathol, 2011; 135:182-189.
Roberts, et al., "Detection of group A *Streptococcus* in tonsils from pediatric patients reveals high rate of asymptomatic streptococcal carriage," BMC Pediatr, 2012; 12:3.
Robinson, "Colonization and infection of the respiratory tract: What do we know?" Pediatr Child Health, Jan. 2004; 9(1):21-4.
Ronni, et al., "Control of IFN-inducible MxA gene expression in human cells," J Immunol, 1993, 150:1715-1726.
Ronni, et al., "Regulation of IFB-alpha/beta, MxA, 2',5'-oligoadenylate synthetase, and HLA gene expression in influenza A-infected human lung epithelial cells," J Immunol, 1997; 158:2363-2374.
Rosenthal, et al., "Prevalence of Gram-negative rods in the normal pharyngeal flora," Annals of Internal Medicine, 1975, 83:355-357.
Rothenberger, et al., "Detection of acute phase response and infection. The role of procalcitonin and C-reactive protein," Clin Chem Lab Med, 1999, 37:275-9.
Salonen, et al., "C-reactive protein in acute viral infections," J Med Virol, 1981; 8(3):161-167.
Sambursky, "510-K Summary of Safety and Effectiveness" (Sep. 14, 2005).
Sambursky, et al., "The RPS Adeno Detector for Diagnosing Adenoviral Conjunctivitis," Ophthalmology, vol. 113, No. 10, pp. 1758-1764 (Oct. 2006).
Sambursky, et al., "Evaluating the accuracy of a point-of-care immunoassay to identify a viral and/or bacterial immune response in patients with acute febrile respiratory infection," presented at European Congress of Clinical Microbiology and Infectious Diseases (ECCMID), May 2014, Barcelona, Spain.
Sambursky, et al., "Evaluating the accuracy of combining two biomarkers to differentiate viral and/or bacterial immune response in patients with acute febrile respiratory infection," presented at ID week, Oct. 2014, Philadelphia, Pennsylvania.
Sambursky, et al., "FebriDx™: the ability of a 10-minute rapid point-of-care immunoassay to reduce antibiotic prescriptions for acute febrile respiratory infection," presented at European Congress of Clinical Microbiology and Infectious Diseases (ECCMID), Apr. 2015, Copenhagen, Denmark.
Sambursky, et al., "Rapidly and Accurately Diagnosing Viral Respiratory Infection Leads to Better Patient Management," presented at Making a Difference in Infectious Disease (MAD-ID), May 2013, Orlando Florida.
Sangil, et al., "Aetiology of community-acquired pneumonia among adults in an H1N1 pandemic year: the role of respiratory viruses," Eur J Clin Microbiol Infect Dis (2012), 31:2765-2772.
Sato, et al., "Differences in serum cytokine levels between influenza virus A and B infections in children," Cytokine, 2009; 47(1):65-68.
Sauteur, et al., "Mycoplasma pneumoniae in children: carnage, pathogenesis, and antibiotic resistance," Curr Opin Infect Dis, 2014, 27:220-227.
Saxon, et al., "Immediate hypersensitivity reactions to beta-lactam antibiotics," Ann Intern Med, 1987; 107:204-15.
Schmidt, et al., "Chlamydia pneumoniae Carriage and Infection in Hospitalized Children with Respiratory Tract Diseases," Infection, 2003; 31:410-416.
Schuetz, et al., "Blood biomarkers for personalized treatment and patient management decisions in community-acquired pneumonia," Curr Opin Infect Dis, 2013, 26:159-167.
Schuetz, et al., "Clinical Outcomes Associated With Procalcitonin Algorithms to Guide Antibiotic Therapy in Respiratory Tract Infections," JAMA, Feb. 20, 2013, vol. 309, No. 7, pp. 717-718.
Schuetz, et al., "Procalcitonin Algorithms for Antibiotic Therapy Decisions: A Systematic Review of Randomized Controlled Trials and Recommendations for Clinical Algorithms," Arch Intern Med, 2011; 171 (15):1322-1331.
Schuetz, et al., "Procalcitonin for diagnosis of infection and guide to antibiotic decisions: past, present and future," BMC Med, 2011; 9:107.
Schuetz, et al., "Procalcitonin to Guide Initiation and Duration of Antibiotic Treatment in Acute Respiratory Infections: An Individual Patient Data Meta-Analysis," Clin Infect Dis, 2012; 55(5):651-62.
Schuetz, et al., "Procalcitonin to initiate or discontinue antibiotics in acute respiratory tract infections (Review)," Cochrane Database of Systematic Reviews, 2012, Issue 9. Art. No. CD007498. DOI:10.1002/14651858.CD007498.pub2.
Schuetz, et al., "Role of Procalcitonin in Managing Adult Patients With Respiratory Tract Infections," Chest, 2012; 141(1):1063-1073.
Schuetz, et al., "Serum Procalcitonin for Discrimination of Blood Contamination from Bloodstream Infection due to Coagulase-Negative Staphylococci," Infection, 2007; 35:352-355.
Horisberger MA. Interteron-induced human protein MxA is a GTPase which binds transiently to cellular proteins. J Virol 1992;66:4705-4709.
Huang N, et al. Antibiotic prescribing for children with nasopharyngitis (common colds), upper respiratory infections, and bronchitis who have health-professional parents. Pediatrics 2005;116:826-832.
International Search Report and Written Opinion dated Feb. 18, 2010, International Application No. PCT/US2009/050645.
International Search Report and Written Opinion dated Jan. 22, 2010, International Application No. PCT/US2009/046848.
International Search Report and Written Opinion dated Mar. 12, 2010, International Application No. PCT/US2009/050653.
International Search Report and Written Opinion for International Application No. PCT/US2010/058827 dated Nov. 30, 2011.
Itazawa T, et al. Increased lymphoid MxA expression in acute asthma exacerbation in children. Allergy 2001;56:895-898.
Itazawa T, et al. Theophylline metabolism in acute asthma with MxA-indicated viral infection. Pediatr Int 2006;48:54-57.
Jaskiewicz JA, et al. Febrile infants at low risk for serious bacterial infection—an appraisal of the Rochester criteria and implications for management. Pediatrics 1994;94: 390-396.
Jennings LC, Anderson TP, Beynon KA, et al., Incidence and characteristics of viral community-acquired pneumonia in adults 1Thorax 2008;63:42-48.
Karle, et al., Application of FTA-based Technology for Sample Collection, Transport, Purification, and Storage of PCR-ready Plant DNA (Nov. 2003).
Kawamura M, et al. New sandwich-type enzyme-linked immunosorbent assay for human MxA protein in a whole blood using monoclonal antibodies against GTP-binding domain for recognition of viral infection. J Clin Lab Anal. 2012;26:174-83.
Le Bon A, Tough DF, Links between innate and adaptive immunity via type I interferon, Curr Opin Immunol. 2002; 14:432-436.
Lindback S, Hellgren U, Julander I, Hansson LO, The value of C-reactive protein as a marker of bacterial infection in patients with septicaemia/endocarditis and influenza, Scand J Infect Dis 1989;21:543-9.
International PCT Search Report for PCT/US2014/019771; Jun. 27, 2014; 14 pages.
Search Report and Written Opinion dated Sep. 25, 2014 for PCT/US2014/019773.
Advani et al., "Detecting Respiratory Viruses in Asymptomatic Children," Pediatr Infect Dis J. Dec. 2012.
Akkerman, et al., "Prescribing antibiotics for respiratory tract infections by GPs: management and prescriber characteristics," Br J Gen Pract 2005; 55(511): 114-118.
Andreola, et al., "Procalcitonin and C-Reactive Protein as Diagnostic Markers of Severe Bacterial Infections in Febrile Infants and Children in the Emergency Department," Pediatr Infect Dis J, 2007; (8):672-7.
Atmar, "Chlamydia Species and Mycoplasma pneumoniae," Curr Infect Dis Rep., Apr. 1, 1999(1):73-79.
Ayoub, et al., "Evaluation of the streptococcal deoxyribonuclease B and diphosphopyridine nucleotide antibody tests in acute rheumatic fever and acute glomerulonephritis," Pediatrics, 1962, 29:527-538.
Baraldo, et al., "Deficient antiviral immune responses in childhood: distinct roles of atopy and asthma," J Allergy Clin Immunol. 2012, 130:1307-1314.

(56) References Cited

OTHER PUBLICATIONS

Bardin, et al., "Experimental rhinovirus infection in volunteers," Eur. Respir. J., 1996, 9:2250-2255.
Barlow, et al., "Observations on the carriage of Candida albicans in man," British Journal of Dermatology, 1969,81, 103-106.
Bell, et al., Quantitative throat-swab culture in the diagnosis of streptococcal pharyngitis in children,: Lancet, Jul. 10, 1976; 2(7976):62-3.
Berger, et al., "A predictive model to estimate the risk of serious bacterial infections in febrile infants" Eur J Pediatr, 1996; 155:468-73.
Berkley, et al., "Viral etiology of severe pneumonia among Kenyan infants and children," JAMA, 2010; 303(20):2051-2057.
Berkovitch, et al., "Colonization rate of bacteria in the throat of healthy infants," Int. J. Pediatr. Otorhinolaryngol., 2002, 63:19-24.
Bierbaum, et al., "Performance of a novel microarray multiplex PCR for the detection of 23 respiratory pathogens (SYMP-ARI study)," Eur J Clin Microbiol Infect Dis. 2012; 31:2851-61.
Bisno et al., "Practice Guidelines for the Diagnosis and Management of Group A Streptococcal Pharyngitis," Clinical Infectious Diseases 2002; 35:113-25.
Bjerrum, et al., "C-reactive protein measurement in general practice may lead to lower antibiotic prescribing for sinusitis," Br J Gen Pract 2004; 54(506): 659-662.
Blaschke, "Interpreting assays for the detection of *Streptococcus pneumoniae*," Clin Infect Dis. May 2011; 52 Suppl 4: S331-7.
Blomqvist, et al., Virological and serological analysis of rhinovirus infections during the first two years of life in a cohort of children, J Med Virol 2002; 66:263-8.
Boe, et al., "Perineal carriers of staphylococci," Br. Med. J., 1964, 5404:280-281.
Boersma, et al., "Reliability of radiographic findings and the relation to etiologic agents in community-acquired pneumonia," Respiratory Medicine. 2006; 100:92-932.
Bouadma, et al., "PRORATA trial group: Use of procalcitonin to reduce patients' exposure to antibiotics in intensive care units (PRORATA trial): a multicentre randomised controlled trial," Lancet 2010; 375:463-474.
Brahmadathan, et al., "Microbiological diagnosis of streptococcal pharyngitis: lacunae and their implications," Indian J Med Microbiol. Apr. 2006; 24(2):92-6.
Briel, et al., "Procalcitonin-guided antibiotic use versus a standard approach for acute respiratory tract infections in primary care: study protocol for a randomised controlled trial and baseline characteristics of participating general practitioners," BMC Fam Pract 2005, 6:34.
Briel, et al., "Procalcitonin-Guided Antibiotic Use vs a Standard Approach for Acute Respiratory Tract Infections in Primary Care," Arch Intern Med. 2008; 168 (18): 2000-2007.
Burkhardt, et al., "Procalcitonin guidance and reductions of antibiotic use in acute respiratory tract infection" Eur Resp J. 2010; 36: 601-607.
Caliendo, et al., "Better Tests, Better Care: Improved Diagnostics for Infectious Diseases," Clin Infect Dis. Dec. 2013; 57 Suppl 3:S139-70.
Cals, et al., "Enhanced Communication Skills and C-reactive Protein Point-of-Care Testing for Respiratory Tract Infection: 3.5-year Follow-up of a Cluster Randomized Trial," Ann Fam Med 2013; 11:157-164.
Cals, et al., "Improving management of patients with acute cough by C-reactive protein point of care testing and communication training (IMPAC3T): study protocol of a cluster randomised controlled trial," BMC Family Practice 2007, 8:15.
Cals, et al., "Point-of-Care C-Reactive Protein Testing and antibiotic Prescribing for Respiratory Tract Infections: A Randomized Controlled Trial," Ann Fam Med 2010; 8: 124-133.
Cals, et al., "Procalcitonin-based guidelines and lower respiratory tract infections," JAMA, 2010; 303(5):418.

Calvino, et al., "Association between C-Reactive Protein Rapid Test and Group A *Streptococcus* Infection in Acute Pharyngitis," J Am Board Fam Med 2014; 27:424-426.
Capelastegui, et al., "Etiology of community-acquired pneumonia in a population-based study: link between etiology and patients characteristics, process-of-care, clinical evolution and outcomes," BMC Infect Dis. 2012; 12:134.
Cevey-Macherel, et al., "Etiology of community-acquired pneumonia in hospitalized children based on WHO clinical guidelines," Eur J Pediatr (2009) 168:1429-1436.
Chalmers, et al., "C-Reactive Protein Is an Independent Predictor of Severity in Community-acquired Pneumonia," The American Journal of Medicine (2008) 121, 219-225.
Chartrand, et al., "Accuracy of rapid influenza diagnostic tests: a meta-analysis," Ann Intern Med 2012; 156:500.
Van der Zalm, et al., "Respiratory Pathogens in Children with and without Respiratory Symptoms," J Pediatr, 2009; 154:396-400.
Van Duijn, et al., "Determinants of prescribing of second-choise antibiotics for upper and lower respiratory tract episodes in Dutch general practice," J Antimicrob Chemother 2005; 56(2):420-422.
Van Gageldonk-Lafeber, et al., "A Case-Control Study of Acute Respiratory Tract Infection in General Practice Patients, in The Netherlands," Clinical Infectious Diseases, 2005; 41:490-7.
Van Gageldonk-Lafeber, et al., "The aetiology of community-acquired pneumonia and implications for patient management," Neth J Med, 2013; 71:418-25.
Van Nieuwkoop, et al., "Procalcitonin reflects bacteremia and bacterial load in urosepsis syndrome: a prospective observational study," Crit Care, 2010, 14:R206.
Verbakel, et al., "Analytical accuracy and user-friendliness of the afinion point-of-care CRP test," J Clin Pathol, 2014; 67(1):83-86.
Verheij, et al., "NHGStandard Acuut hoesten; Dutch College of General Practitioners Guidelines on Acute Cough," Huisarts West 2003; 46(9):496-506. (Original reference in Dutch together with English machine translation.).
Viallon, et al., "Serum and ascetic procalcitonin levels in cirrhotic patients with spontaneous bacterial peritonitis: diagnostic value and relationship to pro-inflammatory cytokines," Intensive Care Med 2000, 26: 1082-8.
Vincent, et al., "Pharyngitis," Am Farn Physician, 2004; 69(6):1465-70.
Von Wussow, et al., "The human intracellular Mx-homologous protein is specifically induced by type I interferons," Eur J Immunol, 1990; 20:2015-2019.
Walsh et al., "Clinical impact of human coronaviruses 229E and OC43 infection in diverse adult populations," J Infect Dis, 2013; 208(10):1634-42.
Wannamaker, et al., "Antibody titers in acute rheumatic fever," Circulation 21, 1960; 598-614.
Wark, et al., "Asthmatic bronchial epithelial cells have a deficient innate immune response to infection with rhinovirus," J Exp Med, 2005; 201:937-947.
Wenzel, et al., "Clinical practice: acute bronchitis," N Engl J Med, 2006; 355:2125-30.
Wheat et al., "Effect of Rifampin on nasal carriers of coagulase-positive staphylococci," Journal of Infectious Diseases, 1981; 144,177.
Winther, et al., "Histopathologic examination and enumeration of polymorphonuclear leukocytes in the nasal mucosa during experimental rhinovirus colds," Acta Otolaryngol (Stockh), 1984; 413 (Suppl.):19-24.
Wiselka, et al., "Prophylactic intranasal α 2-interferon and viral exacerbations of chronic respiratory disease," Thorax, 1991; 46:706-11.
Wright, et al., "Patterns of illness in the highly febrile young child: epidemiologic, clinical and laboratory correlates," Pediatrics, 1981; 67:694-700.
Yates, "Management of patients with a history of allergy to beta-lactam antibiotics," Am J Med, 2008; 121:572-6.
Yo, et al., "Comparison of the test characteristics of procalcitonin to C-reactive protein and leukocytosis for the detection of serious bacterial infections in children presenting with fever without source: a systematic review and meta-analysis," Ann Emerg Med, Nov. 2012; 60(5):591-600.

(56) References Cited

OTHER PUBLICATIONS

Young, et al., "C-reactive protein: a critical review," Pathology 1991; 23:118-24.
Zambrano, et al. "Experimental rhinovirus challenges in adults with mild asthma: response to infection in relation to IgE," J Allergy Clin Immunol, May 2003; 111(5)1008-16.
Zimmerman, et al., "Influenza and other respiratory virus infections in outpatients with medically attended acute respiratory infection during the 2011-12 influenza season," Influenza and Other Respiratory Viruses, 2014; 8(4):397-405.
Zurcher, et al., "Mechanism of human MxA protein action: variants with changed antiviral properties," EMBO Journal 1992; 11(4):1657-1661.
Polzin et al. "Procalcitonin as a diagnostic tool in lower respiratory tract infections and tuberculosis" Eur Respir J, Jun. 2003; 21(6):939-43.
Schuetz, et al., "Effect of procalcitonin-based guidelines vs standard guidelines on antibiotic use in lower respiratory tract infections: the ProHOSP randomized controlled trial," JAMA 2009; 302:1059-66.
Hyuck, "Procalcitonin as a biomarker of infectious diseases," Korean J Intern Med, May 2013; 28(3): 285-291.
Centor et al. "The Diagnosis of Strep Throat in Adults in the Emergency Room", Med. Decision Making; vol. 1, No. 3, 1981.
National Committee for Quality Assurance, "HEDIS 2012 Measures," retrieved from https://www.google.com/url?sa=t&rct=j&q=&esrc=s&source=web&cd=1&ved=2ahUKEwi236jr1tzgAhVSJt8KHfQ4By4QFJAAegQICxAC&url=https%3A%2F%2Fwww.opm.gov%2Fhealthcare-insurance%2Fhealthcare%2Fcarriers%2F2012%2F2012-02attachment.pdf&usg=AOvVaw1IViS53a3GCNJkW14yQmyN; as early as 2012.
World Health Organization (WHO), "Who Report on Infectious Disease: Overcoming Antimicrobial Resistance," Geneva, Switzerland, 2000.
Winther, et al., "Light and scanning electron microscopy of nasal biopsy material from patients with naturally acquired commmon colds," Acta Otolaryngol, 1984; 97:309-318.
American Academy of Pediatrics, Committee on Infectious Diseases, "Red Book: Report of the Committee on Infectious Diseases," 26th Ed. Elk Grove Village, IL: American Academy of Pediatrics; 2003:573-584.
Eskerud, et al., "Fever in general practice: Frequency and diagnoses," Fam Pract, 1992; 263-69.
Jartti, et al., "New molecular virus detection methods and their clinical value in lower respiratory tract infections in children," Paediatr Respir Rev. 2013; 14(1):38-45.
Nokso-Koivisto, et al., "Human picomavirus and coronavirus RNA in nasopharynx of children without concurrent respiratory symptoms," J Med Virol, Mar. 2002; 66(3):417-20.
Schuetz et al., "Procalcitonin to initiate or discontinue antibiotics in acute respiratory tract infections," Evid Based Child Health. Jul. 2013; 8(4):1297-371.
Kumar, et al., "Inhibition of translation by IFIT family members is determined by their ability to interact selectively with the 50-terminal regions of cap0-, cap1- and 50ppp-mRNAs," Nucleic Acids Research Advance Access, Dec. 25, 2013, pp. 1-18.
Germ, et al., "Rhinovirus infection preferentially increases lower airway responsiveness in allergic subjects," Am. J. Respir. Crit. Care Med., 1997,155:1872-1876.
Centers for Disease Control and Prevention (CDC), "Annual number and percent distribution of ambulatory care visits by setting type according to diagnosis group, United States, 2009-2010," http://www.cdc.gov/nchs/data/ahcd/combined_tables.AMC_2009--2010_combined_web_ta ble01.pdf.
Johnson, et al., "Laboratory diagnosis of group A streptococcal infections," World Health Organization, Geneva 1996.
Reed, et al., "Prevalence of Chlamydia trachomatis and Mycoplasma pneumoniae in children with and without pharyngitis," J Fam Pract, 1988; 26(4):387-392.

World Health Organization (WHO), "Antimicrobial resistance: Global report on surveillance 2014: Estimates of burden of antibacterial resistance," http://www.who.int/drugresistance/documents/AMR_report_Web_slide_set.pdf.
Vegelin, et al., "Guidelines for severe community acquired pneumonia in the western world," Neth J Med, 1999; 55:110-117.
Lee, et al., "IFN-gamma production during initial infection determines the outcome of reinfection with respiratory syncytial virus," Am J Resp Crit Care Med, 2008; 177(2):208-218.
Leekha, et al., "Viral detection using a multiplex polymerase chain reaction-based assay in outpatients with upper respiratory infection," Diagn Microbiol Infect Dis, 2013; 75:169-73.
Leung et al., "InfectCheck CRP barcode-style lateral flow assay for semi-quantitative detection of C-reactive protein in distinguishing between bacterial and viral infections," Journal of Immunological Methods, 336 (2008), pp. 30-36.
Lieberman, et al., "Aetiology of respiratory tract infections: Clinical assessment versus serological tests," Br J Gen Pract, 2001; 51(473):998-1000.
Lieu, et al., "Clinical evaluation of a latex agglutination test for streptococcal pharyngitis: performance and impact on treatment rates," Pediatr Infect Dis J, 1988; 7(12):847-854.
Lindbæk, et al., "Clinical symptoms and signs in sore throat patients with large colony variant beta-haemolytic streptococci groups C or G versus group A," Br J Gen Pract 2005; 55:615-9.
Linde, "The importance of specific virus diagnosis and monitoring for antiviral treatment," Antiviral Res, Aug. 2001; 51:81-94; Review.
Little, et al., "Amoxicillin for acute lower-respiratory-tract infection in primary care when pneumonia is not suspected: a 12-country, randomised, placebo-controlled trial," Lancet Infect Dis, 2013; 13:123-129.
Little, et al., "Sore throat management in general practice," Fam Pract, 1996; 13(3): 317-321.
Liu, et al., "Serum C-reactive protein as a biomarker for early detection of bacterial infection in the older patient," Age Ageing, 2010; 559-65.
Long, et al., "Procalcitonin-guidance for reduction of antibiotic use in low-risk outpatients with community acquired pneumonia," Respirology, 2011, 16:819-824.
Long, et al., "Widespread silent transmission of pertussis in families: antibody correlates of infection and symptomatology," J Infect Dis, Mar. 1990; 161(3):480-6.
Louie, et al., "Characterization of viral agents causing acute respiratory infection in a San Francisco University Medical Center Clinic during the influenza season," Clin Infect Dis, Sep. 15, 2005; 41(6):822-8.
MacFarlane, et al., "Prospective Study of Aetiology and Outcome of Adult-Lower-Respiratory Tract Infections in the Community," Lancet, Feb. 27, 1993, vol. 341 Issue 8844, p. 511.
Mackie, et al., "C-reactive protein for rapid diagnosis of infection in leukaemia," J Clin Pathol, 1979; 32(12):1253-1256.
Makela, et al., "Viruses and bacteria in the etiology of the common cold," J Clin Microbiol. 1998; 36:539-542.
Makela, et al., "Lack of Induction by Rhinoviruses of Systemic Type I Interferon Production or Enhanced MxA Protein Expression During the Common Cold," Eur J Clin Microbiol Infect Dis (1999), 18:665-668.
Maniaci, et al., "Procalcitonin in young febrile infants for the detection of serious bacterial infections," Pediatrics, Oct. 2008; 122(4):701-10.
Marik, "The clinical features of severe community-acquired pneumonia presenting as septic shock: Norasept II Study Investigators," J Crit Care, 2000, 15:85-90.
Marsh, "Role of the Oral Microflora in Health," Microbial Ecology in Health and Disease, 2000; 12: 130-137.
Martin, et al., "Group A streptococci among school-aged children: clinical characteristics and the carrier state," Pediatrics, Nov. 2004; 114(5):1212-9.
Martin, et al., "The epidemiology of sepsis in the united states from 1979 through 2000," N Engl J Med, 2003; 348:1546-1554.
Masiá, et al., "Clinical characterisation of pneumonia caused by atypical pathogens combining classic and novel predictors," Clin Microbiol Infect, Feb. 2007; 13(2):153-61.

(56) References Cited

OTHER PUBLICATIONS

Mathisen, et al., "Respiratory viruses in Nepalese children with and without pneumonia: A case-control study," Pediatr Infect Dis J, 2010; 29(8):731-735.
Mayo Clinic, "Test ID: PCT, Procalcitonin, Serum," (http://www.mayomedicallaboratories.com/testcatalog/Clinical+and+Interpretive/83169).
McCaig, et al., "Antimicrobial drug prescription in ambulatory care settings, United States 1992-2000," Emerg Infect Dis, 2003; 9:432-7. [Published correction appears in Emerg Infect Dis, 2003; 9:609].
McCarthy, et al., "Value of C-reactive protein test in the differentiation of bacterial and viral pneumonia," J Pediatr 1978; 92:454-6.
Melbye, et al., "The diagnosis of adult pneumonia in general practice. The diagnostic value of history, physical examination and some blood tests," Scand J Prim Health Care 1988; 6:111-7.
Melbye, et al., "Daily reduction in C-reactive protein values, symptoms, signs and temperature in group-A streptococcal pharyngitis treated with antibiotics," Scand J Clin Lab Invest, 2002; 62:521-5.
Melbye, et al., "Diagnosis of pneumonia in adults in general practice, relative importance of typical symptoms and abnormal chest signs evaluated against a radiographic reference standard," Scand J Prim Health Care, 1992; 10(3)226-233.
Melbye, et al., "Point of care testing for C-reactive protein: A new path for Australian GPs?" Australian Family Physician vol. 35, No. 7, Jul. 2006, pp. 513-516.
Melbye, et al., "The course of C-reactive protein response in untreated upper respiratory tract infection," Br J Gen Pract, 2004, 54, 653-658.
Melendi, et al., "Cytokine profiles in the respiratory tract during primary infection with human metapneumovirus, respiratory syncytial virus or influenza virus in infants," Pediatrics, 2007; 120(2):e410-e415.
Metlay, et al., "Testing strategies in the initial management of patients with community-acquired pneumonia," Ann Intern Med, 2003; 138(2):109-118.
Michaelidis, et al., "Cost-Effectiveness of Procalcitonin-Guided Antibiotic Therapy for Outpatient Management of Acute Respiratory Tract Infections in Adults," J Gen Intern Med, 2013, 29(4):579-86.
Michelow, et al., "Systemic Cytokine Profile in Children With Community-Acquired Pneumonia," Pediatric Pulmonology, 2007,42:640-645.
Miller, "A study of techniques for the examination of sputum in a field survey of chronic bronchitis," Am Rev Respir Dis, 1963; 88:473-483.
Morley, et al., "Serum C-reactive protein levels in disease," Ann N Y Acad Sci, 1982; 389:406-418.
Moulin, et al., "Procalcitonin in children admitted to hospital with community acquired pneumonia," Arch Dis Child 2001;84:332-336.
Muller, et al., "Calcitonin precursors are reliable markers of sepsis in a medical intensive care unit," Crit Care Med. 2000, 28: 977-83.
Muller, et al., "Procalcitonin levels predict bacteremia in patients with community-acquired pneumonia: a prospective cohort trial," Chest, 2010; 138:121-129.
Muller-Doblies, et al., "Innate Immune Responses of Calves during Transient Infection with a Noncytopathic Strain of Bovine Viral Diarrhea Virus," Clinical and Diagnostic Laboratory Immunology, Mar. 2004, vol. 11(2), p. 302-312.
Mundy, et al., "Community-acquired pneumonia: impact of immune status," Am J Respir Crit Care Med, 1995; 152:1309-15.
Murray, et al., "Panel size: how many patients can one doctor manage?" Fam Pract Manag, 2007; 14(4):44-51.
Musher, et al., "Can an etiologic agent be identified in adults who are hospitalized for community-acquired pneumonia: results of a one-year study," J Infect, Jul. 2013; 67(1):11-8.
Nakabayashi, et al., "MxA-based recognition of viral illness in febrile children by a whole blood assay," Pediatr Res, 2006; 60:770-4.

Nakhoul, et al., "Management of Adults with Acute Streptococcal Pharyngitis: Minimal Value for Backup Strep Testing and Overuse of Antibiotics," J Gen Intern Med, 2012, 28(6):830-4.
National Institute for Health and Care Excellence (NICE), "Pneumonia Guidelines: Diagnosis and management of commmunity- and hospital-acquired pneumonia in adults," NICE Clinical Guideline 191; Dec. 2014.
Neumark T, et al., "Use of rapid diagnostic tests and choice of antibiotics in respiratory tract infections in primary healthcare—a 6-y follow-up study," Scand J Infect Dis 2010; 42:90-96.
NICE Guideline Development Group, "Self-limiting respiratory tract infections—antibiotic prescribing overview," 2014.
Rapid test for pink eye may curb overuse of antibiotics, Jan. 26, 2009. http://www.stjohnshealthplans.net/news/pinkeyetest.aspx.
Cheung, et al., "Rhinovirus inhalation causes long-lasting excessive airway narrowing in response to methacholine in asthmatic subjects in vivo," Am J Respir Crit Care Med, 1995, 152:1490-1496.
Chirgwin, et al., "Infection with Chlamydia pneumoniae in Brooklyn," The Journal of Infectious Diseases 1991; 163:757-761.
Chirouze, et al., "Low serum procalcitonin level accurately predicts the absence of bacteremia in adult patients with acute fever," Clin Infect Dis. Jul. 15, 2002; 35(2):156-61.
Choroszy-Król, et al., "Infections Caused by Chlamydophila pneumoniae," Adv Clin Exp Med. Jan.-Feb. 2014; 23(1):123-6.
Christ-Crain, et al., "Clinical review: The role of biomarkers in the diagnosis and management of community acquired pneumonia," Critical Care 2010, 14:203.
Christ-Crain, et al. "Effect of procalcitonin-guided treatment on antibiotic use and outcome in lower respiratory tract infections: cluster-randomised, single-blinded intervention trial," Lancet 2004; 363: 600-607.
Christ-Crain, et al., "Procalcitonin Guidance of Antibiotic Therapy in Community-acquired Pneumonia: A Randomized Trial," Am J Respir Crit Care Med 2006; 174: 84-93.
Christensen, et al., "Are procalcitonin or other infection markers useful in the detection of group A streptococcal acute tonsillitis?" Scand J Infect Dis. May 2014; 46:376-83.
Chua, et al., "Procalcitonin in severe acute respiratory syndrome (SARS)," J. Infect. 2004; 48:303-306.
Chung, et al., "Cytokines in asthma," Thorax 1999; 55:825-857.
Coelho, et al., "Usefulness of C-reactive protein in monitoring the severe community-acquired pneumonia clinical course," Critical Care 2007, 11:R92.
Dahler-Eriksen, et al., "Evaluation of a near-patient test for C-reactive protein used in daily routine in primary healthcare by use of difference plots," Clinical Chemistry 43:11 2064-2075 (1997).
Danchin, et al., "Burden of acute sore throat and group A streptococcal pharyngitis in school-aged children and their families in Australia," Pediatrics, 2007; 120:950-957.
Del Mar, et al., "Antibiotics for sore throat," Cochrane Database Syst Rev. Oct. 18, 2006; (4):CD000023.
Denlinger, et al., "Lower airway rhinovirus burden and the seasonal risk of asthma exacerbation," Am J Respir Crit Care Med. Nov. 1, 2011; 184(9):1007-14.
Denny, et al., "Prevention of rheumatic fever," JAMA, 1950; 143:151-153.
Dinant, et al., "The necessary shift from diagnostic to prognostic research," BMC Fam Pract 2007; 8:53.
Dittrich, "Meeting of Experts on Biomarkers to Discriminate Bacterial From Other Infectious Causes of Acute Fever," Nov. 10, 2015, World Health Organization.
Dorigo-Zetsma, et al., "Results of Molecular Detection of Mycoplasma pneumoniae Among Patients with Acute Respiratory Infection and in Their Household Contacts Reveals Children as Human Reservoirs," J Infect Dis. 2001; 183:675-8.
Drummond, et al., "Community acquired pneumonia—a prospective UK study," Arch Dis Child. Nov. 2000; 83(5):408-12.
Duff, et al., "Risk factors for acute wheezing in infants and children: viruses, passive smoke, and IgE antibodies to inhalant allergens," Pediatrics. 1993; 92:535-540.
Durrani, et al., "Innate immune responses to rhinovirus are reduced by the high-affinity IgE receptor in allergic asthmatic children," J Allergy Clin Immunol. 2012; 130:489-495.

(56) References Cited

OTHER PUBLICATIONS

El-Sahly, et al., "Spectrum of clinical illness in hospitalized patients with "common cold" virus infections," Clin Infect Dis. Jul. 2000; 31(1):96-100.

Elsammack, et aL, "Diagnostic Value of Serum Procalcitonin and C-Reactive Protein in Egyptian Children with Streptococcal Tonsillopharyngitis," The Pediatric Infectious Disease Journal, vol. 25, No. 2, Feb. 2006, pp. 174-176.

Endeman, et al., "Clinical features predicting failure of pathogen identification in patients with community acquired pneumonia," Scand J Infect Dis. 2008; 1-6.

Engelmann, et al., "Diagnosis of Viral Infections Using Myxovirus Resistance Protein A (MxA)," Pediatrics, vol. 135, No. 4, Apr. 2015.

Engstrom, et al., "Excessive use of rapid tests in respiratory tract infections in Swedish primary health care," Scand J Infect Dis 2004; 36:213-8.

Esposito, et al., "Aetiology of acute pharyngitis: the role of atypical bacteria," J Med Microbiol, 2004; 53:645-51.

Esposito, et al., "Do We Know When, What and For How Long to Treat?" Antibiotic Therapy for Pediatric Community-acquired Pneumonia, Pediatr Infect Dis J 2012; 00:e78-85.

Esposito, et al., "Evaluation of a rapid bedside test for the quantitative determination of C-reactive protein," Clin Chem Lab Med. 2005; 43(4):438-440.

Ewig, et al., "Factors associated with unknown aetiology in patients with community-acquired pneumonia," Eur Respir J. 2002; 20:1254-62.

Extended European Search Report, European Application No. 09815363.8, dated Feb. 9, 2012.

Extended European Search report, European Application No. 14760721.2, dated Oct. 19, 2015.

Falsey, et al., "Bacterial complications of respiratory tract viral illness: a comprehensive evaluation," J Infect Dis. Aug. 1, 2013; 208(3):432-41.

FebriDx Brochure, Oct. 2015.

FebriDx Package Insert, May 2015.

Feldman, et al., "Prognostic factors in severe community-acquired pneumonia in patients without co-morbid illness," Respirology 2001, 6:323-330.

Fensterl and Sen, "Interferon-Induced Ifit Proteins: Their Role in Viral Pathogenesis," J. Virology, Mar. 2015, vol. 89, No. 5, pp. 2462-2468.

File, "Community Acquired Pneumonia," Lancet. 2003; 362:1991-2001.

Flanders, et al., "Performance of a bedside c-reactive protein test in the diagnosis of community-acquired pneumonia in adults with acute cough," Am J Med. 2004; 116(8):529-535.

Fraenkel, et al., "Lower airway inflammation during rhinovirus colds in normal and in asthmatic subjects," Am J Respir. Crit. Care Med., 1995, 151:879-886.

Galetto-Lacour, et al., "Bedside Procalcitonin and C-Reactive Protein Tests in Children With Fever Without Localizing Signs of Infection Seen in a Referral Center," Pediatrics, vol. 112, No. 5, Nov. 2003.

Gendrel, et al., "Comparison of procalcitonin with C-reactive protein, interleukin 6 and interferon-alpha for differentiation of bacterial vs. viral infections," Pediatr Infect Dis J. Oct. 1999; 18(10):875-81.

Gerber, et al., "Antigen detection test for streptococcal pharyngitis: evaluation of sensitivity with respect to true infection," J Pediatr., 1986, 108:654-658.

Gerber, et al., "Rapid Diagnosis of Pharyngitis Caused by Group A Streptococci," Clin Microbiol Rev 2004; 17:571-580.

Gerber, et al., "The group A streptococcal carrier state: A reexamination," Am. J. Dis. Child., 1988, 142:562-565.

Gieseker, et al., "Comparison of two rapid *Streptococcus* pyogenes diagnostic tests with a rigorous culture standard," Pediatr Infect Dis J, 2002; 21:922-6.

Gilbert, "Use of Plasma Procalcitonin Levels as an Adjunct to Clinical Microbiology," J Clin Microbiol., Jul. 2010; 48(7):2325-9.

Gilbert, "Procalcitonin as a Biomarker in Respiratory Tract Infection," Clinical Infectious Diseases, 2011; 52(S4):S346-S350.

Schuetz, et al."Using procalcitonin-guided algorithms to improve antimicrobial therapy in ICU patients with respiratory infections and sepsis," Curr Opin Crit Care, 2013; 19(5):453-60.

Schutzle, et al., "Is serum procalcitonin a reliable diagnostic marker in children with acute respiratory tract infections?: A retrospective analysis," Eur J Pediatr, 2009; 168:1117-1124.

Schwartz, et al., "Penicillin V for group a streptococcal pharyngotonsillitis: A randomized trial of seven vs ten days' therapy," JAMA, 1981; 246:1790.

Schwarz, et al., "Serum procalcitonin levels in bacterial and abacterial meningitis," Crit Care Med 2000, 28: 1828-32.

Selberg et al., "Discrimination of sepsis and systemic inflammatory response syndrome by determination of circulating plasma concentraions of procalcitonin, protein complement 3a, and interleukin-6," Crit Care Med 2000, 28: 2793-8.

Sen, et al., "Interferon-induced antiviral actions and their regulation," Adv Virus Res, 1993, 42:57-102.

Shapiro, et al., "A Prospective, Multicenter Clinical Evaluation of a Rapid Diagnostic Test to Detect Clinically Significant Immune Responses to Viral and Bacterial Acute Respiratory Infections," presented at ID week, Oct. 2015, San Diego, California.

Shehab, et al., "Emergency department visits for antibiotic-associated adverse events," Clin Infect Dis, 2008; 47(6):735-43.

Shulman, et al., "Streptococcal pharyngitis: The case for penicillin therapy," Pediatr Infect Dis J, 1994; 13:1-7.

Simon, et al., "Interferon-regulated Mx genes are not responsive to interleukin-1, tumor necrosis factor, and other cytokines," J Virol. 1991; 65:968-971.

Simon, et al., "Serum Procalcitonin and C-reactive Protein Levels as Markers of Bacterial Infection: A Systematic Review and Meta-analysis," Clin Infect Dis, 2004, 39:206-217.

Singleton, et al., "Viral Respiratory Infections in Hospitalized and Community Control Children in Alaska," J Med Virol, 2010; 82(7): 1282-90.

Smith, et al., "Antibiotics for acute bronchitis," Cochrane Database Syst Rev 2004, Issue 4.

Smith, et al., "C-reactive protein in simple community-acquired pneumonia," Chest 1995; 107:1028-1031.

Smith, et al., "C-reactive protein; A clinical marker in community-acquired pneumonia," Chest 1995; 108:1288-1291.

Snow, et al., "Principles of appropriate antibiotic use for treatment of acute bronchitis in adults," Ann Intern Med, 2001; 134:518-520.

Soto-Quiros, et al., "High titers of IgE antibody to dust mite allergen and risk for wheezing among asthmatic children infected with rhinovirus," J Allergy Clin Immunol, 2012; 129:1499-1505, e5.

Spijkervet, et al. "Colonization index of the oral cavity: a novel technique for monitoring colonization defense," Microbial Ecology in Health and Disease, 1989; 2:145-151.

Spuesens, et al., "Carriage of Mycoplasma pneumoniae in the Upper Respiratory Tract of Symptomatic and Asymptomatic Children: An Observational Study," PLoS Med, 2013; 10:e1001444.

Staeheli, et al., "Mx protein: constitutive expression in 3T3 cells transformed with cloned Mx cDNA confers selective resistance to influenza virus," Cell. 1986; 44:147-158.

Staeheli, et al., "Identification of a second interferon-regulated murine Mx gene," Mol Cell Biol, 1988, 8:4524-4528.

Steer, et al., "Normal ranges of streptococcal antibody titers are similar whether streptococci are endemic to the setting or not," Clin Vaccine Immunol, Feb. 2009; 16(2):172-5.

Steinman, et al., "Changing Use of Antibiotics in Community-Based Outpatient Practice, 1991-1999," Ann Intern Med 2003, 138(7):525-533.

Stolz, et al., "Antibiotic Treatment of Exacerbations of COPD: A Randomized, Controlled Trial Comparing Procalcitonin-Guidance With Standard Therapy," Chest 2007; 131:9-19.

Stolz, et al., "Antibiotic treatment of exacerbations of COPD: standard approach for acute respiratory tract infections in primary care: study protocol for a randomised controlled trial and baseline characteristics of participating general practitioners," BMC Fam Pract, 2005; 6:34.

(56) References Cited

OTHER PUBLICATIONS

Stolz, et al., "Diagnostic value of signs, symptoms and laboratory values in lower respiratory tract infection," Swiss Med Wkly, 2006; 136:434-440.
Stolz, et al., "Procalcitonin for reduced antibiotic exposure in ventilator-associated pneumonia: a randomised study," Eur Respir J, 2009; 34:1364-1375.
Stover, et al., "The Epidemiology of Upper Respiratory Infections at a Tertiary Care Center: Prevalence, Seasonality, and Clinical Symptoms," Journal of Respiratory Medicine, vol. 2014 (2014), Article ID 469393, 8 pages.
Strömberg, et al., "Throat carrier rates of beta-hemolytic streptococci among healthy adults and children," Scand J Infect Dis, 1988; 20(4):411-7.
Stuart, et al., "Monitoring the acute phase response [Editorial]," BMJ 1988; 297:1143-4.
Summah, et al., "Biomarkers: a definite plus in pneumonia, Mediators of Inflammation," 2009; Article ID 675753, 9 pages.
Suprin, et al., Procalcitonin: a valuable indicator of infection in a medical ICU, Intensive Care Med 2000, 26: 1232-8.
Tan, et al., "Guideline Development Group. Antibiotic prescribing for self limiting respiratory tract infections in primary care: summary of NICE guidance," BMJ 2008; 337: a437.
Tanz, et al., "Performance of a Rapid Antigen-Detection Test and Throat Culture in Community Pediatric Offices: Implications for Management of Pharyngitis," Pediatrics, 2009; 123:437.
Templeton, et al., "Improved diagnosis of the etiology of community-acquired pneumonia with real-time polymerase chain reaction," Clin Infect Dis, 2005; 41:345-51.
Ten Oever, et al. "Combination of biomarkers for the discrimination between bacterial and viral lower respiratory tract infections," Journal of Infection (2012) 65, 490-495.
Thompson, et al., "The value of acute phase protein measurements in clinical practice," Ann Clin Biochem 1992; 29:123-31.
Thorpe, et al., "Trends in emergency department antibiotic prescribing for acute respiratory tract infections," Ann Pharmacother, 2004; 38(6): 928-935.
Toikka, et al., "Serum procalcitonin, C-reactive protein and interleukin-6 for distinguishing bacterial and viral pneumonia in children," Pediatr Infec Dis J 2000; 19(7):598-602.
Towbin, et al., "A whole blood immunoassay for the interferon-inducible human Mx protein," J Interferon Res. 1992; 12:67-74.
Trigg, et al., "A double-blind comparison of the effects of cefaclor and amoxycillin on respiratory tract and propharyngeal flora and clinical response in acute exacerbations of bronchitis," Respir Med, 1991; 85:301-8.
Tsolia, et al., "Etiology of Community-Acquired Pneumonia in Hospitalized School-Age Children: Evidence for High Prevalence of Viral Infections," Clinical Infectious Diseases, 2004; 39:681-6.
Turner, et al., "Shedding of infected ciliated epithelial cells in rhinovirus colds," J Infect Dis, 1982, 145:849-853.
Uchio, et al., "Rapid Diagnosis of Adenoviral Conjunctivitis on Conjunctival Swabs by 10-Minute Immunochromatography," Opthalmology, vol. 104, No. 8, Aug. 1997, pp. 1294-1299.
Udeh, et al., "Cost Effectiveness of a Point-of-Care Test for Adenoviral Conjunctivitis," The American Journal of the Medical Sciences, vol. 336, No. 3, pp. 254-264 (Sep. 2008).
Uemura, et al., "Comparative characterization of *Staphylococcus aureus* isolates from throats and noses of healthy volunteers," Jpn J Infect Dis, 2004, 57:21-24.
Ugarte, et al., "Procalcitonin as a marker of infection in the intensive care unit," Crit Care Med 1999, 27: 498-504.
Van Benten, et al., "Predominance of rhinovirus in the nose of symptomatic and asymptomatic infants," Pediatr Allergy Immunol, 2003; 14: 363-370.
Van der Bliek, "Functional diversity in the dynamin family," Trends Cell Biol. 1999; 9:96-102.
Van der Meer, et al., "Diagnostic value of C reactive protein in infections of the lower respiratory tract: systematic review," BMJ, doi:10.1136/bmj.38483.478183.EB (published Jun. 24, 2005).
'The Role of Band Counts in Bacterial and Viral Infections'; Am Fam Physician; 634-636; Aug. 1999.
Band Count; ClinLab Navigator; retrieved from http://www.clinlabnavigator.com/band-count.html; as early as Oct. 2012.
Cavallazzi et al. "Is the band count useful in the diagnosis of infection? An accuracy study in critically ill patients."; J Intensive Care Med. Nov.-Dec. 2010;25(6):353-7.

\* cited by examiner

Fig. 5A

| Patient | PCT level (ng/ml) | MxA level (ng/ml) | ThroatCulturesOrganism | Final Diagnosis | Description/comments |
|---|---|---|---|---|---|
| 1 | 0.38 | 4.218 | Beta Hemolytic Streptococcus Group A | bacterial | Greater than $10^6$ β hemolytic Group A Strep with elevated PCT |
| 2 | 0.37 | | Beta Hemolytic Streptococcus Group A | bacterial | |
| 3 | 0.3 | 0.045 | | bacterial | Respiratory viral and atypical PCR negative; Elevated PCT No microbial confirmation; diagnosed with novel diagnostic method |
| 4 | 0.27 | 1.333 | Enterobacter cloacae complex | bacterial | Respiratory viral and atypical PCR negative; Elevated PCT No microbial confirmation; diagnosed with novel diagnostic method |
| 5 | 0.2 | 0.65 | Beta Hemolytic Streptococcus Group A | bacterial | Respiratory viral and atypical PCR negative; Elevated PCT No microbial confirmation; diagnosed with novel diagnostic method |
| 6 | 0.18 | 0.29 | Enterobacter gergoviae | bacterial | Respiratory viral and atypical PCR negative; Elevated PCT No microbial confirmation; diagnosed with novel diagnostic method |
| 7 | 0.16 | 9.125 | | bacterial | Respiratory viral and atypical PCR negative; Elevated PCT No microbial confirmation; diagnosed with novel diagnostic method |
| 8 | 0.16 | 0.432 | | bacterial | Respiratory viral and atypical PCR negative; Elevated PCT No microbial confirmation; diagnosed with novel diagnostic method |
| 9 | 0.15 | 0.418 | | bacterial | Respiratory viral and atypical PCR negative; Elevated PCT No microbial confirmation; diagnosed with novel diagnostic method |
| 10 | 0.14 | 0.781 | | bacterial | Respiratory viral and atypical PCR negative; Elevated PCT No microbial confirmation; diagnosed with novel diagnostic method |
| 11 | 0.13 | 4.174 | STAPHYLOCOCCUS AUREUS | bacterial | Normal oral flora; Respiratory viral and atypical PCR negative; No microbial confirmation; diagnosed with novel diagnostic method |
| 12 | 0.13 | 0 | STAPHYLOCOCCUS AUREUS BETA LACTAMASE negative | bacterial | PCR positive for Rhinovirus with elevated MxA < 27; diagnosed with novel diagnostic method |
| 13 | 0.13 | 6.608 | | bacterial | PCR positive for Parainfluenza Virus |

Fig. 5B

| Patient | PCT level (ng/ml) | MxA level (ng/ml) | ThroatCulturesOrganism | Final Diagnosis | Description/comments |
|---|---|---|---|---|---|
| 14 | 0.11 | 1.063 | BETA HEMOLYTIC STREPTOCOCCUS GROUP C | bacterial | Chest X-ray negative; PCR positive for Rhinovirus with MxA < 27ng/ml which is consistent with colonization; > $10^6$ β hemolytic Group A Strep with elevated PCT |
| 15 | 0.11 | 0.726 | PROTEUS MIRABILIS/PENNERI GROUP | bacterial | Throat culture positive for proteus with elevated PCT |
| 16 | 0.11 | 8.358 | STAPHYLOCOCCUS AUREUS | bacterial | PCR positive for Influenza B Virus |
| 17 | 0.11 | 0.304 | | bacterial | Respiratory viral and atypical PCR negative; Non elevated PCT No microbial confirmation; diagnosed with novel diagnostic method |
| 18 | 0.11 | 0.03 | | bacterial | Respiratory viral and atypical PCR negative; Elevated PCT No microbial confirmation; diagnosed with novel diagnostic method |
| 19 | 0.1 | 0.122 | Streptoccus Group C | bacterial | Throat culture positive for Less than $10^6$ β Hemolytic Group C Strep with elevated PCT |
| 20 | 0.1 | 1.784 | BETA HEMOLYTIC STREPTOCOCCUS GROUP A | bacterial | Throat culture positive for Less than $10^6$ β Hemolytic Group C Strep with elevated PCT |
| 21 | 2.8 | 0.03 | | bacterial | Respiratory viral and atypical PCR negative; high PCT; diagnosed with novel diagnostic method |
| 22 | 0.74 | | Staphylococcus aureus | bacterial | Staph aureus Culture > than $10^6$ with elevated PCT |
| 23 | 0.09 | 0.03 | Beta Hemolytic Streptococcus Group A | bacterial | Chest x ray negative; PCR positive for Rhinovirus with MxA < 27ng/ml which is consistent with colonization; > $10^6$ β hemolytic Group A Strep with elevated PCT |
| 24 | 0.73 | | | bacterial | Atypical PCR Positive for Chlamydia |
| 25 | 0.64 | 0.562 | BETA HEMOLYTIC STREPTOCOCCUS GROUP C | bacterial | Less than 106 β hemolytic Group C Strep with elevated PCT; diagnosed with novel diagnostic method |
| 26 | 0.55 | | Gram negative rod isolated. No further ID | bacterial | Gram negative rod bacteria with elevated PCT |

Fig. 5C

| Patient | PCT level (ng/ml) | MxA level (ng/ml) | ThroatCulturesOrganism | Final Diagnosis | Description/comments |
|---|---|---|---|---|---|
| 27 | 0.52 | 0.03 | HAEMOPHILUS PARAINFLUENZAE | bacterial | Less than 106 β Hemophilus with elevated PCT; diagnosed with novel diagnostic method |
| 28 | 0.5 | 0.026 | | bacterial | Respiratory viral and atypical PCR negative; Elevated PCT; No microbial confirmation; diagnosed with novel diagnostic method |
| 29 | 0.39 | 0.03 | | bacterial | Respiratory viral and atypical PCR negative; Elevated PCT No microbial confirmation; diagnosed with novel diagnostic method |
| 30 | 0.1 | 15.265 | | False negative viral | PCR and IgM positive for EBV |
| 31 | 0.05 | 13.134 | | False negative viral | PCR positive for Influenza A |
| 32 | 0.05 | 0.03 | BETA HEMOLYTIC STREPTOCOCCUS GROUP B | False negative viral | Throat culture positive with normal flora and nonelevated PCT; PCR positive for Coronavirus with MxA < 27ng/ml which is consistent with colonization; PCR positive for Influenza A |
| 33 | 0.05 | 14.813 | ENTEROBACTER AEROGENES | False negative viral | Throat culture positive with normal flora and nonelevated PCT; PCR positive for Influenza A |
| 34 | 0.05 | 12.994 | STREPTOCOCCUS GROUP A | False negative viral | Throat culture positive for Group A Strep > $10^6$ and nonelevated PCT; PCR positive for parainfluenzavirus 3 |
| 35 | 0.05 | 0.036 | | False negative viral | PCR positive for Influenza B |
| 36 | 0.07 | 0.03 | | False negative viral | PCR positive for Parainfluenza Virus 2 and Metapneumovirus |
| 37 | 0.05 | 15.775 | | False negative viral | EBV IgM Positive |
| 38 | 0.05 | 8.062 | ACINETOBACTER BAUMANNII | False negative viral | Throat culture positive with normal flora less than $10^6$ and nonelevated PCT; PCR positive for Influenza A |
| 39 | 0.05 | 6.51 | | False negative viral | PCR positive for Influenza A |

Fig. 5D

| Patient | PCT level (ng/ml) | MxA level (ng/ml) | ThroatCulturesOrganism | Final Diagnosis | Description/comments |
|---|---|---|---|---|---|
| 40 | 0.05 | 13.953 | | negative | Rhinovirus PCR positive with MxA < 20ng/ml which is consistent with colonization; Less than $10^6$ β hemolytic Group A Strep with nonelevated PCT; negative for infection |
| 41 | 0.05 | 34.978 | | False Positive Viral | Respiratory viral and atypical PCR negative; Non elevated PCT No microbial confirmation; diagnosed with novel diagnostic method |
| 42 | 0.05 | 50.608 | BETA HEMOLYTIC STREPTOCOCCUS GROUP A | negative | Throat culture positive Less than $10^6$ β Hemolytic Group C Strep without elevated PCT; No microbial confirmation, diagnosed with novel diagnostic method |
| 43 | 0.05 | 30.764 | | False Positive Viral | Respiratory viral and atypical PCR negative; Non elevated PCT along with Strep pneumo not a primary pathogen of pharyngitis; No microbial confirmation; diagnosed with novel diagnostic method |
| 44 | 0.05 | 19.127 | BETA HEMOLYTIC STREPTOCOCCUS Group B | negative | Less than $10^6$ β hemolytic Group A Strep with nonelevated PCT |
| 45 | 0.05 | 12.595 | | negative | PCR positive for rhinovirus with MxA < 20ng/ml which is consistent with colonization; diagnosed with novel diagnostic method |
| 46 | 0.05 | 11.064 | | negative | Respiratory viral and atypical PCR negative; Non elevated PCT No microbial confirmation; diagnosed with novel diagnostic method |
| 47 | 0.05 | 10.948 | | negative | Respiratory viral and atypical PCR negative; Non elevated PCT No microbial confirmation; diagnosed with novel diagnostic method |
| 48 | 0.05 | 10.299 | Klebsiella pneumonia | negative | Normal oral flora with no elevated PCT; PCT positive for Rhinovirus with MxA < 20ng/ml which is consistent with colonization; |
| 49 | 0.05 | 9.939 | | negative | Respiratory viral and atypical PCR negative; Non elevated PCT No microbial confirmation; diagnosed with novel diagnostic method |
| 50 | 0.05 | 9.804 | | negative | PCR positive for Rhinovirus with nonelevated MxA; diagnosed with novel diagnostic method |
| 51 | 0.05 | 9.05 | | negative | Respiratory viral and atypical PCR negative; Non elevated PCT No microbial confirmation; diagnosed with novel diagnostic method |

Fig. 5E

| Patient | PCT level (ng/ml) | MxA level (ng/ml) | ThroatCulturesOrganism | Final Diagnosis | Description/comments |
|---|---|---|---|---|---|
| 52 | 0.05 | 8.716 | | negative | No microbial confirmation; diagnosed with novel diagnostic method |
| 53 | 0.05 | 7.819 | | negative | PCR positive for Coronavirus with MxA < 20ng/ml which is consistent with colonization; No microbial confirmation, diagnosed with novel diagnostic method |
| 54 | 0.05 | 6.477 | STREPT. PNEUMONIAE | negative | PCR positive for Rhinovirus with MxA < 20ng/ml which is consistent with colonization; Less than 106 β hemolytic Group A Strep with nonelevated PCT; diagnosed with novel diagnostic method |
| 55 | 0.05 | 6.271 | STAPHYLOCOCCUS AUREUS ACINETOBACTER SPECIES | negative | Throat culture positive with normal flora and nonelevated PCT;PCR positive for Coronavirus with MxA < 27ng/ml which is consistent with colonization; No microbial confirmation, diagnosed with novel diagnostic method |
| 56 | 0.05 | 4.492 | | negative | Respiratory viral and atypical PCR negative; Non elevated PCT No microbial confirmation; diagnosed with novel diagnostic method |
| 57 | 0.05 | 3.72 | | negative | Respiratory viral and atypical PCR negative; Non elevated PCT No microbial confirmation; diagnosed with novel diagnostic method |
| 58 | 0.05 | 3.434 | STAPHYLOCOCCUS AUREUS | negative | Throat culture positive with normal flora Less than 106 and nonelevated PCT; No microbial confirmation, diagnosed with novel diagnostic method |
| 59 | 0.05 | 3.069 | | negative | Respiratory viral and atypical PCR negative; Non elevated PCT No microbial confirmation; diagnosed with novel diagnostic method |
| 60 | 0.05 | 2.987 | | negative | Respiratory viral and atypical PCR negative; Non elevated PCT No microbial confirmation; diagnosed with novel diagnostic method |
| 61 | 0.05 | 2.549 | Group A Strep | negative | Throat culture positive for Group A Strep > $10^6$ and nonelevated PCT microbial confirmation; diagnosed with novel diagnostic method |
| 62 | 0.05 | 2.44 | | negative | Respiratory viral and atypical PCR negative; Non elevated PCT No microbial confirmation; diagnosed with novel diagnostic method |

Fig. 5F

| Patient | PCT level (ng/ml) | MxA level (ng/ml) | ThroatCulturesOrganism | Final Diagnosis | Description/comments |
|---|---|---|---|---|---|
| 63 | 0.05 | 2.438 | | negative | PCR positive for Rhinovirus with MxA < 20ng/ml which is consistent with colonization; Less than 106 β hemolytic Group A Strep with nonelevated PCT; diagnosed with novel diagnostic method |
| 64 | 0.05 | 2.285 | | negative | Respiratory viral and atypical PCR negative; Non elevated PCT No microbial confirmation; diagnosed with novel diagnostic method |
| 65 | 0.06 | | BETA HEMOLYTIC STREPTOCOCCUS GROUP A | negative | Strep Culture with no associated elevation in PCT; diagnosed with novel diagnostic method |
| 66 | 0.05 | 1.987 | | negative | PCR positive for Rhinovirus with MxA < 20ng/ml which is consistent with colonization; no significant elevation in PCT; diagnosed with novel diagnostic method |
| 67 | 0.05 | 1.588 | Streptococcus pneumoniae | negative | Throat culture positive with Strep Pneumoniae Less than 106 and nonelevated PCT; No microbial confirmation, diagnosed with novel diagnostic method |
| 68 | 0.05 | 1.539 | | negative | PCR positive for Rhinovirus with MxA < 20ng/ml which is consistent with colonization; Less than 106 β hemolytic Group A Strep with nonelevated PCT; diagnosed with novel diagnostic method |
| 69 | 0.05 | 1.331 | BETA HEMOLYTIC STREPTOCOCCUS GROUP B | negative | Throat culture positive with normal flora and nonelevated PCT;No microbial confirmation, diagnosed with novel diagnostic method |
| 70 | 0.05 | 1.213 | BETA HEMOLYTIC STREPTOCOCCUS GROUP A | negative | Less than 106 β hemolytic Group A Strep with nonelevated PCT; diagnosed with novel diagnostic method |
| 71 | 0.05 | 0.595 | Hemolytic Group A Streptococcus | negative | PCR positive for Rhinovirus with MxA < 27ng/ml which is consistent with colonization; diagnosed with novel diagnostic method |
| 72 | 0.05 | 0.538 | | negative | Chest X-ray negative; no elevated PCT; Group A cell culture likely colonization |
| 73 | 0.05 | 0.276 | STAPHYLOCOCCUS AUREUS BETA HEMOLYTIC STREPTOCOCCUS GROUP B | negative | Throat culture positive with normal flora Less than 106 and nonelevated PCT; Coronavirus PCR + with MxA < 27ng/ml which is consistent with colonization; No microbial confirmation, diagnosed with novel diagnostic method |

Fig. 5G

| Patient | PCT level (ng/ml) | MxA level (ng/ml) | ThroatCulturesOrganism | Final Diagnosis | Description/comments |
|---|---|---|---|---|---|
| 74 | 0.05 | 0.276 | BETA HEMOLYTIC STREPTOCOCCUS GROUP B STAPHYLOCOCCUS AUREUS | negative | Throat culture positive with normal flora Less than 106 and nonelevated PCT; No microbial confirmation, diagnosed with novel diagnostic method |
| 75 | 0.05 | 0.275 | | negative | Respiratory viral and atypical PCR negative; Non elevated PCT No microbial confirmation; diagnosed with novel diagnostic method |
| 76 | 0.05 | 0.215 | | negative | Respiratory viral and atypical PCR negative; Non elevated PCT No microbial confirmation; diagnosed with novel diagnostic method |
| 77 | 0.05 | 0.179 | Streptococcus group C | negative | Throat culture positive with Group C Strep Less than 10^6 and nonelevated PCT; No microbial confirmation, diagnosed with novel diagnostic method |
| 78 | 0.05 | 0.174 | | negative | Respiratory viral and atypical PCR negative; Non elevated PCT No microbial confirmation; diagnosed with novel diagnostic method |
| 79 | 0.05 | 0.103 | | negative | Respiratory viral and atypical PCR negative; Non elevated PCT No microbial confirmation; diagnosed with novel diagnostic method |
| 80 | 0.06 | 0.03 | Staphylococcus aureus | negative | Respiratory viral and atypical PCR negative; Non elevated PCT No microbial confirmation; diagnosed with novel diagnostic method |
| 81 | 0.05 | 0.03 | Proteus mirabilis penneri group | negative | PCR negative; Culture negative; diagnosed with novel diagnostic method |
| 82 | 0.08 | 0.03 | STAPHYLOCOCCUS AUREUS | negative | Respiratory viral and atypical PCR negative; Non elevated PCT No microbial confirmation; diagnosed with novel diagnostic method |
| 83 | 0.05 | 0.03 | STAPHYLOCOCCUS AUREUS | negative | Throat culture positive with normal flora and nonelevated PCT;No microbial confirmation, diagnosed with novel diagnostic method |
| 84 | 0.05 | 0.03 | | negative | Respiratory viral and atypical PCR negative; Non elevated PCT No microbial confirmation; diagnosed with novel diagnostic method |
| 85 | 0.08 | 0.03 | | negative | Respiratory viral and atypical PCR negative; Non elevated PCT No microbial confirmation; diagnosed with novel diagnostic method |
| 86 | 0.07 | 0.03 | | negative | Respiratory viral and atypical PCR negative; Non elevated PCT No microbial confirmation; diagnosed with novel diagnostic method |

Fig. 5H

| Patient | PCT level (ng/ml) | MxA level (ng/ml) | ThroatCulturesOrganism | Final Diagnosis | Description/comments |
|---|---|---|---|---|---|
| 87 | 0.07 | 0.03 | STAPHYLOCOCCUS AUREUS | negative | Respiratory viral and atypical PCR negative; Non elevated PCT No microbial confirmation; diagnosed with novel diagnostic method |
| 88 | 0.05 | 0.03 | | negative | Respiratory viral and atypical PCR negative; Non elevated PCT No microbial confirmation; diagnosed with novel diagnostic method |
| 89 | 0.05 | 0.03 | | negative | Respiratory viral and atypical PCR negative; Non elevated PCT No microbial confirmation; diagnosed with novel diagnostic method |
| 90 | 0.05 | 0.03 | | negative | Respiratory viral and atypical PCR negative; Non elevated PCT No microbial confirmation; diagnosed with novel diagnostic method |
| 91 | 0.05 | 0.03 | | negative | Respiratory viral and atypical PCR negative; Non elevated PCT No microbial confirmation; diagnosed with novel diagnostic method |
| 92 | 0.05 | 0.03 | | negative | Respiratory viral and atypical PCR negative; Non elevated PCT No microbial confirmation; diagnosed with novel diagnostic method |
| 93 | 0.05 | 0.03 | | negative | Respiratory viral and atypical PCR negative; Non elevated PCT No microbial confirmation; diagnosed with novel diagnostic method |
| 94 | 0.05 | 0.03 | | negative | Respiratory viral and atypical PCR negative; Non elevated PCT No microbial confirmation; diagnosed with novel diagnostic method |
| 95 | 0.05 | 0.03 | | negative | Respiratory viral and atypical PCR negative; Non elevated PCT No microbial confirmation; diagnosed with novel diagnostic method |
| 96 | 0.05 | 0.03 | | negative | Respiratory viral and atypical PCR negative; Non elevated PCT No microbial confirmation; diagnosed with novel diagnostic method |
| 97 | 0.05 | 0.03 | Staphylococcus aureus group B | negative | No microbial confirmation; diagnosed with novel diagnostic method |
| 98 | 0.05 | 0.03 | | negative | PCR positive for HSV in an older patient and low MxA consistent with shedding; No microbial confirmation, diagnosed with novel diagnostic method |
| 99 | 0.05 | | | negative | PCR positive for HSV in an older patient and low MxA consistent with shedding; No microbial confirmation, diagnosed with novel diagnostic method |

Fig. 5I

| Patient | PCT level (ng/ml) | MxA level (ng/ml) | ThroatCulturesOrganism | Final Diagnosis | Description/comments |
|---|---|---|---|---|---|
| 100 | 0.05 | 0.03 | | | PCR positive for Rhinovirus with MxA < 20ng/ml which is consistent with colonization; no significant elevation in PCT; diagnosed with novel diagnostic method |
| 101 | 0.05 | 0.03 | CITROBACTER FREUNDII | negative | Throat culture positive with normal flora Less than 106 and nonelevated PCT; No microbial confirmation, diagnosed with novel diagnostic method |
| 102 | 0.05 | 0.03 | STAPHYLOCOCCUS AUREUS | negative | Respiratory viral and atypical PCR negative; Non elevated PCT No microbial confirmation; diagnosed with novel diagnostic method |
| 103 | 0.05 | 0 | | negative | PCR positive for Rhinovirus with elevated MxA < 20; diagnosed with novel diagnostic method |
| 104 | 0.05 | 0 | CANDIDA ALBICANS | negative | PCR positive for Rhinovirus with elevated MxA < 20; diagnosed with novel diagnostic method |
| 105 | 0.05 | 0 | | negative | PCR positive for Rhinovirus with elevated MxA < 20; diagnosed with novel diagnostic method |
| 106 | 0.05 | | | negative | Respiratory viral and atypical PCR negative; Non elevated PCT No microbial confirmation; diagnosed with novel diagnostic method |
| 107 | 0.05 | | | negative | Respiratory viral and atypical PCR negative; Non elevated PCT No microbial confirmation; diagnosed with novel diagnostic method |
| 108 | 0.05 | | | negative | Respiratory viral and atypical PCR negative; Non elevated PCT No microbial confirmation; diagnosed with novel diagnostic method |
| 109 | 0.05 | | | negative | Respiratory viral and atypical PCR negative; Non elevated PCT No microbial confirmation; diagnosed with novel diagnostic method |
| 110 | 0.05 | | Beta hemolytic Streptococcus group B | negative | Respiratory viral and atypical PCR negative; Non elevated PCT No microbial confirmation; diagnosed with novel diagnostic method |
| 111 | 0.05 | | | negative | Respiratory viral and atypical PCR negative; Non elevated PCT No microbial confirmation; diagnosed with novel diagnostic method |
| 112 | 0.05 | | | negative | Respiratory viral and atypical PCR negative; Non elevated PCT No microbial confirmation; diagnosed with novel diagnostic method |

Fig. 5J

| Patient | PCT level (ng/ml) | MxA level (ng/ml) | ThroatCulturesOrganism | Final Diagnosis | Description/comments |
|---|---|---|---|---|---|
| 113 | 0.05 | | Enterobacter cloacae complex | negative | Respiratory viral and atypical PCR negative; Non elevated PCT No microbial confirmation; diagnosed with novel diagnostic method |
| 114 | 0.05 | | | negative | Respiratory viral and atypical PCR negative; Non elevated PCT No microbial confirmation; diagnosed with novel diagnostic method |
| 115 | 0.05 | | | negative | Respiratory viral and atypical PCR negative; Non elevated PCT No microbial confirmation; diagnosed with novel diagnostic method |
| 116 | 0.07 | | | negative | No microbial confirmation; diagnosed with novel diagnostic method |
| 117 | 0.05 | | MRSA | negative | No microbial confirmation; diagnosed with novel diagnostic method |
| 118 | 0.05 | | | negative | No microbial confirmation; diagnosed with novel diagnostic method |
| 119 | 0.06 | | | negative | Respiratory viral and atypical PCR negative; Non elevated PCT No microbial confirmation; diagnosed with novel diagnostic method |
| 120 | 0.05 | | | negative | Respiratory viral and atypical PCR negative; Non elevated PCT No microbial confirmation; diagnosed with novel diagnostic method |
| 121 | 0.05 | | | negative | PCR positive for Rhinovirus with MxA < 20ng/ml which is consistent with colonization; diagnosed with novel diagnostic method |
| 122 | 0.05 | | Beta hemolytic Streptococcus Group A pyogenes | negative | Throat culture + with Group A Strep Less than $10^6$ and nonelevated PCT; No microbial confirmation, diagnosed with novel diagnostic method |
| 123 | 0.05 | 67.715 | | Viral | PCR positive for Influenza B virus |
| 124 | 0.05 | 52.343 | | Viral | PCR positive for Influenza B virus |
| 125 | 0.05 | 48.03 | STAPHYLOCOCCUS AUREUS | viral | Throat culture positive with normal flora and nonelevated PCT; PCR positive for Influenza B |
| 126 | 0.05 | 47.526 | STREPTOCUCCUS GROUP C | viral | Throat culture for with Group C Strep Less than $10^6$ and nonelevated PCT; PCR positive for Influenza A |

Fig. 5K

| Patient | PCT level (ng/ml) | MxA level (ng/ml) | ThroatCulturesOrganism | Final Diagnosis | Description/comments |
|---|---|---|---|---|---|
| 127 | 0.05 | 44.474 | STAPHYLOCOCCUS AUREUS | viral | Throat culture positive with normal flora and nonelevated PCT; PCR + Influenza A |
| 128 | 0.05 | 42.426 | | Viral | PCR positive for Rhinovirus with elevated MxA > 20 |
| 129 | 0.05 | 41.398 | | viral | PCR positive for Influenza B |
| 130 | 0.05 | 31.997 | | viral | PCR positive for Para influenza 3 |
| 131 | 0.05 | 30.732 | | viral | PCR positive for Influenza B |
| 132 | 0.05 | 30.614 | | viral | PCR positive for Influenza B |
| 133 | 0.05 | 29.462 | | viral | PCR positive for Influenza B |
| 134 | 0.05 | 27.961 | STREPTOCOCCUS GROUP C | viral | Throat culture positive with Group C Strep Less than $10^6$ and nonelevated PCT; PCR + Influenza B |
| 135 | 0.05 | 27.734 | | viral | PCR positive for Influenza A |
| 136 | 0.06 | 23.883 | | Viral | PCR positive for CMV |
| 137 | 0.05 | 70.206 | | viral | PCR positive for Influenza A |
| 138 | 0.05 | 68.514 | | viral | PCR positive for RSV |
| 139 | 0.05 | 61.15 | | viral | PCR positive for Influenza B |

Fig. 5L

| Patient | PCT level (ng/ml) | MxA level (ng/ml) | ThroatCulturesOrganism | Final Diagnosis | Description/comments |
|---|---|---|---|---|---|
| 140 | 0.05 | 56.589 | STAPHYLOCOCCUS AUREUS | | Throat culture positive with normal flora and nonelevated PCT; No microbial confirmation, diagnosed with novel diagnostic method; PCR positive for HSV associated with elevated MxA consistent with new infection in younger patient |
| 141 | 0.05 | 47.396 | | viral | PCR positive for Rhinovirus in presence of elevated MxA > 20ng/ml is a sign of a true infection |
| 142 | 0.05 | 32.068 | | viral | PCR positive for Rhinovirus in presence of elevated MxA > 20ng/ml is a sign of a true infection |
| 143 | 0.05 | 29.817 | ENTEROBACTER CLOACAE KLEBSIELLA PNEUMONIAE CRONOBACTER | viral | Throat culture with polymicrobial growth of normal oral flora; PCR positive for Rhinovirus in presence of elevated MxA > 27ng/ml is a sign of a true infection |
| 144 | 0.05 | 28.834 | | viral | PCR positive for Rhinovirus in presence of elevated MxA > 20ng/ml is a sign of a true infection |
| 145 | 0.05 | 22.095 | STAPHYLOCOCCUS AUREUS | viral | Throat culture positive with normal flora and nonelevated PCT; No microbial confirmation, diagnosed with novel diagnostic method; PCR positive for Influenza A and Chlamydia with elevated MxA and normal PCR is consistent with Influenza and chlamydia colonization |
| 146 | 0.07 | 20.189 | | viral | PCR positive for Rhinovirus with MxA > 20ng/ml |
| 147 | 0.07 | 20.153 | | viral | PCR positive for Influenza A |
| 148 | 0.05 | 20.074 | | viral | PCR positive for Influenza B Virus |

BACTERIAL CONFIRMATION BY PCR AND CELL CULTURE: 22

| | |
|---|---|
| GROUP A STREP | (8) |
| GROUP C STREP | (1) |
| STAPHAUREUS | (6) |
| PROTEUS SPECIES | (1) |
| ENTEROBACTER | (4) |
| HEMOPHILUS | (1) |
| KLEBSIELLA | (1) |
| TOTAL: | 22 |

BACTERIAL WITHOUT CO-INFECTION: 10

| | |
|---|---|
| GROUP A STREP | (4) |
| STAPHAUREUS | (2) |
| PROTEUS | (1) |
| ENTEROBACTER | (2) |
| HEMOPHILUS | (1) |
| TOTAL: | 10 |

BACTERIAL/CO-INFECTION: 12

| | |
|---|---|
| HSV + GROUP A STREP | (1) |
| RHINOVIRUS + GROUP A STREP | (2) |
| PARAINFLUENZA + GROUP A STREP | (1) |
| RHINOVIRUS + GROUP C STREP | (1) |
| INFLUENZA B + STAPHAUREUS | (1) |
| CORONAVIRUS + INFLUENZA A + STAPHAUREUS | (1) |
| INFLUENZA A + ENTEROBACTER | (1) |
| INFLUENZA A + RHINOVIRUS + STAPHAUREUS | (1) |
| HSV + STAPHAUREUS | (1) |
| RHINOVIRUS + ENTEROBACTER | (1) |
| RHINOVIRUS + KLEBSIELLA | (1) |
| TOTAL: | 12 |

FIG. 6

METHODS AND DEVICES FOR ACCURATE DIAGNOSIS OF INFECTIONS

REFERENCE TO RELATED APPLICATIONS

This application claims one or more inventions which were disclosed in Provisional Application No. 62/245,431, filed Oct. 23, 2015, entitled "MxA TO DRIVE INCREASED SPECIFICITY AND AUGMENT SENSITIVITY OF BACTERIAL BIOMARKERS". The benefit under 35 USC § 119(e) of the United States provisional application is hereby claimed, and the aforementioned application is hereby incorporated herein by reference.

BACKGROUND OF THE INVENTION

Field of the Invention

The invention pertains to the field of identifying infections. More particularly, the invention pertains to using the biomarkers MxA, C-reactive protein and/or procalcitonin to accurately screen for and diagnose viral and bacterial infections and to differentiate colonization from active infection.

Description of Related Art

Fever is a common cause of childhood visits to urgent care centers for both family practice and pediatric offices. Most commonly, this relates to either a respiratory infection or gastroenteritis. The high incidence of fever in children and the precautious administration of unnecessary antibiotics is reason to develop a more accurate screening test for viral and/or bacterial infection.

Differentiating bacterial and viral infection, as well as active infection from colonization, is often challenging, especially in young children that cannot verbalize their symptoms and in the outpatient setting where access to laboratory diagnostics is expensive, time consuming, and requires several days to produce a result. Several diagnostic markers show great promise to differentiate viral from bacterial infections. Three such markers include the proteins MxA (myxovirus resistance protein A), procalcitonin (PCT) and C-Reactive Protein (CRP). Most respiratory infections are related to pharyngitis of which 40%-60% are caused by viruses and 10-30% by group A beta hemolytic *streptococcus*. Other acute respiratory infections include sinusitis, otitis media, rhinopharyngitis, rhinosinusitis, pharyngotonsillitis, epiglottitis, laryngitis, rhinitis, bronchitis, bronchiolitis and pneumonia.

Severe community-acquired pneumonia is caused by bacterial infections in around 60% of cases, requiring admission to an intensive care unit (ICU) for about 10% of patients. The remaining 30% are related to respiratory viruses.

About 80% of all antimicrobials are prescribed in primary care, and up to 80% of these are for respiratory tract indications. Respiratory tract infections are by far the most common cause of cough in primary care. Broad spectrum antibiotics are often prescribed for cough, including acute bronchitis, and many of these prescriptions will benefit patients only marginally, if at all, and may cause side effects and promote antibiotic resistance. Some of the factors that urge physicians to give antibiotics include the absence of an adequate diagnostic marker of bacterial infections, the concern about lack of patient follow-up, and the time pressure.

Mx proteins are members of the superfamily of high molecular weight GTPases. Accordingly, these GTPases are upregulated by type I alpha/beta or type II interferons (IFN). The Mx GTPases are expressed exclusively in IFN alpha/beta but not IFN gamma treated cells. Type I interferons play important roles in innate immune responses and have immunomodulatory, antiproliferative, and antiviral functions. Human MxA, a 78 kDa protein, accumulates in the cytoplasm of IFN α/β treated cells and inhibits the replication of a wide range of viruses. MxA protein may offer certain advantages as a biomarker for viral infection over the other induced proteins such as 2', 5'-oligoadenylate synthetase, because of its lower basal concentration, longer half-life (2.3 days) and fast induction. MxA mRNA is detectable in isolated peripheral blood white blood cells stimulated with IFN within 1 to 2 h of IFN induction, and MxA protein begins to accumulate shortly thereafter.

Studies have shown that MxA protein expression in peripheral blood is a sensitive and specific marker for viral infection. The higher MxA levels in the viral infection group compared with the bacterial infection group can be explained by the fact that the MxA protein is induced exclusively by type I IFN and not by IFN-gamma, IL-1, TNF-alpha, or any of the other cytokines by bacterial infection. Serum type I IFN levels remain within normal limits, even in patients with severe bacterial infections.

Similarly, most viral infections have been reported to cause little acute phase response, and low C-Reactive Protein (CRP) concentrations have been used to distinguish illnesses of viral origin from those of bacterial etiology. Because the plasma concentration of C-reactive protein increases rapidly after stimulation and decreases rapidly with a short half-life, C-reactive protein can be a very useful tool in diagnosing and monitoring infections and inflammatory diseases. In Scandinavia, point of care C-reactive protein testing is part of the routine evaluation of patients with respiratory infections in general practice, and its use has proved cost-effective. In general practice, C-reactive protein is found to be valuable in the diagnosis of bacterial diseases and in the differentiation between bacterial and viral infections, however, it lacks specificity. Several viruses such as Influenza A and B as well as Adenovirus, frequently cause elevations in CRP levels. In spite of this limitation, the diagnostic value of C-reactive protein is found to be superior to that of the erythrocyte sedimentation rate (ESR) and superior or equal to that of the white blood cell count (WBC).

Procalcitonin is another marker of bacterial infection. While procalcitonin has no known hormonal activity, it is a 116 amino acid peptide precursor of the hormone calcitonin which is involved with calcium homeostasis. When a patient is healthy, procalcitonin is only present in the parafollicular cells (C cells) of the thyroid gland and by the neuroendocrine cells of the lung and the intestine. If a bacterial infection is present, however, intact procalcitonin is found in the blood. The level of procalcitonin is related to the proinflammatory stimulus by severity of bacterial infection and sepsis. Procalcitonin levels do not rise significantly with viral or non-infectious inflammations. Interestingly, the high procalcitonin levels produced during infections are not followed by a simultaneous increase in calcitonin levels or a decrease in serum calcium levels. Procalcitonin has been used in identifying bacterial infections, however, similar to C-reactive protein, some viral infections such as Influenza A and B and Adenovirus may cause modest elevations in procalcitonin levels.

Clinically, it can be challenging to differentiate certain systemic viral and bacterial infections. Bacterial cultures are usually performed in cases of severe infection such as pneumonia, or when the consequence of missing a diagnosis can lead to severe complications, such as with Strep throat. Often times, cultures are difficult to obtain. Unfortunately, viral cultures are not routinely performed due to the significant time delay in receiving results. Viral screening PCR panels are useful, but they are expensive and do not provide information at the point of care. Thus, there remains a need for diagnostic tests that are capable of confidently identifying viral and bacterial infections, as well as distinguishing active infection from colonization/carrier state, in a point of care setting.

Another problem in screening and diagnosis is that, often, despite extensive testing, pathogens are frequently not identified. Numerous prospective clinical studies utilized PCR for identifying respiratory viruses and atypical bacteria, bacterial cell cultures, and/or serology to identify suspected pathogens. In these studies, a pathogen was not identified in approximately 32-70% of URIs (upper respiratory tract infections) and approximately 39-68% of LRTIs (lower respiratory tract infections).

In two studies of upper respiratory infections in adults, 32% and 67%, respectively, of the infections were microbiologically unconfirmed (Huovinen et al. Pharyngitis in Adults: The Presence and Coexistence of Viruses and Bacterial Organisms Ann Intern Med. 1989; 110(8):612-616; Nicholson et al. Acute viral infections of upper respiratory tract in elderly people living in the community: comparative, prospective, population based study of disease burden. BMJ. 1997; 315:1060-4, both herein incorporated by reference). In four studies of upper respiratory infections in adults and children, 44%, 20%, 45%, and 60-70%, respectively, of the infections were microbiologically unconfirmed (Melbye et al. The course of C-reactive protein response in untreated upper respiratory tract infection, Br J Gen Pract. 2004 September; 54(506):653-8; Leekha S et al. Viral detection using a multiplex polymerase chain reaction-based assay in outpatients with upper respiratory infection. Diagn Microbiol Infect Dis. 2013; 75:169-73; Blaschke, Interpreting assays for the detection of *Streptococcus pneumoniae*. Clin Infect Dis. 2011 May; 52 Suppl 4:S331-7; Stover and Litwin, The Epidemiology of Upper Respiratory Infections at a Tertiary Care Center: Prevalence, Seasonality, and Clinical Symptoms. Journal of Respiratory Medicine. Volume 2014 (2014), Article ID 469393, 8 pages, all herein incorporated by reference).

Two pediatric studies, one for upper respiratory infections and the other for lower respiratory tract infections, showed microbiologically unconfirmed infection in 63% and 40% of the patients, respectively (Chi et al. Etiology of acute pharyngitis in children: is antibiotic therapy needed? J Microbiol Immunol Infect. 2003 March; 36(1):26-30; Drummond et al. Community acquired pneumonia—a prospective UK study. Arch Dis Child. 2000 November; 83(5): 408-12, both herein incorporated by reference). In seven studies of adults with lower respiratory tract infections, 50%, 42%, 68%, 46%, 45%, 39% and 47%, respectively, of the infections were microbiologically unconfirmed (Oosterheert et al. Impact of rapid detection of viral and atypical bacterial pathogens by real-time polymerase chain reaction for patients with lower respiratory tract infection. Clin Infect Dis. 2005 Nov. 15; 41(10):1438-44; Jennings et al. Incidence and characteristics of viral community-acquired pneumonia in adults. Thorax. 2008 January; 63(1):42-8; Laing et al. Community-acquired pneumonia in Christchurch and Waikato 1999-2000: microbiology and epidemiology. N Z Med J. 2001 Nov. 9; 114(1143):488-92; Musher D M et al. Can an etiologic agent be identified in adults who are hospitalized for community-acquired pneumonia: results of a one-year study. J Infect. 2013 July; 67(1):11-8; Bierbaum et al. Performance of a novel microarray multiplex PCR for the detection of 23 respiratory pathogens (SYMP-ARI study). Eur J Clin Microbiol Infect Dis. 2012; 31:2851-61; van Gageldonk-Lafeber et al. The aetiology of community-acquired pneumonia and implications for patient management. Neth J Med. 2013; 71:418-25; Falsey A R et al. Bacterial complications of respiratory tract viral illness: a comprehensive evaluation. J Infect Dis. 2013 Aug. 1; 208 (3):432-41, all herein incorporated by reference).

SUMMARY OF THE INVENTION

Diagnostic and screening devices and methods test for the presence of immune response markers for viral infection and immune response markers for bacterial infection, to effectively assist in the identification of the presence of a clinically significant infection, assist in the differentiation of viral and bacterial infections and to distinguish colonization/carrier state from active infection.

One method of differentiating between colonization/carrier state and active infection includes the step of performing a test for a presence of bacteria and/or virus in a sample. This first test may include, but is not limited to, PCR, viral culture, viral or bacterial IFA, viral antigen testing, bacterial antigen testing, or a bacterial culture. If the sample is positive for a typical pathogen (viral or bacterial), a second test is performed to confirm the existence of a bonafide infection. Bacterial confirmation in the presence of at least approximately 0.10 ng/ml to 0.015 ng/ml procalcitonin and/or a presence of at least approximately 15 mg/L to 20 mg/L of C-reactive protein represents a true infection and not a carrier state or colonization. If the original sample is confirmed for the presence of a virus, a third test is performed to detect a presence of the mean plus 2-3.5 times the standard deviation of the normal population baseline values of the viral biomarker, or at least approximately 25 ng/ml to 35 ng/ml of MxA depending on the reference standard. A presence of at least approximately 25 ng/ml MxA indicates an active viral infection. The absence of at least approximately 25 ng/ml MxA indicates an absence of a bonafide viral infection and represents the carrier state or colonization. In other embodiments, tests for only bacteria or only viruses are performed. The biomarkers may be qualitative and set with thresholds at the cut-off or provide quantitative results or a combination of qualitative or quantitative results.

A method for differentiating between colonization/carrier state and an active infection includes the step of determining the presence of a viral or bacterial pathogen utilizing antigen testing, molecular testing, and/or cell culture in combination with serological confirmation of a systemic response via an elevation in MxA, CRP, procalcitonin or any other specific bacterial biomarker. Other potential biomarkers include but are not limited to serum amyloid A, IL-6 (Interleukin-6), IFIT, or human neutrophile lipocalin (HNL).

In other embodiments, MxA, procalcitonin, and/or C-reactive protein are used to distinguish between bacterial infection, viral infection, and colonization/carrier state. In some of these embodiments, these markers of immune response are used to diagnose patients with an illness that was microbiologically unconfirmed with the standard laboratory methods (for example, PCR, culture, and radiography).

In other embodiments, after standard tests to determine infection (including tests using MxA, C-reactive protein, and/or procalcitonin) have been performed and the cause of a patient's illness is still microbiologically unconfirmed, additional steps are taken to try to determine a diagnosis. Use of MxA in combination with either C-reactive protein or procalcitonin, or another serologic bacterial marker, helps to confirm the presence of a clinically significant infection from an insignificant infection that does not require immediate treatment.

In some preferred embodiments, a first sample is assayed for the presence of elevated MxA, C-reactive protein and/or procalcitonin. If these assays give a negative result, a second sample is taken from the patient within four to seventy two hours (preferably, within 48 hours) of the initial sample, and tested a second time for the presence of elevated MxA, C-reactive protein and/or procalcitonin. In some of these embodiments, the first and second sample are tested for MxA, with the second sample being taken within four to forty-eight hours of the first sample. In other embodiments, the first sample and the second sample are tested for MxA and either C-reactive protein or procalcitonin. In other embodiments HNL (human neutrophil lipocalin) IL-6, or serum amyloid A are assayed instead of C-reactive protein or procalcitonin. The second sample in this embodiment is taken within four to forty-eight hours of the first sample. In other embodiments, additional research and testing is done to try to determine if a patient with a microbiologically unconfirmed diagnosis has an emergent disease or illness.

In other embodiments, a method of increasing the specificity of detection of a bacterial host biomarker without compromising sensitivity includes the step of assaying for at least one viral host biomarker and at least one bacterial host biomarker. In one preferred embodiment, the bacterial host biomarker is C-reactive protein and the viral host biomarker is MxA. In another preferred embodiment, the bacterial host biomarker is procalcitonin and the viral host biomarker is MxA. In another preferred embodiment, the viral host biomarker is interferon or an IFIT (an interferon-induced protein with tetratricopeptide repeats).

A method for determining whether an infection is bacterial and/or viral includes the step of determining a presence of MxA, C-reactive protein, and procalcitonin in a sample. One or more additional levels of CRP at 80 mg/ml-100 mg/ml or PCT between 0.25 ng/ml and 1.0 ng/ml may be added to the assay to determine the intensity or severity of the bacterial infection.

A kit for diagnosing whether an infection is bacterial and/or viral includes at least one reagent for determining a presence of a first level of C-reactive protein in a sample, at least one reagent determining a presence of a second level of C-reactive protein that is higher than the first level of C-reactive protein in the sample, at least one reagent for determining a presence of MxA in the sample, and at least one reagent for determining a presence of procalcitonin in the sample.

In one preferred embodiment, a single multiparametric device tests for the presence of MxA, a low level of C-reactive protein, a high level of C-reactive protein, and procalcitonin in a sample. In another preferred embodiment, a single multiparametric device tests for the presence of MxA and procalcitonin in a sample.

One method screens a patient with a respiratory infection for bacterial colonization. A first test is performed for a presence of bacteria. If the first test indicates bacteria is present, a second test is performed to quantitatively determine a level of procalcitonin or C-reactive protein in a patient sample. A patient sample testing positive for atypical bacteria using PCR in the first test and a level of procalcitonin in a patient sample is less than 0.1 ng/ml or a level of C-reactive protein in the patient sample is less than 20 mg/l indicates negative for infection. A cell culture result of greater than $1\times10^6$ CFU/ml atypical bacteria in the first test and a level of procalcitonin less than 0.15 ng/ml indicates colonization. A cell culture result of greater than $1\times10^6$ CFU/ml atypical bacteria in the first test, a level of procalcitonin greater than or equal to 0.15 ng/ml and less than 0.25 ng/ml, a white blood cell count less than 12,000, and no bands indicates colonization. A cell culture result of greater than $1\times10^6$ CFU/ml atypical bacteria in the first test and a level of C-reactive protein less than 20 mg/l indicates colonization. A cell culture result of greater than $1\times10^6$ CFU/ml atypical bacteria in the first test, a level of C-reactive protein greater than or equal to 20 mg/l and less than 80 mg/l, a white blood cell count less than 12,000, and no bands also indicates colonization. If the patient tests positive for Strep A or Strep C using cell culture and a level of procalcitonin is less than 0.1 ng/ml or a level of C-reactive protein is less than 20 mg/l, the method tests for Streptolysin O antibody and a white blood cell count. A Streptolysin O antibody of less than 80% and a white blood cell count of less than 12,000 indicates colonization. Negative paired serology also indicates colonization.

A method of screening a patient with a respiratory infection for colonization includes the step of performing a first test for a presence of a bacterial or viral infection. If the first test is positive for presence of a virus, a second test is performed to determine a level of MxA in a patient sample. A level of MxA in the patient sample greater than or equal to 25 ng/ml indicates a viral infection and a level of MxA in the patient sample less than 25 ng/ml indicates no systemic host response. The method may also include a third test for a presence of bacteria. If the third test indicates bacteria is present, a fourth test is performed to determine a level of procalcitonin or C-reactive protein in a patient sample. A patient sample testing positive for atypical bacteria using PCR in the third test and a level of procalcitonin in a patient sample less than 0.1 ng/ml or a level of C-reactive protein in the patient sample is less than 20 mg/l indicates negative for infection. A cell culture result of greater than $1\times10^6$ CFU/ml atypical bacteria in the third test and a level of procalcitonin less than 0.15 ng/ml indicates colonization. A cell culture result of greater than $1\times10^6$ CFU/ml atypical bacteria in the third test, a level of procalcitonin greater than or equal to 0.15 ng/ml and less than 0.25 ng/ml, a white blood cell count less than 12,000, and no bands indicates colonization. A cell culture result of greater than $1\times10^6$ CFU/ml atypical bacteria in the third test and a level of C-reactive protein less than 20 mg/l indicates colonization. A cell culture result of greater than $1\times10^6$ CFU/ml atypical bacteria in the third test, a level of C-reactive protein greater than or equal to 20 mg/l and less than 80 mg/l, a white blood cell count less than 12,000, and no bands also indicates colonization. If the patient tests positive for Strep A or Strep C using cell culture and a level of procalcitonin is less than 0.1 ng/ml or a level of C-reactive protein is less than 20 mg/l, a sample is tested for Streptolysin O antibody and a white blood cell count. A Streptolysin O antibody of less than 80% and a white blood cell count of less than 12,000 indicates colonization and negative paired serology also indicates colonization.

A method of screening a symptomatic patient for active infection includes performing a test to assay for a host viral biomarker selected from the group consisting of MxA and an interferon induced protein with tetratricopeptide repeats and a host bacterial biomarker selected from the group consisting of C-reactive protein, procalcitonin, interleukin-6, serum amyloid A, and human neutrophil lipocalin. The first test is performed using a membrane and buffer that directly lyses cells, separates blood into plasma/serum, and filters cellular debris to detect the host viral biomarker and the host viral biomarker without any pre-processing steps. A value of the host viral biomarker greater than approximately 2 times the mean in the normal population times the standard deviation indicates a viral infection. A value of the host bacterial biomarker greater than approximately 2 times the mean in the normal population times the standard deviation indicates a bacterial infection. A value of the host viral biomarker greater than approximately 2 times the mean in the normal population times the standard deviation and a value of the host bacterial biomarker greater than approximately 2 times the mean in the normal population times the standard deviation indicates a viral infection. A value of the host viral biomarker less than approximately 2 times the mean in the normal population times the standard deviation and a value of the host bacterial biomarker less than approximately 2 times the mean in the normal population times the standard deviation indicates a microbiologically unconfirmed state.

A method includes the step of assaying a patient sample for MxA. If the patient sample has an MxA level greater than or equal to 25 ng/ml, the patient is diagnosed with a viral infection, regardless of elevated levels of at least one bacterial host biomarker in the sample.

A method of differentiating between colonization and active infection includes the step of performing at least one first test for a presence of bacteria or virus in a sample. If the sample is positive for bacteria, a second test is performed for a presence of at least approximately 0.10 ng/ml procalcitonin and/or a presence of at least approximately 20 mg/L of C-reactive protein. A presence of at least approximately 0.10 ng/ml procalcitonin or at least approximately 20 mg/L of C-reactive protein indicates an active bacterial infection. An absence of at least approximately 0.10 ng/ml procalcitonin or at least approximately 20 mg/L C-reactive protein indicates bacterial colonization. If the sample is positive for virus, a third test is performed for a presence of at least approximately 25 ng/ml MxA. A presence of at least approximately 25 ng/ml MxA indicates an active viral infection. An absence of at least approximately 25 ng/ml MxA indicates viral colonization.

A method of differentiating between colonization and active infection includes the step of performing at least one first test for a presence of bacteria in a sample. If the sample is positive for bacteria, a second test is performed to assay for a presence of at least approximately 0.10 ng/ml procalcitonin and/or a presence of at least approximately 20 mg/L of C-reactive protein. A presence of at least approximately 0.10 ng/ml procalcitonin or at least approximately 20 mg/L indicates an active bacterial infection. An absence of at least approximately 0.10 ng/ml procalcitonin or at least approximately 20 mg/L C-reactive protein indicates bacterial colonization.

A method of differentiating between colonization and active infection includes the step of performing at least one first test for a presence of virus in a sample. If the sample is positive for virus, a second test is performed to assay for a presence of at least approximately 25 ng/ml MxA. A presence of at least approximately 25 ng/ml MxA indicates an active viral infection and an absence of at least approximately 25 ng/ml MxA indicates viral colonization.

A method of screening a patient for a bacterial or viral infection includes the steps of testing for a level of MxA greater than 25 ng/ml in a first sample and testing the first sample for a level of a host bacterial biomarker. The host bacterial biomarker is selected from the group consisting of a level of C-reactive protein in the first sample greater than 20 mg/L and a level of procalcitonin in the first sample greater than 0.10 ng/ml. If the levels of MxA and the host bacterial biomarker are undetected in the first sample, a second sample is taken approximately 4-48 hours after the first sample has been taken and the sample is re-assayed for a presence of MxA and either C-reactive protein or procalcitonin. In some preferred embodiments, the second sample is taken 6-8 hours after the first sample has been taken. In some preferred embodiments, both the first sample are assayed using a quantitative assay or both samples are assayed using a qualitative assay.

In one embodiment, a method determines a presence of MxA and procalcitonin in a sample using a single multi-parametric assay device that assays for the presence of both MxA and procalcitonin.

BRIEF DESCRIPTION OF THE DRAWINGS

FIGS. 5A-5L show diagnoses for patients in a clinical trial using the diagnostic methods described herein.

FIG. 6 shows the bacteria identified in a clinical trial.

DETAILED DESCRIPTION OF THE INVENTION

Figure 1:
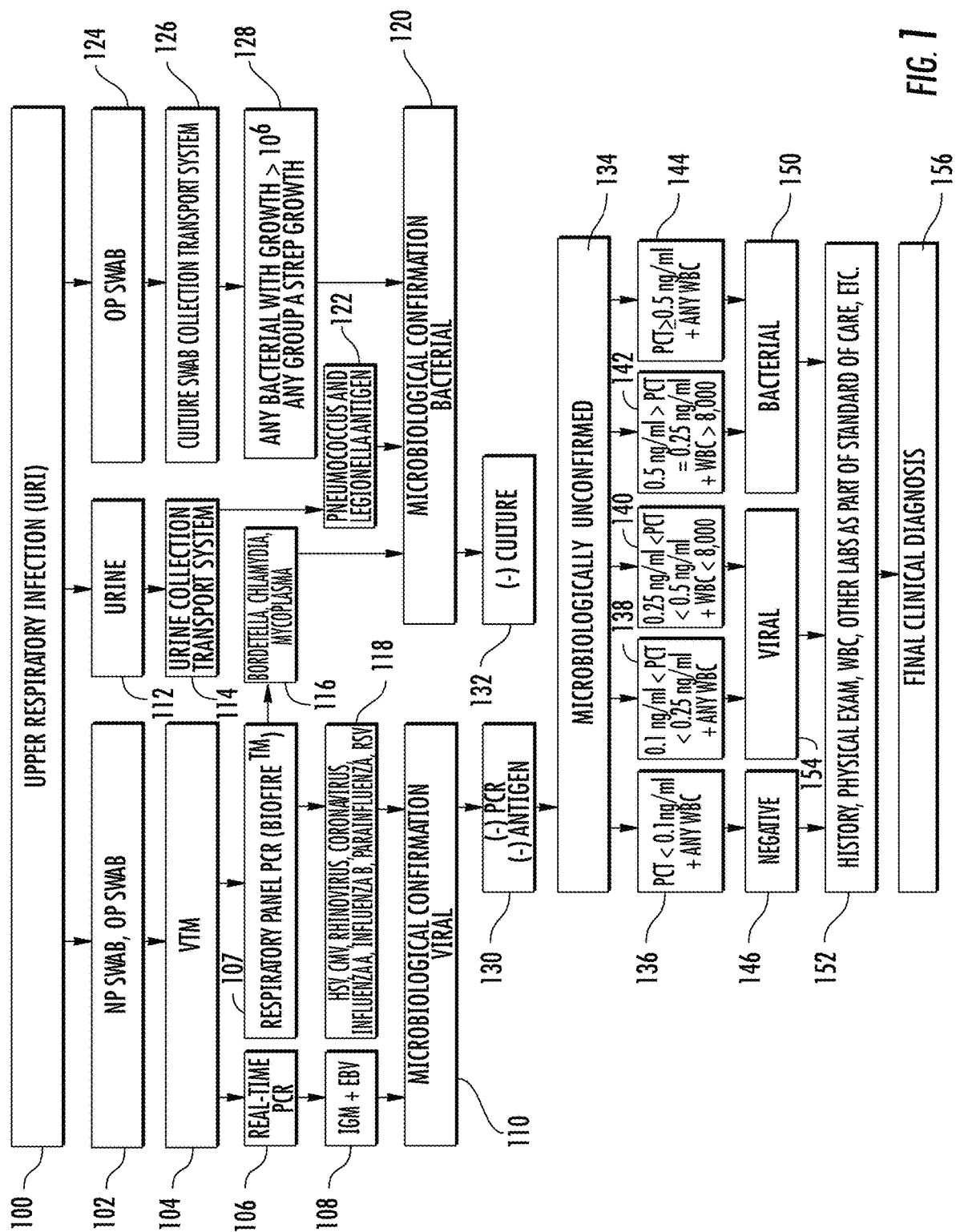
FIG. 1 shows a clinical method for diagnoses of upper respiratory infections.

Challenges in the clinical differentiation of viral and/or bacterial respiratory infection lead to the misappropriation of antibiotics and increased healthcare costs. A tool to facilitate rapid and accurate point-of-care differentiation is needed.

The methods and devices described herein, which assay for MxA, IFIT proteins, other viral host markers, C-reactive protein, procalcitonin, and/or other bacterial host markers may be used on any test platform. Other potential biomarkers include, but are not limited to, serum amylase A, or human neutrophil lipocalin (HNL). Some device examples include, but are not limited to, lateral flow devices, ELISA, fluorescence, or chemiluminescence. The results may be qualitative or quantitative or a combination thereof. The test may represent a single use disposable format or a portable or desktop analyzer. Other examples are also described herein.

The present invention provides methods and devices for differentiating between viral and bacterial infections. Instead of testing for analytes specific to a particular bacterial or viral infection, the assays and methods described herein test for diagnostic markers that are specifically produced in a host in response to general, unspecified bacterial infection and general, unspecified viral infection. The diagnostic markers are preferably markers of an unspecified and/or unknown illness of bacterial or viral origin. In preferred embodiments, the diagnostic markers are specific markers for an immune response to an unspecified and/or unknown bacterial and/or viral infection.

The methods and devices herein are also able to distinguish between colonization and active infection. It was unexpected that someone can have an active infection and be asymptomatic. Conversely, someone who is symptomatic may not have an active infection.

As described herein, "colonization" or a "carrier state" refer to a clinically insignificant local infection without an associated systemic immune or serological response. These two terms will be used interchangeably herein.

A multiplexed diagnostic device tests markers for both viral and bacterial infection and can effectively identify clinically significant infections by choosing a threshold significantly above baseline values seen in the normal population and based on the relative values of the biomarkers, and can assist in the rapid differentiation between viral and bacterial infections and/or between active infection and colonization, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance.

The methods and devices described herein test for the presence of MxA, C-reactive protein (preferably a first level and a second level, where the second level of C-reactive protein is higher than the first level of C-reactive protein but alternatively one level of C-reactive protein may be assayed), and/or procalcitonin, or another bacterial biomarker. Testing for this unique combination of viral (MxA) and bacterial (C-reactive protein and procalcitonin) immune response markers allows for a much more accurate diagnosis of a patient.

The combination of MxA, interferon, or IFIT in the presence of C-reactive protein, procalcitonin, or another bacterial biomarker shifts the receiver operator curve to allow for higher sensitivity thresholds to be used for bacterial infection confirmation because the specificity of the bacterial biomarker is enhanced by the presence of the viral marker. Thus, if a patient has an elevated viral marker in the presence of elevated C-reactive protein and/or procalcitonin or other bacterial biomarkers, it confirms a viral infection yet an elevation of the bacterial markers independent of the viral markers would confirm a bacterial infection. Without the presence of the viral biomarkers, the cutoff for the bacterial infection determination would need to be set much higher to generate improved specificity at the cost of sensitivity. This combination of the biomarkers dramatically improves the bacterial sensitivity by shifting the receiver operator curves in favor of higher sensitivity cutoffs.

In some preferred embodiments, a combined single diagnostic sample analysis device tests for a presence of MxA, a low level of C-reactive protein, a high level of C-reactive protein, and procalcitonin. In other preferred embodiments, a first combined diagnostic device tests for a presence of two or more of MxA, a low level of C-reactive protein, a high level of C-reactive protein, or procalcitonin and one or more additional diagnostic devices tests for a presence of at least one of MxA, a low level of C-reactive protein, a high level of C-reactive protein, or procalcitonin. In another preferred embodiment, a first combined diagnostic sample analysis device tests for a presence of MxA, a low level of C-reactive protein, and a high level of C-reactive protein, and a second sample analysis device tests for the presence of procalcitonin. In yet another embodiment, different devices test for each of MxA, a low level of C-reactive protein, a high level of C-reactive protein, and procalcitonin.

In some embodiments, obtaining results for two levels of C-reactive protein differentiates between a non-aggressive bacterial infection needing appropriate oral antibiotics (positive result for low level of C-reactive protein only in the range of 20 mg/L) versus an aggressive, severe bacterial infection needing aggressive therapeutic intervention such as intravenous antibiotics or other more drastic interventions (positive result for both low level and high level of C-reactive protein in the range of greater than 80 mg/L). The presence of a second higher cutoff line may also assist in identifying patients more likely requiring hospital admission. High C-reactive protein levels help determine the aggressiveness or clinical significance of a bacterial infection because of the semi-quantitative aspect of the test.

Some examples of assay formats for determining the presence of C-reactive protein, MxA and/or procalcitonin include, but are not limited to, immunoassays, immunoblotting methods, agglutination reactions, a complement-fixation reaction, a hemolytic reaction, a precipitation reaction, a gold colloid method, a chromatography method, phosphorescence, radioactivity, colorimetry, gravimetry, X-ray diffraction, X-ray absorption, magnetism, fluorescent resonant emissions, or an immunostaining method. Some examples for immunoassays include, but are not limited to, immunoprecipitation, radioimmunoassays (RIA), enzyme immunoassays (EIA or ELISA), a Vidas® immunoassay device (Biomerieux, Hazelwood, Mo.), an i-Stat® portable handheld system (Abbott Laboratories, Abbott Park, Ill.), a Philips Handheld diagnostic system (Philips Handheld Diagnostics, The Netherlands), fluorescent immunoassays (FIA), chemiluminescent immunoassays, physiochemical assays (TIA, LAPIA, or PCIA), lateral flow immunoassays, or flow cytometry. MxA monoclonal antibodies have been used in modified flow cytometry (Itazawa et al., Increased lymphoid MxA expression in acute asthma exacerbation in children., Allergy September 2001 56(9): 895-8). Some preferred immunoassays for these biomarkers include, but are no limited to, ELISAs, fluorescence immunoassays, magnetic assays, paramagnetic assays, and chemiluminiscent assays. In other embodiments, the mRNA or gene transcripts may be used. In some preferred embodiments, the assays are automated.

One particular example of a device to determine the presence of C-reactive protein, MxA and/or procalcitonin is a multiparametric immunoassay system that is able to detect two or more of these targets in the same device. One such device is a Vidas® immunoassay device (Biomerieux, Hazelwood, Mo.), which could test for the presence of one, two, three, or all four of these targets simultaneously. The Vidas® immunoassay device is an Enzyme Linked Fluorescent assay (ELFA) (also available in a compact version called Mini Vidas®) and is widely used in clinical laboratories. Other devices that could be used include a Vitek® immunodiagnostic system (Biomerieux, Hazelwood, Mo.), or a Luminex® immunoassay system (Luminex Corporation, Austin, Tex.). Another example is a device similar to an i-Stat® portable handheld system (Abbott Laboratories, Abbott Park, Ill., see the devices disclosed in U.S. Pat. Nos. 5,638,828, 5,666,967, 5,653,243, 5,779,650, 6,010,463, 6,845,327, 6,896,778, 7,419,821, and 8,017,382, all herein incorporated by reference). Yet another example is a device that combines magnetic particle separation with chemiluminescent detection, such as the BioFlash multiparametric immunoassay system (Biokit, Barcelona, Spain). Another example is a Philips handheld diagnostics device (Philips Handheld Diagnostics, The Netherlands).

Viral and bacterial infections are highly contagious and difficult to clinically differentiate due to a significant overlap in signs and symptoms, which often leads to the over prescription of systemic antibiotics and fosters antibiotic resistance. In developed countries, acute respiratory infections are the leading cause of morbidity, accounting for: 20% of medical consultations, 30% of absences from work, and 75% of all antibiotic prescriptions. In the U.S., there are approximately 76 million physician office visits annually for acute respiratory infection. The ability to detect an immune response to an infection aids in the clinical diagnostic ability to differentiate clinically significant infections and those resulting from a viral and/or bacterial etiology and to differentiate between colonization and active infection.

In preferred embodiments, the marker for viral infection is MxA and the markers for bacterial infection are procalcitonin (PCT), and two levels of C-reactive protein. High MxA protein levels are strongly correlated with systemic viral infection and increased C-reactive protein and procalcitonin are more associated with bacterial infections. The present invention includes infectious screening tests for identifying MxA, C-reactive protein and procalcitonin in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates. In one preferred embodiment, the sample is taken from whole blood.

In some embodiments, lysing buffer is used to treat the whole blood in a vacuum tube. In some embodiments, whole blood is preferably lysed before the sample is assayed for the host biomarkers. In some embodiments, a membrane and buffer are used to directly lyse the whole blood cells, separate blood into plasma/serum, and filter cellular debris, to detect a combination of intracellular and extracellular biomarkers. In some preferred embodiments, there are no external or pre-processing steps.

The $C_{50}$ concentration for a particular test, where 50% of the time a visually read test is interpreted as positive, depends on an individual's visual acuity. The $C_{50}$ concentration is also known as the cut-off concentration or the threshold concentration above which the test is considered positive. Some times it is also called a Medical Decision Point above which a relevant decision is made by the clinician The Applicant has found the $C_{50}$ values to be ≥25 ng/ml to 35 ng/ml for MxA, ≥15 mg/L to 20 mg/L for low CRP (serum equivalent) and ≥80 mg/L to 100 mg/L for high CRP (serum equivalent). Below $C_{50}$, for example at $C_5$ there is a 5% chance the result is scored as positive. The $C_5$ concentrations begin at 10 ng/ml for MxA, at about 10 mg/L for low CRP and about 30 mg/L for high CRP. These are not false positives because there is some analyte present in the sample.

In some preferred embodiments of testing for the presence of procalcitonin (including, but not limited to, those embodiments testing also for MxA, and/or one or both levels of C-reactive protein), the threshold concentration of procalcitonin in a sample needed to elicit a positive result is greater than approximately 0.1 ng/ml. In another preferred embodiment, the threshold concentration of procalcitonin in a sample to elicit a positive result is equal to or greater than approximately 0.15 ng/ml. In another preferred embodiment, the threshold concentration of procalcitonin in a sample to elicit a positive result is equal to or greater than approximately 0.25 ng/ml. In one preferred embodiment, the procalcitonin cut off value is defined as the mean in the normal population +2-3.5 times the standard deviation.

In other preferred embodiments of testing for the presence of MxA (including, but not limited to, those embodiments testing also for procalcitonin, and/or one or both levels of C-reactive protein), the threshold concentration of MxA in a sample to elicit a positive result may be as low as approximately 15 ng/ml; however, the threshold concentration may by higher, in a range from approximately 20 ng/ml to approximately 400 ng/ml. In one preferred embodiment, the threshold concentration to obtain a positive result for MxA is equal to or greater than approximately 25 ng/ml. In another preferred embodiment, the threshold concentration to obtain a positive result for MxA is equal to or greater than approximately 30 ng/ml. In other preferred embodiments, a threshold concentration to obtain a positive result for MxA is equal to or greater than approximately 40 ng/ml.

The cutoff value (threshold concentration) for assaying MxA depends on whether a quantitative or qualitative assay is being performed. For example, the cutoff value for assaying MxA in lateral flow assays is preferably 40 ng/ml because it is a qualitative assay. In some preferred embodiments, a 25 ng/ml cut off value or a 35 ng/ml cut off value is preferable when performing a quantitative assays. Any MxA values between approximately 25 ng/ml and 40 ng/ml could preferably used in a quantitative assay. The cut off values are preferably technology independent and the standards used may alter the cut off values slightly. The important thing is to determine whether the MxA biomarker is elevated. In one preferred embodiment, the MxA cut off value is defined as the mean in the normal population +2-3.5 times the standard deviation.

In some preferred embodiments of testing for the presence of a low level of C-reactive protein (including, but not limited to, those embodiments testing also for MxA, procalcitonin, and/or a high level of C-reactive protein), a threshold concentration to obtain a positive result for the low level of C-reactive protein is equal to or greater than a serum equivalent of approximately 6-20 mg/L of C-reactive protein. In other preferred embodiments, the threshold concentration to obtain a positive result for the low level of C-reactive protein is equal to or greater than a serum equivalent of approximately 10 mg/L of C-reactive protein. In still other preferred embodiments, the threshold concentration to obtain a positive result for the low level of C-reactive protein is equal to or greater than a serum equivalent of approximately 20 mg/L. In one preferred embodiment, the C-reactive protein cut off value is defined as the mean in the normal population +2-3.5 times the standard deviation.

In some preferred embodiments of testing for the presence of a high level of C-reactive protein (including, but not limited to, those embodiments testing also for MxA, procalcitonin, and/or a low level of C-reactive protein), the threshold concentration to obtain a positive result for the high level of C-reactive protein is equal to or greater than a serum equivalent of approximately 60-100 mg/L. In another preferred embodiment, the threshold concentration to obtain a positive result for the high level of C-reactive protein is equal to or greater than a serum equivalent of approximately 80 mg/L. In other preferred embodiments, the threshold concentration to obtain a positive result for the high level of C-reactive protein is equal to or greater than a serum equivalent of approximately 65 mg/L.

The threshold concentrations of each of the targets may depend on the size of the sample being applied to the assay device (for example a test strip), as well as its dilution, if applicable.

In some embodiments, the devices and methods described herein allow for the rapid, visual, qualitative in vitro detection of MxA, C-reactive protein and procalcitonin directly from peripheral whole blood. In one preferred embodiment, the test measures an immune response to a suspected viral and/or bacterial infection in patients older than one year that present within seven days of onset of a fever, with respiratory symptoms consistent with respiratory disease, and with a suspected diagnosis of acute pharyngitis or community acquired pneumonia. Negative results do not necessarily preclude respiratory infection and should not be used as the sole basis for diagnosis, treatment, or other management decisions. In some embodiments, additional laboratory testing (e.g., bacterial and viral culture, immunofluorescence, viral polymerase chain reaction, and radiography) and clinical presentation are preferably additionally used to confirm whether a specific lower respiratory or pharyngeal pathogen exists.

In addition, there are some conditions that lead to erroneous false positives or negatives. These include, but are not limited to, current use of immunosuppressive drugs by the patient providing the sample, current use of oral anti-infective drugs by the patient providing the sample, current use of interferon therapy (e.g. for multiple sclerosis, Human Immunodeficiency Virus (HIV), Hepatitis B virus (HBV), or Hepatitis C virus (HCV)) by the patient providing the sample, and live viral immunization within the last 30 days by the patient providing the sample. Both false negatives and false positives are possible since the levels can fluctuate due to therapy.

In preferred embodiments, the devices and methods are intended for professional use in an outpatient office or urgent care clinic and should be used in conjunction with other clinical (laboratory or radiographic) and epidemiological information.

In some preferred embodiments, a method of differentiating between colonization and active infection includes the step of performing a first test for a presence of bacteria or virus in a sample. The first test may include, but is not limited to, PCR, a radiological test, IFA, a rapid antigen test, or a bacterial culture. If the sample is positive for bacteria, a second test is performed for a presence of at least approximately 0.10 ng/ml procalcitonin and/or a presence of at least approximately 15-20 mg/L of C-reactive protein. A presence of at least approximately 0.10 ng/ml procalcitonin or at least approximately 15-20 mg/L C-reactive protein indicates an active bacterial infection. An absence of at least approximately 0.10 ng/ml procalcitonin or at least approximately 15-20 mg/L C-reactive protein in combination with other factors indicates bacterial colonization. If the sample is positive for virus, a third test is performed for a presence of at least approximately 25 ng/ml MxA. A presence of at least approximately 25 ng/ml MxA indicates an active viral infection. The absence of at least approximately 25 ng/ml MxA indicates negative or a non-systemic host response. In other embodiments, tests for only bacteria or only viruses are performed.

In one embodiment, the infections being distinguished are respiratory infections. In other embodiments, other types of infections, which can be bacterial or viral, are differentiated using the system of the present invention. Some examples include, but are not limited to, gastric infections, encephalitis, meningitis, gastroenteritis, febrile respiratory illness (including bronchitis, pharyngitis, pneumonia), cellulitis, sinusitis, otitis media, urinary tract infections, and conjunctivitis.

US Patent Publication 2010/0297611, published Nov. 25, 2010, entitled "Method and Device for Combined Detection of Viral and Bacterial Infections", US Patent Publication 2013/0196310, published Aug. 1, 2013, entitled "Method and Device for Combined Detection of Viral and Bacterial Infections", U.S. Pat. No. 8,962,260, issued Feb. 24, 2015, entitled "Method and Device for Combined Detection of Viral and Bacterial Infections", and US Patent Publication 2013/0130367, published May 23, 2013, entitled "Method and Device for Combined Detection of Viral and Bacterial Infections", all incorporated herein by reference, disclose methods and devices for distinguishing between bacterial and viral infections by detecting bacterial and viral markers on lateral flow immunoassays. In some preferred embodiments of these applications, the viral marker is MxA and the bacterial marker is C-reactive protein.

"Sensitivity" is the ability to detect a positive result. For example, a more sensitive test is less likely to miss a positive with a very low concentration. In a qualitative test where the results are scored either as positive or negative, the ability to determine correctly the positive samples which have low concentrations of the analyte by having a lower limit of detection is of paramount importance. This is especially true during the early time course of any infection or disease where the target analyte is generally at low concentrations. The higher the sensitivity, the lower the false negatives in the system.

"Specificity" is the ability to identify the specific analyte without interference from other components. Specificity is also the likelihood that a test will be negative when the analyte is absent from the sample. The higher the specificity, the lower the false positives in the system.

In isolation, neither MxA nor procalcitonin alone is sensitive or specific at identifying both viral and bacterial infection. Procalcitonin is specific to identify bacterial infection, but is not sensitive for viral infection. MxA is specific to identify viral infection, but it is not sensitive for bacterial infection. Using both procalcitonin and MxA together provides a sensitive and specific way to identify an immune response to a viral and/or bacterial infection.

In one preferred embodiment of a multiplexed assay using MxA and procalcitonin, the fingerstick blood pattern of test results shows a positive result with a serum equivalence to a procalcitonin cut-off between approximately 0.10 ng/ml and 0.15 ng/ml and a MxA cut-off in a range between approximately 25 ng/ml and 40 ng/ml. These preferred values are shown in Table 1.

TABLE 1

| Biomarker | Location | Fingerstick Cut-off value |
|---|---|---|
| MxA | Intracellular (Peripheral Blood Mononuclear Cells) | 25-40 ng/ml |
| Procalcitonin | Extracellular (Serum) | 0.10-0.15 ng/ml |

Similarly, in isolation, neither MxA nor C-reactive protein alone is sensitive or specific at identifying both viral and bacterial infection. Low cut-off values of C-reactive protein show high sensitivity and low specificity for detecting bacterial infection. High cut-off values of C-reactive protein show low sensitivity and high specificity for detecting bacterial infection. MxA is specific to identify viral infection, but it is not sensitive for bacterial infection. A multiplexed pattern of results including medical decision points reflecting cut-off levels of low CRP, high CRP, and MxA together provide a sensitive and specific way to identify an immune response to a viral and/or bacterial infection.

In one preferred embodiment of a multiplexed assay using MxA and two levels of C-reactive protein, the fingerstick blood pattern of test results shows a positive result with a serum equivalence to a low CRP level cut-off between approximately 10 mg/L and 20 mg/L, a serum equivalence to a high CRP level cut-off between approximately 65 mg/L and 100 mg/L, and a MxA cut-off between approximately 25 ng/ml and 40 ng/ml. These preferred values are shown in Table 2.

TABLE 2

| Biomarker | Location | Fingerstick Cut-off value |
|---|---|---|
| MxA | Intracellular (Peripheral Blood Mononuclear Cells) | 25-40 ng/ml |
| CRP-low | Extracellular (Serum) | 10-20 mg/L |
| CRP-high | Extracellular (Serum) | 65-100 mg/L |

In a preferred embodiment of a multiplexed visually read qualitative assay using MxA and two levels of C-reactive protein, the blood pattern of test results shows a positive result with a serum equivalence to a low CRP level cut-off between approximately 10 mg/L and 20 mg/L, a serum equivalence to a high CRP level cut-off between approximately 60 mg/L and 100 mg/L, and a MxA cut-off between approximately 15 ng/ml and 25 ng/ml.

In another preferred embodiment of a multiplexed assay using MxA, procalcitonin, and two levels of C-reactive protein, the fingerstick blood pattern of test results shows a positive result with a serum equivalence to a low CRP level cut-off between approximately 10 and 20 mg/L, a serum equivalence to a high CRP level cut-off between approximately 80 mg/L and 100 mg/L, a serum equivalence of procalcitonin between approximately 0.10 ng/ml and 0.15 ng/ml and a MxA cut-off between approximately 25 ng/ml and 40 ng/ml. These preferred values are shown in Table 3.

TABLE 3

| Biomarker | Location | Fingerstick Cut-off value |
|---|---|---|
| MxA | Intracellular (Peripheral Blood Mononuclear Cells) | 25-40 ng/ml |
| CRP-low | Extracellular (Serum) | 10-20 mg/L |
| CRP-high | Extracellular (Serum) | 65-100 mg/L |
| Procalcitonin | Extracellular (Serum) | 0.10-0.15 ng/ml |

Elevated C-reactive protein or procalcitonin levels alone are nonspecific indicators. For example, in influenza infection, there is an elevated level of C-reactive protein which may erroneously lead a clinician to prescribe antibiotics. When C-reactive protein or procalcitonin are multiplexed with MxA, the true etiology (viral or non-viral) is identified which can lead to appropriate and timely therapeutic intervention.

The specificity of these tests are further enhanced by restricting the intended use. For example, in preferred embodiments, only certain ages of the patient population are tested (preferably one year of age or older) and/or patients with specific underlying conditions that may lead to confounding factors are preferably not screened with these tests.

Colonization/Carrier State Versus Active Infection

Microbial clinical relevance is based on a host response. Overtreatment of colonizing bacteria and under-treatment of potential significant bacterial infection is thwarted with the methods described herein.

Delayed antibiotic prescription is recommended in international guidance (NICE guideline development group. Prescribing of antibiotics for self-limiting respiratory tract infections in adults and children in primary care. 2014, herein incorporated by reference). The National Institute for Health and Care Excellence (NICE) currently recommends using a strategy of either no antibiotic prescriptions or a delayed antibiotic prescription for dealing with uncomplicated acute sore throats and other respiratory infections.

The NICE draft guidelines recommend considering a point-of-care C-reactive protein (CRP) test for patients presenting with lower respiratory tract infection in primary care if it is not clear after clinical assessment whether antibiotics should be prescribed. The results of the C-reactive protein test should be used to guide antibiotic prescribing as follows:

Do not routinely offer antibiotic therapy if the C-reactive protein concentration is less than 20 mg/L Consider a delayed antibiotic prescription (a prescription for use at a later date if symptoms worsen) if the C-reactive protein concentration is between 20 mg/L and 100 mg/L Offer antibiotic therapy if the C-reactive protein concentration is greater than 100 mg/L Guidelines-IDSA and NICE According to the Infectious Diseases Society of America (IDSA) (Caliendo A M et al. Better tests, better care: improved diagnostics for infectious diseases. Clin Infect Dis. 2013 December; 57 Suppl 3:S139-70, incorporated herein by reference), future diagnostic tests should have the following characteristics:

Performed directly from accessible, minimally invasive clinical specimens, such as blood, respiratory samples, urine, and stool Able to rule out infection with high certainty (negative predictive value) as a first step for a variety of clinical syndromes Able to support differentiation of viral from bacterial infection Incorporating biomarkers that are either pathogen- or host-derived and capable of indicating host response to a pathogen or further classifying clinically significant infectious processes into relevant categories (e.g., bacterial or viral)

A diagnostic strategy that incorporates sensitive biomarkers (e.g., infection present yes/no) followed by pathogen-specific tests that are linked to a rapid assessment of drug resistance could not only bring antibiotic stewardship to the outpatient setting but also revolutionize sepsis management. Clinical studies that evaluated the presence of respiratory viruses in asymptomatic patients indicate that the old doctrine, which considered the presence of any respiratory virus clinically significant, is no longer true. Detected nucleic acids may be from nonviable organisms or from commensal (nonpathogenic) or colonizing bacteria or viruses that are noncontributory to the disease. Pathogen-based testing also needs to take into account colonization rates in children, especially due to their high pneumococcal colonization rates. The challenge with typical bacteria and some viral pathogens is the need to determine if the identified pathogen is colonizing or invading. Procalcitonin, MxA and C-reactive protein are promising biomarkers that can be used in addition to fever, leukocytosis, and clinical syndrome as a predictor of bacterial (PCT and CRP) or viral (MxA) infection.

Currently, the medical definition of colonization is the presence of a bacteria or virus without an associated immune antibody response detectable in the blood. The ability to use serology to detect antibody responses requires two patient visits, an initial visit at the start of symptoms and a subsequent visit 2-4 weeks later. Because of the inherent time delay, it is not practical to perform this testing to confirm an active infection. Thus, most doctors simply rely on antigen testing, culture, or PCR to identify the presence of a bacteria or virus instead of using paired serology, which combines identification with an antibody response. This results in the significant over-estimation of true infection and subsequent over-prescription of unnecessary antibiotics.

Traditionally the confirmation of an infection is measured against the presence or absence of microbial antigen, culture growth, or nucleic acid. However, none of these tests distinguish between colonization and active infection. In reality, more than the presence or absence of a microbial antigen is required in order to indicate infection. An active, true infection also requires an associated immune response. Without the immune response, colonization of the bacteria or virus is occurring. Only a true infection requires antibiotic therapy. Colonized bacteria are not typically contagious and do not require therapeutic intervention.

There is a challenge to define true infection from bacterial colonization or a local viral infection without a systemic host response. There needs to be a change in definition of infection, which will change the diagnostic parameters and reported performance of a test. The new definition that should be adopted and standardized for a clinically significant respiratory infection requires confirmation of the presence of a pathogen via antigen, culture, or molecular detection in association with a systemic host response.

As newly defined herein, a clinically significant infection is the local microbiological confirmation of a pathogen by cell culture, molecular techniques, and antigen in association with a systemic immune response (C-reactive protein, procalcitonin, MxA, or serological response).

Patients with acute febrile respiratory symptoms may be first categorized as having a clinically significant immune response or not. The definition of a bona fide infection is one where a virus or bacteria is identified via antigen detection, cell culture or PCR and is associated with an immune response. The lack of an associated immune response confirms colonization. Of the patients with a clinically significant immune response, they may be categorized as viral or bacterial. Of the clinically insignificant immune response (colonizers), these are typically allergic and driven through an IgE pathway as a result of exposure to an allergen (which may be a noninvasive virus such as rhinovirus or coronavirus), leading to a subsequent exacerbation of reactive airway disease in patients with a history of underlying allergies, atopy, asthma, or Chronic Obstructive Pulmonary Disease (COPD).

A more appropriate approach to estimate the likelihood of bacterial or viral infection and the severity of disease is to use blood biomarkers mirroring the host response to infection, and indirectly, the severity of infection. MxA may be used to differentiate an invasive viral infection from asymptomatic/colonization. In addition, procalcitonin and/or C-reactive protein may be used to differentiate bacterial colonization from infection.

Distinguishing asymptomatic infection (carrier state) without a host response from a clinically significant infection is critically important in defining an objective comparative gold standard. Routine oropharyngeal bacterial cultures frequently grow bacteria that are not pathogenic or responsible for an active infection. Bacterial growth in the presence of a host immune response is far more indicative of a clinically significant bacterial infection. Molecular tests are so sensitive, used independently, that they will often provide clinically misleading information, since molecular tests cannot differentiate an active infection from a carrier state. For some viral pathogens, the combination of a positive molecular test in association with a host response is the differentiating feature of a clinically important infection.

The methods described herein are able to distinguish between infection/immune response (for example, using MxA, procalcitonin and/or C-reactive protein levels) and colonization (concentration of organisms at a site, although the organism is causing no deleterious signs or symptoms). Colonization can persist for days to years, with resolution influenced by the immune response to the organism, competition at the site from other organisms and, sometimes, use of antimicrobials. A carrier is a colonized person that may transmit the organism to other people. Separately, contamination occurs when a microbe is introduced into the specimen from another site.

Very recent studies have shown that the high sensitivity of PCR has made the interpretation of positive results in acute infections challenging. PCR assays allow detection of even trace amounts of viral nucleic acids. This may lead to positive results even in the absence of symptoms or without the pathogen being the etiological agent. It is very likely that this is at least partly explained by the extreme sensitivity of PCR which makes it prone to detect subclinical infections, carriage, persistence, and contamination.

Clinical specificity of PCR testing for acute respiratory tract infections has recently been questioned in several separate studies (van Gageldonk-Lafeber A B, Heijnen M L, Bartelds A I, et al. A case-control study of acute respiratory tract infection in general practice patients in The Netherlands. Clin Infect Dis. 2005 Aug. 15; 41(4):490-7; Jansen R R, Wieringa J, Koekkoek S M, et al. Frequent detection of respiratory viruses without symptoms: toward defining clinically relevant cutoff values. J Clin Microbiol. 2011 July; 49(7):2631-6; Rhedin S, Lindstrand A, Rotzén-Östlund M, et al. Clinical utility of PCR for common viruses in acute respiratory illness. Pediatrics. 2014 March; 133(3):e538-45. Advani et al. Detecting respiratory viruses in asymptomatic children. Pediatr Infect Dis J. 2012 December; 31 (12):1221-6; van der Zalm M M, van Ewijk B E, Wilbrink B, et al. Respiratory pathogens in children with and without respiratory symptoms. J Pediatr. 2009 March; 154(3):396-400, 400; Linde A. The importance of specific virus diagnosis and monitoring for antiviral treatment. Antiviral Res. 2001 August; 51:81-94. Review, all herein incorporated by reference).

One example of widespread colonization of gram negative bacteria is the fact that more than half of healthy people carry *Streptococcus pneumonia, Hemophilus influenzae* and *Moraxella catarrhalis* in their mouths (O'Brien K L et al. Pediatr Infect Dis J. 2003; 22:133-40, herein incorporated by reference). *Staphylococcus aureus* can be isolated from the oral cavity in 20-40% of healthy people (Barlow and Chattaway. (1969). Observations on the carriage of Candida albicans in man British Journal of Dermatology 81, 103-106; Wheat et al. (1981). Effect of Rifampin on nasal carriers of coagulase-positive staphylococci. Journal of Infectious Diseases 144,177; Le et al. Arch Otolaryngol Head Neck Surg. 2007; 133(10):969-72, all herein incorporated by reference). By use of a sensitive enrichment broth, *S. aureus* was cultured from the two sites from 259 patients upon admission to an orthopedic ward and from 87 staff members of the same ward. The throat was the most common carriage site in both groups. Forty percent of the patients and 54% of the staff were positive for *S. aureus* in the throat (Nilsson and Ripa, *Staphylococcus aureus* throat colonization is more frequent than colonization in the anterior nares. J Clin Microbiol. 2006; 44:3334-9, herein incorporated by reference).

Boe et al. reported an isolation rate of 31% in patients admitted to a medical ward (Boe et al., 1964. Perineal carriers of staphylococci. Br. Med. J. 5404:280-281, herein incorporated by reference) and Uemura et al. reported an isolation rate of 29% in a group of healthy adult volunteers (Uemura et al., 2004. Comparative characterization of *Staphylococcus aureus* isolates from throats and noses of healthy volunteers. Jpn. J. Infect. Dis. 57:21-24, herein incorporated by reference). Berkovitch et. al. found bacteria in the throats of 10% of healthy children under the age of 2 years (Berkovitch et al., 2002. Colonization rate of bacteria in the throat of healthy infants. Int. J. Pediatr. Otorhinolaryngol. 63:19-24, herein incorporated by reference). These species are called 'community' acquired strains because of their high prevalence in normal hosts. The oral carriage of Enterobacteriaceae, Pseudomonadaceae and Acinetobacter species are less common in healthy people (Rosenthal and Tager, (1975). Prevalence of Gram-negative rods in the normal pharyngeal flora. Annals of Internal Medicine 83,355-357, herein incorporated by reference).

Opportunistic colonization with resistant Gram-negative organisms (*Enterobacter cloacae, Klebsiella* species, present in sputum) was found in 56% of patients admitted to the hospital with severe exacerbations of chronic bronchitis and persisted at follow-up (48%) with a significant excess of new organisms (Trigg C J et al. Respir Med. 1991; 85:301-8).

Examples of widespread colonization of gram positive bacteria include the fact that up to 25%-40% of patients are colonized with group A *streptococcus* (GAS) in the oropharynx (Schwartz R H et al. Penicillin V for group A *streptococcal* pharyngotonsillitis. A randomized trial of seven vs ten days' therapy. JAMA 1981; 246:1790; Strömberg A et al. Scand J Infect Dis. 1988; 20(4):411-7; Shulman S T et al. Pediatr Infect Dis J. 1994; 13:1-7; Le T M et al. Arch Otolaryngol Head Neck Surg. 2007; 133(10):969-72; Del Mar C. Managing sore throat: a literature review. I. Making the diagnosis. Med J Aust 1992; 156: 572-575, all herein incorporated by reference). Only 60% of patients with culture positive Group A Strep had an associated antibody response with either anti-streptolysin O (ASO) or anti-DNase B (ADB) (Johnson D R et al. The human immune response to *streptococcal* extracellular antigens: clinical, diagnostic, and potential pathogenetic implications. Clin Infect Dis. 2010 Feb. 15; 50(4):481-90, incorporated herein by reference). Heavy growth of *Streptococcus pyogenes* grew out of the throats of nearly 10% of healthy children (Bell S M and Smith D D. Lancet. 1976; 2(7976):62-3, herein incorporated by reference).

The oropharyngeal cavity possesses defense mechanisms against colonization with aerobic Enterobacteriaceae, Pseudomonadaceae and Acinetobacter species. Several factors contribute to the colonization defense integrity, including the appropriate anatomy and physiology (e.g. pH of saliva), motility, secretory immunoglobulin A, mucosal cell turnover, and indigenous oral flora (Spijkervet et al., Colonization index of the oral cavity: a novel technique for monitoring colonization defense. Microbial Ecology in Health and Disease; 1989; 2:145-151, incorporated herein by reference). All of these factors interact within the host to contribute to an effective clearance of Enterobacteriaceae, Pseudomonadaceae, Acinetobacter species. If one of the defense factors is altered such as with ageing, underlying disease, medical intervention, or history of antibacterial agents, these gram negative bacteria tend to colonize.

In order for colonization to occur, prolonged mucosal contact with bacteria is needed, and, not surprisingly, diseases associated with impaired mucociliary clearance are exactly the conditions that are complicated by chronic airway colonization. Thus, the patient with chronic bronchitis is commonly colonized by *H. influenzae* and *M. catarrhalis*, whilst the patient with cystic fibrosis or bronchiectasis is commonly colonized by *P. aeruginosa* (Niederman, Gram-negative colonization of the respiratory tract: pathogenesis and clinical consequences. Semin Respir Infect 1990; 5: 173-184, herein incorporated by reference).

*Chlamydophila* carriers who represent 2-5% of the population may be the source of the infection but they do not exhibit the symptoms of an acute infection. The infection can take a symptomatic form in immunocompromised conditions. Carrier-state does not require treatment (Choroszy-Krol et al., Infections caused by *Chlamydophila pneumoniae*. Adv Clin Exp Med. 2014 January-February; 23(1): 123-6, herein incorporated by reference).

There is a large spectrum of symptoms of the respiratory tract in case of *C. pneumoniae* and *M. pneumonia* detection ranging from asymptomatic infection (or carriage) to severe pneumonia. Both *C. pneumoniae* and *M. pneumoniae* can colonize or persist in the respiratory tract for weeks and even months after acute infection and resolution of symptoms associated with the initial infection.

In an unselected pediatric population of kindergarten and school children, the rate of asymptomatic infection exceeded 50%. If there were respiratory tract symptoms, they were usually not severe (Schmidt et al., *Chlamydia pneumoniae* carriage and infection in hospitalized children with respiratory tract diseases. Infection. 2003 December; 31(6):410-6, herein incorporated by reference). When examining 65 symptomatic patients with pharyngitis, Esposito et al showed that C-reactive protein was elevated to a mean of 34-38 mg/L for *Chlamydia, Mycoplasma*, and Group A Strep cases. In addition 5% of healthy controls had either *Chlamydia* or *Mycoplasma* and 21% had Group A Strep. Further, 28% (7/25) of patients that tested positive for *Chlamydia* DNA had no serological evidence of true infection (Esposito et al., Aetiology of acute pharyngitis: the role of atypical bacteria. J Med Microbiol. 2004; 53:645-51, herein incorporated by reference). *C. pneumoniae* was detected in throat swabs by PCR-EIA in 9.3% (74 of 798 children). By using PCR, prevalence of *Chlamydia* is found to 1-2% of asymptomatic adults and 4-6% of asymptomatic children (4-6%). There was a low confirmatory power between detection of *C. pneumoniae* in the upper airways and systemic immune response resulting in acute infection based on serology. Detection of *C. pneumoniae* at the upper airways without systemic antibody response, which occurred in 17% (9/52), suggests carriage.

Asymptomatic children (n=405) and children with respiratory symptoms (n=321) aged 3 months to 16 years were enrolled in a cross-sectional study from Jul. 1, 2008, to Nov. 30, 2011. Clinical data, pharyngeal and nasopharyngeal specimens, and serum samples were collected. The primary objective was to differentiate between colonization and symptomatic infection with *M. pneumoniae* by current diagnostic methods, especially real-time PCR. *M. pneumoniae* DNA was detected in 21.2% (95% CI 17.2%-25.2%) of the asymptomatic children and in 16.2% (95% CI 12.2%-20.2%) of the symptomatic children (p=0.11). Neither serology, quantitative PCR, nor culture, differentiated asymptomatic carriage from infection. A total of 202 children were tested for the presence of other bacterial and viral pathogens. Two or more pathogens were found in 56% (63/112) of the asymptomatic children and in 55.5% (50/90) of the symptomatic children. Finally, longitudinal sampling showed persistence of *M. pneumoniae* in the URT for up to 4 months (Spuesens et al., Carriage of *Mycoplasma pneumoniae* in the upper respiratory tract of symptomatic and asymptomatic children: an observational study. PLoS Med 2013; 10:e1001444, herein incorporated by reference).

During a 30-month prospective study in the Netherlands, the distribution of *Mycoplasma pneumoniae* and respiratory viruses among 1172 patients with acute respiratory infection (ARI) who were treated in the outpatient general practitioner setting were studied. *M. pneumoniae*, as detected by polymerase chain reaction analysis, was present in 39 (3.3%) patients. Nine of the 12 *M. pneumoniae*-positive household contacts were <16 years old (p=0.02), and 4 (44%) of them did not develop ARI. Apparently, children are a relevant reservoir for *M. pneumoniae*. (Dorigo-Zetsma et al., Results of molecular detection of *Mycoplasma pneumoniae* among patients with acute respiratory infection and in their household contacts reveals children as human reservoirs. J Infect Dis. 2001 Feb. 15; 183(4):675-8, herein incorporated by reference).

Even Pertussis can lead to asymptomatic infection. In fact, immunizations have led to the harboring of bacteria with adults serving as the reservoir. In one study, four children with pertussis and their 18 family members were subjects of a 1-year study to detect infection and antibody responses to *Bordetella pertussis*. Attack rate for pertussis infection in contacts was 83%. Two-thirds of cases in these immunized contacts were subclinical. After pertussis immunization, immunity to disease is greater than is protection from infection (Long et al., Widespread silent transmission of pertussis in families: antibody correlates of infection and symptomatology. J Infect Dis. 1990 March; 161(3):480-6.1990, herein incorporated by reference).

In the upper respiratory tract, up to 26% of children are colonized with group A *streptococcus* (GAS) (Reed et al., Prevalence of *Chlamydia trachomatis* and *Mycoplasma pneumoniae* in children with and without pharyngitis. J Fam Pract. 1988; 26(4):387-392; Lieu et al., Clinical evaluation of a latex agglutination test for *streptococcal* pharyngitis: performance and impact on treatment rates. Pediatr Infect Dis J. 1988; 7(12):847-854; Shulman et al., *Streptococcal* pharyngitis: The case for penicillin therapy. Pediatr Infect Dis J 1994; 13:1-7; Roberts et al., Detection of group A *Streptococcus* in tonsils from pediatric patients reveals high rate of asymptomatic *streptococcal* carriage. BMC Pediatr 2012; 12:3, all herein incorporated by reference) and according to the Infectious Disease Society of America Clinical Guidelines, the clinical significance of the number of group A β-hemolytic *streptococcal* colonies present on the throat culture plate is problematic. If a sensitive culture procedure results in detection of either few or many colonies of the organism, the patient may be infected or merely colonized (Gerber et al., 1986. Antigen detection test for *streptococcal* pharyngitis: evaluation of sensitivity with respect to true infection. J. Pediatr. 108:654-658; Kaplan et al., 1971. Diagnosis of *streptococcal* pharyngitis: differentiation of active infection from the carrier state in the symptomatic child, The Journal of Infectious Diseases, Vol. 123, No. 5 (May, 1971), pp. 490-501; Kellogg et al., 1986. Detection of group A streptococci in the laboratory of physician's office. Culture vs. antibody methods. J. Am. Med. Assoc. 255: 2638-2642, all herein incorporated by reference). Bell et. al. (Quantitative throat-swab culture in the diagnosis of *streptococcal* pharyngitis in children. Lancet. 1976 Jul. 10; 2(7976):62-3, herein incorporated by reference) demonstrated a difference in the detection of a heavy growth of *Streptococcus pyogenic* in throat swabs taken from 1054 children with pharyngitis compared with those from 462 normal children when a standardized technique of quantitative culture was used. In patients with pharyngitis, 71% of the isolates were heavy whereas a heavy culture was obtained in nearly 10% of healthy children. Other authors report a rate of 6%-40% of false-positive asymptomatic carriers of β-hemolytic streptococci throat swabs in healthy persons (Del March, 1992. Managing sore throat: a literature review. I. Making the diagnosis. Med J Aust 1992; 156: 572-575, herein incorporated by reference).

For clinical as well as technical reasons, there is no significant correlation between colony counts and the presence or absence of infection (Kellogg et al., 1986. Detection of group A streptococci in the laboratory of physician's office. Culture vs. antibody methods. J. Am. Med. Assoc. 255:2638-2642). Differentiation of infection from colonization requires the demonstration of an antibody response to the organism, a response which is both time-consuming (requiring 2 to 3 weeks or more between serum samples) and subject to false-negative results following prompt and appropriate antibiotic therapy (Gerber et al., 1988. The group A *streptococcal* carrier state. A reexamination. Am. J. Dis. Child. 142:562-565, herein incorporated by reference). Although patients with true acute group A *streptococcal* pharyngitis are likely to have more strongly positive cultures than are patients who are *Streptococcus* carriers, there is so much overlap in the degree of positivity of throat culture results that the differentiation cannot be made accurately on this basis alone (Bisno et al. Practice Guidelines for the Diagnosis and Management of Group A *Streptococcal* Pharyngitis, Clinical Infectious Diseases 2002; 35:113-25, herein incorporated by reference).

Group A beta-haemolytic *Streptococcus* (GAS) is considered to be the predominant bacterial cause (10-26% of all acute tonsillitis cases) of acute tonsillitis and in most countries is the only pathogen for which antibiotic therapy is currently recommended (Christensen et al., Are procalcitonin or other infection markers useful in the detection of group A *streptococcal* acute tonsillitis? Scand J Infect Dis. 2014 May; 46(5):376-83. 2014, herein incorporated by reference). The clinical specificity is decreased due to the poor capability of the test to differentiate between patients with GAS acute tonsillitis and GAS carriers with a tonsillar infection of other origin.

Not only can bacteria colonize, but so can viruses. Respiratory viruses such as Influenza A/B, Parainfluenza virus 1-4, Metapneumovirus, and Respiratory Syncytial Virus 1-2 are considered true pathogens. Herpes Simplex virus, Epstein Barr virus, and Cytomegalovirus can result in asymptomatic shedding in the pharynx and mouth, which is of no clinical significance. Rhinovirus and Coronavirus are known to colonize the nasopharynx (van der Zalm et al., Respiratory pathogens in children with and without respiratory symptoms. J Pediatr. 2009 March; 154(3):396-400, 400.e1, herein incorporated by reference) Rhinovirus and Coronaviruses are the most frequently identified of the respiratory viruses found in nasopharyngeal testing of both symptomatic cases and asymptomatic cases (van der Zalm, 2009). Human Rhinoviruses were detected in 20% to 50% of samples and Coronaviruses in 10% of asymptomatic patients (van Benten I et al. Pediatr Allergy Immunol. 2003; 14(5): 363-70; van der Zalm M M et al. J Pediatr. 2009; 154(3): 396-400, 400.e1; Rhedin S et al. Pediatrics. 2014; 133(3): e538-45; Nokso-Koivisto J et al. Human picornavirus and coronavirus RNA in nasopharynx of children without concurrent respiratory symptoms. J Med Virol. 2002; 66(3): 417-20, all herein incorporated by reference). Coronavirus and Rhinovirus do not typically cause fever but are highly associated with nasal congestion (Zimmerman et al. Influenza Other Respir Viruses. 2014; 8(4):397-405, herein incorporated by reference).

It has been suggested that not merely presence, but rather a certain viral load, is needed above which respiratory symptoms occur (Jansen et al., (2011). Frequent detection of respiratory viruses without symptoms: toward defining clinically relevant cutoff values. J Clin Microbiol 49: 2631-2636, herein incorporated by reference). Human rhinovirus and coronavirus were found in equal levels of 22% and 6% respectively in both healthy and symptomatic patients while all other viruses were not found in healthy children at significant levels (van Benten et al., Predominance of rhinovirus in the nose of symptomatic and asymptomatic infants. Pediatr Allergy Immunol. 2003 October; 14(5):363-70; Rhedin et al. Clinical utility of PCR for common viruses in acute respiratory illness. Pediatrics. 2014 March; 133(3): e538-45, both herein incorporated by reference). The fact that rhinovirus is often found in asymptomatic children is not surprising, because it is generally a relatively mild pathogen that can colonize the nasal mucosa without causing symptoms (van Benten et al., 2003) and the van Benten studies indicate that respiratory pathogens are frequently found in samples from children with no respiratory symptoms (40%). Nokso-Kovisto showed the rate of viral detection was 45% in children with related past or recent respiratory infection. Thirty-one (29%) of the nasopharyngeal aspirates were positive for viral RNA, 18% for rhinovirus, and 11% for enterovirus RNA. In addition, 81% of the children with virus-positive samples had had previously respiratory symptoms or there were concurrent respiratory symptoms in other family members (Nokso-Koivisto et al., Human picornavirus and coronavirus RNA in nasopharynx of children without concurrent respiratory symptoms. J Med Virol. 2002 March; 66(3):417-20, herein incorporated by reference).

According to the literature, coronavirus and rhinovirus do not typically cause fever although they colonize the nasopharynx and oropharynx in up to 10-40% of normal, healthy persons. During January-April 2012, 662 outpatients with acute respiratory illness (≤7 days) were tested with a multiplex MRT-PCR (SRT-PCR) to examine the distribution of viruses and characteristics of patients using multinomial logistic regression. Of the rhinovirus and coronavirus detected as a single virus resulted in an accompanying fever in less than 10% of their infections. When a multinomial regression analysis was performed with adjusted odd ratios, the risk of fever associated with rhinovirus and coronavirus was between 0.85-1.15; however they were both highly associated with nasal congestion (Zimmerman et al., Influenza and other respiratory virus infections in outpatients with medically attended acute respiratory infection during the 2011-12 influenza season. Influenza Other Respir Viruses. 2014 July; 8(4):397-405, herein incorporated by reference).

Up to 68% of asymptomatic healthy children carry multiple respiratory viruses in their nasopharynx at any given time (Jartti T et al. Pediatr Infect Dis J 2008; 27(12): 1103-1107, herein incorporated by reference).

Viral contributing factors for disease equal the proportion of all hospitalized cases related to a specific virus/rate of presence in asymptomatic children (Singleton et al. J Med Virol 2010; 82(7): 1282-90, herein incorporated by reference). Group 1 includes viruses with a significantly greater contribution to respiratory symptoms, including RSV, Metapneumovirus, Parainfluenza viruses, and Influenza viruses. Group 2 viruses, including human Rhinoviruses, Adenoviruses, and Coronaviruses, are less likely to cause significant active infection.

Rhinovirus infection remains localized in the upper respiratory tract. This occurs for one very important reason: rhinoviruses are extremely inefficient replicators at temperatures above 33° C. The virus may find its way to the lower portion of the lungs, but temperatures there will be several degrees warmer (approximately 37° C.) and will not be conducive to rhinoviral infection. The virus will also be swallowed and end up in the stomach where both increased temperature and decreased pH work to prevent infection. Unlike Poliovirus, the Rhinovirus capsid (protective protein coat) irreversibly disassembles at low pH, effectively inactivating the virus Rhinovirus mRNA has been detected in children for prolonged periods, even after symptoms have resolved (Blomqvist et al. Virological and serological analysis of rhinovirus infections during the first two years of life in a cohort of children. J Med Virol 2002; 66:263-8.; Jartti et al. Serial viral infections in infants with recurrent respiratory illnesses. Eur Respir J 2008; 32:314-20. 15; Jartti et al., Persistence of rhinovirus and enterovirus RNA after acute respiratory illness in children. J Med Virol 2004; 72:695-9; Peltola et al., Rhinovirus transmission within families with children: incidence of symptomatic and asymptomatic infections. J Infect Dis 2008; 197:382-9, all herein incorporated by reference), and is possibly more prolonged for asthma patients (Kling et al., Persistence of rhinovirus RNA after asthma exacerbation in children. Clin Exp Allergy 2005; 35:672-8, herein incorporated by reference).

It has been reported that MxA protein is not induced by human rhinovirus (HRV) infections when PCR was used to detect rhinoviruses in nasopharyngeal aspirates. This discrepancy between PCR detection and lack of systemic MxA was thought to be due to lack of a genuine respiratory infection related to long-term carriage of, or a latent infection by, rhinovirus (Mäkelä et al., Eur J Clin Microb Inf Dis., 18: 655-668, 1999, incorporated herein by reference). Koskenvuo demonstrated that laboratory-confirmed viral infections other than rhinovirus resulted in elevated MxA protein expression levels in children receiving anticancer treatment compared to their confirmed bacterial infections or control samples (Koskenvuo et al., Pediatr Hematol Oncol., 23(8): 649-660, December 2006, herein incorporated by reference). The observation of rhinoviruses not being able to induce a significant systemic MxA protein expression is also in accordance with other findings by Mäkelä et al (Mäkelä 1999).

While other respiratory viruses, such as influenza virus and respiratory syncytial virus (RSV), cause a destruction of airway epithelial cells, rhinovirus is seldom associated with cytopathology of the upper respiratory tract. Using light and scanning electron microscopy of nasal biopsy specimens from subjects with natural colds, Winther et al. found that epithelial cells were sloughed; however, the epithelial cell lining and borders remained structurally intact (Winther et al., Acta Otolaryngol. 97: 309-318, 1984, herein incorporated by reference). A similar preservation of cell morphology and composition was observed for the nasal epithelium during studies of experimental HRV infection, where the amount of viral shedding did not correlate with the severity of symptoms (Winther et al., Acta Otolaryngol. 97: 309-318, 1984; Turner et al., J. Infect. Dis. 145: 849-853, 1982; Winther et al., Acta Otolarynogol.(Stockh), 413(Suppl.):19-24, 1984, all herein incorporated by reference).

The presence of the combination of the viral and bacterial biomarkers discussed herein in a patient sample indicate the presence of clinically significant infection. When a symptomatic patient is negative for the viral or bacterial biomarkers, it is much more likely the patient has an underlying hypersensitivity reaction such as asthma, hayfever, or COPD exacerbation. Viruses and some bacteria may induce this allergic reaction without causing invasive disease. Without the biomarkers, these patients would be diagnosed as having a primary infectious condition that likely would lead to overtreatment. Another embodiment of the methods and devices described herein includes the inclusion of allergic biomarkers such as total serum IgE.

Several studies have demonstrated that the production of innate, antiviral type I and type III IFNs in bronchial epithelial cells from patients with asthma is reduced compared with levels secreted by cells from the lower airway of patients without asthma following infection with HRV (Wark et al., J Exp Med. 201: 937-947, 2005; Baraldo et al., J Allergy Clin Immunol. 130:1307-1314, 2012, both herein incorporated by reference). This impaired antiviral response correlated inversely with increasing quantities of HRV-RNA detected by quantitative polymerase chain reaction (qPCR) in culture supernatants (Wark 2005; Baraldo 2012). In two other studies, the secretion of innate IFNs from plasmacytoid dendritic cells in peripheral blood was significantly decreased in cells from subjects with asthma compared with those without after stimulation with influenza in one study, or HRV in the other (Gill et al., J Immunol. 184: 5999-60006, 2010; Durrani et al., J. Allergy Clin Immunol. 130: 489-495, 2012, both herein incorporated by reference). Additionally, the production of these cytokines correlated inversely with serum IgE levels or FcεRIα expression on plasmacytoid dendritic cells, and IgE cross-linking on plasmacytoid dendritic cells before stimulation with influenza or HRV further diminished this innate response. Taken together, these observations suggest that people with asthma may be at risk for higher viral loads and symptoms affecting their respiratory tract during HRV infection. Although various kinds of cytokines are involved in asthma, there have been no findings of increased production of type I IFNs in acute exacerbation. Therefore, MxA protein found induced and elevated in patients with asthma would likely be caused by an invasive viral infection, whereas this cannot secondarily occur from other cytokines associated with allergic inflammation (Chung and Barnes, Thorax, 55: 825-857, 1999, herein incorporated by reference).

In the RV-16 challenge study, Zambrano et al. (Zambrano et al., J Allergy Clin Immunol. 111(5): 1008-1116, May 2003, herein incorporated by reference) reported that the subjects with asthma and high levels of total IgE had lower respiratory tract symptoms that were significantly greater than symptoms reported by the subjects with asthma and low IgE levels or by the control subjects without asthma, despite having viral loads that were, if anything, lower throughout the infection in the evaluation. Additionally, the subjects with asthma with high and low IgE levels had respiratory tract symptoms (both upper and lower) that were increased compared with control subjects during the period of symptom resolution, even though the viral loads were not significantly different from the control subjects without asthma. Taken together, the results indicate that viral load is not likely to influence the persistence of symptoms in the subjects with asthma, which supports the hypothesis that the prolongation of symptoms may result from the amplification of allergic inflammation provoked by HRV.

It is clear that most children and adults who experience HRV-induced exacerbations are atopic and have high titers of serum IgE antibody (Ab) to allergens, such as dust mites, which have been shown to significantly increase the risk of wheezing with HRV (Soto-Quiros et al., J Allergy Clin Immunol. 129:1499-1505, e5, 2012; Duff et al., Pediatrics 92; 535-540, 1993; Green et al., BMJ 324:763, 2002, all herein incorporated by reference).

One of the cardinal features of asthma is airway hyperresponsiveness, which is defined as the increased sensitivity of the small airways to bronchoconstriction in response to inhaled substances, such as histamine or methacholine. It is therefore of great interest that viral respiratory infections can transiently increase airway responsiveness in humans and in animals. The use of an experimentally induced infection of volunteers with HRV or influenza viruses has enabled longitudinal examination of lung physiology before, during, and after infections. Cheung et al. inoculated 14 subjects with mild asthma with either HRV-16 (type 16 rhinovirus) or placebo and found that airway responsiveness transiently increased during the acute infection, and returned to baseline levels by 1 week after the inoculation. In addition to increasing the sensitivity of the airway, HRV-16 infection increased the maximal response to inhaled methacholine, and, in contrast to changes in airway responsiveness, the maximal responses remained elevated for up to 15 days after the acute infection. Thus, viral infections can enhance both the reactivity of the lower airway and the magnitude of bronchoconstriction in response to inhaled contractile substances in asthma, and the latter effect can persist for weeks after the acute infection (Cheung et al Rhinovirus inhalation causes long-lasting excessive airway narrowing in response to methacholine in asthmatic subjects in vivo. Am. J. Respir. Crit. Care Med. 1995. 152:1490-1496, herein incorporated by reference).

There is evidence that allergy and asthma can influence the effect of respiratory viral infection on airway responsiveness. Experimental infection with HRV-16 induces greater changes in airway responsiveness in volunteers with respiratory allergy (Bardin et al., Eur. Respir. J. 9: 2250-2255, 1996; Gem et al., Am. J. Respir. Crit. Care Med. 155:1872-1876, 1997, both incorporated herein by reference) or mild allergic asthma than in normal control subjects (Fraenkel et al., Am J Respir. Crit. Care Med. 151:879-886, 1997, both incorporated herein by reference). Wiselka et. al evaluated its efficacy for the prevention of respiratory virus infections and the resulting complications in patients with chronic lung disease. No beneficial effects of IFN-α were seen in this population of patients with asthma and COPD (Wiselka et al., Thorax 46:706-11, 1991, incorporated herein by reference), which may be related to the primary IgE driven allergic response and less a direct infectious response.

Viral loads among the children with and without asthma were similar and the same was true among the adults who were infected with HRV experimentally. Taken together, these studies suggest that the asthmatic response to RV is likely to result from inflammatory pathways that are amplified or independently provoked by HRV, rather than from a higher viral load in the asthmatic airway (Kennedy et al., Am J Respir Crit Care Med. 189(5): 532-9, 2014, incorporated herein by reference).

Most asthma exacerbations are initiated by viral upper respiratory illnesses. It is unclear whether HRV—induced exacerbations are associated with greater viral replication and neutrophilic inflammation compared with HRV colds. The absence of large differences in viral burden among groups suggests differential lower airway sensitization to the effects of neutrophilic inflammation in the patients having exacerbations. A total of 52 persons with asthma and 14 control subjects without atopy or asthma were studied for over 10 weeks per subject on average; 25 participants developed an asthma exacerbation. Detection of HRVs in the preceding 5 days was the most common attributable exposure related to exacerbation. Compared with other infections, those by a minor group A HRV were 4.4-fold more likely to cause exacerbation (P=0.038) (Denlinger et al., Am J Respir Crit Care Med. 184(9): 1007-14, 2011, incorporated herein by reference).

Using PCR along with standard viral diagnostic tests, Johnston et al. determined that 80 to 85% of school-aged children with wheezing episodes tested positive for a virus and that the virus most commonly detected was HRV (Johnston et al., Br. Med. J. 310:1226-1229, 1995, incorporated herein by reference) followed by coronavirus. Furthermore, about half of the exacerbations in adults with asthma are associated with HRV infection (Nicholson et al., Br. Med. J. 307: 982-986, 1993, incorporated herein by reference). Moreover, virus-induced asthma may be severe: seasonal patterns of upper respiratory virus prevalence correlate closely with hospital admissions for asthma, especially in children (Johnston et al., Am. J. Respir. Crit. Care Med. 154:654-660, 1996, incorporated herein by reference). Furthermore, HRV and other respiratory viruses are frequently detected in children hospitalized for asthma. Together, these studies indicate that viral infections, and particularly respiratory illnesses from HRV, are the most common cause of asthma exacerbations in children and also contribute substantially to the asthma morbidity in adults.

The Applicant ran MxA ELISA (using Biovendor's commercially available CE marked MxA ELISA) tests on samples that had been confirmed to be Rhinovirus positive using the BioFire™ PCR system. The quantitative data demonstrates that Rhinovirus was only elevated above 40 ng/mL in 3/51 patients or 5.9% of the subjects, independent of age, that tested Biofire PCR positive, as seen in the Table 4. Table 4 shows the age of the patient, that all of the samples were positive in the BioFire™ PCR test, and the MxA ELISA result.

TABLE 4

| Age | BioFire PCR Rhinovirus | MxA ELISA Result (ng/mL) |
| --- | --- | --- |
| 3 | POSITIVE | 34.573 |
| 3 | POSITIVE | 29.817 |

TABLE 4-continued

| Age | BioFire PCR Rhinovirus | MxA ELISA Result (ng/mL) |
|---|---|---|
| 3 | POSITIVE | 0.263 |
| 4 | POSITIVE | 72.908 |
| 4 | POSITIVE | 36.894 |
| 4 | POSITIVE | 0.03 |
| 6 | POSITIVE | 0.03 |
| 7 | POSITIVE | 0.03 |
| 8 | POSITIVE | 0.03 |
| 10 | POSITIVE | 13.606 |
| 10 | POSITIVE | 0.03 |
| 11 | POSITIVE | 11.07 |
| 11 | POSITIVE | 1.213 |
| 14 | POSITIVE | 42.426 |
| 16 | POSITIVE | 9.608 |
| 16 | POSITIVE | 0.378 |
| 19 | POSITIVE | 9.804 |
| 19 | POSITIVE | 0.063 |
| 20 | POSITIVE | 2.177 |
| 21 | POSITIVE | 1.063 |
| 21 | POSITIVE | 0.301 |
| 23 | POSITIVE | 20.53 |
| 23 | POSITIVE | 2.065 |
| 24 | POSITIVE | 12.595 |
| 25 | POSITIVE | 22.185 |
| 25 | POSITIVE | 10.299 |
| 25 | POSITIVE | 0.03 |
| 29 | POSITIVE | 20.189 |
| 31 | POSITIVE | 0.538 |
| 32 | POSITIVE | 2.196 |
| 33 | POSITIVE | 19.127 |
| 33 | POSITIVE | 0.03 |
| 34 | POSITIVE | 2.988 |
| 34 | POSITIVE | 1.539 |
| 36 | POSITIVE | 1.245 |
| 37 | POSITIVE | 32.068 |
| 39 | POSITIVE | 26.269 |
| 40 | POSITIVE | 8.716 |
| 40 | POSITIVE | 3.428 |
| 41 | POSITIVE | 47.396 |
| 44 | POSITIVE | 0.03 |
| 46 | POSITIVE | 2.438 |
| 48 | POSITIVE | 16.148 |
| 48 | POSITIVE | 1.987 |
| 50 | POSITIVE | 4.507 |
| 52 | POSITIVE | 0.72 |
| 52 | POSITIVE | 0.595 |
| 59 | POSITIVE | 13.953 |
| 59 | POSITIVE | 0.33 |
| 60 | POSITIVE | 28.834 |
| 63 | POSITIVE | 6.477 |

Differentiation of infection from colonization requires the demonstration of an antibody response to the organism and is subject to false-negative results following prompt and appropriate antibiotic therapy (Gerber, et al. 1988. The group A *streptococcal* carrier state. A reexamination. Am. J. Dis. Child. 142:562-565, herein incorporated by reference). Antibody responses are impractical to perform to clinically differentiate colonization from true infection; therefore another immune response is needed. Patients with clinical evidence of infection but normal procalcitonin levels are highly unlikely to have an infection caused by a pathogenic bacteria (Gilbert, Use of plasma procalcitonin levels as an adjunct to clinical microbiology. J Clin Microbiol. 2010 July; 48(7):2325-9, herein incorporated by reference).

Evidence supports the use of procalcitonin to: differentiate bacterial from viral respiratory diagnoses, to help risk stratify patients, and to guide antibiotic therapy decisions about initial need for, and optimal duration of therapy (Schuetz et al. Role of procalcitonin in managing adult patients with respiratory tract infections. Chest. 2012 April; 141(4):1063-73, herein incorporated by reference).

Anti-streptolysin O (ASO) titer is a blood test to measure antibodies against streptolysin O, a substance produced by group A *Streptococcus* bacteria. The presence of an immune response to either GAS somatic or extracellular antigens remains the most reliable means for documentation of bona fide infection. Approximately 60% of patients with culture positive group A cultures had an elevation of either anti-streptolysin O (ASO) and anti-DNase B (ADB) confirming an immune response. The *streptococcal* upper respiratory tract carrier state with persistence of pharyngeal GAS for periods of a few weeks to many months accompanied by elevated—but not increasing—antibody titers, is one important example. Were such a carrier to develop a sore throat due to another etiology, for example, a single positive culture and/or antibody determination would very likely lead the practicing clinician or the epidemiologist to a false-positive association with GAS (Johnson et al., 2010. The human immune response to *streptococcal* extracellular antigens: clinical, diagnostic, and potential pathogenetic implications. Clin Infect Dis. 2010 Feb. 15; 50(4):481-90, herein incorporated by reference). To overcome potential limitations of procalcitonin to serve as a sole differentiator of colonization, in some embodiments, the addition of anti-streptolysin antibody titers are performed.

In one embodiment, the presence of antistreptolysin O antibody is used in association with elevated procalcitonin values to define true infection since the presence of the antistreptolysin O antibody supports the existence of an immune response.

Antistreptococcal antibody (ASO) titers have no value in the diagnosis of acute GAS pharyngitis, but are useful in prospective epidemiologic studies to differentiate true GAS infections from GAS carriage. The determination of anti-streptolysin O antibodies used to be the mainstay of confirming a diagnosis of GAS pharyngitis. Demonstration of a significant or four-fold rise in titer on paired serum samples taken at an interval of 7 to 14 days apart will indicate an ongoing or an acute infection (Johnson et al., Laboratory diagnosis of group A *streptococcal* infections. World Health Organization, Geneva, 1996, incorporated herein by reference). On the other hand, presence of GAS in throat in the absence of a significant rise in antibodies indicates a carrier state and no GAS infection. Practical difficulties in getting two serum samples and the time taken to demonstrate a four-fold rise in titer make this unfeasible on a routine basis. For instance, it is not always possible to obtain a second sample for titer determination, particularly in developing countries, where acute rheumatic fever is the most common. Therefore, it is generally accepted that if only a single specimen is available, a titer greater than the upper limit of normal at the initial testing can be considered presumptive evidence of a preceding *streptococcal* infection (Kaplan et al., J. Infect. Dis. 123: 490-501, 1971; Klein et al. Appl. Microbiol. 21:999-1001, 1971; Wannamaker and Ayoub, Circulation 21: 598-614, 1960, all incorporated herein by reference). Alternately, titer obtained with a single serum sample can be interpreted based on a cut-off value defined as the upper limit of normal (ULN). ULN represents the highest level of antibodies that can be observed in 20% of normal individuals who have demonstrable antibodies in them. Any ASO titer above these cut-off values would be suggestive of a GAS infection (Brahmadathan and Gladstone, Indian J Med Microbiol., 24(2): 92-6, April 2006, incorporated herein by reference).

The upper limit of normal for *streptococcal* serology has been defined by separating the upper 20% from the lower 80% of the group distribution in a dichotomous fashion (Ayoub and Wannamaker, Pediatrics 29: 527-538, 1962; Klein, 1971; Wannamaker 1960, all incorporated herein by reference). The choice of the 80th percentile cutoff rather than more traditional upper-limit-of-normal calculations (e.g., 2 standard deviations from the mean) is based upon studies that found that more than 80 to 90% of patients with acute rheumatic fever or post-*streptococcal* glomerulonephritis have *streptococcal* titers that are above the 80th percentile for the healthy controls with no clinical evidence of recent *streptococcal* infection (Ayoub 1962; Wannamaker 1960). Therefore, it is assumed that in any population a proportion of apparently healthy individuals will have had a recent, subclinical GAS infection (Ayoub 1962). In developed countries, where impetigo caused by GAS is uncommon, *streptococcal* titers in the population primarily reflect the incidence of pharyngeal infection with GAS; therefore, the titers in healthy people are low in early childhood, rise to a peak in children aged 5 to 15 years, decrease in late adolescence and early adulthood, and then flatten off after that. The U.S. ULN have been defined. The estimated titers that were 80% of the upper limit or normal at age 10 years were 276 IU/ml for ASO which is similar to other reported values (Kaplan et al., Pediatrics 101:86-88, 1998; Steer et al., Clin Vaccin Immunol 16(2): 172-5, February, 2009, both incorporated herein by reference).

Table 5 shows the differences between contamination, colonization, and active infection (adapted from Lorrot M et al. Procalcitonin in pediatric emergencies: comparison with C-reactive protein, interleukin 6 and interferon alpha in the differentiation between bacterial and viral infections. Presse Med 2000; 29:128-134, herein incorporated by reference). Normal WBC, IgG, and C-reactive protein values excluded bacterial infections with a predictive value of 100% in children presenting with fever. Lorrot compared procalcitonin with C reactive protein, interleukin-6 and interferon-alpha. MxA levels (a way of measuring host immune response) were not measured in the Lorrot study.

The primary bacterial pathogens for upper respiratory infections are shown in Table 6 (Bisno et al. Clin Infect Dis 2002; 15; 35(2):113-25; Wenzel and Fowler. Clinical practice: acute bronchitis. N Engl J Med 2006; 355:2125-30, both herein incorporated by reference). The primary lower respiratory tract infection bacterial pathogens include *S. pneumoniae, M pneumoniae, C pneumoniae, H influenzae, Staph auereus, Moraxella catarrhalis, Legionella* spp, Enterobacteriaceae, *Pseudomonas* spp, *Anaerobes, Pneumocysis* spp, *M Tubercolosis, C psittaci* and *C burnetii* (File T M. Community Acquired Pneumonia. Lancet. 2003; 362: 1991-2001, incorporated herein by reference).

TABLE 6

| Primary Bacterial Pathogens | Syndrome | Estimated Prevalence |
| --- | --- | --- |
| Bacterial Pathogens *Streptococcus pyogenes* | | |
| Group A β-hemolytic streptococcus | Pharyngitis, tonsillitis, and scarlet fever | 5%-30% (5%-10% in adults; 15-30% in children) |
| Group C β-hemolytic streptococcus | Pharyngitis and tonsillitis | >5% |
| *Neisseria gonorrheae* | Pharyngitis | <1% (rare) |
| *Corynebacterium diphtheria* | Diptheria | <1% (rare) |
| *Arcanobacterium haemolyticum* | Pharyngitis and scarlatiniform rash | <1% (rare) |
| Atypical Bacterial pathogens | | |
| *Chlamydia pneumoniae* | Pneumonia, bronchitis, and pharyngitis | 5%* |
| *Myoplasma pneumoniae* | Pneumonia, bronchitis, and pharyngitis | <1%* |
| *Bordetella pertussis* | Pneumonia, bronchitis, and pharyngitis | <1%* |

*Less than 10% for all 3 pathogens combined

In current rapid tests for strep, sensitivity for the *streptococcal* Rapid antigen detection test (RADT) ranges from 70-90 percent and specificity ranges from 90-100 percent in multiple studies (Del Mar et al. Antibiotics for sore throat. Cochrane Database Syst Rev. 2006 Oct. 18; (4):CD000023; Gerber M A and Shulman S T. Rapid diagnosis of pharyngitis caused by group A streptococci. Clin Microbiol Rev 2004; 17:571; Gieseker et al. Comparison of two rapid *Streptococcus pyogenes* diagnostic tests with a rigorous culture standard. Pediatr Infect Dis J 2002; 21:922; Nakhoul and Hickner, Management of adults with acute *streptococcal* pharyngitis: minimal value for backup strep testing and overuse of antibiotics. J Gen Intern Med 2013; 28:830; Tanz et al. Performance of a rapid antigen-detection test and throat culture in community pediatric offices: implications for management of pharyngitis. Pediatrics 2009; 123:437, all herein incorporated by reference). In a meta-analysis of 159 studies that evaluated rapid influenza antigen tests, the pooled sensitivity was 62.3 percent (95% CI 57.9-66.6 percent) and the pooled specificity was 98.2 percent (95% CI 97.5-98.7 percent). The sensitivity was lower in adults than in children (53.9 versus 66.6 percent), and was higher for influenza A than for influenza B (64.6 versus 52.2 percent) (Chartrand et al. Accuracy of rapid influenza diagnostic tests: a meta-analysis. Ann Intern Med 2012; 156:500, herein incorporated by reference).

Since procalcitonin can be found in the serum of a healthy person (<0.12 ng/mL) and the current assays demonstrate an interassay precision of approximately 10% (Aouifi et al. Usefulness of procalcitonin for diagnosis of infection in

TABLE 5

| Condition | DNA Detection | Culture Growth | Antigen Detection | Host Immune Response |
| --- | --- | --- | --- | --- |
| Contamination | No | Yes | No | No |
| Colonization (carrier state) | Yes | Yes | Yes | No |
| Active infection | Yes | Yes | Yes | Yes | cardiac surgical patients. Crit Care Med 2000; 28:3171-6, herein incorporated by reference), a recommended cutoff for definitive bacterial infection is 0.15 ng/ml.

The Mayo Clinic reaffirmed this recommendation by stating, in children older than 72 hours and in adults, levels <0.15 ng/mL make a diagnosis of significant bacterial infection unlikely (http://www.mayomedicallaboratories.com/testcatalog/Clinical+and+Interpretive/83169, herein incorporated by reference).

Moreover, procalcitonin between 0.15 and 0.25 ng/ml does not exclude an infection, because localized infections (without systemic signs) may be associated with such low levels. To increase the likelihood of a positive bacterial infection identification, WBC level is linked to this elevated procalcitonin for bacterial infection and elevated procalcitonin ≥0.15 ng/ml and <0.25 ng/ml in the presence of low WBC level will be deemed viral. In patients with a procalcitonin level below 0.15 ng/ml, the diagnosis of a bacterial respiratory tract infection is considered highly unlikely, and the use of antibiotics is discouraged. In patients with a procalcitonin level above 0.25 ng/mL, a bacterial respiratory tract infection is considered the most likely diagnosis and the use of antibiotics is recommended (Mayo Clinic).

During a multicenter clinical trial, experts determined the presence of a true active bacterial infection from culture positive colonization via the presence of elevated procalcitonin ± an elevated WBC≥15,000. The results are shown in Table 7. The WBC values are shown in thousands in the table. While all of the patients were positive for bacteria in a throat culture, the final diagnosis for 21 out of the 26 patients was a negative diagnosis, or colonization. None of those 21 patients had WBC counts of greater than or equal to 15,000 and procalcitonin levels of greater than 0.10 ng/ml, or, if the WBC counts were less than 15,000, procalcitonin levels greater than 0.15 ng/ml. Patients 5, 7, and 8, who each had WBC levels of 12,180, 12,350 and 12,200, respectively, had procalcitonin levels of 0.19 ng/ml, 0.37 ng/ml and 0.38 ng/ml, respectively. Each of these patients was diagnosed with a bacterial infection due to their procalcitonin levels being elevated above 0.15 ng/ml. Patient 6, who had WBC levels of 17,100 and procalcitonin level of 0.2 ng/ml, was also diagnosed with a bacterial infection. Patient 26, who had WBC levels of 16,690, 2 bands, and a procalcitonin level of 0.74 ng/ml, was also diagnosed with a bacterial infection.

TABLE 7

| Patient | WBC | Bands | Procalcitonin Result (ng/ml) | Throat Culture Organism Isolated | Final Diagnosis |
|---|---|---|---|---|---|
| 1 | 7.5 | 0 | 0.05 | Beta Hemolytic Group A *Streptococcus* | Negative |
| 2 | 8.7 | 0 | 0.05 | Beta Hemolytic Group A *Streptococcus* | Negative |
| 3 | 11 | 0 | 0.05 | Beta Hemolytic Group A *Streptococcus* | Negative |
| 4 | 3.41 | 0 | 0.05 | Beta Hemolytic Group A *Streptococcus* | Negative |
| 5 | 12.18 | 0 | 0.19 | Beta Hemolytic Group A *Streptococcus* | Bacterial |
| 6 | 17.1 | 0 | 0.2 | Beta Hemolytic Group A *Streptococcus* | Bacterial |
| 7 | 12.35 | 0 | 0.37 | Beta Hemolytic Group A *Streptococcus* | Bacterial |
| 8 | 12.2 | 0 | 0.38 | Beta Hemolytic Group A *Streptococcus* | Bacterial |
| 9 | 9.31 | 0 | 0.05 | Beta Hemolytic Group A *Streptococcus* | Negative |
| 10 | 8.5 | 0 | 0.05 | *Staphylococcus aureus* | Negative |
| 11 | 9.83 | 0 | 0.05 | *Staphylococcus aureus* | Negative |
| 12 | 9.67 | 0 | 0.05 | *Staphylococcus aureus* | Negative |
| 13 | 10.82 | 0 | 0.05 | *Staphylococcus aureus* | Negative |
| 14 | 7.44 | 0 | 0.05 | *Staphylococcus aureus* | Negative |
| 15 | 10.1 | 0 | 0.05 | *Staphylococcus aureus* | Negative |
| 16 | 12.7 | 0 | 0.05 | *Staphylococcus aureus* | Negative |
| 17 | 8.36 | 0 | 0.05 | *Staphylococcus aureus* | Negative |
| 18 | 5.45 | 0 | 0.05 | *Staphylococcus aureus* | Negative |
| 19 | 10.49 | 0 | 0.06 | *Staphylococcus aureus* | Negative |
| 20 | 9 | 0 | 0.07 | *Staphylococcus aureus* | Negative |
| 21 | 9 | 0 | 0.08 | *Staphylococcus aureus* | Negative |
| 22 | 5.1 | 0 | 0.05 | *Staphylococcus aureus* | Negative |
| 23 | 4.1 | 0 | 0.05 | *Staphylococcus aureus* | Negative |
| 24 | 11.57 | 0 | 0.13 | *Staphylococcus aureus* | Negative |
| 25 | 16.69 | 2 | 0.74 | *Staphylococcus aureus* | Bacterial |
| 26 | 8.37 | 0 | 0.05 | *Staphylococcus aureus* | negative |

Table 8 shows how procalcitonin may be used in the embodiments described herein to determine active viral or bacterial infection, or colonization. If there are no viral or bacterial pathogens detected, and the procalcitonin level is less than 0.15 ng/ml, the diagnosis is no bacterial or viral infection. If only a viral pathogen is detected, and the procalcitonin level is less than 0.15 ng/ml, the diagnosis is viral infection. In some embodiments, this is preferably further confirmed by testing for a level of ≥25 ng/ml MxA in the sample. In other embodiments, this is preferably further confirmed by testing for a level ranging from 15 ng/ml to 40 ng/ml in the sample. If only a bacterial pathogen is detected, but the procalcitonin level is less than 0.15 ng/ml, the diagnosis is bacterial colonization from non-primary pathogens. If only a bacterial pathogen is detected, and the procalcitonin level is greater than or equal to 0.10 ng/ml, the diagnosis is bacterial infection from primary pathogens. If only a bacterial pathogen is detected, and the procalcitonin level is greater than or equal to 0.15 ng/ml, the diagnosis is bacterial infection from non-primary pathogens. If both a bacterial and a viral pathogen are detected, and the procalcitonin level is greater than or equal to 0.10 ng/ml, the diagnosis is viral and bacterial co-infection, with the bacterial infection being from primary pathogens. In some embodiments, this is preferably further confirmed by testing for a level of ≥25 ng/ml MxA in the sample. In other embodiments, this is preferably further confirmed by testing for a level ranging from 15 ng/ml to 40 ng/ml in the sample. If both a bacterial and a viral pathogen are detected, and the procalcitonin level is greater than or equal to 0.15 ng/ml, the diagnosis is viral and bacterial co-infection, with the bacterial infection being from non-primary pathogens. In some embodiments, this is preferably further confirmed by testing for a level of ≥25 ng/ml MxA in the sample In other embodiments, this is preferably further confirmed by testing for a level ranging from 15 ng/ml to 40 ng/ml in the sample.

TABLE 8

| Bacterial Pathogen Detected | Viral Pathogen Detected | Procalcitonin level ng/ml | Interpretation |
| --- | --- | --- | --- |
| No | No | <0.15 | No evidence of bacterial or viral infection |
| No | Yes | <0.15 | Viral infection |
| Yes | No | <0.15 | Bacterial colonization (non-primary pathogens) |
| Yes | No | ≥0.10 | Bacterial infection (primary pathogens) |
| Yes | No | ≥0.15 | Bacterial infection (non-primary pathogens) |
| Yes | Yes | ≥0.10 | Viral and bacterial (primary) co-infection |
| Yes | Yes | ≥0.15 | Viral and bacterial (non-primary) co-infection |

A rapid differentiating point of care (POC) test has profound clinical implications since distinguishing viral from bacterial infections has been shown to be challenging, especially early in the disease process (Metlay and Fine. Testing strategies in the initial management of patients with community-acquired pneumonia. Ann Intern Med. 2003; 138(2):109-118.; Martin et al., The epidemiology of sepsis in the united states from 1979 through 2000. N Engl J Med. 2003; 348:1546-1554. doi: 10.1056/NEJMoa022139, both herein incorporated by reference). Van Gageldonk-Lafeber et al observed no association between detected bacterial and viral pathogens and either diagnoses made by general practitioners (GP) or subject's reported symptoms (van Gageldonk-Lafeber et al., A case-control study of acute respiratory tract infection in general practice patients in the Netherlands. Clin Infect Dis. 2005; 41(4):490-497, herein incorporated by reference). Moreover, physical examination alone was shown to have a sensitivity of 50% to 70% and specificity of 60% to 75% (Lieberman et al., Aetiology of respiratory tract infections: Clinical assessment versus serological tests. Br J Gen Pract. 2001; 51(473):998-1000, herein incorporated by reference) as well as a negative and positive predictive value of 50% to 60% (Lähde et al., HRCT findings in the lungs of primary care patients with lower respiratory tract infection. Acta Radiol. 2002; 43(2):159-163, herein incorporated by reference). The difficulty with establishing an etiologic outpatient diagnosis in acute febrile respiratory illness stems from overlap in signs and symptoms, limitations with available diagnostic tests, empirical treatment regimens, and the time lag to receive results from laboratory tests.

According to Korppi, C-reactive protein measurement is recommended as the first-line method of screening suspected bacterial inflammation (Korppi et al., White blood cells, C-reactive protein and erythrocyte sedimentation rate in pneumococcal pneumonia in children. Eur Respir J. 1997; 10(5):1125-1129, herein incorporated by reference). Several studies have indicated that C-reactive protein is feasible and accurate at differentiating pneumonia from acute bronchitis (van der Meer et al., Diagnostic value of C reactive protein in infections of the lower respiratory tract: Systematic review. BMJ. 2005; 331(7507):26. doi: 10.1136/bmj.38483.478183.EB; Hopstaken et al., Contributions of symptoms, signs, erythrocyte sedimentation rate, and C-reactive protein to a diagnosis of pneumonia in acute lower respiratory tract infection. Br J Gen Pract. 2003; 53(490): 358-364; Flanders et al. Performance of a bedside c-reactive protein test in the diagnosis of community-acquired pneumonia in adults with acute cough. Am J Med. 2004; 116(8): 529-535; Melbye et al., Diagnosis of pneumonia in adults in general practice. relative importance of typical symptoms and abnormal chest signs evaluated against a radiographic reference standard. Scand J Prim Health Care. 1992; 10(3): 226-233, all herein incorporated by reference). Pneumonia is associated with elevated serum C-reactive protein levels greater than 10 mg/L, while severe pneumonia has serum C-reactive protein typically greater than 100 mg/L (Smith and Lipworth, C-reactive protein in simple community-acquired pneumonia. Chest. 1995; 107(4):1028-1031; Chalmers et al., C-reactive protein is an independent predictor of severity in community-acquired pneumonia. Am J Med. 2008; 121(3):219-225, both herein incorporated by reference). In Scandinavia, POC C-reactive protein testing is part of the routine evaluation of patients with LRTI, and its use has proved cost-effective (Diederichsen et al., Randomised controlled trial of C-reactive protein rapid test as a guide to treatment of respiratory infections in general practice. Scand J Prim Health Care. 2000; 18(1):39-43; Dahler-Eriksen et al., Near-patient test for C-reactive protein in general practice: Assessment of clinical, organizational, and economic outcomes. Clin Chem. 1999; 45(4):478-485 . . . 42, 43, both herein incorporated by reference).

Both C-reactive protein and procalcitonin (PCT) concentrations have been used to initiate and monitor antibiotic use for LRTI (Cals et al., Effect of point of care testing for C reactive protein and training in communication skills on antibiotic use in lower respiratory tract infections: Cluster randomised trial. BMJ. 2009; 338:b1374. doi: 10.1136/bmj.b1374; Schuetz et al., Effect of procalcitonin-based guidelines vs standard guidelines on antibiotic use in lower respiratory tract infections: The ProHOSP randomized controlled trial. JAMA. 2009; 302(10):1059-1066. doi: 10.1001/jama.2009.1297, both herein incorporated by reference). Procalcitonin has been suggested (Briel et al., Procalcitonin-guided antibiotic use vs a standard approach for acute respiratory tract infections in primary care. Arch Intern Med. 2008; 168(18):2000-7; discussion 2007-8, herein incorporated by reference) for monitoring community-acquired outpatient infections, but since it is not available as a POC test, costs for measuring procalcitonin are relatively higher, making it undesirable for high-incidence infections in family practice (Cals et al., Procalcitonin-based guidelines and lower respiratory tract infections. JAMA. 2010; 303(5):418. doi: 10.1001/jama.2010.52, herein incorporated by reference). In general, the specificity of single biomarkers in terms of etiologic distinction between bacterial and viral infections remains a problem (Simon et al., Serum procalcitonin and C-reactive protein levels as markers of bacterial infection: A systematic review and meta-analysis. Clin Infect Dis. 2004; 39(2):206-217. doi: 10.1086/421997; Oshita et al., Semi-quantitative procalcitonin test for the diagnosis of bacterial infection: Clinical use and experience in Japan. J Microbiol Immunol Infect. 2010; 43(3):222-227, both herein incorporated by reference). C-reactive protein as a single biomarker is a useful and highly specific parameter to suggest the bacterial etiology of an infection at high concentrations, but lower concentrations of C-reactive protein are often observed during both viral and bacterial infections (ten Oever et al., Combination of biomarkers for the discrimination between bacterial and viral lower respiratory tract infections. J Infect Dis. 2012; 65(6):490-495, herein incorporated by reference). Attempts at panel tests, including C-reactive protein combined with IL-18 because of its role in anti-viral immunity, have been unsuccessful at differentiating viral from bacterial infection (ten Oever et al., 2012)

Higher MxA levels in patients with viral infection compared with patients with bacterial infection can be explained by the fact that MxA protein is induced exclusively by type 1 IFN and not by IFN-gamma, IL-1, TNF-alpha, or any of the other cyotokines induced by bacterial infection (Simon et al., Interferon-regulated mx genes are not responsive to interleukin-1, tumor necrosis factor, and other cytokines. J Virol. 1991; 65(2):968-971, herein incorporated by reference). Serum type 1 IFN levels remain within normal limits, even in patients with severe bacterial infections (Calandra et al., Prognostic values of tumor necrosis factor/cachectin, interleukin-1, interferon-alpha, and interferon-gamma in the serum of patients with septic shock. swiss-dutch J5 immunoglobulin study group. J Infect Dis. 1990; 161(5):982-987; Girardin E, Grau G E, Dayer J M, Roux-Lombard P, Lambert P H. Tumor necrosis factor and interleukin-1 in the serum of children with severe infectious purpura. N Engl J Med. 1988; 319(7):397-400. doi: 10.1056/NEJM198808183190703, both herein incorporated by reference). There is substantive data that demonstrates that human infection with respiratory syncitial virus (RSV), influenza, adenovirus, and metapneumovirus stimulate a robust cytokine response that includes gamma interferon (Melendi et al., Cytokine profiles in the respiratory tract during primary infection with human metapneumovirus, respiratory syncytial virus or influenza virus in infants. Pediatrics. 2007; 120(2):e410-e415; Sato et al., Differences in serum cytokine levels between influenza virus A and B infections in children. Cytokine. 2009; 47(1):65-68, both herein incorporated by reference). The magnitude of the IFN response varies with the type of inciting virus (Melendi et al., 2007). Moreover, a deficiency in the receptor for IFN is reported to increase the severity of respiratory viral infection (Lee et al., IFN-gamma production during initial infection determines the outcome of reinfection with respiratory syncytial virus. Am J Resp Crit Care Med. 2008; 177(2):208-218, herein incorporated by reference).

MxA has been found to be elevated in common respiratory viral infections as well as common viral gastrointestinal infections (Forster et al., MxA protein in infants and children with respiratory tract infection. Acta Paediatr. 1996; 85(2):163-167; Halminen et al., Expression of MxA protein in blood lymphocytes discriminates between viral and bacterial infections in febrile children. Pediatr Res. 1997; 41(5):647-650; Chieux et al., The MxA protein levels in whole blood lysates of patients with various viral infections. J Virol Methods. 1998; 70(2):183-191.25-27; Chieux et al., MxA protein in capillary blood of children with viral infections. J Med Virol. 1999; 59(4):547-551; Nakabayashi et al., MxA-based recognition of viral illness in febrile children by a whole blood assay. Pediatr Res. 2006; 60(6):770-774; Kawamura et al., New sandwich-type enzyme-linked immunosorbent assay for human MxA protein in a whole blood using monoclonal antibodies against GTP-binding domain for recognition of viral infection. J Clin Lab Anal. 2012; 26(3):174-183, all herein incorporated by reference). Bacterial cultures are usually only performed in cases of presumed severe infection, such as suspected pneumonia, or when the consequence of missing a diagnosis can lead to severe complications, such as with Strep throat. Bacterial cultures are often difficult to obtain, especially in children or uncooperative patients, and viral cultures are not routinely performed due to the significant time delay in receiving results. New molecular-based viral screening panels are useful but they are expensive and do not provide information at the point of care. Additionally, venous blood samples can be difficult to collect from children in ambulatory care settings. A POC test, provided at the bedside, presents an immediate result from a droplet of blood and is especially useful in children (Verbakel et al., Analytical accuracy and user-friendliness of the afinion point-of-care C-reactive protein test. J Clin Pathol. 2014; 67(1):83-86, herein incorporated by reference).

The high sensitivity of PCR allows the detection of minimal amounts of viral nucleic acids, but the clinical relevance of positive test results is not clear because small amounts of a respiratory virus could represent asymptomatic colonization or post-infectious shedding (Jansen et al., Frequent detection of respiratory viruses without symptoms: Toward defining clinically relevant cutoff values. J Clin Microbiol. 2011; 49(7):2631-2636, herein incorporated by reference). When asymptomatic control patients are compared to patients with respiratory illnesses, PCR detects the presence of viruses in 19-44% of the control patients, suggesting transient colonization or persistence, most commonly associated with rhinovirus and coronavirus (van Gageldonk-Lafeber et al., A case-control study of acute respiratory tract infection in general practice patients in the Netherlands. Clin Infect Dis. 2005; 41(4):490-497; Jansen et al., Frequent detection of respiratory viruses without symptoms: Toward defining clinically relevant cutoff values. J Clin Microbiol. 2011; 49(7):2631-2636; Rhedin et al., Clinical utility of PCR for common viruses in acute respiratory illness. Pediatrics. 2014; 133(3):e538-e545; van der Zalm et al., Respiratory pathogens in children with and without respiratory symptoms. J Pediatr. 2009; 154(3):396-400.e1; van Benten et al., Predominance of rhinovirus in the nose of symptomatic and asymptomatic infants. Pediatr Allergy Immunol. 2003; 14(5):363-370, all herein incorporated by reference). Nokso-Koivisto showed that 81% of the children with virus-positive samples had previous respiratory symptoms or had family members with concurrent respiratory symptoms (Nokso-Koivisto et al., Human picornavirus and coronavirus RNA in nasopharynx of children without concurrent respiratory symptoms. J Med Virol. 2002; 66(3):417-420, herein incorporated by reference). However, viruses such as influenza, parainfluenza, metapneumovirus, and RSV are rarely detected in asymptomatic subjects and when present, suggest active infection (Rhedin et al., Clinical utility of PCR for common viruses in acute respiratory illness. Pediatrics. 2014; 133(3):e538-e545; Mathisen et al., Respiratory viruses in Nepalese children with and without pneumonia: A case-control study. Pediatr Infect Dis J. 2010; 29(8):731-735; Berkley et al., Viral etiology of severe pneumonia among Kenyan infants and children. JAMA. 2010; 303(20):2051-2057, all herein incorporated by reference).

Since these viruses all seem to be rapidly cleared from the respiratory tract after an infection, PCR is a suitable diagnostic method to determine their infection (Jartti et al., New molecular virus detection methods and their clinical value in lower respiratory tract infections in children. Paediatr Respir Rev. 2013; 14(1):38-45, herein incorporated by reference).

Rhinovirus is considered a relatively mild pathogen that can colonize the nasal mucosa without causing symptoms (van Benten et al., Predominance of rhinovirus in the nose of symptomatic and asymptomatic infants. Pediatr Allergy Immunol. 2003; 14(5):363-370, herein incorporated by reference). Viruses such as rhinovirus and coronavirus cause the common cold and do not typically cause an invasive infection, fever in immunocompetent hosts, or stimulate IFN or MxA (Nokso-Koivisto et al., Human picornavirus and coronavirus RNA in nasopharynx of children without concurrent respiratory symptoms. J Med Virol. 2002; 66(3): 417-420; Johnston et al., Use of polymerase chain reaction for diagnosis of picornavirus infection in subjects with and without respiratory symptoms. J Clin Microbiol. 1993; 31(1):111-117, both herein incorporated by reference). This suggests that a causal inference based on the detection of these viruses in symptomatic patients should be made with caution. In particular, coronavirus, and rhinovirus must be interpreted with discretion due to high detection rates among healthy subjects. All other viruses were found to be positive in in less than 5% of patients (Rhedin et al., Clinical utility of PCR for common viruses in acute respiratory illness. Pediatrics. 2014; 133(3):e538-e545; herein incorporated by reference).

Molecular testing, antigen testing and cell culture only determine the presence or absence of a pathogen. They do not differentiate a bonafide infection from a carrier state or colonization. The presence of a systemic response is required to confirm a true active infection. A novel diagnostic method must be able to differentiate between bacterial cell culture growth, a colonizing bacteria, and a host immune response.

Clinical Diagnostic Methods

FIG. 1 shows an existing clinical method for diagnoses of upper respiratory infections (100). Nasopharyngeal or oropharyngeal swabs may be taken (102), viral transport medium (104) is taken, and may be subject to real time PCR (106) or respiratory panel PCR (107) (for example Biofire® respiratory panel PCR). If IgM is positive (108) in the real time PCR for Epstein barr virus, the diagnosis (110) is a viral infection. If the respiratory panel PCR is positive for HSV, CMV, Rhinovirus, Coronavirus, Influenza A, Influenza B, Parainfluenza, or RSV (118), the diagnosis (110) is also a viral infection. If the respiratory panel PCR is positive for *Bordetella, Chlamydia*, or *Mycoplasma* (116), the diagnosis (120) is a bacterial infection.

An alternative sample that could be collected is a urine sample (112), collected via a urine collection transport system (114). If the urine sample is positive for *Pneumococcus* or *Legionella* antigen (122), the diagnosis (120) is a bacterial infection. An oropharyngeal sample (124) may alternatively be subject to cell culture, using a culture swab collection transport system (126). Any bacteria with growth >$10^6$ or any group A strep growth (128) indicates (120) a bacterial infection.

If the samples are negative for PCR, antigen (130), and cell culture (132), they are considered microbiologically unconfirmed (134) and subject to further testing. If the procalcitonin levels in the sample are less than 1.0 ng/ml and there are any white blood cells (136), the diagnosis (146) is negative. If the procalcitonin levels are between 0.1 ng/ml and 0.25 ng/ml plus any white blood cells (138), the diagnosis (154) is a viral infection. If the procalcitonin levels are between 0.25 ng/ml and 0.5 ng/ml and the white blood cell count is less than 8,000 (140), the diagnosis (154) is also a viral infection. If the procalcitonin levels are greater than or equal to 0.25 ng/ml up to 0.5 ng/ml and there is a white blood cell count greater than 8,000 (142), the diagnosis (150) is a bacterial infection. If the procalcitonin levels are greater than or equal to 0.5 ng/ml and there are any white blood cells (144), the diagnosis (150) is also a bacterial infection. Patient history, physical exam, white blood cell count and other laboratory tests (152) may be taken to confirm a final clinical diagnosis (156).

Figure 2:
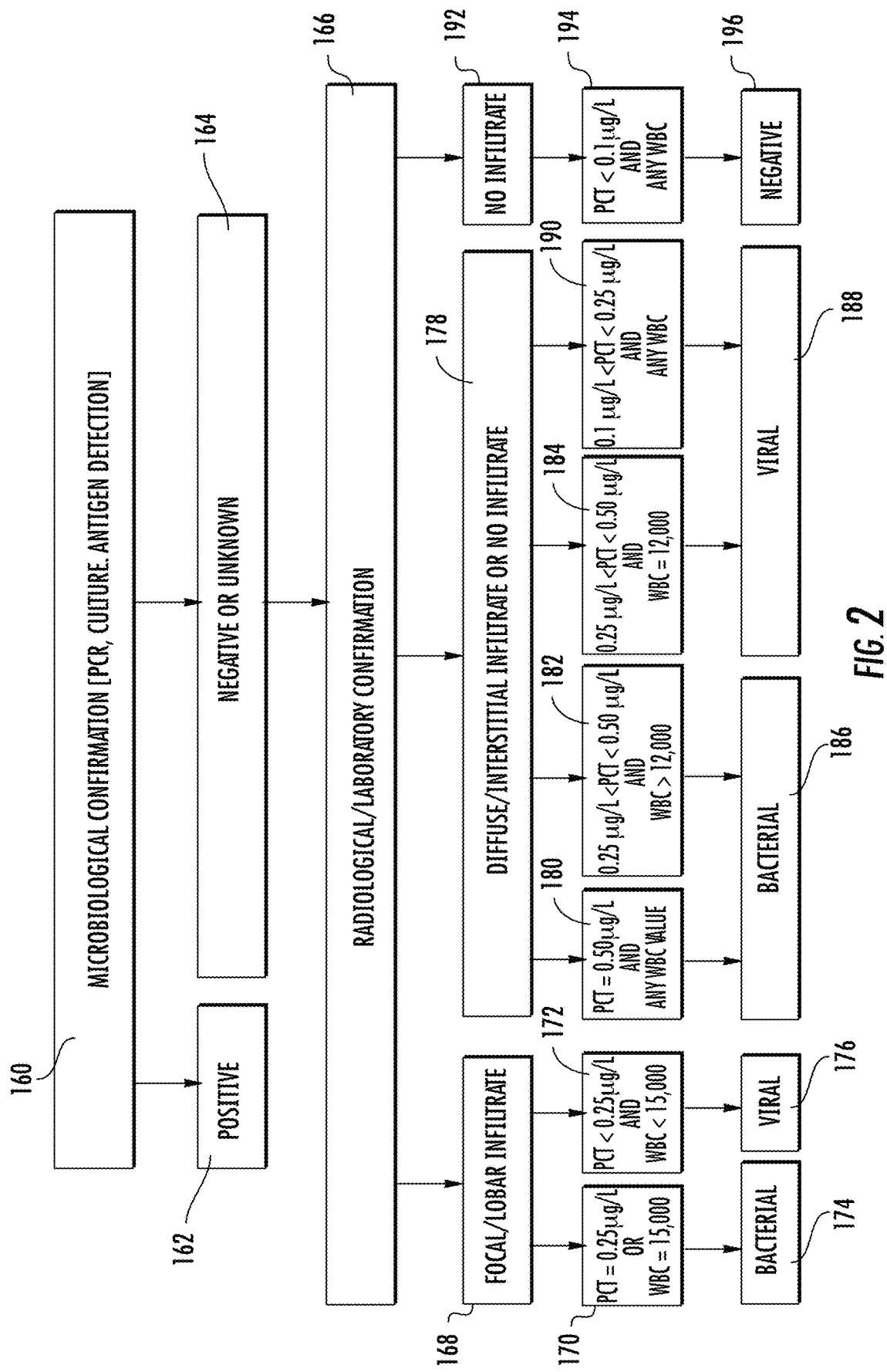
FIG. 2 shows a clinical method for diagnoses of lower respiratory infections.

FIG. 2 shows an existing clinical method for diagnoses of lower respiratory tract infections. The initial testing (160) for diagnosis, including PCR, culture, and antigen detection, is similar to what is described with respect to FIG. 1. Positive samples (162) are identified with either a bacterial or viral diagnosis.

For samples that are negative or microbiologic ally unconfirmed (164) based on the initial testing, there is first a radiological/laboratory confirmation (166), for example using a chest x-ray. For patients with focal/lobar infiltrates (168) identified in the chest x-ray, if the procalcitonin levels are at least 0.25 µg/L or the white blood cell count is at least 15,000 (170), the diagnosis (174) is a bacterial infection. For the patients with focal/lobar infiltrates (168), if the procalcitonin levels are less than 0.25 µg/L and the white blood cell count is less than 15,000 (172), the diagnosis (176) is a viral infection.

For patients with a diffuse/interstitial infiltrate or no infiltrate (178) identified in the chest x-ray, if the procalcitonin levels are greater than or equal to 0.50 µg/L with any white blood cell count value (180), the diagnosis (186) is a bacterial infection. If the procalcitonin levels in these patients are between 0.25 µg/L and 0.50 µg/L and the white blood cell count is greater than 12,000 (182), the diagnosis (186) is also a bacterial infection. In these patients, if their procalcitonin levels are between 0.25 µg/L and 0.50 µg/L and the white blood cell count is less than or equal to 12,000 (184), the diagnosis (188) is a viral infection. In these patients, if the procalcitonin values are between 0.1 µg/L and 0.25 µg/L and there are any white blood cells (190), the diagnosis (188) is also a viral infection.

In patients with no infiltrate (192) detected in a chest x-ray, if the procalcitonin levels are less than 0.1 µg/L (194), the diagnosis (196) is negative regardless of the white blood cell count.

Both FIG. 1 and FIG. 2 primarily test for specific pathogens or a general immune response. These methods do not differentiate between colonization and active infection.

Identifying an appropriate immune response is best accomplished in two ways. First, bacterial cell culture growth without an associated elevation of procalcitonin or C-reactive protein is unlikely to represent a clinically significant bacterial infection and is more likely to represent colonization. Secondly, PCR studies have repeatedly demonstrated that both Rhinovirus and Coronavirus can persist in the nasopharynx without a host response and are not related to a clinically significant infection. Similarly, patients with a history of HSV and CMV may have periodic DNA shedding which is not associated with active infection. Although molecular testing can be very useful for viral detection, molecular testing alone cannot determine clinical significance. It is common for patients to not have a confirmed microbiological diagnosis. Reliance on the host response is therefore critical for the safe and effective management of these patients.

The methods described herein use MxA to differentiate between an active viral infection, and a non-systemic host response. Following negative molecular testing for viral pathogens, the methods described herein also use elevated procalcitonin or C-reactive protein as a differentiator of the presence of a probable bacterial infection.

One method of differentiating between colonization, a non-systemic host response and active infection includes the step of performing a first test for a presence of bacteria or virus in a sample. The first test may include, but is not limited to, PCR, a radiological test, viral culture, viral IFA, viral antigen testing, or a bacterial culture. If the sample is positive for virus, a second test is performed for a presence of at least approximately 25 ng/ml MxA in the sample (or is positive for paired serology). In the absence of 25 ng/ml MxA or paired serology, the sample is classified as no systemic host response. If the sample is positive for at least 25 ng/ml MxA, the infection is classified as a viral infection, regardless of whether or not there are additional indications of a bacterial infection.

If the first test is positive for bacteria, a second test is performed to determine a level of procalcitonin or C-reactive protein in a patient sample. In the absence of at least 0.1 ng/ml procalcitonin or 20 mg/L of C-reactive protein, in combination with other factors, indicates bacterial colonization. Other levels of procalcitonin between 0.10 ng/ml and 0.25 ng/ml, in combination with other factors, or C-reactive protein between 20 mg/l and 80 mg/l, in combination with other factors, may also indicate colonization. In other embodiments, tests for only bacteria or only viruses are performed.

In other embodiments, the host biomarkers (such as MxA, C-reactive protein, and/or procalcitonin) levels are determined initially, and if they are negative in a symptomatic patient, it is assumed clinically insignificant and additional testing is not necessary. However, if additional tests are performed and show any growth or detection of pathogen, this would represent colonization.

Typical/IDSA-listed bacteria include Group A and C beta-hemolytic *streptococcous*, *Neisseria gonorrhea*, *Arcanobacterium haemolyticum*, and *Fusobacterium necrophorum*. Atypical (non-IDSA) bacteria include *Bordetella pertussis*, *Chlamydophila pneumoniae* and *Mycoplasma pneumoniae*.

Paired serology, as defined herein, is a pathogen-specific antibody titer increase by a factor of 4 or more between the acute-phase serum specimen and the convalescent-phase.

Figure 3:
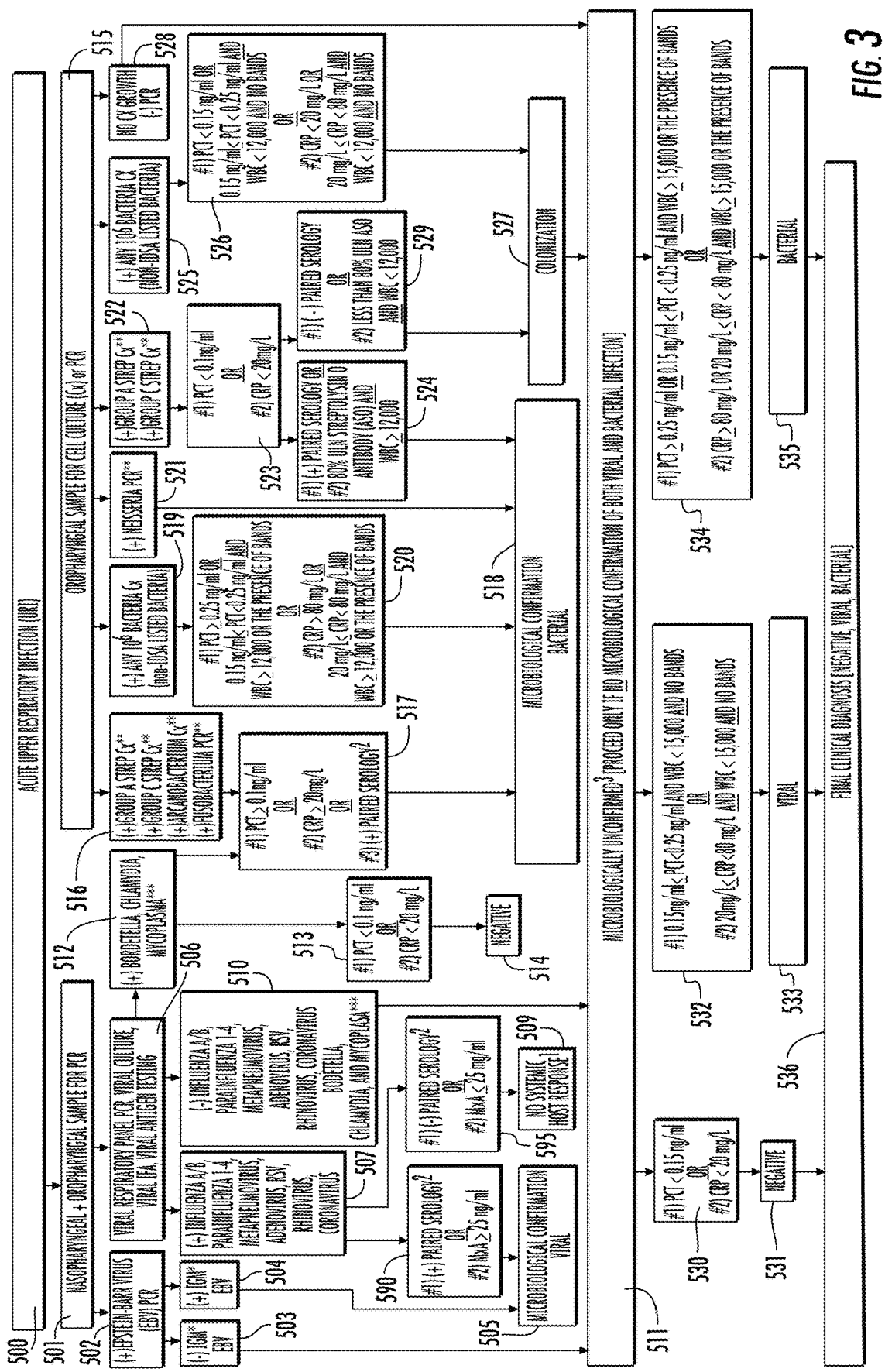
FIG. 3 shows a novel method for diagnosing upper respiratory infections and identifying colonization.

FIG. 3 shows an embodiment of a method to diagnose upper respiratory infections and colonization using MxA, procalcitonin and/or CRP and other sample testing.

FIG. 3 shows a variety of different testing that can be performed to screen and diagnose an upper respiratory infection (500), for example in a clinical trial. In clinical settings, however, typically very few, if any, of these tests are initially performed. Instead, a rapid test, if available, is preferably performed to initially screen for pathogens.

Nasopharyngeal and oropharyngeal samples may be collected for PCR (501) (see top left side of FIG. 3). If Epstein-Barr virus (EBV) PCR (502) is negative (503) for IgM EBV (serum sample), the result is considered microbiologically unconfirmed (511). If the EBV PCR is positive (504) for IgM EBV (serum sample), there is microbiological confirmation (505) of a viral infection.

Respiratory panel PCR, viral IFA or viral antigen testing (506) may also or alternatively be performed. One example of the respiratory panel PCR that could be performed is BioFire® respiratory panel PCR, but alternative respiratory panel PCR systems could be used. A sample positive for influenza A/B, parainfluenza 1-4, Metapneumovirus, Adenovirus, Respiratory Synctial Virus (RSV), Rhinovirus or Coronovirus (507), combined with either a positive paired serology or a level of MxA greater than or equal to 25 ng/ml (590), confirms a viral infection (505). Positive (+) viral PCR, viral culture, viral IFA, or viral antigen testing for Influenza, Parainfluenza 1-4, Metapneumovirus, Adenovirus, RSV, Rhinovirus, or Coronavirus (507) without positive paired serology or elevated MxA (≥25 ng/ml) (595) is classified as a non-systemic host response (509).

If the sample is positive for any of the atypical bacteria *Bordetella pertussis*, *Chlamydophila pneumoniae* or *Mycoplasma pneumoniae* (512), and either procalcitonin levels are less than 0.1 ng/ml or C-reactive protein levels are less than 20 mg/l (513), the diagnosis (514) is negative. If the sample is positive (512) for any of these atypical bacteria and the procalcitonin level is greater than or equal to 0.1 ng/ml or the C-reactive protein levels are greater than or equal to 20 mg/l or there is paired serology (517), a bacterial infection is microbologically confirmed (518).

If the sample is negative for Influenza A/B, Parainfluenza 1-4, Metapneumovirus, Adenovirus, RSV, Rhinovirus, Coronavirus, *Bordetella*, *Chlamydia*, and *Mycoplasma* (510), the illness is classified as microbiologically unconfirmed (511).

Oropharyngeal samples for cell culture (Cx) or PCR (515) (top right side of FIG. 3) may alternatively or additionally be taken. If the sample is positive for Group A Strep (cell culture), Group C strep (cell culture), *Arcanobacterium* (cell culture), or *Fusobacterium* (PCR) (516), which are all typical IDSA-listed bacteria, and procalcitonin levels are greater than or equal to 0.1 ng/ml or C-reactive protein levels are greater than or equal to 20 mg/l or there is positive paired serology (517), there is microbiological confirmation (518) of a bacterial infection. If there are levels of non-IDSA listed bacteria of $10^6$ or greater in cell culture (519) (bacterial growth greater than $1 \times 10^6$ colony forming units (CFU)/mL), and the procalcitonin level is greater than or equal to 0.25 ng/ml, the procalcitonin levels are greater than or equal to 0.15 ng/ml but less than 0.25 ng/ml and either the white blood cell count is greater than 12,000 or bands are present, the C-reactive protein level is greater than 80 mg/l, or the C-reactive protein is greater than or equal to 20 mg/l but less than 80 mg/l and either the white blood cell count is greater than or equal to 12,000 or there are bands (520), there is also microbiological confirmation (518) of bacterial infection. If PCR is positive for *Neisseria* (521), the infection is confirmed (518) as bacterial. If cell culture is positive for Group A or Group C strep (522), the procalcitonin levels are less than 0.1 ng/ml or the C-reactive protein levels are less than 20 mg/l (523), there is positive paired serology or at least 80% ULN Streptolysin O antibody (ASO) and a white blood cell count greater than or equal to 12,000 (524), the infection is confirmed (518) as bacterial. If cell culture is positive for Group A or Group C strep (522), the procalcitonin levels are less than 0.1 ng/ml or the C-reactive protein levels are less than 20 mg/l (523), there is negative paired serology or less than 80% ULN Streptolysin O antibody (ASO) and the white blood cell count is less than 12,000 (529), there is colonization (527) (and the sample is considered microbiologically unconfirmed (511)).

If there are levels of non-IDSA listed bacteria of $10^6$ or greater in cell culture (525) (bacterial growth greater than $1 \times 10^6$ colony forming units (CFU)/mL), and the levels of procalcitonin are less than 0.15 ng/ml, the procalcitonin levels are greater than or equal to 0.15 ng/ml but less than 0.25 ng/ml and the white blood cell count is less than 12,000 and there are no bands, the C-reactive protein levels are less than 20 mg/l, or the C-reactive protein levels are greater than or equal to 20 mg/l but less than 80 mg/l and the white blood cell count is less than 12,000 and there are no bands (526), there is colonization (527) (and the sample is considered microbiologically unconfirmed (511)). If there is no cell culture growth and the sample is negative for PCR (528), the sample is considered microbiologically unconfirmed (511). Since PCR is highly sensitive, it is unlikely that a viral or atypical bacterial will not be detected. Thus, any elevated procalcitonin greater than or equal to 0.1 ng/ml is more likely bacterial.

All of the microbiologically unconfirmed (511) results may then be further analyzed (see bottom portion of FIG. 3). Further analysis is only performed if there has been no confirmation of bacterial or viral infection. The clinician does not perform further analysis if he has confirmed either bacterial or viral infection.

If procalcitonin levels are less than 0.15 ng/ml or C-reactive protein levels are less than 20 mg/l in these samples (530), the patient is diagnosed (531) as negative. If procalcitonin levels are greater than or equal to 0.15 ng/ml but less than 0.25 ng/ml in these samples, the white blood cell count is less than 15,000 and there are no bands, or the C-reactive protein levels are greater than or equal to 20 mg/l but less than 80 mg/l, the white blood cell count is less than 15,000 and there are no bands (532), the patient is diagnosed (533) with a viral infection. If procalcitonin levels are greater than or equal to 0.25 ng/ml, procalcitonin levels are greater than or equal to 0.15 ng/ml but less than 0.25 ng/ml and the white blood cell count is greater than or equal to 15,000 or bands are present, the C-reactive protein levels are greater or equal to 80 mg/l, or the C-reactive protein levels are greater than or equal to 20 mg/l but less than 80 mg/l and the white blood cell count is greater than or equal to 15,000 or bands are present (534), the patient is diagnosed (535) with a bacterial infection. The final clinical diagnosis (536) is either negative, viral or bacterial.

Note that, if the MxA levels are greater than 25 ng/ml, the diagnosis is considered viral regardless of what the C-reactive protein or procalcitonin value is. The practitioner should not prescribe antibiotics, and instead take a watchful waiting approach, re-evaluating later or doing reflex testing.

Figure 4:
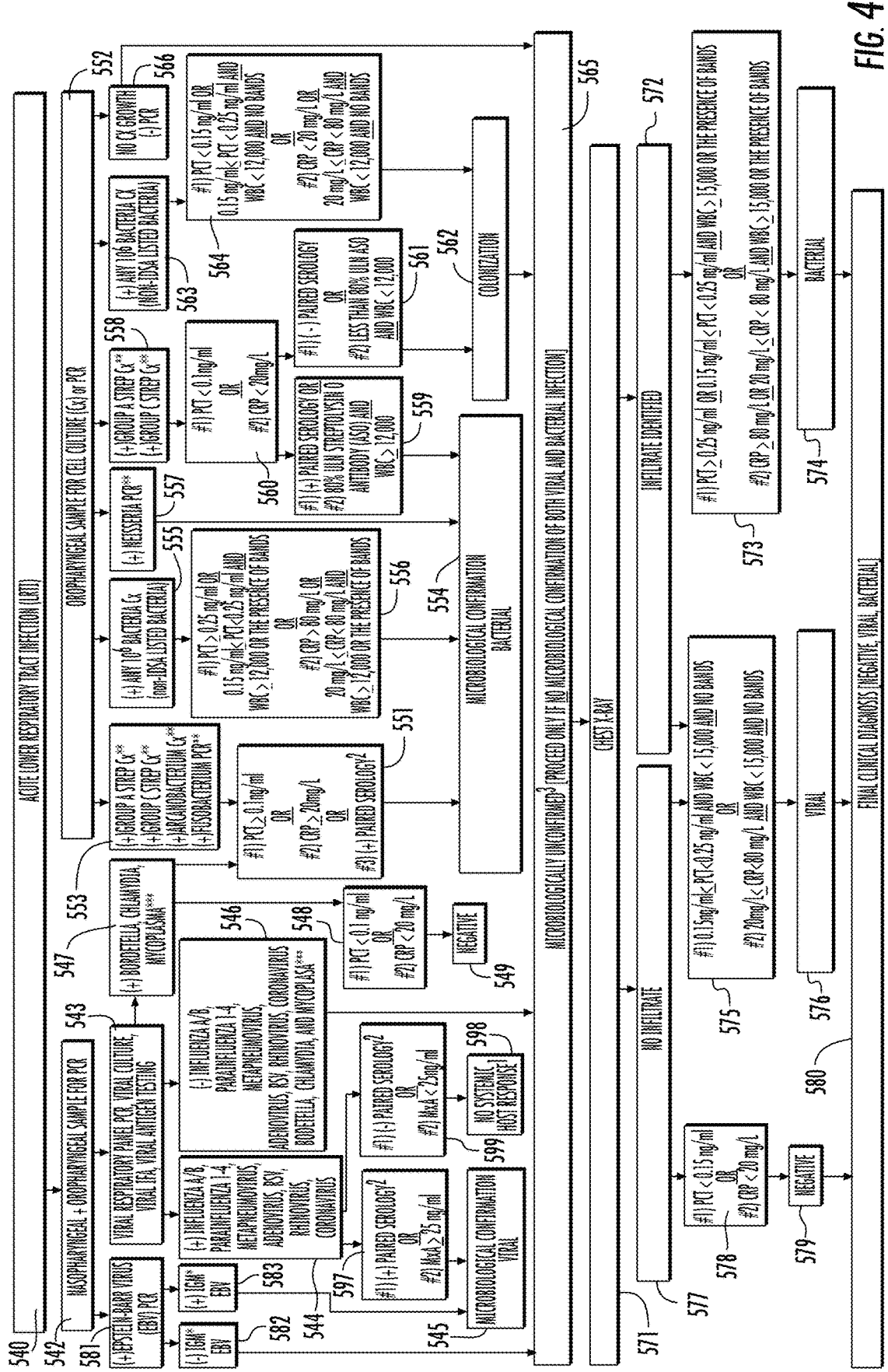
FIG. 4 shows a novel method for diagnosing lower respiratory infections and identifying colonization.

FIG. 4 shows an embodiment of a method to diagnose lower respiratory infections (540) and colonization using MxA, C-reactive protein, procalcitonin and other assays. FIG. 4 shows a variety of different testing that can be performed to screen and diagnose a lower respiratory tract infection (540), for example in a clinical trial. In clinical settings, however, typically very few, if any, of these tests are initially performed. Instead, a rapid test, if available, is preferably performed to initially screen for pathogens.

Nasopharyngeal and oropharyngeal samples may be collected for PCR (542) (top left side of FIG. 4). If Epstein-Barr virus (EBV) PCR (581) is negative (582) for IgM EBV (serum sample), the result is considered microbiologically unconfirmed (565). If the EBV PCR is positive (583) for IgM EBV (serum sample), there is microbiological confirmation (545) of a viral infection.

Respiratory panel PCR, viral IFA or viral antigen testing (543) may also or alternatively be performed. Although a Biofire® respiratory panel PCR is identified in this figure, other respiratory panel PCR systems could alternatively be used. A sample positive for influenza A/B, parainfluenza 1-4, Metapneumovirus, Adenovirus, Respiratory Synctial Virus (RSV), Rhinovirus or Coronovirus (544), combined with either a positive paired serology or a level of MxA greater than or equal to 25 ng/ml (597), confirms a viral infection (545). Positive (+) viral PCR, viral culture, viral IFA, or viral antigen testing for Influenza, Parainfluenza 1-4, Metapneumovirus, Adenovirus, RSV, Rhinovirus, or Coronavirus (544) without positive paired serology or elevated MxA (>25 ng/ml) (599) is classified as a non-systemic host response (598).

If the sample is positive for *Bordetella pertussis, Chlamydophila pneumoniae* or *Mycoplasma pneumoniae* (547), and procalcitonin levels are less than 0.1 ng/ml or C-reactive protein levels are less than 20 mg/l (548), the diagnosis (549) is negative. If the sample is positive for any of these atypical bacteria (547) and the procalcitonin level is greater than or equal to 0.1 ng/ml or the C-reactive protein levels are greater than or equal to 20 mg/l or there is paired serology (551), a bacterial infection is microbologically confirmed (554).

If the sample is negative for Influenza A/B, Parainfluenza 1-4, Metapneumovirus, Adenovirus, RSV, Rhinovirus, Coronavirus, *Bordetella, Chlamydia*, and *Mycoplasma* (546), the illness is classified as microbiologically unconfirmed (565).

Urinary antigen testing or PCR (not shown in the Figures) may be used for *Pneumococcus* and *Legionella* testing according to use for lower respiratory tract infections.

Oropharyngeal samples for cell culture (Cx) or PCR (552) (top right side of FIG. 4) may alternatively or additionally be taken. If the sample is positive for Group A Strep (cell culture), Group C strep (cell culture), *Arcanobacterium* (cell culture), or *Fusobacterium* (PCR) (553), which are all typical IDSA-listed bacteria, and procalcitonin levels are greater than or equal to 0.1 ng/ml or C-reactive protein levels are greater than or equal to 20 mg/l or there is positive paired serology (551), there is microbiological confirmation (554) of a bacterial infection. If there are levels of non-IDSA listed bacteria of $10^6$ or greater in cell culture (555) (bacterial growth greater than $1\times10^6$ colony forming units (CFU)/mL), and the procalcitonin level is greater than or equal to 0.25 ng/ml, the procalcitonin levels are greater than or equal to 0.15 ng/ml but less than 0.25 ng/ml and either the white blood cell count is greater than 12,000 or bands are present, the C-reactive protein level is greater than 80 mg/l, or the C-reactive protein is greater than or equal to 20 mg/l but less than 80 mg/l and either the white blood cell count is greater than or equal to 12,000 or there are bands (556), there is also microbiological confirmation (554) of bacterial infection. If PCR is positive for *Neisseria* (557), the infection is confirmed (554) as bacterial. If cell culture is positive for Group A or Group C strep (558), the procalcitonin levels are less than 0.1 ng/ml or the C-reactive protein levels are less than 20 mg/l (560), there is positive paired serology or at least 80% ULN Streptolysin O antibody (ASO) and a white blood cell count greater than or equal to 12,000 (559), the infection is confirmed (554) as bacterial. If cell culture is positive for Group A or Group C strep (559), the procalcitonin levels are less than 0.1 ng/ml or the C-reactive protein levels are less than 20 mg/l (560), there is negative paired serology or less than 80% ULN Streptolysin O antibody (ASO) and the white blood cell count is less than 12,000 (561), there is colonization (562) (and the sample is considered microbiologically unconfirmed (565)).

If there are levels of non-IDSA listed bacteria of $10^6$ or greater in cell culture (563) (bacterial growth greater than $1\times10^6$ colony forming units (CFU)/mL), and the levels of procalcitonin are less than 0.15 ng/ml, the procalcitonin levels are greater than or equal to 0.15 ng/ml but less than 0.25 ng/ml and the white blood cell count is less than 12,000 and there are no bands, the C-reactive protein levels are less than 20 mg/l, or the C-reactive protein levels are greater than or equal to 20 mg/l but less than 80 mg/l and the white blood cell count is less than 12,000 and there are no bands (564), there is colonization (562) (and the sample is considered microbiologically unconfirmed (565)). If there is no cell culture growth and the sample is negative for PCR (566), the sample is considered microbiologically unconfirmed (565). Since PCR is highly sensitive, it is unlikely that a viral or atypical bacterial will not be detected; thus, any elevated procalcitonin greater than or equal to 0.1 ng/ml is more likely bacterial.

The patients with microbiologically unconfirmed results (565) may be subject to a chest X-ray (571) to determine if infiltrate is identified. Further analysis is only performed if there has been no confirmation of bacterial or viral infection. The clinician does not perform further analysis if he has confirmed either bacterial or viral infection.

If an infiltrate is identified (572), and procalcitonin levels are greater than or equal to 0.15 ng/ml but less than 0.25 ng/ml in these samples, the white blood cell count is less than 15,000 and there are no bands, or the C-reactive protein levels are greater than or equal to 20 mg/l but less than 80 mg/l, the white blood cell count is less than 15,000 and there are no bands (575), the patient is diagnosed (576) with a viral infection. If procalcitonin levels are greater than or equal to 0.25 ng/ml, procalcitonin levels are greater than or equal to 0.15 ng/ml but less than 0.25 ng/ml and the white blood cell count is greater than or equal to 15,000 or bands are present, the C-reactive protein levels are greater or equal to 80 mg/l, or the C-reactive protein levels are greater than or equal to 20 mg/l but less than 80 mg/l and the white blood cell count is greater than or equal to 15,000 or bands are present (573), the patient is diagnosed (574) with a bacterial infection. If the procalcitonin levels are greater than or equal to 0.15 ng/ml but less than 0.25 ng/ml in these samples, the white blood cell count is less than 15,000 and there are no bands, or the C-reactive protein levels are greater than or equal to 20 mg/l but less than 80 mg/l, the white blood cell count is less than 15,000 and there are no bands (575), the patient is diagnosed (576) with a viral infection.

If no infiltrate is identified (577), and the procalcitonin levels are greater than or equal to 0.15 ng/ml but less than 0.25 ng/ml in these samples, the white blood cell count is less than 15,000 and there are no bands, or the C-reactive protein levels are greater than or equal to 20 mg/l but less than 80 mg/l, the white blood cell count is less than 15,000 and there are no bands (575), the patient is diagnosed (576) with a viral infection. If the procalcitonin level is less than 0.15 ng/ml or the C-reactive protein levels are less than 20 mg/l (578), the illness is classified as negative (579). The final clinical diagnosis (580) is either negative, viral or bacterial.

Note that, if the MxA levels are greater than 25 ng/ml, the diagnosis is considered viral regardless of what the C-reactive protein or procalcitonin value is. The practitioner should not prescribe antibiotics, and instead take a watchful waiting approach, re-evaluating later or doing reflex testing.

Although FIGS. 3 and 4 show embodiments for diagnosing respiratory infections, the MxA, C-reactive protein and procalcitonin values in the figures could alternatively be used to diagnose other types of bacterial and viral infections (for example gastric infections, meningitis, encephalitis, cellulitis, urinary tract infections, otitis and conjunctivitis), as well as identifying colonization.

Figure 17:
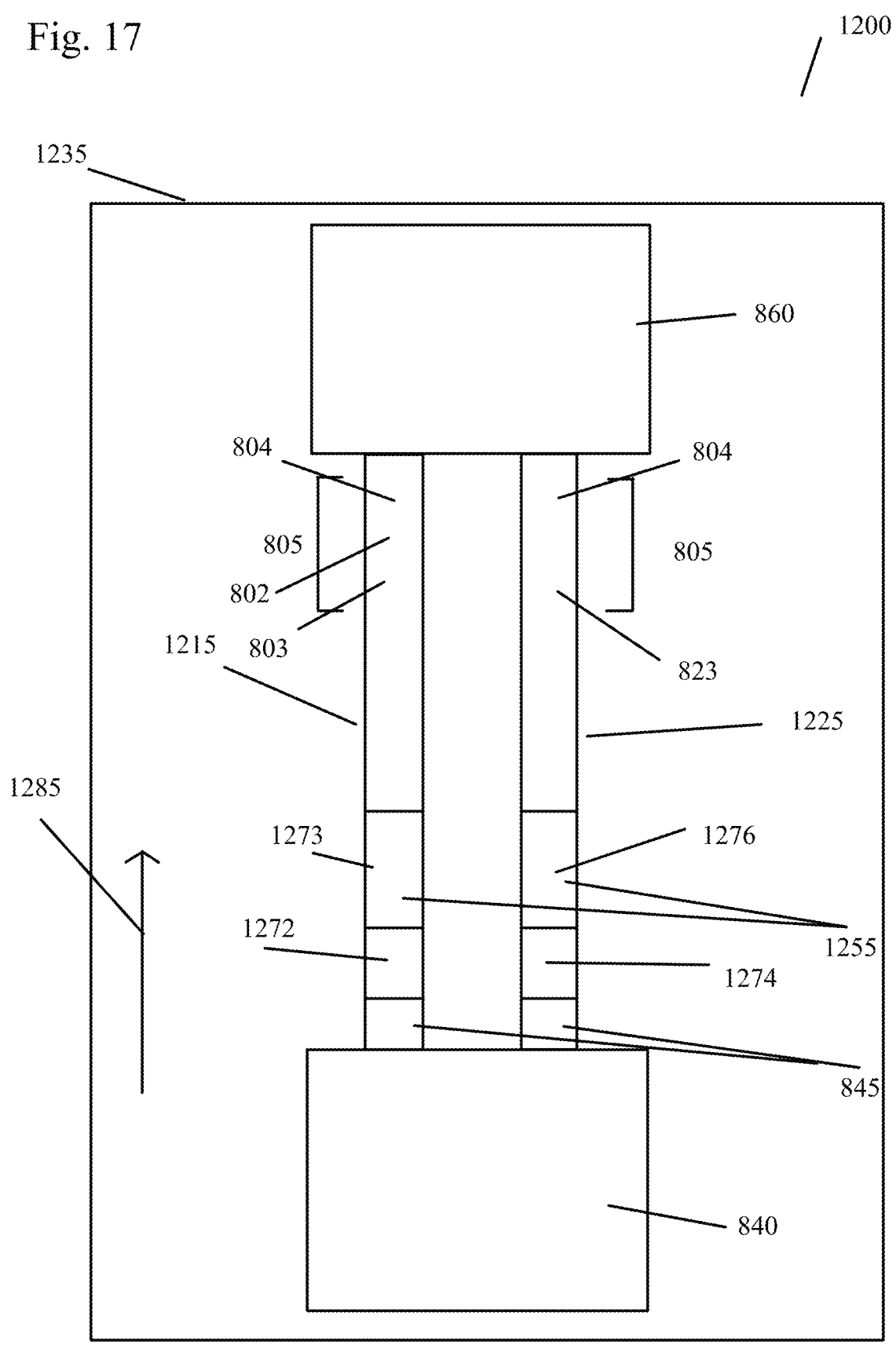
FIG. 17 shows a sample analysis device with dual test strips.

In one example, any of the devices shown in FIG. 13, 15 or 17 could be used to differentiate an active infection from colonization of a virus or bacteria. A direct Antigen detection test such as Strep test or any PCR cannot differentiate colonization from active infection. Only a test that detects the host's immune response such as biomarkers of the host's origin is able to accomplish such a differentiation. Assaying for both MxA and C-reactive protein (or PCT) permits the user to obtain screening data for both bacterial and viral infections, increasing the ability of determining colonization.

No treatment is needed for colonization. This type of "localized infection" clears by itself without becoming an active infection.

Figure 18:
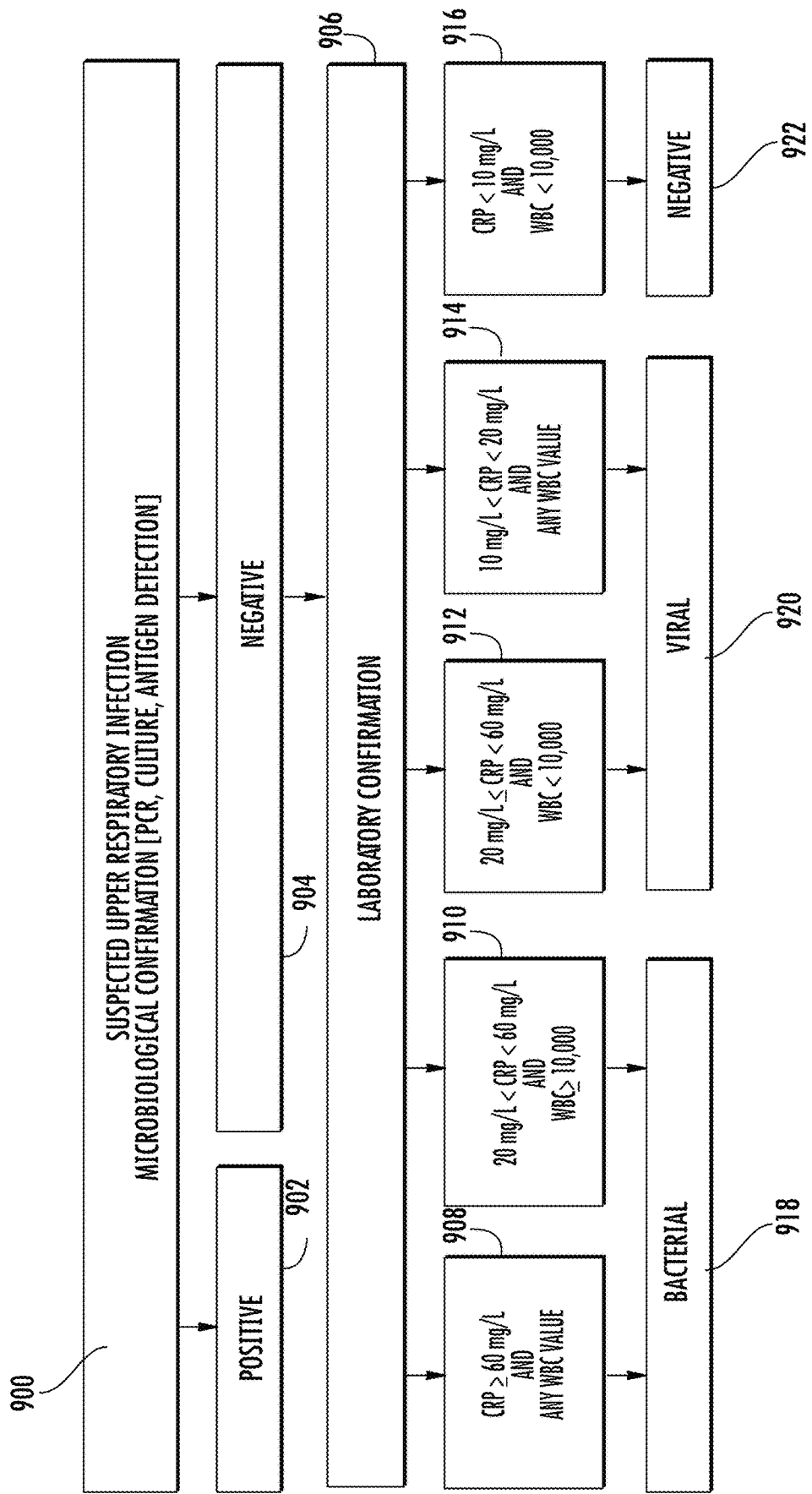
FIG. 18 shows a method of confirming whether a suspected, but microbiologically unconfirmed, upper respiratory infection is bacterial or viral.
Figure 19:
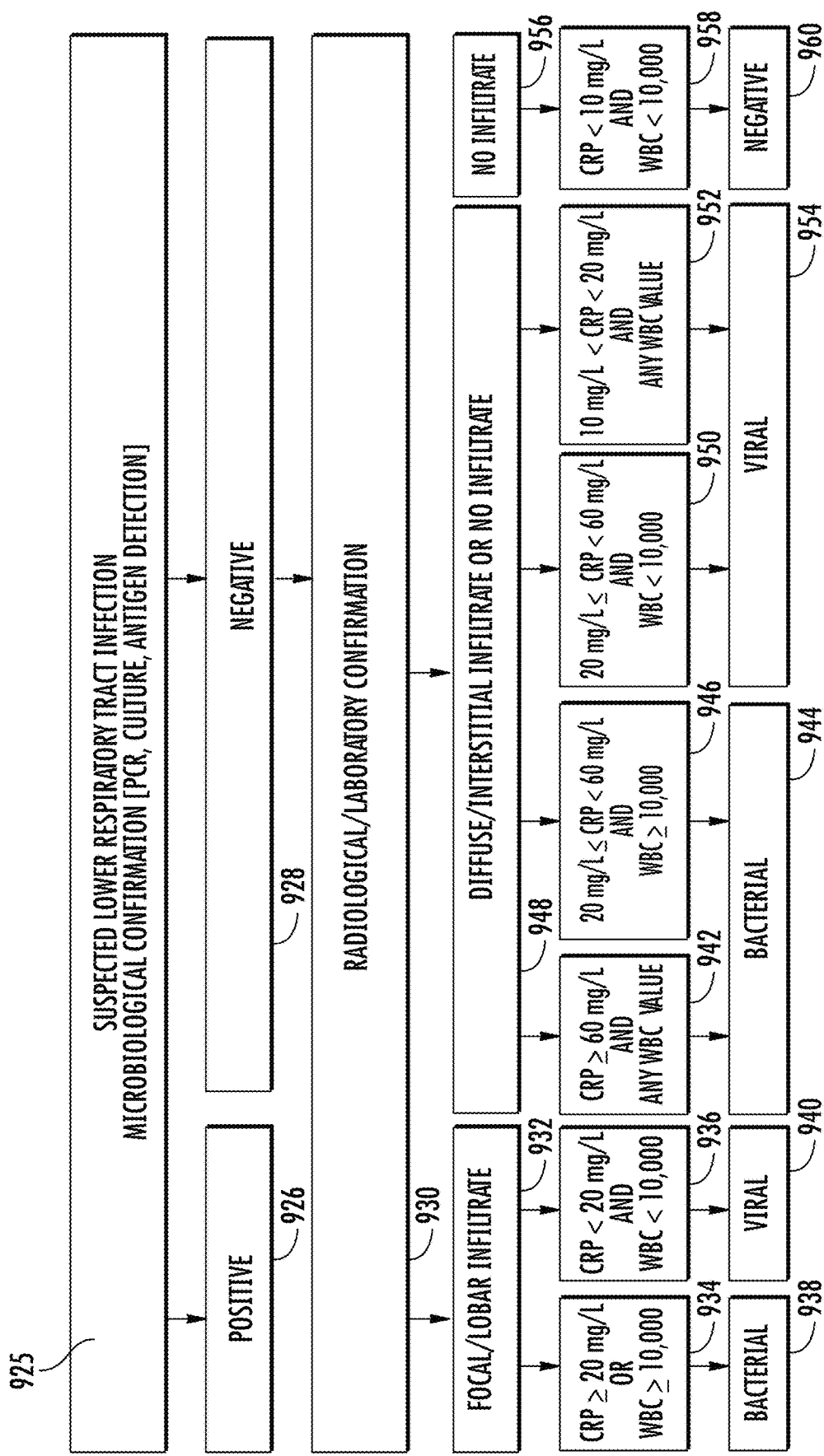
FIG. 19 shows a method of confirming whether a suspected, but microbiologically unconfirmed, lower respiratory infection is bacterial or viral.
Figure 20:
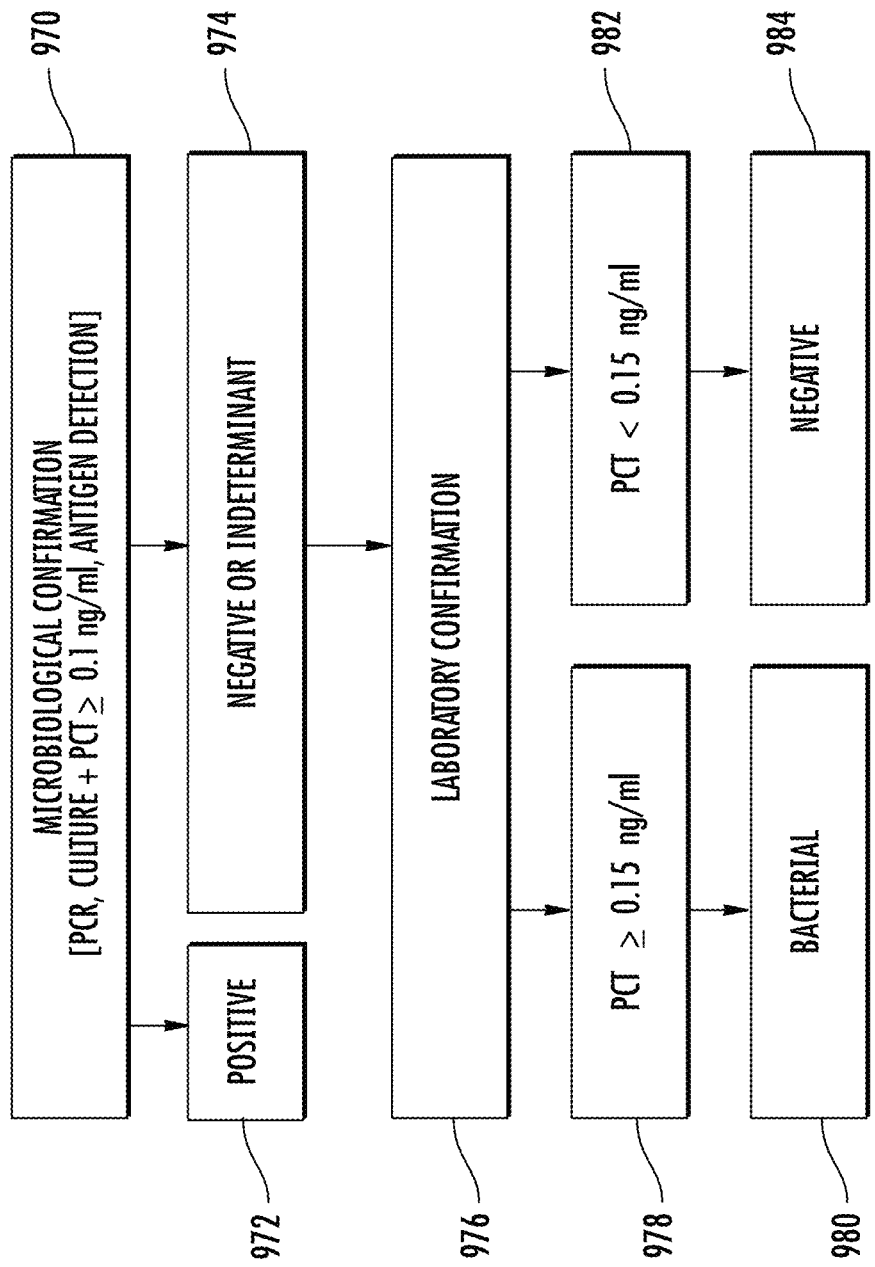
FIG. 20 shows a method for confirming bacterial infection in microbiologically unconfirmed patients.

FIGS. 18 and 19 use C-reactive protein to diagnose microbiologically unconfirmed patients with a respiratory infection. FIG. 18 shows diagnostic methods for patients with a suspected upper respiratory infection. If microbiological tests, such as PCR, culture, or antigen detection (900), are positive (902) for bacterial or virus, the patient is diagnosed (918), (920) with a bacterial or viral infection. If the microbiologically confirmatory tests (e.g. —PCR, culture, and/or antigen detection) are negative (904), further laboratory confirmation (906) is performed. If the patient has C-reactive protein values of greater than or equal to 60 mg/L and any white blood cell value (908), the patient is diagnosed (918) with a bacterial infection. If the patient has a C-reactive protein value 20 mg/L<CRP<60 mg/L and a white blood cell count greater than or equal to 10,000 (910), they are also diagnosed (918) with a bacterial infection. If the patient has a C-reactive protein value 20 mg/L<CRP<60 mg/L and a white blood cell count less than 10,000 (912), the patient is diagnosed (920) with a viral infection. If the patient has a C-reactive protein value 10 mg/L<CRP<20 mg/L and any white blood cell value (914), the patient is also diagnosed (920) with a viral infection. If the patient has a C-reactive protein value of less than 10 mg/L and a white blood cell count of less than 10,000 (916), the patient is diagnosed (922) as negative for infection. White blood cell counts are less than 50% specific and cannot differentiate a viral or bacterial infection. White blood cell count elevation is not diagnostic of a clinically significant infection.

FIG. 19 shows diagnostic methods for patients with a suspected lower respiratory infection. If microbiological tests, such as PCR, culture, or antigen detection (925), are positive (926) for bacteria or virus, the patient is diagnosed with a bacterial or viral infection. In the presence of a systemic immune response, any PCR is considered positive or if the patient has a radiologically confirmed pneumonia. If the microbiologically confirmatory tests (e.g.—PCR, culture, and/or antigen detection) are negative (928), further radiological or laboratory confirmation (930) is performed. The presence of radiologic evidence of diffuse infiltrates by chest X-ray suggests a viral infection while the presence of radiologic evidence of a focal lobar process or infiltrate by chest X-ray suggests a bacterial infection. If the patient has a focal/lobar infiltrate (932) and the C-reactive protein levels are greater than or equal to 20 mg/L or the white blood cell count is greater than or equal to 10,000 (934), the patient is diagnosed (938) with a bacterial infection. If the patient has a focal/lobar infiltrate (932) and the C-reactive protein levels are less than 20 mg/L and the white blood cell count is less than 10,000 (936), the patient is diagnosed (940) with a viral infection. If a patient has C-reactive protein levels less than 20 mg/L and a white blood cell count greater than 10,000

(not shown), they may have a noninfectious conditions such as asthma or COPD exacerbation. If the patient has diffuse/interstitial infiltrate or no infiltrates (948), a C-reactive protein level greater than or equal to 60 mg/L and any white blood cell value (942), the patient is diagnosed (944) with a bacterial infection. If the patient has diffuse/interstitial infiltrate or no infiltrates (948), a C-reactive protein level 20 mg/L<CRP<60 mg/L and a white blood cell count of greater than or equal to 10,000 (946), the patient is also diagnosed (944) with a bacterial infection. If the patient has diffuse/interstitial infiltrate or no infiltrates (948), a C-reactive protein level 20 mg/L<CRP<60 mg/L and a white blood cell count of less than 10,000 (950), the patient is diagnosed (954) with a viral infection. If the patient has diffuse/interstitial infiltrate or no infiltrates (948), a C-reactive protein level 10 mg/L<CRP<20 mg/L and any white blood cell count (952), the patient is also diagnosed (954) with a viral infection. If the patient has no infiltrate (956), a C-reactive protein value of less than 10 mg/L and a WBC count of less than 10,000 (958), the patient is diagnosed as negative (960) for infection, and the result may indicate colonization.

The methods in FIGS. 18 and 19 could be used in combination with determining MxA levels, to better diagnose patients with a viral or bacterial infection, colonization, or a microbiologically unconfirmed illness.

The Applicants note that they have found that co-infection is very unusual. Many peer reviewed studies did not differentiate colonization from infection so all colonized people would appear to have a pseudo-co-infection. This is actually untrue because using C-reactive protein alone at 20 mg/ml to determine treatment did not lead to increased morbidity despite not treating many culture positive patients.

During a dual test strip prospective, multicenter clinical trial, rhinovirus was confirmed present by PCR in 52 subjects; however, only 8/52 patients actually demonstrated an elevation in MxA. Of those patients with confirmed rhinovirus and elevated MxA, the Applicant's dual test strip correctly identified 5/8. Because rhinovirus is not included in the intended use and 8 patients had an elevated MxA, these patients were deemed "false positive," despite being correct, which led to an artificially lower viral specificity. Colonization of viral or bacterial pathogens or periodic viral shedding without an invasive systemic response was not detected. The presence of elevated procalcitonin and/or white blood cell count in association with known pathogens was required to differentiate bacterial colonization from active infection. Since rhinovirus and coronavirus are frequent colonizers of the respiratory tract and only cause a clinically significant active infection in approximately 10% of patients, these two viruses were not included in the intended use.

The novel method may differentiate colonizing virus from active invasive infection in various different ways. In one embodiment, the method is used to detect only Influenza A/B, Metapneumovirus, Adenovirus, RSV, Parainfluenza Virus, and Epstein-Barr Virus while excluding Rhinovirus, Coronavirus, HSV, and CMV. In another embodiment, to differentiate true infection from colonization or latent shedding, Herpes Simplex virus, Cytomegalovirus, Rhinovirus, and Coronavirus will be deemed to be true positives if they are PCR positive and associated with a normal procalcitonin level and elevated MxA≥25 ng/ml. In yet another embodiment, if Epstein-Barr, HSV, or CMV is positive by PCR, the presence of a simultaneous positive IgM blood test would confirm true positive. The risk is that it takes 5-7 days for an IgM antibody to develop. This embodiment is not applicable to Rhinovirus or CMV. In this embodiment, a positive viral (EBV, HSV, or CMV) PCR and a positive (EBV, HSV, or CMV) VCA (viral capsid antigen) IgG Test indicates new viral infection. A positive viral (EBV, HSV, or CMV) PCR and a negative (EBV, HSV, or CMV) VCA IgG Test indicates no acute infection. A negative viral (EBV, HSV, or CMV) PCR and a positive (EBV, HSV, or CMV) VCA IgG Test indicates a false positive.

Current protocols lead to over diagnosis of bacterial infection, inappropriate antibiotic use, and deviate from current antibiotic stewardship recommendations. Outcome studies from 14 randomized clinical trials (Muller, F et al. Procalcitonin levels predict bacteremia in patients with community-acquired pneumonia: a prospective cohort trial. Chest 2010, 138:121-129; van Nieuwkoop, C. et al. Procalcitonin reflects bacteremia and bacterial load in urosepsis syndrome: a prospective observational study. Crit Care 2010, 14:R206; Riedel, S et al. Procalcitonin as a marker for the detection of bacteremia and sepsis in the emergency department. Am J Clin Pathol 2011, 135:182-189; Schuetz, P. et al., Serum procalcitonin for discrimination of blood contamination from bloodstream infection due to coagulase-negative staphylococci. Infection 2007, 35:352-355; Christ-Crain, M. et al., Effect of procalcitonin-guided treatment on antibiotic use and outcome in lower respiratory tract infections: cluster-randomised, single-blinded intervention trial. Lancet 2004, 363:600-607; Schuetz, P. et al., ProHOSP Study Group: Effect of procalcitonin-based guidelines vs standard guidelines on antibiotic use in lower respiratory tract infections: the ProHOSP randomized controlled trial. JAMA 2009, 302:1059-1066; Stolz, D. et al., Antibiotic treatment of exacerbations of COPD: a randomized, controlled trial comparing procalcitonin-guidance with standard therapy. Chest 2007, 131:9-19; Christ-Crain M., Procalcitonin guidance of antibiotic therapy in community-acquired pneumonia: a randomized trial. Am J Respir Crit Care Med 2006, 174:84-93; Kristoffersen, K B et al., Antibiotic treatment interruption of suspected lower respiratory tract infections based on a single procalcitonin measurement at hospital admission—a randomized trial. Clin Microbiol Infect 2009, 15:481-487; Long, W. et al., [The value of serum procalcitonin in treatment of community acquired pneumonia in outpatient]. Zhonghua Nei Ke Za Zhi 2009, 48:216-219; Long, W. et al., Procalcitonin-guidance for reduction of antibiotic use in low-risk outpatients with community acquired pneumonia. Respirology 2011, 16:819-824; Burkhardt, O. et al., Procalcitonin guidance and reduction of antibiotic use in acute respiratory tract infection. Eur Respir J 2010, 36:601-607; Elsammak et al., Diagnostic value of serum procalcitonin and C-reactive protein in Egyptian children with *streptococcal* tonsillopharyngitis. Pediatr Infect Dis J 2006; 25:174-6; Bouadma, L. et al., M, PRORATA trial group: Use of procalcitonin to reduce patients' exposure to antibiotics in intensive care units (PRORATA trial): a multicentre randomised controlled trial. Lancet 2010, 375:463-474; Stolz, D. et al., Procalcitonin for reduced antibiotic exposure in ventilator-associated pneumonia: a randomised study. Eur Respir J 2009, 34:1364-1375; Briel, M. et al., Procalcitonin-guided antibiotic use vs a standard approach for acute respiratory tract infections in primary care. Archives Intern Med. 2008; 168:2000-7, all incorporated herein by reference), as well as the draft NICE guidelines for using C-reactive protein, support this.

Prior art protocols, which used the recommended cut off values of 0.15 ng/ml for procalcitonin and did not assay MxA levels, miscategorized two patients in one of our studies with group C Strep and elevated procalcitonin as viral and an additional two patients without a microbiological bacterial confirmation as viral.

The novel methods described herein use procalcitonin or C-reactive protein to differentiate colonization from true bacterial infection. The novel methods also use MxA to differentiate between a viral infection and no systemic host response.

Testing for C-reactive protein and MxA measures a clinically significant immune response to a suspected invasive viral and/or bacterial infection in patients older than 1 year that present within 3 days of an acute onset fever and within 7 days of new onset respiratory symptoms consistent with a suspected community acquired upper respiratory infection (rhinopharyngitis, tonsillopharyngitis, laryngotracheitis) or lower respiratory tract infection (tracheobronchitis, bronchiolitis, or pneumonia). These tests help to identify 1) patients with an underlying invasive viral infection from either Influenza A/B, Adenovirus, Respiratory Syncytial Virus, Metapneumovirus, Parainfluenza Virus, or Epstein-Barr Virus; 2) patients with a clinically significant elevated host response consistent with an underlying bacterial infection. Testing for MxA and C-reactive protein can result in a positive viral infection (if the MxA level creates a positive MxA result), a positive bacterial infection (if the C-reactive protein levels create positive C-reactive protein results), or co-infection (if both the MxA and C-reactive protein levels are positive). While co-infection is more likely with this assay, the Applicant's studies did not confirm any patients with co-infection. If they are negative, they result in a microbiologically unconfirmed respiratory illness. Some examples of test strips that use MxA and C-reactive protein levels to diagnose infection are described further below.

Additional testing can confirm that the negative result is truly negative for infection. Some examples of ways to confirm that a patient with a respiratory illness is negative for infection, in addition to testing them for MxA, C-reactive protein, and/or procalcitonin, include a negative PCR respiratory panel (for example, a BioFire™ respiratory panel, Biofire Diagnostics, Inc., Salt Lake City, Utah), a negative sputum, blood, or throat cultures, negative additional viral PCR testing, negative urine antigen tests or a negative chest X-ray.

If microbiologically unconfirmed patients have one or more of these negative results, they are presumed noninfectious. These noninfectious patients may have, for example, an allergy, drug fever, cancer, connective tissue disease, thyroid disease, gout, inflammatory bowel disease, sarcoidosis, vaccination, or blood clots. As discussed below, additional testing may be performed to try to microbiologically confirm the etiology of their illness.

Microbiologically Unconfirmed (MU) Diagnoses

As a general comment, the Applicant observed more microbiologically unconfirmed cases than expected in its trials. This was partially due to seasonal timing (the first trial occurred in winter and the second trial in spring and summer), but the results were similar to literature reports. Based on an extensive literature review, an average estimated prevalence of microbiologically unconfirmed (MU) illnesses is 50%.

Microbiologically unconfirmed illnesses can be due to a true negative, colonization, or a microbiologically unconfirmed (MU) illness that could be an emergent, previously unidentified illness.

In some embodiments, when the cause of a patient's illness is still microbiologically unconfirmed after testing, additional steps are taken to try to determine a diagnosis. One additional step is taking a second sample from the patient and retesting for one or more of the same biomarkers tested in the first sample. The second sample is preferably taken between four and seventy two hours after the first sample. In some preferred embodiments, the second sample is taken within twenty four hours after the first sample has been taken. In other preferred embodiments, the second sample is taken within four to twelve hours after the first sample has been taken. In other preferred embodiments, the second sample is taken within six to eight hours after the first sample has been taken.

In some preferred embodiments, another sample is taken from the patient within four to seventy two hours after the initial sample was taken to test for MxA, C-reactive protein, and/or procalcitonin, and tested a second time for the presence of elevated MxA, C-reactive protein and/or procalcitonin.

In some embodiments, the second test is preferably a quantitative test, to determine if the levels of one or more of these biomarkers has increased. In some of these embodiments, the second sample is tested for MxA within four to eight hours of the initial test. In other embodiments, additional research and testing is done to try to determine if a patient with a microbiologically unconfirmed diagnosis has an emergent disease or illness.

With respect to FIGS. 3-4 and 18-20, the patients that are ultimately diagnosed as negative in those methods are considered still microbiologically unconfirmed.

The devices in FIGS. 13 and 15 provide a rapid test that can differentiate an active infection from a respiratory or other type of illness of either viral or bacterial etiology. Procalcitonin and C-reactive protein alone cannot. No treatment is needed for microbiologically unconfirmed illnesses. However, additional MxA and C-reactive protein (or procalcitonin) testing done within a shorter time period, such as taking a second sample four to seventy two hours hours after the first sample and assaying it for the presence of these biomarkers, may be prudent to rule out the prodrome effect. Alternatively, additional testing for MxA, C-reactive protein, and/or procalcitonin, alone or in combination, with a second sample taken four to seventy two hours after the first sample used to identify the presence of these biomarkers could better identify the etiology of the patient's illness. This second test also rules out the prodrome effect.

The second sample to test for MxA, C-reactive protein, and/or procalcitoninis is preferably taken between four and seventy two hours after the first sample. In some preferred embodiments, the second sample is taken within twenty four hours after the first sample has been taken. In other preferred embodiments, the second sample is taken within four to twelve hours after the first sample has been taken. In other preferred embodiments, the second sample is taken within six to eight hours after the first sample has been taken.

Figure 13A:
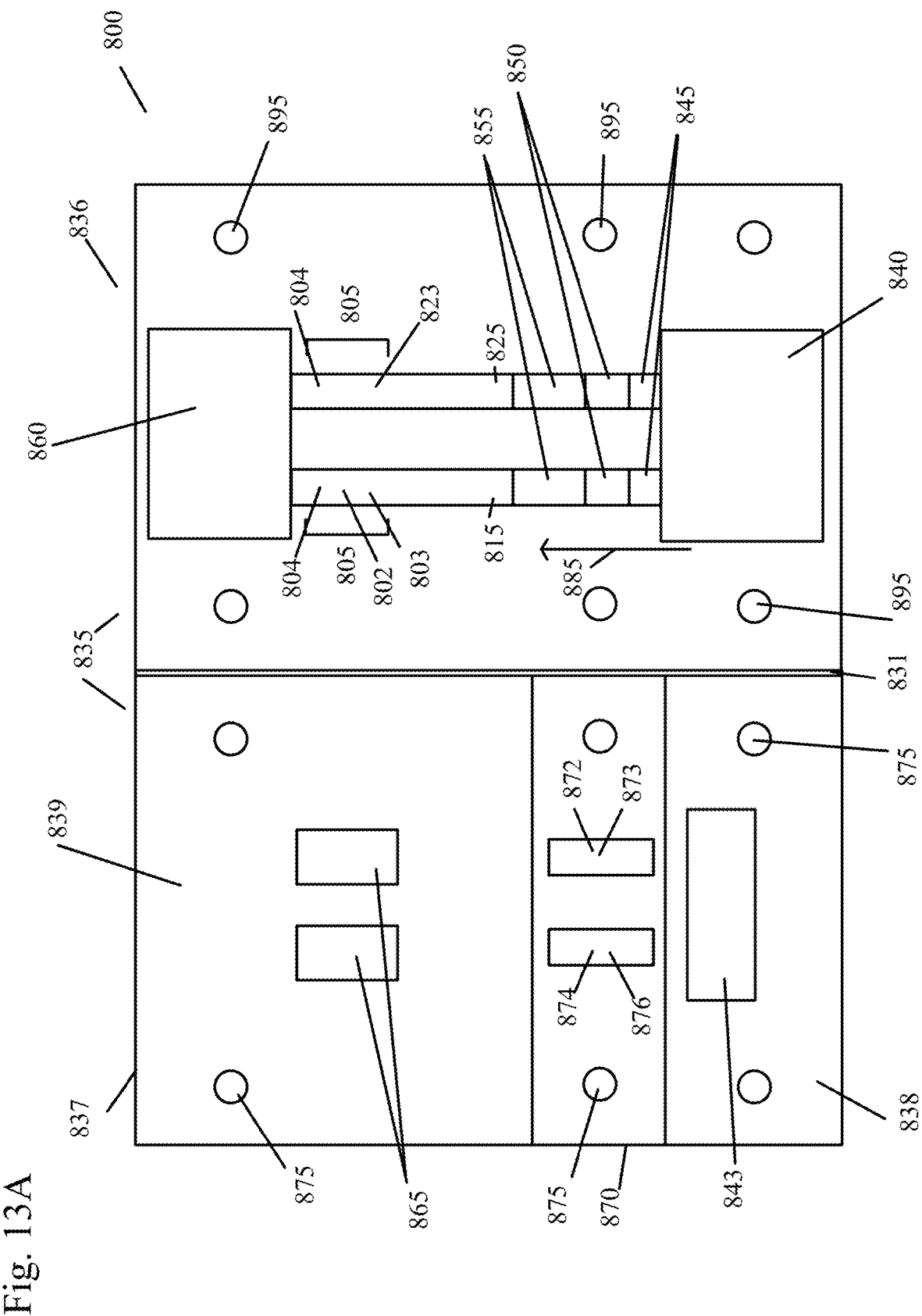
FIG. 13A shows a fully open sample analysis device with dual test strips, as well as a conjugate zone and a sample application zone on a sample compressor in a plane separate from the test strips.
Figure 13B:
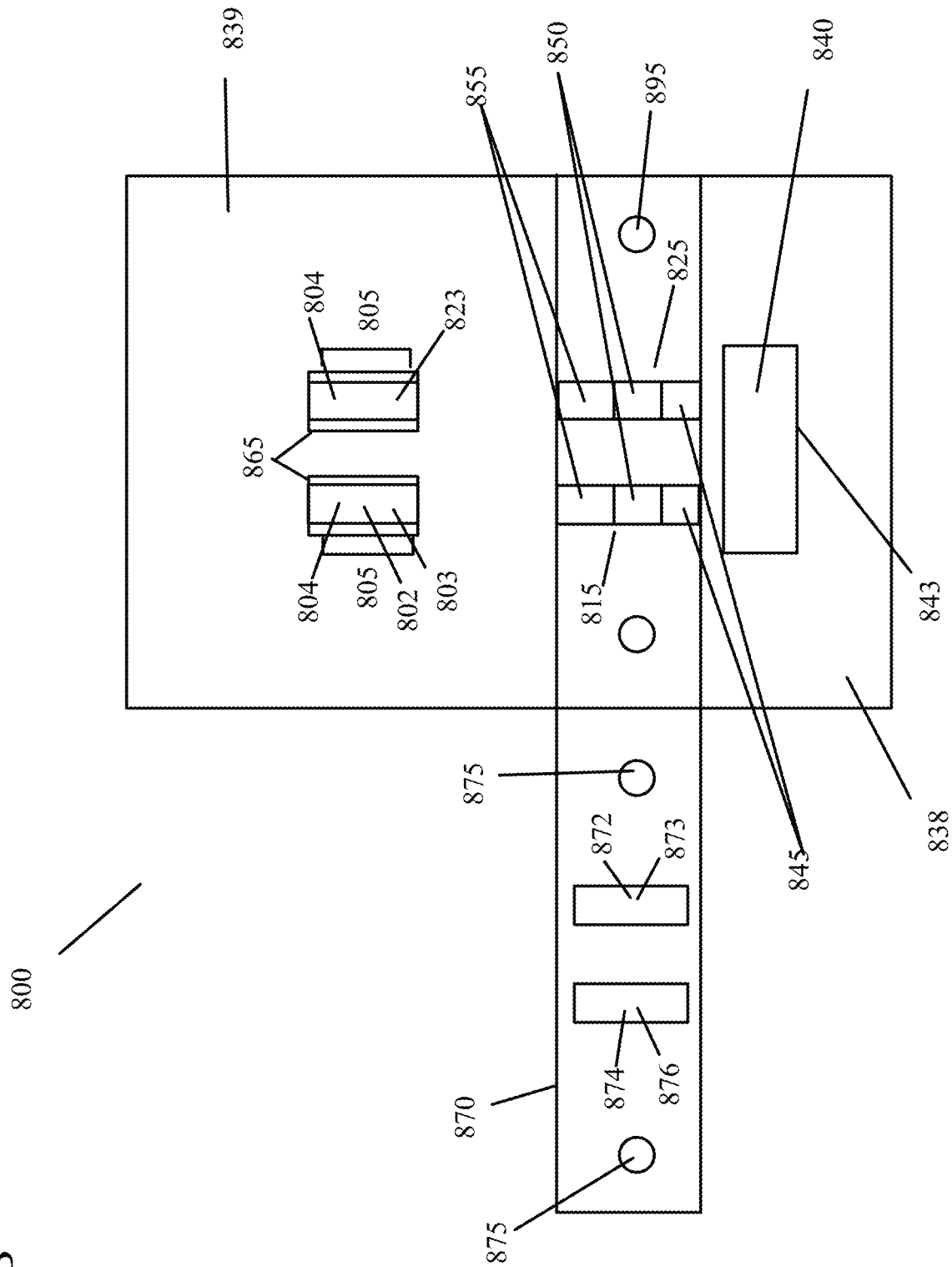
FIG. 13B shows the sample analysis device of FIG. 13A with part of the housing closed, but the conjugate zone still visible on the left side of the device.
Figure 13C:
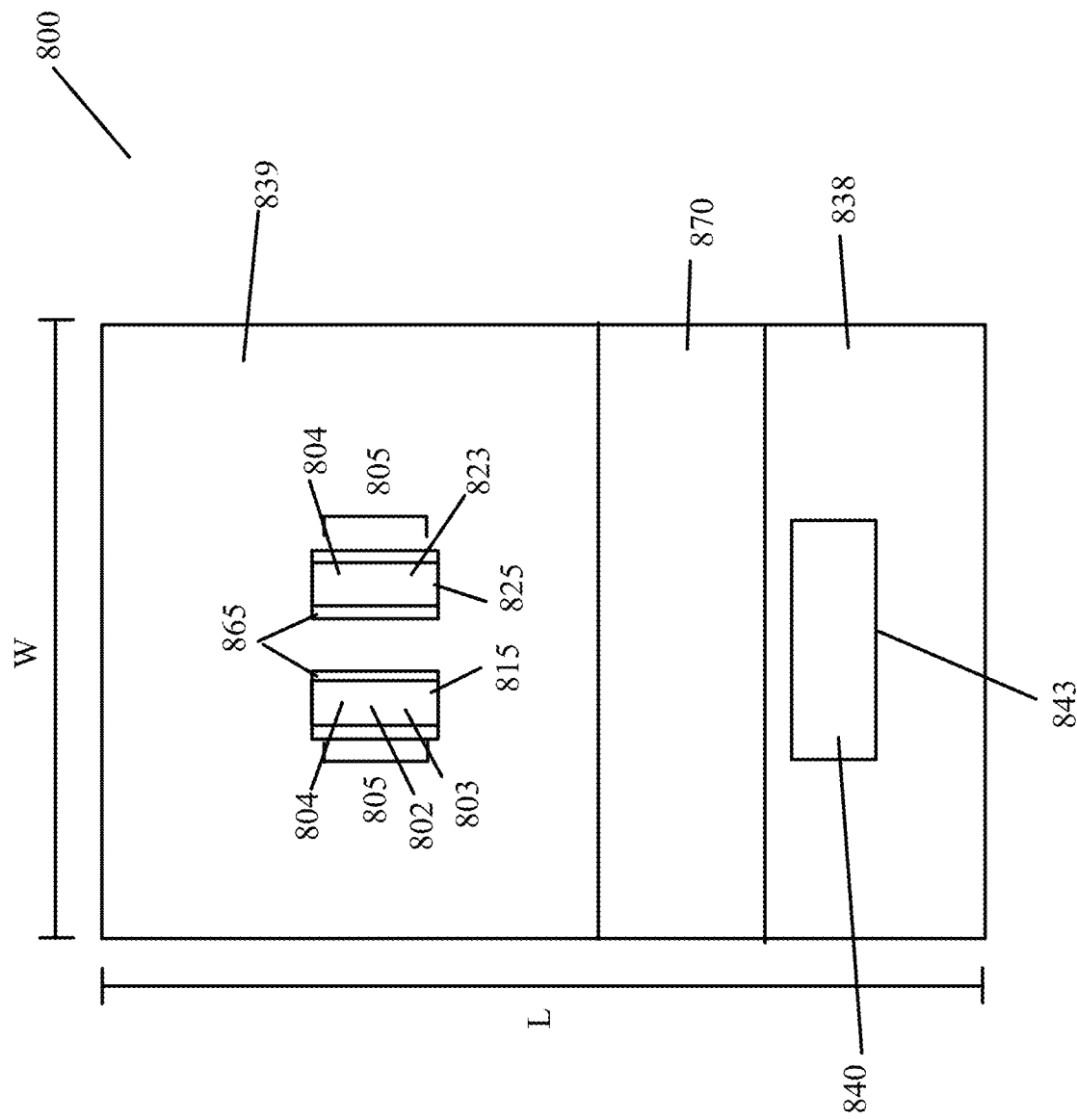
FIG. 13C shows the sample analysis device of FIG. 13A after the test has been initiated.
Figure 14A:
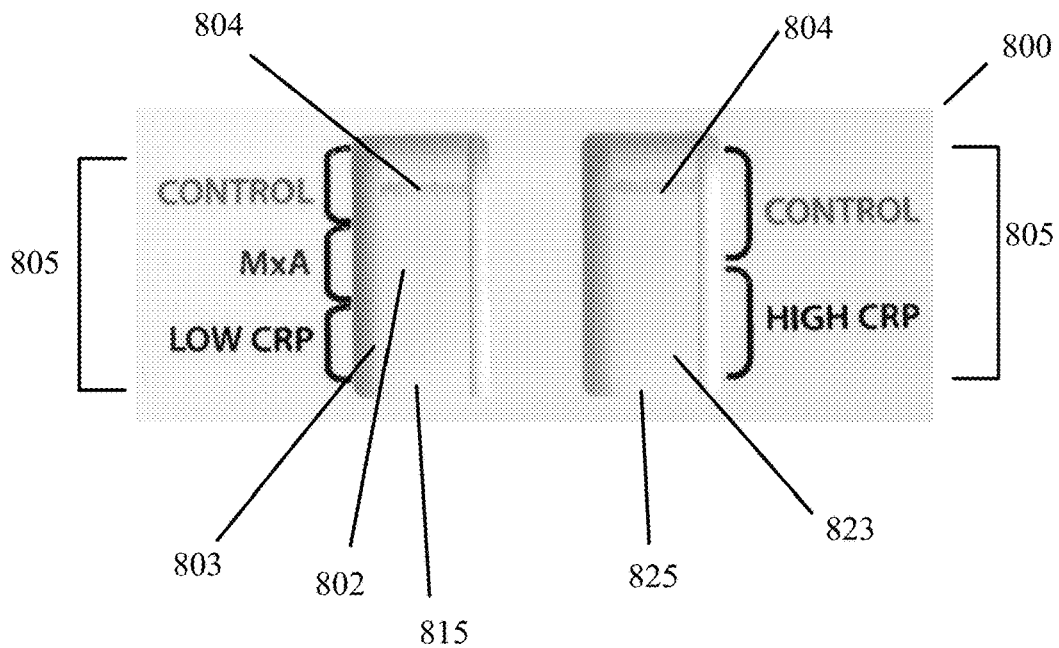
FIG. 14A shows a test result negative for both MxA and C-reactive protein (low and high) in an embodiment of the present invention.

For example, if a sample tested using the device of FIG. 13, 15 or 17 has the results shown in FIG. 14A, a second sample could be taken from that patient and the second sample could be assayed on the device of FIG. 13, 15 or 17 again for MxA, low CRP and high CRP. If that patient has a viral or bacterial infection, the second sample would indicate a positive result for either MxA or C-reactive protein, respectively.

As another example, if a sample tested for C-reactive protein and MxA using the device of FIG. 9 or other assay methods known in the art is negative for both C-reactive protein and MxA, a second sample could be taken from that patient and the second sample could be assayed on the device of FIG. 9 again for MxA and C-reactive protein. If that patient has a viral or bacterial infection, the second sample would indicate a positive result for either MxA or C-reactive protein, respectively.

As a third example, a sample could be tested for procalcitonin and MxA using devices known in the art. If the sample is initially negative for both MxA and procalcitonin, a second sample could be taken from that patient and the second sample could be assayed again for MxA and procalcitonin. If that patient has a viral or bacterial infection, the second sample would indicate a positive result for either MxA or procalcitonin, respectively.

The results from the second test in any of these examples would guide the practitioner in their decisions whether to prescribe antibiotics. This guidance would be provided much earlier than in the prior art diagnostic system, which relied on a "wait and see" approach, and would wait at least 48 hours to see if the patient worsened before performing any additional testing.

Diagnostic Studies Using Immune Response Markers

The Applicant performed prospective, multicenter, blinded clinical trials for identifying an immune response to viral and/or bacterial infection related to an acute community-acquired febrile respiratory infection. The study was performed on subjects older than 1 year of age presenting to primary care and urgent care outpatient offices and emergency departments in geographically diverse clinical trial sites across the United States.

Using a combination of Procalcitonin testing (bioMerieux Vidas® device) and myxovirus resistance protein A (MxA) ELISA testing, the data substantiates the accuracy of combining these markers either in quantitative or qualitative fashion on any type of device including, but not limited to, lateral flow devices, chemoluminescence, bead, fluorescence ELISA, Automated Immunoassay/immunoanalysis testing systems (for example BioMerieux Vidas® or mini-Vidas® immunoassay systems).

FIGS. 5A-5L show results from 148 patients in the trial. Each row identifies a different patient in the trial. Column one identifies each patient with an arbitrary number. Column two shows the quantitative venous procalcitonin levels (ng/ml) and column three shows the quantitative MxA ELISA levels. Column four lists the organism/infection, if any, that was picked up by a throat culture. Column five lists the clinical diagnosis given to that patient. Column six provides a description and comments regarding how the diagnosis was reached. For the negative diagnoses that do not include MxA values, the MxA assay was not run.

Bacterial infection was defined and diagnosed in the trial as follows:

A swab of the Oropharynx was performed and bacterial cultures performed.

Since procalcitonin can be found in the serum of a healthy person (<0.11 ng/mL) and the current assays demonstrate an interassay precision of approximately 10% (Aouifi et al., Crit care Med. 2000, 28:3171-6), the previous protocol cutoff for definitive bacterial infection was reduced from 0.5 ng/ml to a new lower cutoff of 0.15 ng/ml.

Any culture with bacteria cultured >$10^6$ CFU and associated with an elevated procalcitonin greater than or equal to 0.15 ng/ml was deemed a true bacterial infection.

Any culture with a single species of the primary pathogenic bacteria (such as Group A or Group B Strep for upper respiratory tract infections) and associated with an elevated procalcitonin greater than or equal to 0.1 ng/ml was deemed positive for a true bacterial infection even if the bacterial growth is less than >$10^6$ CFU as long as the patient is negative PCR for a viral pathogen.

In patients that were negative for any microbiological testing and had an elevated procalcitonin ≥0.15 ng/ml were also deemed to have a bacterial infection.

Viral infection was defined and diagnosed in the trial as follows:

Both an oropharyngeal and nasopharyngeal swab was sent for polymerase chain reaction analysis using the BioFire™ Respiratory Panel test (Biofire Diagnostics, Inc., Salt Lake City, Utah).

To differentiate true infection from colonization or latent shedding, Herpes Simplex virus, Cytomegalovirus, Rhinovirus and Coronavirus will be deemed to be true positives if they are associated with a normal procalcitonin level and elevated MxA≥20 ng/ml.

The combined test accurately identified 83 out of 84 microbiologically unconfirmed (MU) respiratory infections, 26 out of 35 viral infections, and 29 out of 29 bacterial infections.

The combined test reduces the amount of unnecessary antibiotic prescriptions because of its ability to differentiate between viral and bacterial infection.

Figure 7:
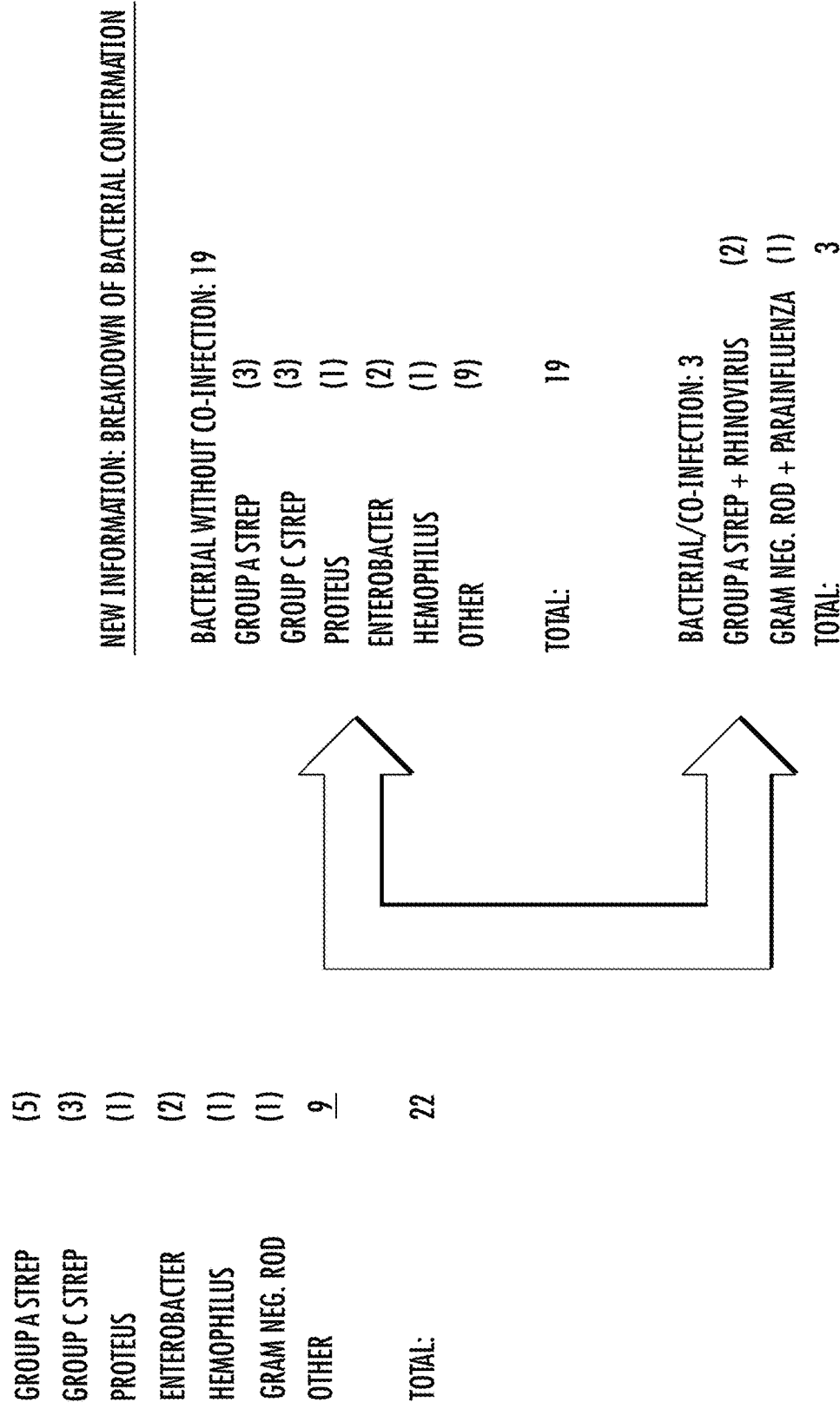
FIG. 7 shows the bacteria identified using one of the novel methods described herein.

FIG. 6 shows the bacteria identified in one trial. FIG. 7 shows the bacteria identified using the novel method described herein. In FIG. 6, all of the bacteria identified in the trial is considered a bacterial infection, and does not consider colonization. In FIG. 7, the patients positive for bacterial infection change because only the true infections are being counted.

Using Lateral Flow Devices in Combination with a Device for Determining Levels of Procalcitonin In some embodiments where procalcitonin is detected in combination with MxA and one or two levels of C-reactive protein, lateral flow devices are used to detect MxA and/or C-reactive protein and other assay devices are used to detect procalcitonin. Lateral flow devices are known, and are described in, e.g., U.S. Pat. No. 7,723,124 and US Patent Publication No. and 2007/0059682. The contents of both of these applications are incorporated herein by reference. Other lateral flow devices known in the art could alternatively be used with the systems and methods of the present invention.

Any of the devices and methods described in US Patent Publication 2010/0297611, published Nov. 25, 2010, entitled "Method and Device for Combined Detection of Viral and Bacterial Infections", US Patent Publication 2013/0196310, published Aug. 1, 2013, entitled "Method and Device for Combined Detection of Viral and Bacterial Infections", U.S. Pat. No. 8,962,260, issued Feb. 24, 2015, entitled "Method and Device for Combined Detection of Viral and Bacterial Infections", and US Patent Publication 2013/0130367, published May 23, 2013, entitled "Method and Device for Combined Detection of Viral and Bacterial Infections", all incorporated herein by reference, could be used in the methods and devices described herein to detect MxA and/or C-reactive protein levels.

U.S. Published Patent Application No. 2007/0059682, incorporated herein by reference, discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Pat. No. 7,723,124, issued May 25, 2010 and incorporated herein by reference, discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. This enables point-of-care testing with results available during a patient visit.

Figure 8:
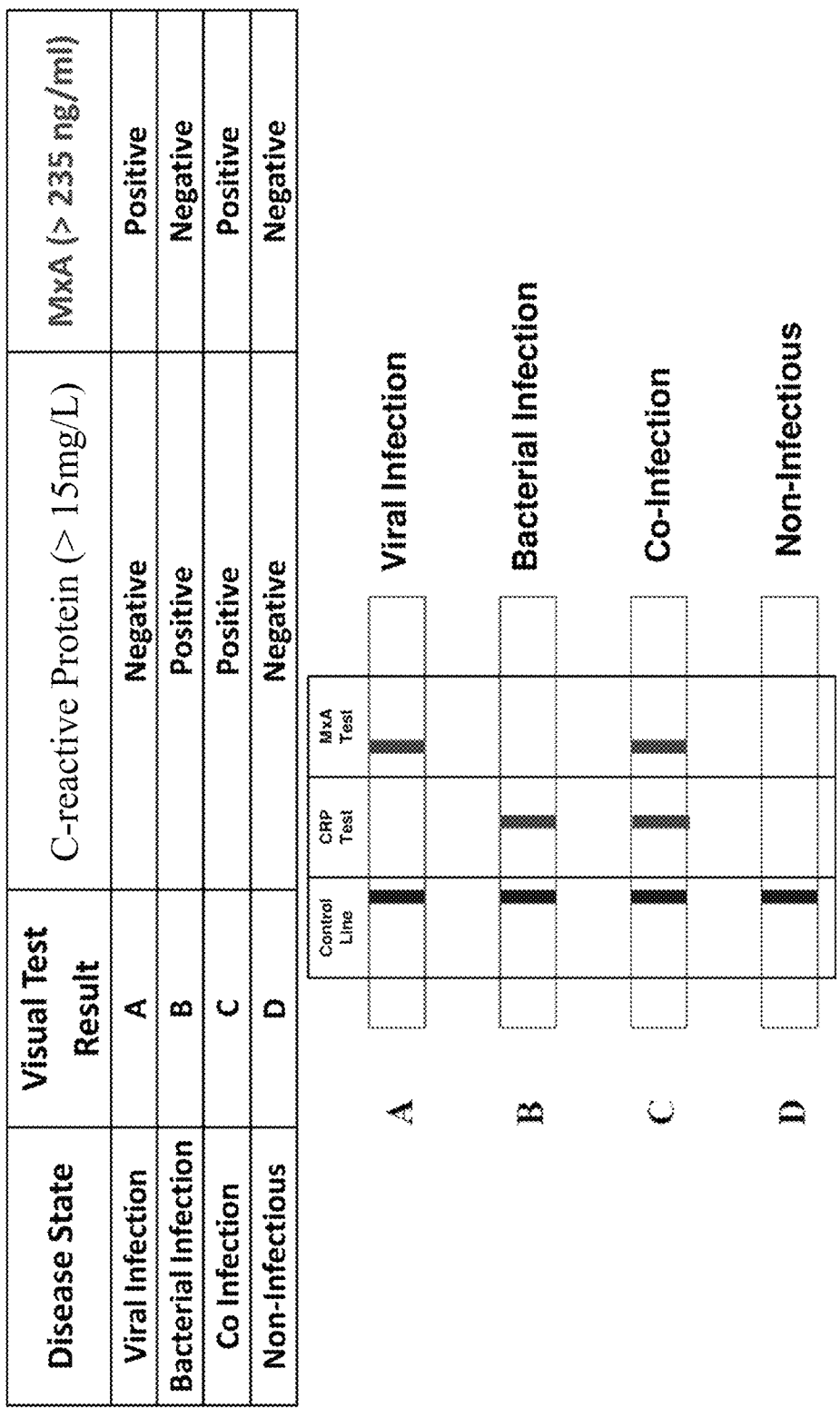
FIG. 8 shows rapid screening test window visual test results to distinguish viral and bacterial infections and an interpretation of those results.

One example of a rapid screening test for distinguishing viral and bacterial infection is shown in FIG. 8. As discussed above, MxA is a diagnostic marker for viral infection, while C-reactive protein is a diagnostic marker for bacterial infection. In this example, a blue line ("control line" in A-D of the Figure) represents the control. A green line represents a C-reactive protein (CRP) level >15 mg/L ("CRP test" in A-D of the figure). A red line represents an MxA level >20 ng/ml ("MxA test" in A-D of the figure). A positive result for the MxA protein, with a negative result for the CRP protein indicates only a viral infection (Visual Test Result A). A positive result for the (CRP) with a negative result for the MxA protein indicates only a bacterial infection (Visual Test Result B). A positive result for both MxA and C-reactive protein indicates co-infection (infection with both a bacteria and a virus) (Visual Test Result C). No bacterial or viral infection is indicated by a negative result for both MxA and C-reactive protein (Visual Test Result D). While particular color lines are discussed in this example, other colors, or the same colors at different locations on the test strip to indicate viral or bacterial markers, are within the spirit of the present invention.

When development of different colored lines is utilized, the lines may or may not be physically separated by space. In the latter instance, the labels are chosen such that the color seen when both markers are present is different from the colors seen when the individual markers are present. For example, the presence of the viral marker may be indicated by a red line; the presence of the bacterial marker by a blue line; and the presence of both by a purple line (combined red and blue).

The test strip may also include a control section which indicates the functionality of the test strip. FIG. 8 shows a control line. If present, the control section can be designed to convey a signal to the user that the device has worked. For example, the control section may contain a reagent (e.g., an antibody) that will bind to the labeled reagents from the reagent zone. In one preferred embodiment, rabbit anti-chicken is used as the control line and chicken IgY conjugated to a label, for example blue latex beads, is the control conjugate. Alternatively, the control section may contain an anhydrous reagent that, when moistened, produces a color change or color formation, e.g. anhydrous copper sulphate which will turn blue when moistened by an aqueous sample. As a further alternative, the control section could contain immobilized viral and bacterial markers which will react with excess labeled reagent from the reagent zone. The control section may be located upstream or downstream from the detection zone. A positive control indicator tells the user that the sample has permeated the required distance through the test device.

Figure 9A:
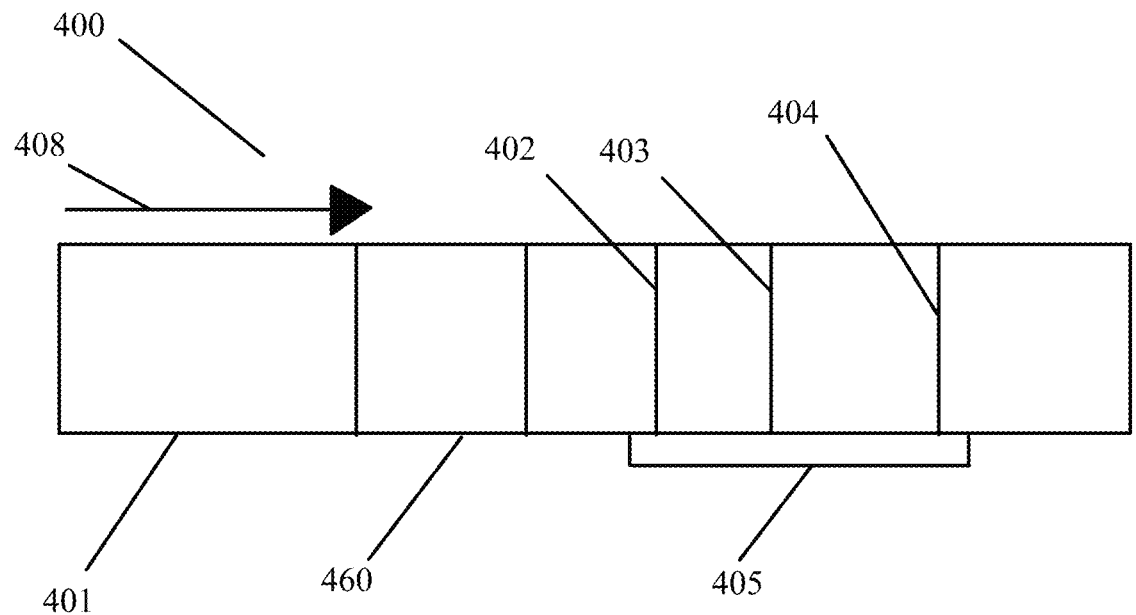
FIG. 9A shows a device with a test line corresponding to the presence of a viral marker and a second, separate test line that detects the presence of a bacterial marker in an embodiment of the present invention.
Figure 9B:
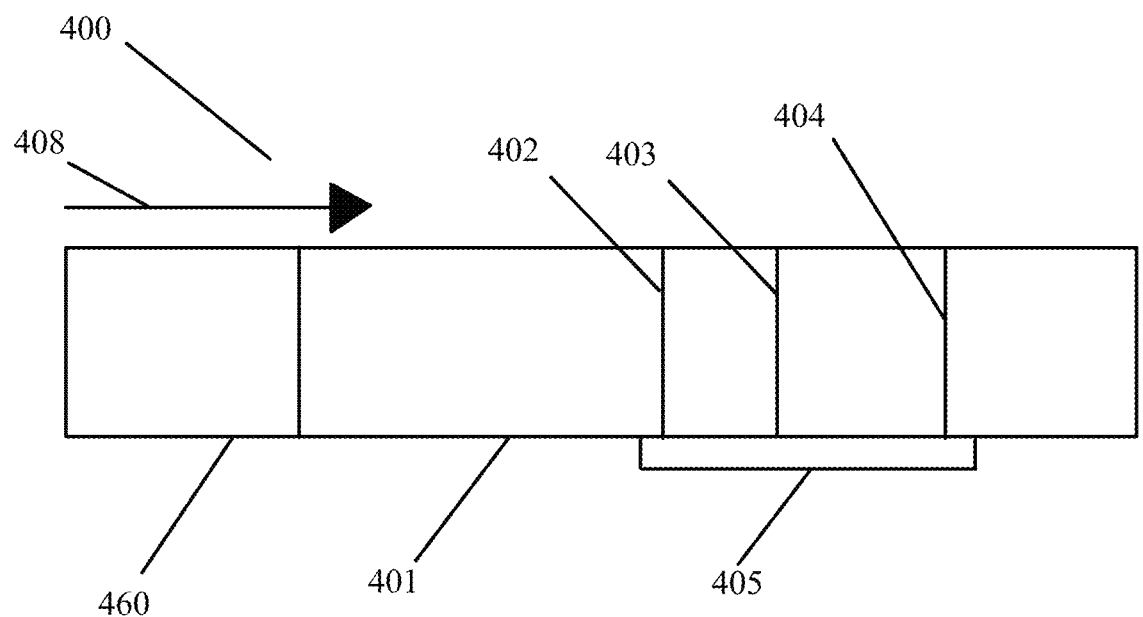
FIG. 9B shows a device with the reagent zone upstream of the sample application zone, and a test line corresponding to the presence of a viral marker and a second, separate test line that detects the presence of a bacterial marker in an embodiment of the present invention.

FIGS. 9A and 9B show a chromatographic test strip (400) with a test line (402) corresponding to the presence of a viral marker such as MxA and a second, separate test line (403) that detects the presence of a bacterial marker such as C-reactive protein or procalcitonin. The sample is applied to the application zone (401) of the chromatographic test strip (400). As shown in FIG. 9A, the sample then passes a reagent zone (460) containing at least one labeled viral binding partner and at least one labeled bacterial binding partner that is eluted by and then able to migrate with a sample transport liquid (e.g. a buffer solution). Alternatively, as shown in FIG. 9B, the reagent zone (460) is located upstream of the sample application zone (401) such that the labeled binding partners in the reagent zone are eluted by the sample transport liquid and travel to the sample. The labeled viral binding partner is capable of specifically binding to a viral marker of interest to form a complex which in turn is capable of specifically binding to another specific reagent or binding partner in the detection zone. The labeled bacterial binding partner is capable of specifically binding to a bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (400) in these embodiments.

The test strip (400) also includes a detection zone (405) containing at least one first section for detection of a viral marker, e.g. a test line (402), including an immobilized specific binding partner, complementary to the viral reagent complex formed by the viral marker and its labeled binding partner. Thus, at the test line (402), detection zone binding partners trap the labeled viral binding partners from the reagent zone (460) along with their bound viral markers. This localization of the viral marker with its labeled binding partners gives rise to an indication at the test line (402). At the test line (402), the presence of the viral marker is determined by qualitative and/or quantitative readout of the test line (402) indication resulting from the accumulation of labeled binding partners.

The detection zone (405) also includes at least one second section for detection of a bacterial marker, e.g. a test line (403), including an immobilized specific binding partner, complementary to the bacterial reagent complex formed by the bacterial marker and its labeled binding partner. Thus, at the test line (403), detection zone binding partners trap the labeled bacterial binding partners from the reagent zone (460) along with their bound bacterial markers. This localization of the bacterial marker with its labeled binding partners gives rise to an indication at the test line (403). At the test line (403), the presence of the bacterial marker is determined by qualitative and/or quantitative readout of the test line (403) indication resulting from the accumulation of labeled binding partners. While test line (402) is upstream of test line (403) relative to the direction of flow (408) in the figures, in alternative embodiments, test line (403) is upstream of test line (402). In still other embodiments, test lines (402) and (403) are located in the same location on the test strip.

Optionally, the detection zone (405) may contain further test lines to detect other viral and/or bacterial markers, as well as a control line (404). For example, C-reactive protein and MxA may be detected on the same test strip. The control line (404) indicates that the labeled specific binding partner traveled through the length of the assay, even though it may not have bound any viral or bacterial markers, thus confirming proper operation of the assay. As shown in FIGS. 9A through 9B, the control zone (404) is preferably downstream of the test lines (402) and (403). However, in other embodiments, the control zone (404) may be located upstream of either or both of the test lines (402) and (403).

In some embodiments, the control line (404) includes an antibody or other recombinant protein which binds to a component of the elution medium or other composition being used in the test. In embodiments where nucleic acids are the targets, the control line (404) preferably includes a nucleic acid complementary to the labeled nucleic acid being used as a binding partner for the target nucleic acid.

Although only one test line is shown in the figures for each of the viral and bacterial markers, multiple test lines for both or either of the viral and bacterial markers may be used within the spirit of the invention. In some embodiments where there are multiple bacterial and/or viral targets, the presence of each target preferably corresponds to a separate test line (402) or (403). In other embodiments, both the bacterial marker and the viral marker are detected on a single test line. In these embodiments, the presence of both a bacterial marker and a viral marker on the same test line has different characteristics than the presence of either a bacterial or viral marker alone. For example, the presence of both a bacterial marker and a viral marker on the same test line may be visually indicated by a different color than the presence of either a bacterial marker or a viral marker alone.

In some preferred embodiments, the devices and methods of the present invention include a lysis zone to help differentiate viral and bacterial infections. In these embodiments, the sample that has been collected is not lysed prior to collection and transfer to the sample analysis device. This decreases the number of steps needed to collect and prepare the sample for analysis. One situation where a lysis agent improves assay efficiency is in assaying for the presence of MxA. As discussed herein, the presence of this protein can help to distinguish between bacterial and viral infection in febrile children. In situ lysis using a combination of 1% to 6% weight/volume CHAPS and 0.5% to 2% weight/volume NP40 as the lysis agent improves detection of MxA in fresh or frozen whole blood. In other embodiments, in situ lysis uses urea, Tween 80, and/or a combination of these two lysis agents.

In the embodiments utilizing a lysis agent, following sample loading, the sample traveling with the transport liquid (buffer) will encounter the lysis agent. The lysis agent will have preferably been pre-loaded onto the test strip and is eluted by the transport liquid. In some preferred embodiments the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded or trapped on the test strip. The initially dried lysis agent is preferably localized between the sample application zone and a reagent zone. In embodiments where the reagent zone is upstream of the sample application zone, the lysis zone is downstream of the sample application zone. The lysing agent is preferably soluble in the sample transport liquid, and the lysing agent is solubilized and activated upon contact with the sample transport liquid. The sample transport liquid then contains both lysing agent in solution or suspension and sample components in suspension. Any lysis-susceptible components in a sample, then being exposed in suspension to the lysing agent, are themselves lysed in situ. The running buffer then carries the analyte, including any lysis-freed components, to the detection zone.

The location where the lysis agent is pre-loaded and dried can be varied as needed. In order to maximize the time that the sample has to interact with the lysis agent as well as to minimize the amount of lysis agent reaching the detection zone, the dried, absorbed, adsorbed, embedded, or trapped lysis agent may be located in or just downstream of the sample application zone. Or, in order to minimize the distance along which the lysis product must travel before reaching the reagent zone, the dried lysis agent may be located closer to the reagent zone. In other embodiments, the lysis agent may be included in the running buffer. In some preferred embodiments, NP-40 and sarkosyl lysis agents are included in a Tris-containing running buffer. In other preferred embodiments, Tween 80 and urea are used as the lysis agents on a lateral flow chromatography test strip. In other preferred embodiments, lysis agents on the strip (including Tween 80 and urea) and lysis agents in a Tris-containing running buffer (including NP-40 and Sarkosyl) are used in combination.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the viral and bacterial markers and the assay. The pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both the high and low ionic strength may be used to lyse. For example, a lower ionic strength (hypotonic) tends to break up erythrocytes. For example, water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, Sodium lauroyl sarcosinate (also known as sarkosyl) and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, NP-40 (for example Tergitol® NP-40), Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

In some preferred embodiments, Tween 80 and urea are used as the lysis agents on a lateral flow chromatography test strip. In other preferred embodiments, lysis agents in a Tris-containing running buffer include NP-40 and Sarkosyl. In other preferred embodiments, lysis agents on the strip (including Tween 80 and urea) and lysis agents in a Tris-containing running buffer (including NP-40 and Sarkosyl) are used in combination.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution and storage before use of a test strip in point-of-care testing.

In preferred embodiments where MxA is the viral marker, in situ lysis using a combination of 1% to 6% weight/volume CHAPS and 0.5% to 2% weight/volume NP40 as the lysis agent is preferably used. As a more specific example, 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume) are dried onto a lysis zone of a test strip.

In FIGS. 10A through 10D, the sample is applied to the application zone (201) on a chromatographic test strip (200). The sample passes a lysis zone (250), where a lysis agent will have preferably been pre-loaded onto the test strip and is eluted by the transport liquid. The lysis agent lyses any lysis-susceptible components in the sample in situ.

The chromatographic test strip contains a sample application zone (201), a lysis zone (250) containing a lysis agent, and a reagent zone (260) containing at least one labeled binding partner that binds to a viral marker and at least one labeled binding partner that binds to a bacterial marker that are eluted by and then able to migrate with a sample transport liquid (e.g. a buffer solution). While the reagent zone (260) is shown downstream of the sample application zone in these figures, in alternative embodiments, the reagent zone (260) could be upstream of the sample application zone (see FIG. 10B), as long as the reagents encounter the sample at some point after the sample reaches the lysis zone and is effectively lysed. The labeled binding partners are capable of specifically binding to a viral or bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (200) in these embodiments.

In some embodiments, the lysis agent is localized in the lysis zone (250) between the sample application zone (201) and the reagent zone (260). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the detection zone (205).

Figure 10A:
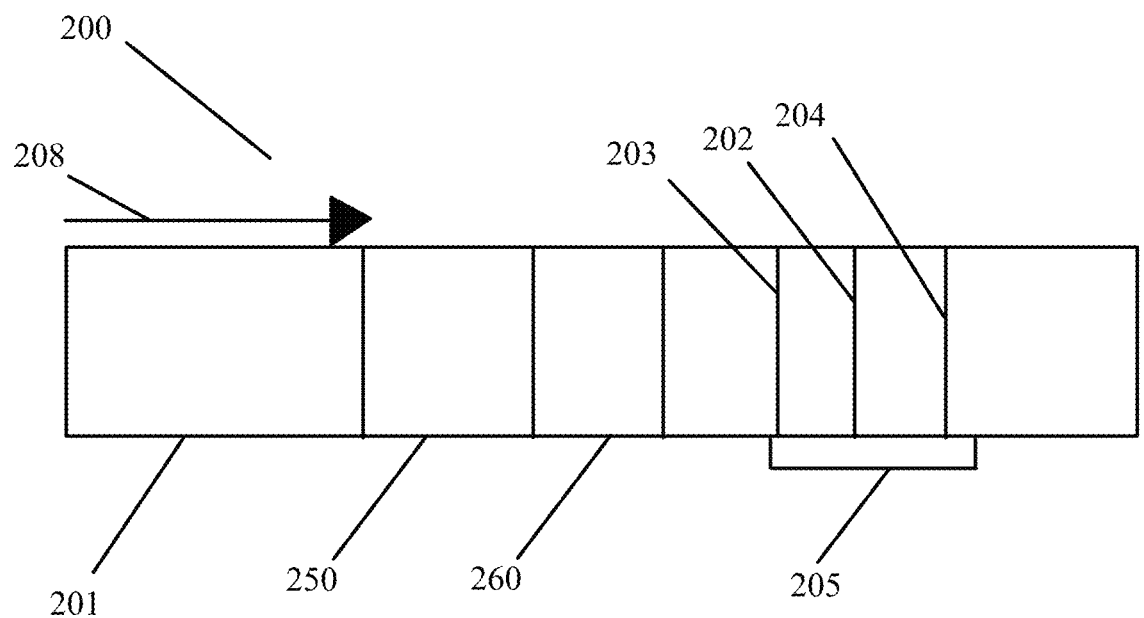
FIG. 10A shows a sample analysis device including a lysis zone located between a sample application zone and a reagent zone.
Figure 10B:
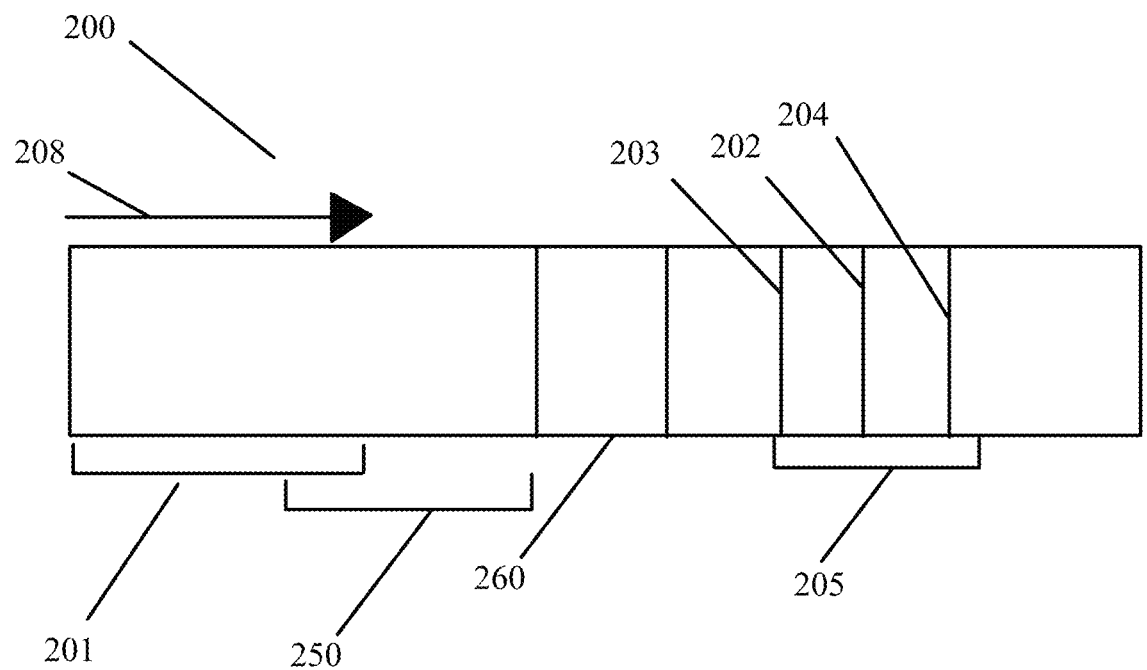
FIG. 10B shows a sample analysis device including a lysis zone overlapping a sample application zone.
Figure 10C:
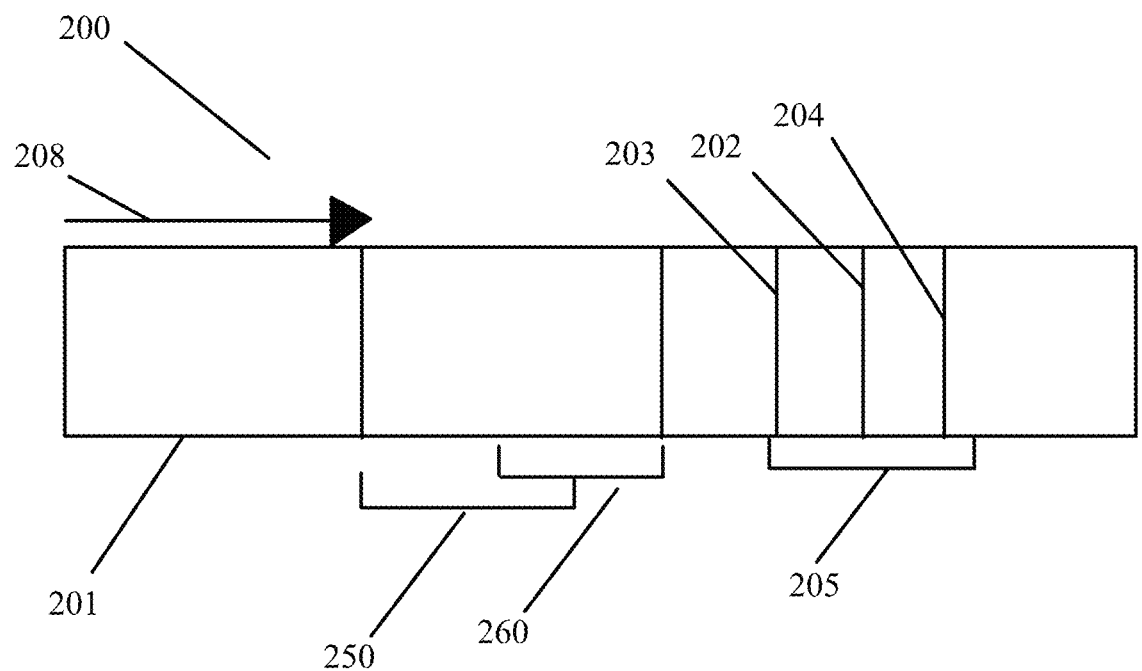
FIG. 10C shows a sample analysis device including a lysis zone overlapping a reagent zone.
Figure 10D:
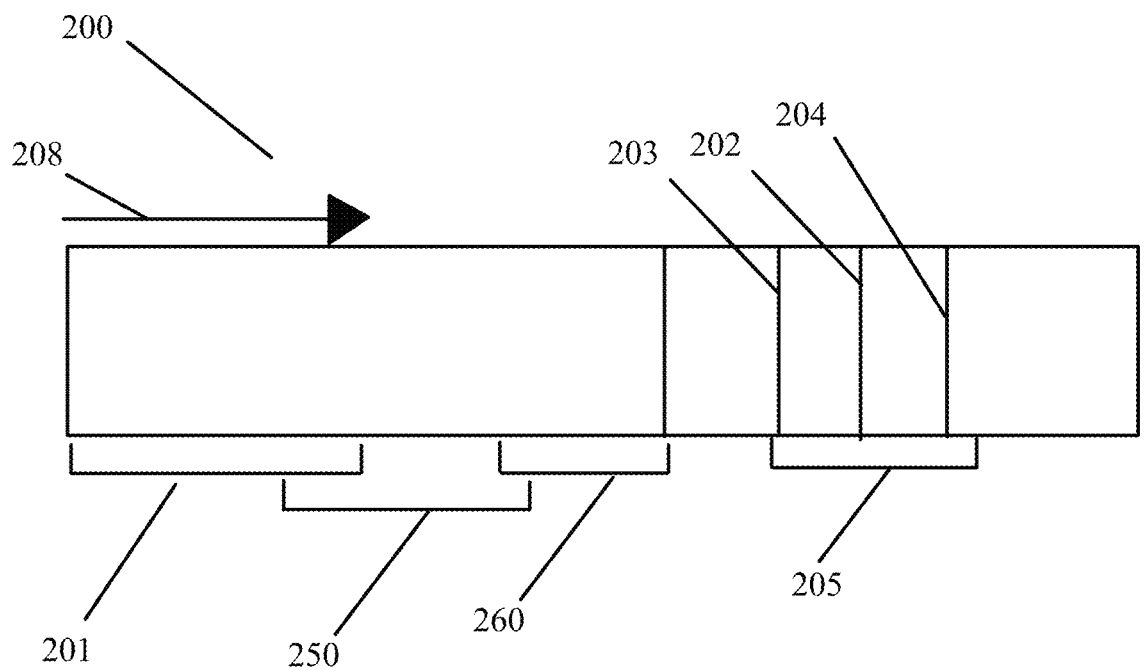
FIG. 10D shows a sample analysis device including a lysis zone overlapping a sample application zone and a reagent zone.

The lysis zone (250) is preferably located between the sample application zone (201) and the reagent zone (260), as shown in FIG. 10A. In other embodiments, the lysis zone (250) overlaps the sample application zone (201), the reagent zone (260) or both the sample application zone (201) and the reagent zone (260) as shown in FIGS. 10B, 10C, and 10D, respectively. Note that the figures are schematic, and are not drawn to scale. The amount of overlap between the different zones (as shown in FIGS. 10B through 10D) may be highly variable.

The test strip (200) also includes a detection zone (205) containing a first section for detection of at least one bacterial marker, e.g. a test line (203), including an immobilized specific binding partner, complementary to the bacterial conjugate formed by the bacterial marker and its labeled binding partner. Thus, at the test line (203), detection zone binding partners trap the bacterial labeled binding partners from the reagent zone (260) along with their bound bacterial markers. This localization of the bacterial markers with their labeled binding partners gives rise to an indication at the test line (203). At the test line (203), the presence of a bacterial marker is determined by qualitative and/or quantitative readout of the test line (203) indication resulting from the accumulation of labeled binding partners.

The detection zone (205) also includes a second section for detection of at least one viral marker, e.g. a test line (202), including an immobilized specific binding partner, complementary to the viral conjugate formed by the viral marker and its labeled binding partner. Thus, at the test line (202), detection zone binding partners trap the viral labeled binding partners from the reagent zone (260) along with their bound viral markers. This localization of the viral markers with their labeled binding partners gives rise to an indication at the test line (202). At the test line (202), the presence of a viral marker is determined by qualitative and/or quantitative readout of the test line (202) indication resulting from the accumulation of labeled binding partners. While test line (203) is upstream of test line (202) relative to the direction of flow (208) in the figures, in alternative embodiments, test line (202) is upstream of test line (203). In still other embodiments, test lines (202) and (203) are located in the same location on the test strip.

Optionally, the detection zone (205) may contain further test lines to detect other bacterial and/or viral markers, as well as a control line (204). The control line (204) indicates that the labeled specific binding partner traveled through the length of the assay, even though it may not have bound any markers, thus confirming proper operation of the assay. As shown in FIGS. 10A through 10D, the control zone (204) is preferably downstream of the test lines (203) and (202).

However, in other embodiments, the control zone (204) may be located upstream of either or both of the test lines (203) and (202).

In some embodiments, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line (202). In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mild lysis agents in the running buffer itself. In these embodiments, there is no adverse effect on the reagent zone which will be downstream and the sample can either be upstream or downstream of the reagent zone. A lysing enzyme in the running buffer can "target" its substrate and cut it to open up the cell membrane or cell wall. As an example, penicillin can excise or "punch a hole" in a susceptible bacteria. In other embodiments, when the lysis agent is applied to the sample collection material, then the reagent zone may be upstream of the sample application zone. In some preferred embodiments, lysis agents in a Tris-containing running buffer include NP-40 and Sarkosyl.

As an example, one or more lysis agents are dried onto the sample application zone of a lateral flow strip. On a per strip basis, the lysis agent is made of approximately 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume). Up to 10 microliters of whole blood are then added to the sample application zone to be lysed in situ. MxA protein is released from inside white blood cells to react with an MxA monoclonal antibody on a visual tag (colloidal gold or visible latex beads). This complex traverses with a running buffer containing Triton X-100 and is captured by MxA monoclonal antibodies immobilized at the test line of the nitrocellulose membrane. This binding at the test line gives rise to a visible indication.

In other examples, Tween 80 and urea are used as the lysis agents on a lateral flow chromatography test strip.

Some examples of assay formats for determining procalcitonin when MxA and/or C-reactive protein are being determined lateral flow include, but are not limited to, immunoassays, immunoblotting methods, agglutination reactions, a complement-fixation reaction, a hemolytic reaction, a precipitation reaction, a gold colloid method, a chromatography method, phosphorescence, radioactivity, colorimetry, gravimetry, X-ray diffraction, X-ray absorption, magnetism, fluorescent resonant emissions, or an immunostaining method. Some examples for immunoassays include, but are not limited to, immunoprecipitation, radioimmunoassays (RIA), enzyme immunoassays (EIA or ELISA), a Vidas® immunoassay device (Biomerieux, Hazelwood, Mo.), fluorescent immunoassays (FIA), an i-Stat® portable handheld system (Abbott Laboratories, Abbott Park, Ill.), a Philips Handheld diagnostic system (Philips Handheld Diagnostics, The Netherlands), chemiluminescent immunoassays, physiochemical assays (TIA, LAPIA, or PCIA), lateral flow immunoassays, or flow cytometry. Some preferred immunoassays for these biomarkers include, but are no limited to, ELISAs, fluorescence immunoassays, magnetic assays, paramagnetic assays, and chemiluminescent assays. In other embodiments, the mRNA or gene transcripts may be used. In some preferred embodiments, the assays are automated. Assays for MxA and/or C-reactive protein may also alternatively use any of the assay systems and devices above.

One particular example of a device to determine the presence of C-reactive protein, MxA and/or procalcitonin is a multiparametric immunoassay system that is able to detect two or more of these targets in the same device. In some preferred embodiments, the devices are able to detect MxA levels greater than or equal to between 25 ng/ml and 35 ng/ml, low CRP levels greater than or equal to 20 mg/l, high CRP levels greater than or equal to 80 mg/L, and procalcitonin levels of at least 0.1 ng/ml. In other embodiments, the devices are able to quantitate the levels of these biomarkers.

One multiparametric immunoassay system that could be used is a Vidas® immunoassay device (Biomerieux, Hazelwood, Mo.), which could test for the presence of one, two, three, or all four of these targets (MxA, procalcitonin, low-CRP and high-CRP) simultaneously. The Vidas® immunoassay device is an Enzyme Linked Fluorescent assay (ELFA) (also available in a compact version called Mini Vidas®) and is widely used in clinical laboratories. Other devices that could be used include a Vitek® immunodiagnostic system (Biomerieux, Hazelwood, Mo.), or a Luminex® immunoassay system (Luminex Corporation, Austin, Tex.). Another example is a device similar to an i-Stat® portable handheld system (Abbott Laboratories, Abbott Park, Ill., see the devices disclosed in U.S. Pat. Nos. 5,638,828, 5,666,967, 5,653,243, 5,779,650, 6,010,463, 6,845,327, 6,896,778, 7,419,821, and 8,017,382, all herein incorporated by reference). Yet another example is a device that combines magnetic particle separation with chemiluminescent detection, such as the BioFlash multiparametric immunoassay system (Biokit, Barcelona, Spain). Any non-subjective read-outs such as machine-read devices could be used to determine the levels of the biomarkers discussed herein.

Sample Analysis Device with Bimodal Dual Test Strips in Combination with Testing for Procalcitonin Bimodal dual test strips can be used to differentiate bacterial and viral infection in humans, but also may be used in veterinary applications for animals. Since C-reactive protein differs depending upon the species, there are not common antibodies to C-reactive protein between species. Therefore, the veterinary tests need to include C-reactive protein specific to the particular species being tested. MxA is well conserved among species, so it is possible to use human MxA in veterinary tests. However, MxA to a particular species could alternatively be used to try to further increase specificity. Veterinary tests using the bimodal dual test strips described herein may be developed for a specific species, including, but not limited to, cats, dogs, rabbits, pigs, sheep, horses, cows, monkeys, chimpanzees, baboons, and orangutans.

A strip with MxA and low CRP could be made with any configuration, for example the configurations shown in FIGS. 9A and 9B, or FIGS. 10A through 10D, where MxA is the viral marker being detected and relatively low levels of C-reactive protein is the bacterial marker being detected. In other embodiments, the MxA test line and the C-reactive protein test line could overlap, or be in the same location on the test strip. In these embodiments, the presence of low CRP and MxA on the same test line has different characteristics than the presence of either a bacterial or viral marker alone. For example, the presence of both low CRP and MxA on the same test line may be visually indicated by a different color than the presence of either MxA or low CRP alone. In these embodiments, a positive result for MxA would give a different color or indication than a positive result for low CRP, so that the person reading the assay could distinguish between a completely negative result, a positive result for MxA, a positive result for low CRP, and a positive result for both MxA and low CRP. For example, a positive result for MxA could result in a red test line, and a positive result for low CRP could result in a blue test line. So, when a sample is positive for both MxA and low CRP, the line is visibly purple.

Some embodiments for lateral flow assay devices to detect high levels of CRP are shown in FIGS. 11A-11B and 12A-12D. These configurations are similar to the configurations shown in FIGS. 9A-9B and 10A-10D, without a test line for a viral marker, and the same reference numerals are used for the same components of the strip (600), (700).

Figure 11A:
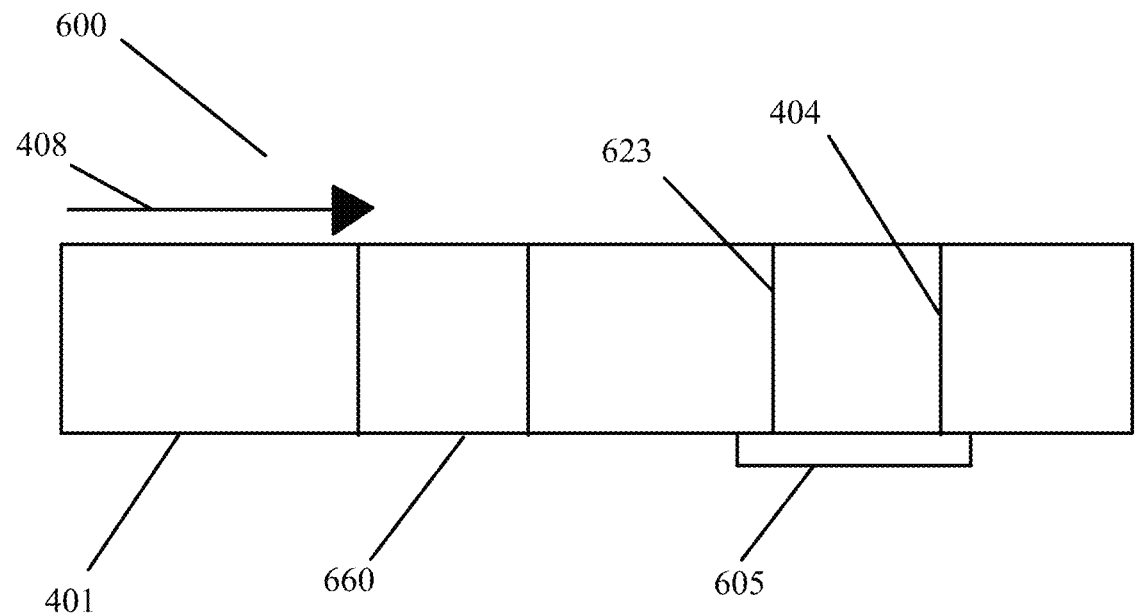
FIG. 11A shows a device with a test line corresponding to the presence of a bacterial marker such as high C-reactive protein levels.
Figure 11B:
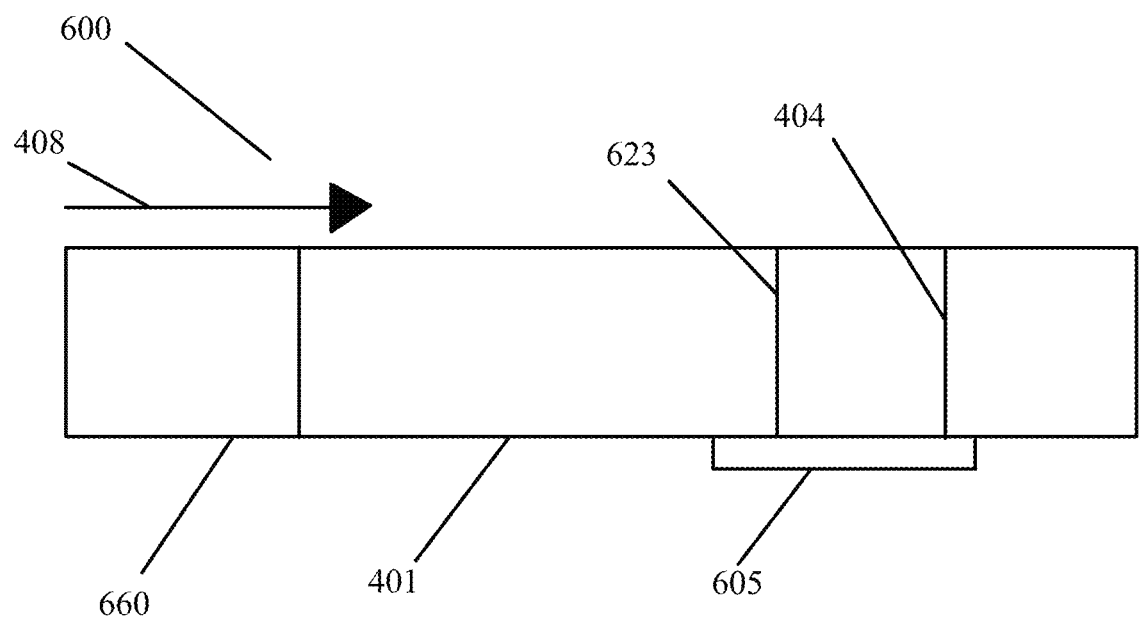
FIG. 11B shows a device with the reagent zone upstream of the sample application zone, and a test line corresponding to the presence of a bacterial marker such as high C-reactive protein levels.

FIGS. 11A and 11B show a chromatographic test strip (600) with a test line (623) that detects the presence of a bacterial marker, such as high levels of C-reactive protein. The sample is applied to the application zone (401) of the chromatographic test strip (600). The sample travels along the direction of flow (408). As shown in FIG. 11A, the sample then passes a reagent zone (660) containing at least one labeled bacterial binding partner that is eluted by and then able to migrate with a sample transport liquid (e.g. a buffer solution). Alternatively, as shown in FIG. 11B, the reagent zone (660) is located upstream of the sample application zone (401) such that the labeled binding partners in the reagent zone are eluted by the sample transport liquid and travel to the sample. The labeled bacterial binding partner is capable of specifically binding to a bacterial marker of interest, for example high levels of C-reactive protein, to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (600) in these embodiments.

The test strip (600) also includes a detection zone (605) containing a section for detection of a bacterial marker, e.g. a test line (623), including an immobilized specific binding partner, complementary to the bacterial reagent complex formed by the bacterial marker and its labeled binding partner. Thus, at the test line (623), detection zone binding partners trap the labeled bacterial binding partners from the reagent zone (660) along with their bound bacterial markers. This localization of the bacterial marker with its labeled binding partners gives rise to an indication at the test line (623). At the test line (623), the presence of the bacterial marker is determined by qualitative and/or quantitative readout of the test line (623) indication resulting from the accumulation of labeled binding partners.

Optionally, the detection zone (605) may contain further test lines to detect other bacterial and/or viral markers, as well as a control line (404). The control line (404) indicates that the labeled specific binding partner traveled through the length of the assay, even though it may not have bound any bacterial markers, thus confirming proper operation of the assay. As shown in FIGS. 11A through 11B, the control zone (404) is preferably downstream of the test line (623). However, in other embodiments, the control zone (404) may be located upstream of the test line (623).

In some embodiments, the control line (404) includes an antibody or other recombinant protein which binds to a component of the elution medium or other composition being used in the test. In embodiments where nucleic acids are the targets, the control line (404) preferably includes a nucleic acid complementary to the labeled nucleic acid being used as a binding partner for the target nucleic acid.

In other embodiments to test for a bacterial marker, such as high CRP levels, as shown in FIGS. 12A through 12D, the sample passes a lysis zone (250), where a lysis agent will have preferably been pre-loaded onto the test strip and is eluted by the transport liquid. The lysis agent lyses any lysis-susceptible components in the sample in situ.

The chromatographic test strip (700) contains a sample application zone (201), a lysis zone (250) containing a lysis agent, and a reagent zone (760) containing at least one labeled binding partner that binds to a bacterial marker, for example high levels of C-reactive protein, that is eluted by and then able to migrate with a sample transport liquid (e.g. a buffer solution). While the reagent zone (760) is shown downstream of the sample application zone in these figures, in alternative embodiments, the reagent zone (760) could be upstream of the sample application zone (see FIG. 11B), as long as the reagents encounter the sample at some point after the sample reaches the lysis zone and is effectively lysed. The labeled binding partner is capable of specifically binding to a bacterial marker of interest, for example high levels of C-reactive protein, to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (700) in these embodiments.

In one embodiment, the lysis agent is localized in the lysis zone (250) between the sample application zone (201) and the reagent zone (760). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the detection zone (705).

Figure 12A:
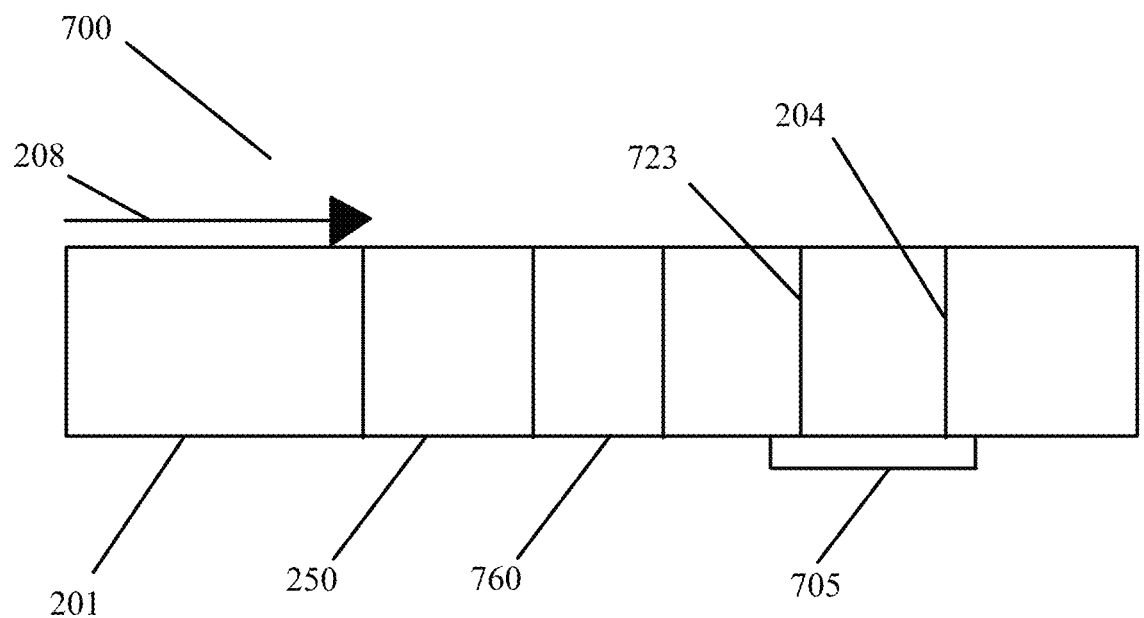
FIG. 12A shows a sample analysis device including a lysis zone located between a sample application zone and a reagent zone.
Figure 12B:
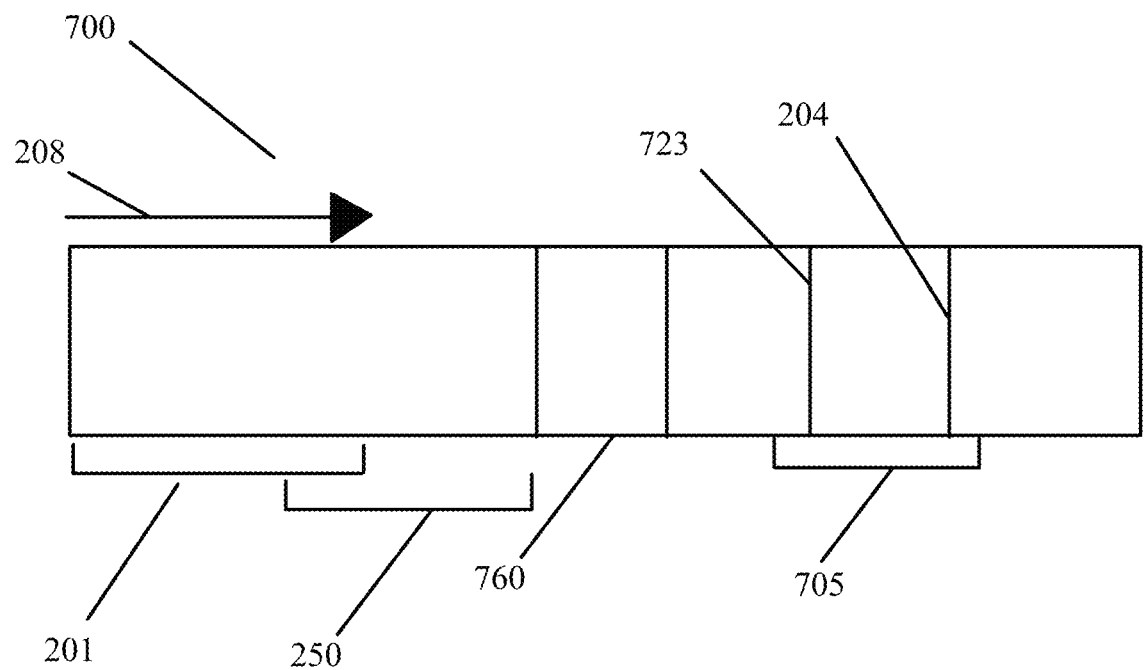
FIG. 12B shows a sample analysis device including a lysis zone overlapping a sample application zone.
Figure 12C:
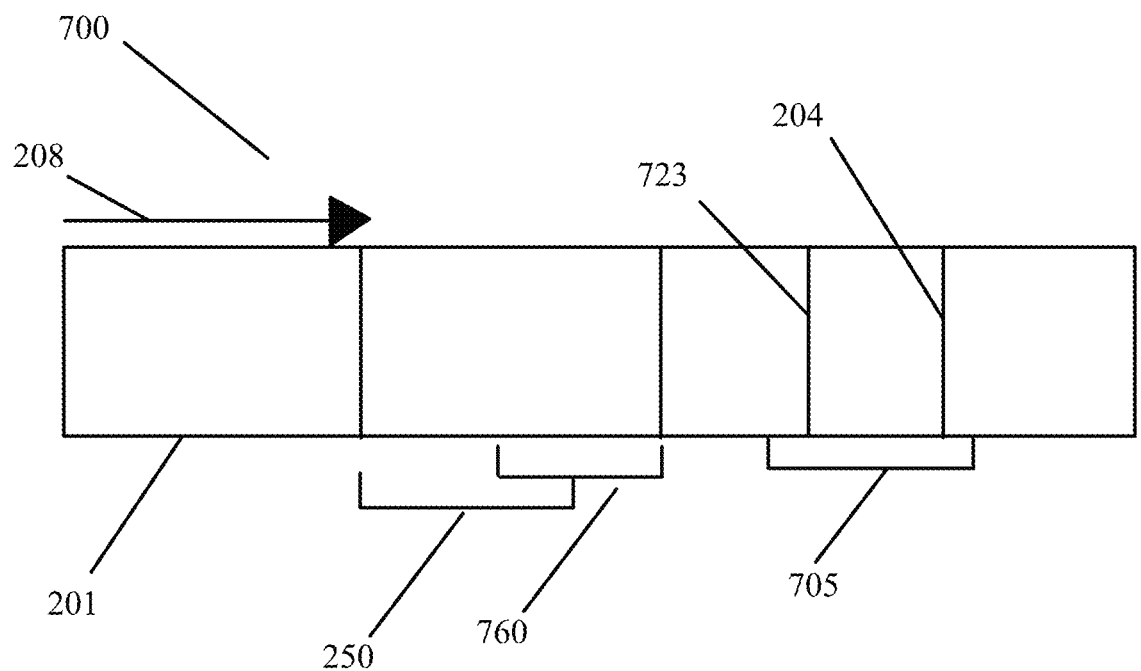
FIG. 12C shows a sample analysis device including a lysis zone overlapping a reagent zone.
Figure 12D:
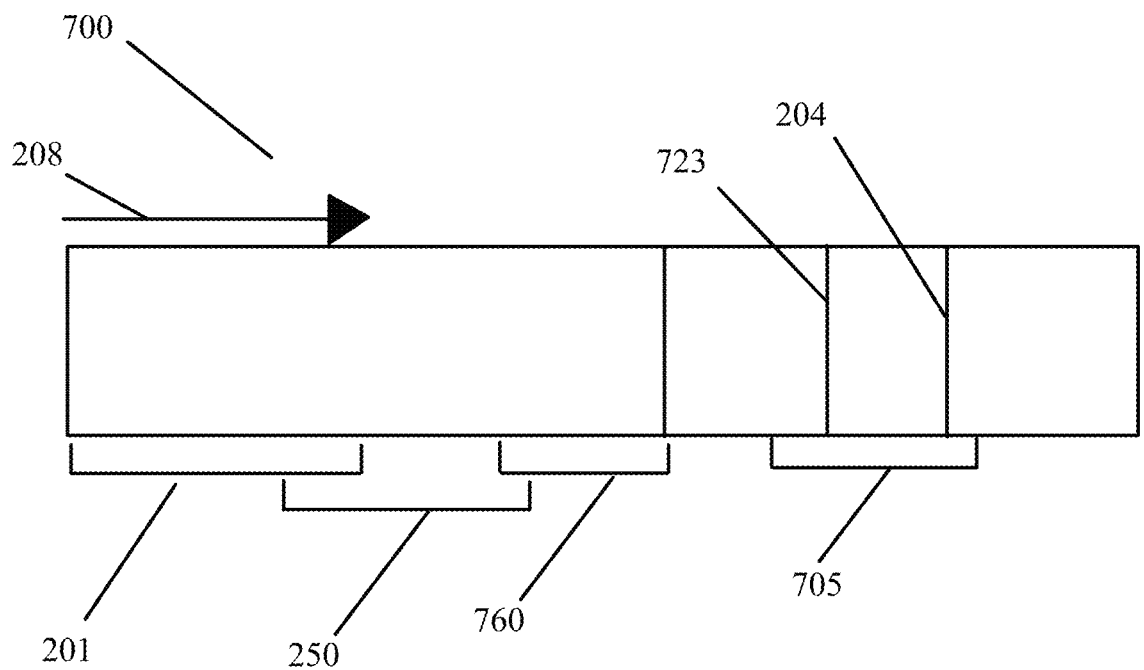
FIG. 12D shows a sample analysis device including a lysis zone overlapping a sample application zone and a reagent zone.

The lysis zone (250) is preferably located between the sample application zone (201) and the reagent zone (760), as shown in FIG. 12A. In other embodiments, the lysis zone (250) overlaps the sample application zone (201), the reagent zone (760) or both the sample application zone (201) and the reagent zone (260) as shown in FIGS. 12B, 12C, and 12D, respectively. Note that the figures are schematic, and are not drawn to scale. The amount of overlap between the different zones (as shown in FIGS. 12B through 12D) may be highly variable.

The test strip (700) also includes a detection zone (705) containing a section for detection of at least one bacterial marker, e.g. a test line (723), including an immobilized specific binding partner, for example, a specific binding partner for a high level of C-reactive protein, complementary to the bacterial conjugate formed by the bacterial marker and its labeled binding partner. Thus, at the test line (723), detection zone binding partners trap the bacterial labeled binding partners from the reagent zone (760) along with their bound bacterial markers. This localization of the bacterial markers with their labeled binding partners gives rise to an indication at the test line (723). At the test line (723), the presence of a bacterial marker is determined by qualitative and/or quantitative readout of the test line (723) indication resulting from the accumulation of labeled binding partners.

Optionally, the detection zone (705) may contain further test lines to detect other bacterial and/or viral markers, as well as a control line (204). The control line (204) indicates that the labeled specific binding partner traveled through the length of the assay, even though it may not have bound any markers, thus confirming proper operation of the assay. As shown in FIGS. 12A through 12D, the control zone (204) is preferably downstream of the test line (723). However, in other embodiments, the control zone (204) may be located upstream of the test line (723).

In some embodiments, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

One preferred configuration for a bimodal dual test strip sample analysis device is shown in FIGS. 13A through 13C. The sample analysis device or test card (800) includes a closable housing (835) with two sides (836), (837) and a spine or hinged portion (831). In one preferred embodiment, the test card (800) is approximately 11.5 cm long (L)×7 cm wide (W) when the two sides (836), (837) are closed. However, any size test card (800) that accommodates all of the components may be used. Within the first side (836) of the housing (835), there are two test strips (815), (825), each including a receiving pad (845), a diverting zone (850), a transfer pad (855) and a detection zone (805). The first side (836) also includes an absorbent pad (840) and preferably a waste pad (860). The first test strip (815) preferably includes a detection zone (805) with an MxA test line (802), a low CRP test line (803) and a control line (804). The second test strip (825) preferably includes a detection zone (805) with a high CRP test line (823) and a control line (804). All of the test lines are visible through the windows (865) on the second side (837) of the housing (835) when the housing (835) is closed. The absorbent pad (840) is preferably a single pad that the running buffer is added to to start lateral flow. Similarly, the waste pad (860) is preferably a single pad that collects excess running buffer at the end of the test. However, in other embodiments, each strip could have a separate absorbent pad (840) and/or waste pad (860).

The second side (837) of the housing (835) includes three separate sections (838), (839) and (870). The middle portion, a sample compressor or flap (870), preferably includes two conjugate zones (872), (874), each including a labeled binding partner for at least one analyte, and a labeled control. In some embodiments, the sample compressor (870) is any of the sample compressors described in U.S. Pat. No. 8,609,433, entitled "Multiplanar Lateral flow Assay with Sample Compressor", issued Dec. 17, 2013, herein incorporated by reference. A window (843) is located in the lower portion (838) of the second side (837) of the housing so that the buffer can be added to the absorbent pad (840) when the housing (835) is closed. The viewing windows (865) for the detection zones (805) are on the upper portion (839) of the second side (837) of the housing (835).

The upper portion (839) and the lower portion (838) of the second side (837) of the housing (835) also preferably each include at least one knob, peg or protrusion (875) that mates with one or more holes (895) so that the upper and lower portions (838), (839) may be easily fastened onto the first side (836) of the housing (835). In a preferred embodiment, there are two pegs (875) on the lower portion (838) that mate with two holes (895) flanking the absorbent pad (840) on the first side (836) of the housing (835) and two pegs (875) on the upper portion (839) that mate with two holes (895) flanking the waste pad (860) on the first side (836) of the housing (835). In other embodiments, the holes (895) are on the second side (837) of the housing (835) and the pegs (875) are on the first side (836) of the housing (835). In yet other embodiments, other reversible fastening mechanisms could be used to secure the upper portion (838) and/or lower portion (839) of the second side (837) of the housing (835) to the first side (836) of the housing (835). In other embodiments, the upper and lower sections (838), (839) are permanently closed, for example using an adhesive, before use.

The flap (870), also known as a sample compressor, on the second side (837) of the housing includes two conjugate zones (872), (874) and two sample application zones (873), (876), and can be easily opened and closed. The flap (870) also preferably includes at least one knob, peg or protrusion (875) that mates with one or more holes (895) so that the flap (870) is easily correctly closed onto the first side (836) of the housing (835) after sample has been added to the sample application zones (873), (876). In other embodiments, the holes (895) are on the second side (837) of the housing (835) and the pegs (875) are on the first side (836) of the housing (835). In yet other embodiments, other reversible fastening mechanisms could be used to secure the flap (870) to the first side (836) of the housing (835).

The conjugate zones (872), (874) and the sample application zones (873), (876) preferably overlap. In preferred embodiments, the conjugate zones (872), (874) are colored due to the dyes in the sample conjugates and control conjugates, and the sample is placed directly on the colored portion of the flap (870). In one preferred embodiment, the conjugate zone (872) that is used for the first test strip (815) contains an MxA binding partner that is labeled with a red dye, a low CRP binding partner that is labeled with a black dye, and a control binding partner that is labeled with a blue dye. In this embodiment, the conjugate zone (872) appears purplish. The other conjugate zone (874) contains a high CRP binding partner that is labeled with a black dye and a control binding partner that is labeled with a blue dye. In this embodiment, the conjugate zone (874) appears bluish.

The diverting zone (850) preferably includes a gap or barrier that interrupts lateral flow, diverting the running buffer up into the flap (870) that includes the conjugate zones (872), (874) and the sample application zones (873), (876). In some embodiments, the diverting zone is any of the diverting zones described in U.S. Pat. No. 8,815,609, entitled "Multiplanar Lateral flow Assay with Zone", issued Aug. 26, 2014, herein incorporated by reference.

In operation, the upper and lower portions (838), (839) of the second side (837) of the housing (835) are preferably snapped closed before use by securing the pegs (875) to the holes (895). The sample analysis device, or test card (800) is preferably placed on a flat surface. If the flap (870) is not already open, the user opens it to access the sample application zones (873), (876). A blood sample to be tested is taken from the patient. The sample may be taken by any procedure known in the art. In a preferred embodiment, a sample of 5 µl of blood is added to each of the sample application zones (873), (876) and then the flap (870) is closed. Each of the 5 µl samples is preferably collected independently of each other. The blood samples are preferably added directly to the device (800), without any pretreatment.

To ensure that the sample compressor or flap (870) has been closed correctly, pressure is preferably applied to the housing (835) above the pegs (875) to snap the pegs (875) closed. The top of the flap (870) needs to be flush with the top of the rest of the second side (837) of the housing (835) for the test to run properly. Running buffer is added to the absorbent pad (840), which initiates lateral flow (885). In preferred embodiments, the running buffer includes one or more lysis agents, for example detergents, to lyse the blood sample and expose the intracellular MxA in the sample. In some preferred embodiments, the lysis agents NP-40 and sarkosyl are included in a Tris-containing running buffer.

When the running buffer reaches the diverting zone (850), it is diverted up into the flap (870). It travels through the conjugate zones (872), (874), collecting any complexes formed between the MxA binding partner and MxA in the sample, the low CRP binding partner and low levels of C-reactive protein in the sample, the high CRP binding partner and high levels of C-reactive protein in the sample, as well as the control conjugate.

Since the conjugate zones (872), (874) bridge the diverting zone (850) on the lateral flow test strips (815), (825), the running buffer, which now contains sample, conjugate, and the complexes described above, then travels into the transfer pad (855), and to the detection zones (805) on each of the test strips (815), (825). If MxA is present in the sample, the MxA test line (802) on the first test strip (815) will be red. If a threshold low level of C-reactive protein is present in the sample, the low CRP test line (803) on the first test strip (815) will be black. If a threshold high level of C-reactive protein is present in the sample, the high CRP test line (823) on the second test strip (825) will be black. If the test is run correctly, the control lines (804) on both the first strip (815) and the second test strip (825) will be blue. In preferred embodiments, the levels of detection are 40 ng/ml for MxA, 10 mg/L for low CRP on the first test strip (815) and 80 mg/L for high CRP on the second test strip (825). In other preferred embodiments, the levels of detection are 25 ng/ml for MxA, 20 mg/L for low CRP on the first test strip (815) and 80 mg/L for high CRP on the second test strip (825). Any combinations of these different cutoff values could be used. The results of the test should be visible after approximately 5-20 minutes, preferably within about 10 minutes.

Since the control binding partner is on the sample compressor or flap (870) and not on either of the test strips (815), (825), there is a true procedural control to this configuration. If the flap (870) is not closed properly, nothing will show up in the detection zone (805), indicating that the test was run improperly.

FIGS. 14A through 14F show test results using the device (800) shown in FIGS. 13A through 13C, with two test strips (815), (825) side by side, where a first test strip (815) tests for the presence of both MxA and low levels of C-reactive protein and the second test strip (825) tests for high levels of C-reactive protein.

FIG. 14A shows a negative result at the MxA test line (802) and a negative result at the low CRP test line (803) on the first test strip (815), as well as a negative result at the high CRP test line (823) on the second test strip (825). More specifically, the only visible lines in the detection zone (805) of the lateral flow assay (800) are the two blue control lines (804). This result indicates that the sample is negative for both viral and bacterial infection. A patient with this result, absent additional testing, would be considered microbiologically unconfirmed.

Figure 14B:
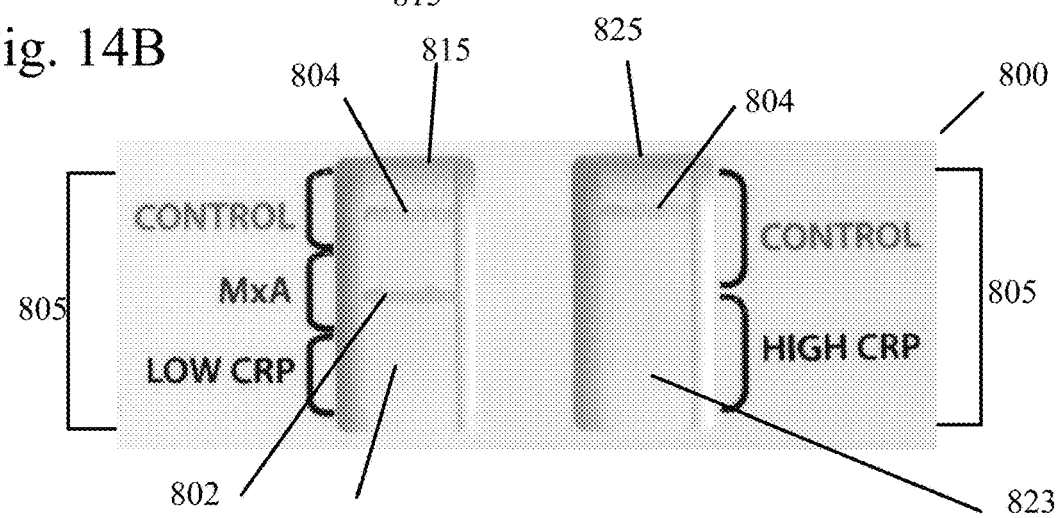
FIG. 14B shows a test result positive for MxA, indicating a viral infection.
Figure 14C:
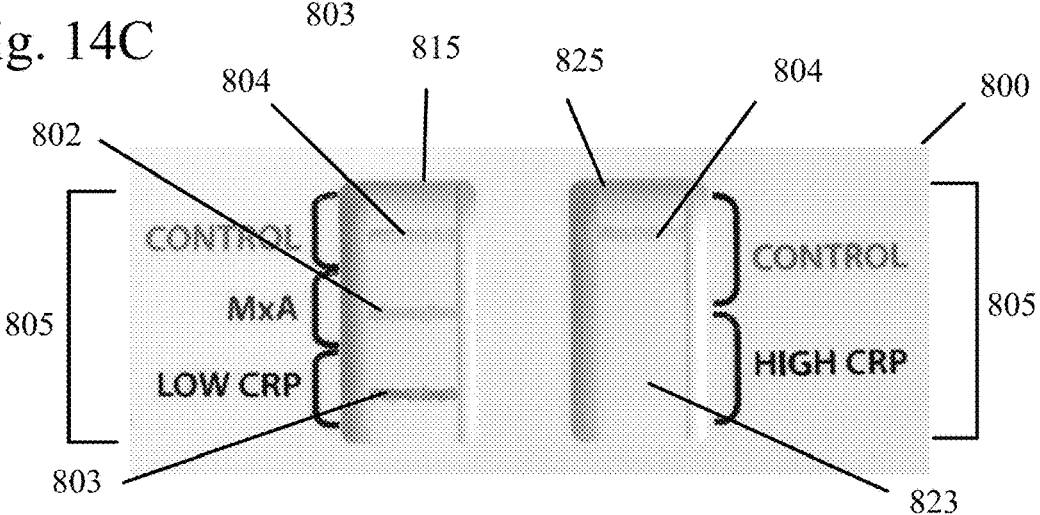
FIG. 14C shows a test result positive for MxA and low CRP, indicating a viral infection.

FIGS. 14B and 14C are positive for viral infection. In FIG. 14B, the presence of two blue control lines (804) and a red MxA line (802) indicate a viral infection. In FIG. 14C, the presence of two blue control lines (804) and a red MxA line (802) indicate a viral infection. Since there is also a black low CRP line (803) in FIG. 14C, there is a possibility of bacterial co-infection, although there is an absence of a high CRP line (823). Any time MxA is positive in this test, it indicates a viral infection.

Figure 14D:
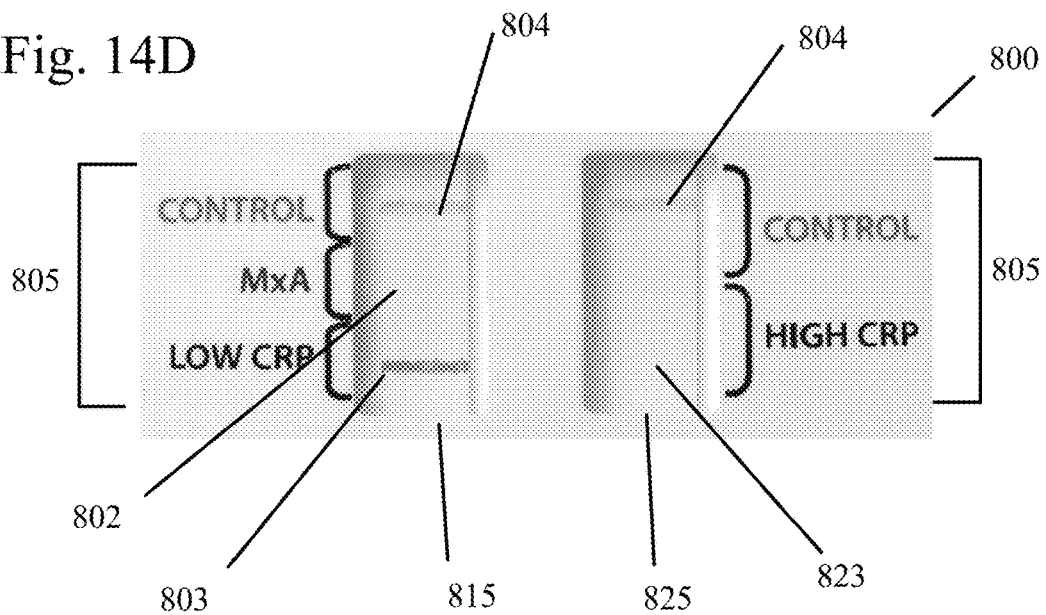
FIG. 14D shows a test result positive for low CRP.
Figure 14E:
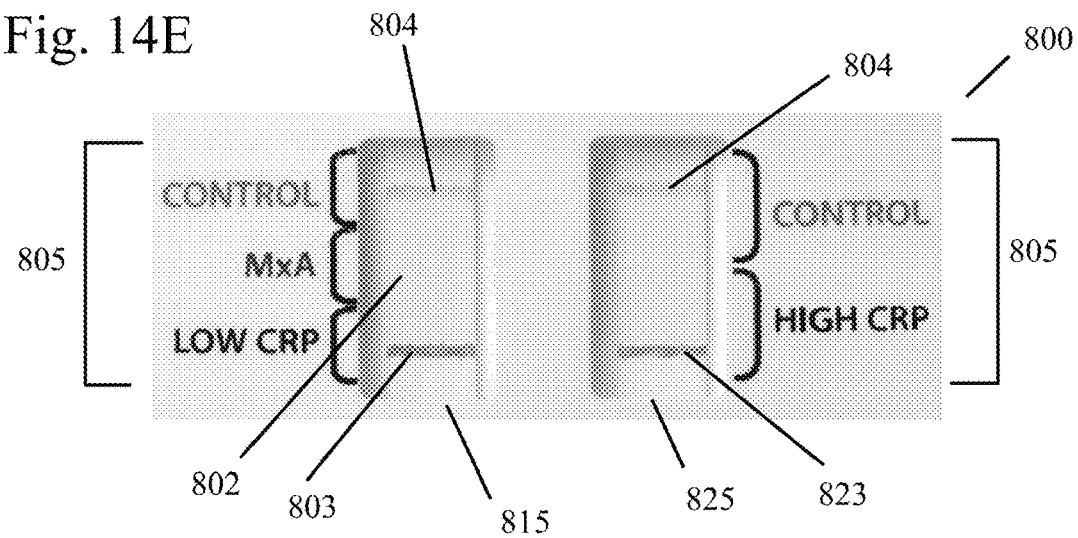
FIG. 14E shows a test result positive for both low and high CRP, on separate strips.

FIGS. 14D and 14E are positive for bacterial infection. In FIG. 14D, the presence of two blue control lines (804) and a black low CRP line (803) indicates a bacterial infection. In FIG. 14E, the presence of two blue control lines (804), a black low CRP line (803), and a black high CRP line (823) also indicates a bacterial infection. The MxA line is absent in both FIGS. 14D and 14E, indicating an absence of a viral infection.

Figure 14F:
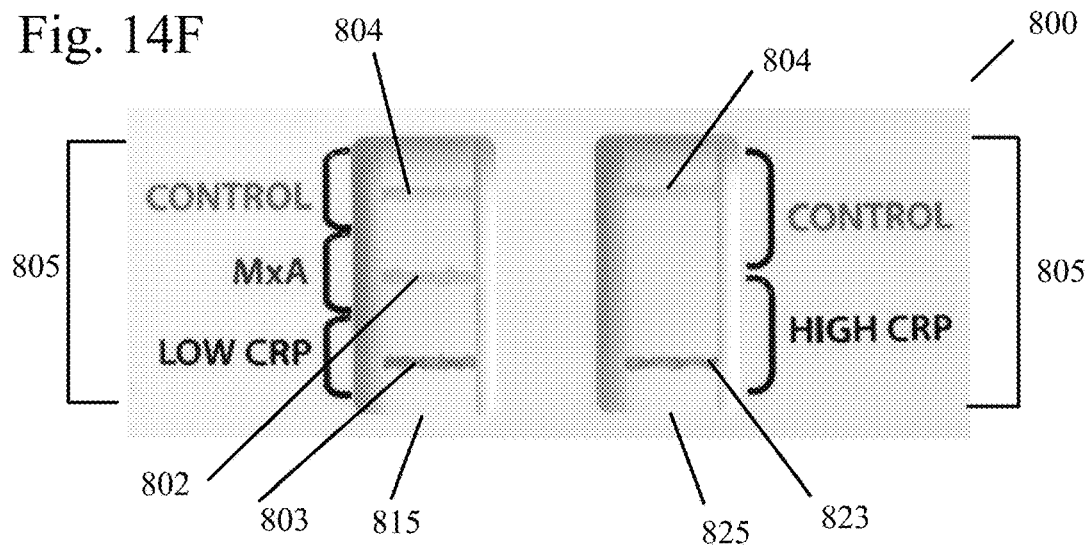
FIG. 14F shows a test result positive for both CRP (low and high) and MxA, indicating a viral infection (or possible co-infection).

FIG. 14F indicates viral infection, or co-infection (both bacterial and viral infection). The presence of two blue control lines (804), a red MxA line (802), a black low CRP line (803), and a black high CRP line (823) indicates viral infection or a possible co-infection. In most cases, the patient will have a viral infection only. While there is a possibility for co-infection, the Applicants have not observed co-infection in their studies.

Figure 15A:
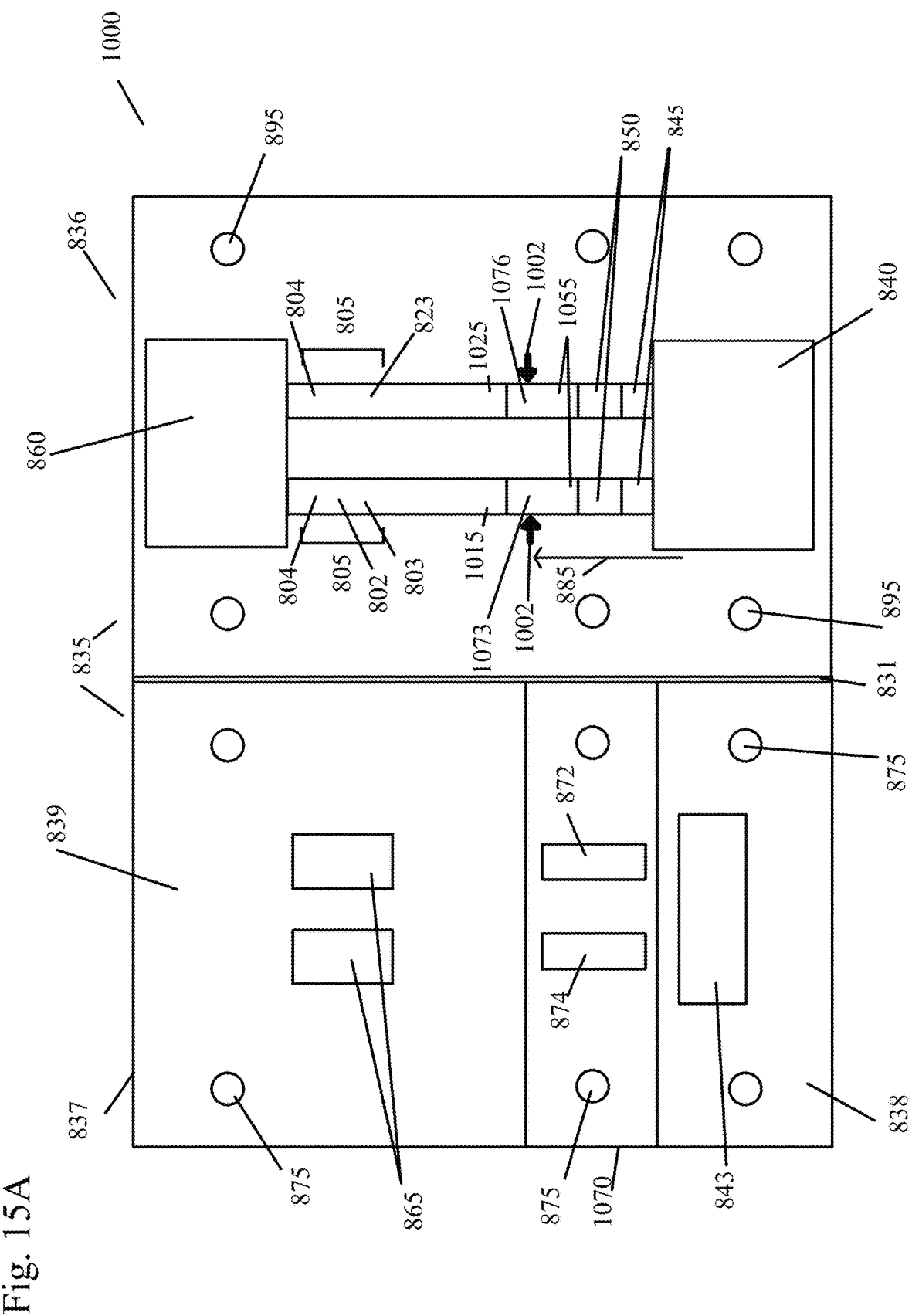
FIG. 15A shows a fully open sample analysis device with dual test strips and a conjugate zone on a sample compressor in a plane separate from the test strips.
Figure 15B:
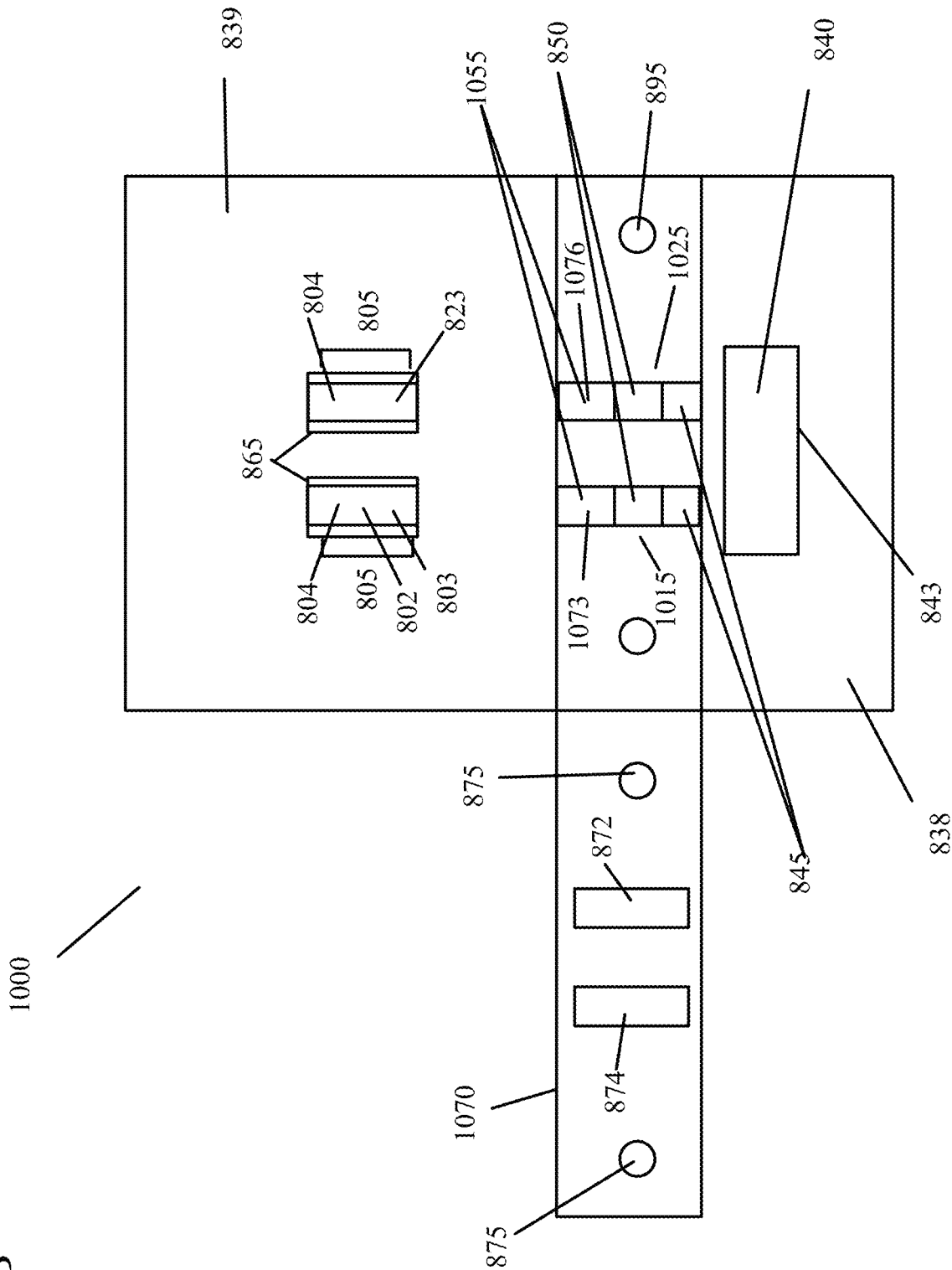
FIG. 15B shows the sample analysis device of FIG. 15A with part of the housing closed, but the conjugate zone still visible on the left side of the device.
Figure 15C:
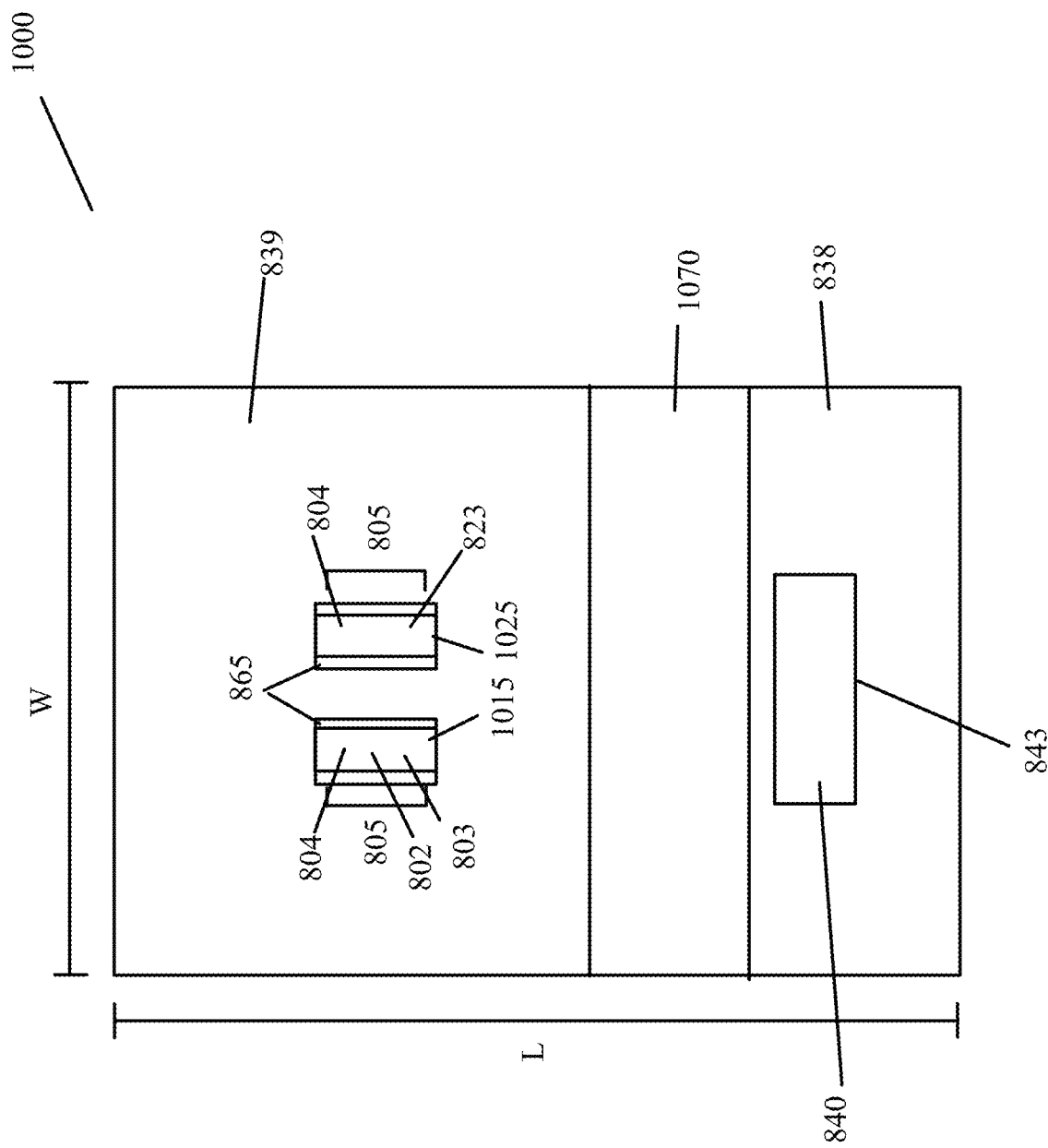
FIG. 15C shows the sample analysis device of FIG. 15A after the test has been initiated.

Another preferred configuration for a bimodal dual test strip sample analysis device (1000) is shown in FIGS. 15A through 15C. This configuration is similar to the configuration (800) shown in FIGS. 13A through 13C, but the sample application zones (1073), (1076) are located on each of the test strips (1015), (1025), downstream of the diverting zone (850). The sample analysis device or test card (1000) includes a closable housing (835) with two sides (836), (837) and a spine or hinged portion (831). In one preferred embodiment, the test card (1000) is approximately 11.5 cm long (L)×7 cm wide (W) when the two sides (836), (837) are closed. However, any size test card (1000) that accommodates all of the components may be used. Within the first side (836) of the housing (835), there are two test strips (1015), (1025), each including a receiving pad (845), a diverting zone (850), a transfer pad (1055) and a detection zone (805). The first side (836) also includes an absorbent pad (840) and preferably a waste pad (860). The first test strip (1015) preferably includes a detection zone (805) with an MxA test line (802), a low CRP test line (803) and a control line (804). The second test strip (1025) preferably includes a detection zone (805) with a high CRP test line (823) and a control line (804). All of the test lines are visible through the windows (865) on the second side (837) of the housing (835) when the housing (835) is closed. The absorbent pad (840) is preferably a single pad to which the running buffer is added to start lateral flow. Similarly, the waste pad (860) is preferably a single pad that collects excess running buffer at the end of the test. However, in other embodiments, each strip could have a separate absorbent pad (840) and/or waste pad (860).

The second side (837) of the housing (835) includes three separate sections (838), (839) and (1070). The middle portion, or flap (1070), also known as a sample compressor, preferably includes two conjugate zones (872), (874), each including a labeled binding partner for at least one analyte, and a labeled control. A window (843) is located in the lower portion (838) of the second side (837) of the housing so that the buffer can be added when the housing (835) is closed. The viewing windows (865) for the detection zones (805) are on the upper portion (839) of the second side (837) of the housing (835).

The upper portion (839) and the lower portion (838) of the second side (837) of the housing (835) also preferably each include at least one knob, peg or protrusion (875) that mates with one or more holes (895) so that the upper and lower portions (838), (839) may be easily fastened onto the first side (836) of the housing (835). In a preferred embodiment, there are two pegs (875) on the lower portion (838) that mate with two holes (895) flanking the absorbent pad (840) on the first side (836) of the housing (835) and two pegs (875) on the upper portion (839) that mate with two holes (895) flanking the waste pad (860) on the first side (836) of the housing (835). In other embodiments, the holes (895) are on the second side (837) of the housing (835) and the pegs (875) are on the first side (836) of the housing (835). In yet other embodiments, other reversible fastening mechanisms could be used to secure the upper portion (838) and/or lower portion (839) of the second side (837) of the housing (835) to the first side (836) of the housing (835). In other embodiments, the upper and lower sections (838), (839) are permanently closed, for example using an adhesive, before use.

The flap (1070) on the second side (837) of the housing includes two conjugate zones (872), (874) and can be easily opened and closed. The flap (1070) also preferably includes at least one knob, peg or protrusion (875) that mates with one or more holes (895) so that the flap (1070) is easily correctly closed onto the first side (836) of the housing (835) after sample has been added to the sample application zones (1073), (1076) on the test strips (1015), (1025). In other embodiments, the holes (895) are on the second side (837) of the housing (835) and the pegs (875) are on the first side (836) of the housing (835). In yet other embodiments, other reversible fastening mechanisms could be used to secure the flap (1070) to the first side (836) of the housing (835).

In some embodiments, the conjugate zones (872), (874) are colored due to the dyes in the sample conjugates and control conjugates. In one preferred embodiment, the conjugate zone (872) that is used for the first test strip (1015) contains an MxA binding partner that is labeled with a red dye, a low CRP binding partner that is labeled with a black dye, and a control binding partner that is labeled with a blue dye. In this embodiment, the conjugate zone (872) appears purplish. The other conjugate zone (874) contains a high CRP binding partner that is labeled with a black dye and a control binding partner that is labeled with a blue dye. In this embodiment, the conjugate zone (874) appears bluish.

The diverting zone (850), which preferably includes a gap or barrier, interrupts lateral flow, diverting the running buffer up into the flap (1070) that includes the conjugate zones (872), (874).

In operation, the upper and lower portions (838), (839) of the second side (837) of the housing (835) are preferably snapped closed before use by securing the pegs (875) to the holes (895). The sample analysis device, or test card (1000) is preferably placed on a flat surface. If the flap (1070) is not already open, the user opens it to access the sample application zones (1073), (1076). The sample application zones (1073), (1076) may be located in any portion of the transfer pad (1055). A blood sample to be tested is taken from the patient. The sample may be taken by any procedure known in the art. In a preferred embodiment, a sample of 5 µl of blood is added to each of the sample application zones (1073), (1076) zones and then the flap (1070) is closed. Each of the 5 µl samples is preferably collected independently of each other. The blood is preferably added directly to the device (1000), without any pretreatment. In preferred embodiments, an arrow (1002) or other indication (shown in FIG. 15A), for example the words "add sample here" shows the user where to place the sample on the test strips (1015), (1025).

To ensure that the flap (1070) has been closed correctly, pressure is preferably applied to the housing (835) above the pegs (875) to snap the pegs (875) closed. The top of the flap (1070) needs to be flush with the top of the rest of the second side (837) of the housing (835) for the test to run properly. Running buffer is added to the absorbent pad (840), which initiates lateral flow (885). In preferred embodiments, the running buffer includes one or more lysis agents, for example detergents, to lyse the blood sample and expose the intracellular MxA in the sample. When the running buffer reaches the diverting zone (850), it is diverted up into the flap (1070). It travels through the conjugate zones (872), (874), collecting the MxA binding partners, the low CRP binding partners, and the high CRP binding partners, as well as the control conjugate.

Since the conjugate zones (872), (874) bridge the diverting zone (850) on the lateral flow test strips (1015), (1025), the running buffer, which now contains conjugate, then travels into the transfer pad (1055), which includes the sample application zones (1073), (1076), and to the detection zones (805) on each of the test strips (1015), (1025). If MxA is present in the sample, the MxA test line (802) on the first test strip (1015) will be red. If a threshold low level of C-reactive protein is present in the sample, the low CRP test line (803) on the first test strip (1015) will be black. If a threshold high level of C-reactive protein is present in the sample, the high CRP test line (823) on the second test strip (1025) will be black. In preferred embodiments, the levels of detection are 40 ng/ml for MxA, 10 mg/L for low CRP on the first test strip (1015) and 80 mg/L for high CRP on the second test strip (1025). In other preferred embodiments, the levels of detection are 25 ng/ml for MxA, 20 mg/L for low CRP on the first test strip (1015) and 80 mg/L for high CRP on the second test strip (1025). Any combinations of these different cutoff values could be used. The results of the test should be visible after approximately 5-20 minutes, preferably within about 10 minutes. If the test was run correctly, the control lines (804) on both the first test strip (1015) and the second test strip (1025) will be blue.

Since the control binding partner is on the flap (1070) and not on either of the test strips (1015), (1025), there is a true procedural control to this configuration. If the flap (1070) is not closed properly, nothing will show up in the detection zone (805), indicating that the test was run improperly.

In an alternative embodiment, the sample application zones (1073), (1076) are located on the receiving pad (845), before the diverting zone (850). In this embodiment, the running buffer travels through the sample application zones (1073), (1076), and then is diverted into the flap (1070).

In preferred embodiments of the configurations shown in FIGS. 13A through 13C and 15A through 15C, greater than approximately 1.2 ml of running buffer is placed on the absorbent pad (840). If less than 1.0 ml is added in embodiments where the diverting zone (850) is a gap, the buffer gets stalled at the gap because the gap holds approximately 1.0 ml.

Figure 16:
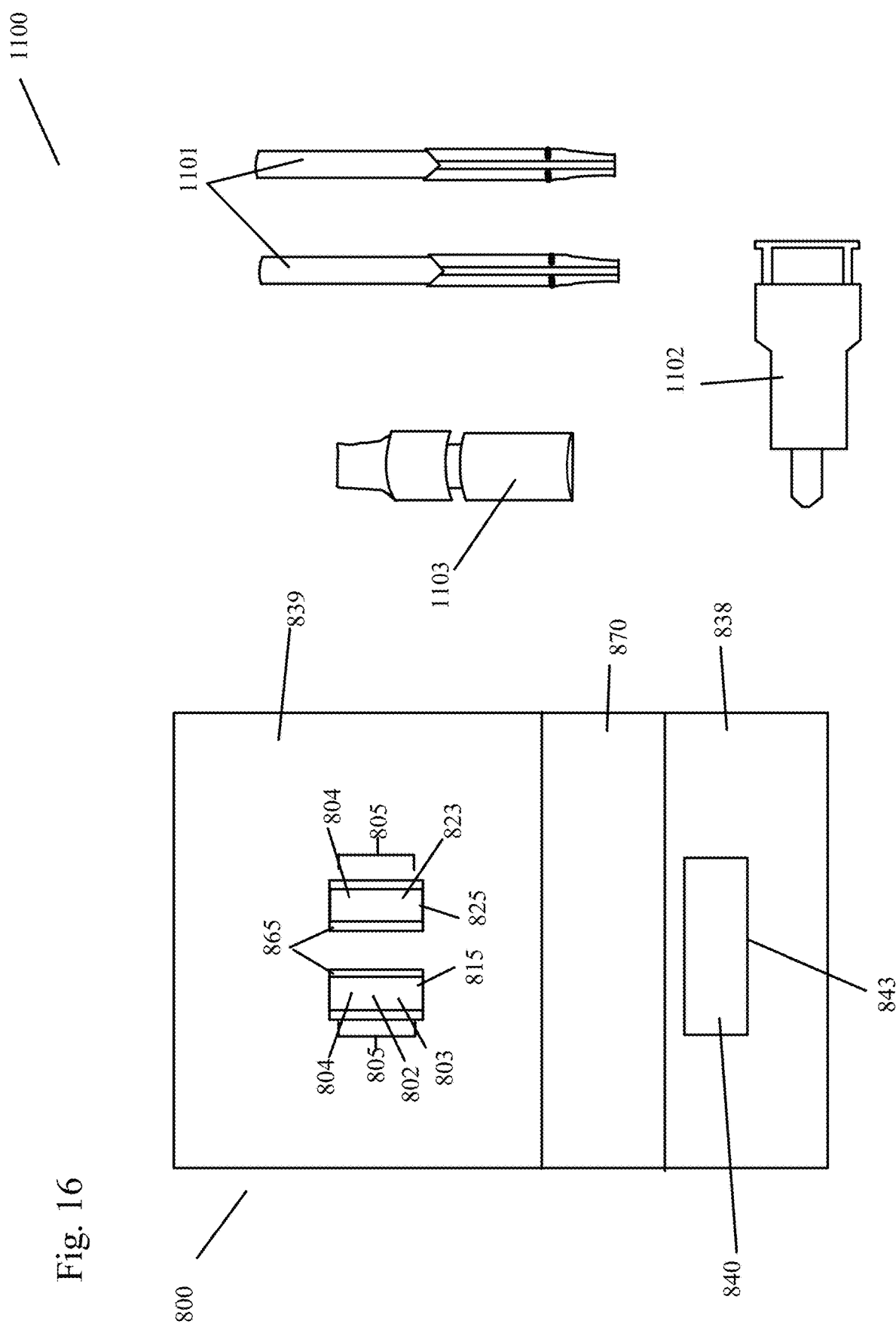
FIG. 16 shows a kit for sample analysis using a sample analysis device.

As shown in FIG. 16, in one preferred embodiment, a kit (1100) includes the sample analysis device (800), (1000), a lancet (1102), one or more pipettes (1101), and a running buffer (1103). The lancet (1102) is used to make a skin puncture and one or more pipettes (1101) are used to collect the blood from the puncture site. In a preferred embodiment, 5 μl of blood is transferred from a first pipette (1101) to the first conjugate zone (872, see FIGS. 13B and 15B) and another 5 μl of blood is transferred from a second pipette (1101) and added to the second conjugate zone (874, see FIGS. 13B and 15B). The flap (870) is closed, and the running buffer (1103) is added to the absorbent pad (840), as described in the description of FIGS. 13A through 13C and 15A through 15C.

The diverting zone (850) preferably includes at least one feature that interrupts flow in the plane in which flow is occurring. The diverting zone may include a barrier, a gap, a ditch, or any combination of these features. The barrier is preferably an impermeable membrane (or substantially impermeable membrane) that may be made of any material that prevents the flow of liquid from continuing to flow in the same plane. Some materials for the barrier include, but are not limited to, inert materials, semi-permeable materials, plastics, hydrocarbons, metal, hydrophobic materials, Sephadex, Sepharose, cellulose acetate, a hygroscopic material (for example $CaCl_2$, $CaSO_4$ or silica gel), or hydrogels. The gap or ditch is any break in the plane of the lateral flow test strip that extends to a depth sufficient to stop flow. In one preferred embodiment, the gap is preferably at least approximately 0.1 mm deep.

The diverting zone (850) in FIGS. 13A through 13C and 15A through 15C delays or completely stops flow until the sample compressor/flap (870), (1070) is brought into contact with the rest of the device, and creates a bridge along which the fluid can flow. The sample compressor (870), (1070) acts as a bridge and redirects flow into a different plane. Flow is diverted into the sample compressor (870), (1070). This increases collection of the reagents on the sample compressor (870), (1070). For example, in embodiments where the conjugate is on the sample compressor (870), (1070), collection of the conjugate increases in devices with a diverting zone (850). In embodiments where both the sample application zones (873), (876), (1073), (1076) and the conjugate are on the sample compressor (870), (1070), the sample and conjugate both encounter the running buffer when it is diverted into the sample compressor (870), (1070), and a ½ sandwich or full sandwich (depending upon where the second binding partner for the analyte is located on the sample analysis device) is formed before the running buffer is diverted back to the test strips if the analyte is present in the sample. Embodiments with a diverting zone (850) and a sample compressor (870), (1070) increase speed, allow for better interactions between the conjugate and the sample, and allow for more sensitivity because more conjugate is placed into the fluid. In these embodiments, all of the fluid preferably interacts with the conjugate. This is a significant improvement over compressor embodiments without redirection, where approximately 20-30% of the fluid interacts with the conjugate.

Another preferred configuration for a bimodal dual test strip sample analysis device (1200) is shown in FIG. 17. This configuration is similar to the configurations (800), (1000) shown in FIGS. 13A through 13C and FIGS. 15A through 15C, without a second section (837) of the housing (1235) or a diverting zone (850). Instead, all of the components of the test are located in the same plane and flow proceeds laterally from the absorbent pad (840) to the waste pad (860). Note that this embodiment could also include a housing with a window to facilitate application of the buffer to the absorbent pad (840), a window located above each sample application zone (1273), (1276) for applying sample to the device (1200), and viewing windows for the detection zone (805). In one preferred embodiment, the sample analysis device (1200) is approximately 11.5 cm long (L)×7 cm wide (W). However, any size test card (1200) that accommodates all of the components may be used. There are two test strips (1215), (1225), each including a receiving pad (845), a conjugate zone (1272), (1274), a transfer pad (1255) containing a sample application zone (1273), (1276), a detection zone (805) and a waste pad (860). 1240 While the conjugate zones (1272), (1274) are shown upstream of the sample application zones (1273), (1276) in this figure, in other embodiments, one or both of the conjugate zones (1272), (1274) are located downstream of the sample application zones (1273), (1276). The detection zone (805) of the first test strip (1215) preferably includes an MxA test line (802), a low CRP test line (803) and a control line (804). The detection zone (805) on the second test strip (1225) also preferably includes a high CRP test line (823) and a control line (804). The absorbent pad (840) is preferably a single pad that the running buffer is added to to start lateral flow. Similarly, the waste pad (860) is preferably a single pad that collects excess running buffer at the end of the test. However, in other embodiments, each strip could have a separate absorbent pad (840) and/or waste pad (860).

In preferred embodiments, the conjugate zones (1272), (1274) are colored due to the dyes in the sample conjugates and control conjugates. In one preferred embodiment, the conjugate zone (1272) that is used for the first test strip (1215) contains an MxA binding partner that is labeled with a red dye, a low CRP binding partner that is labeled with a black dye, and a control binding partner that is labeled with a blue dye. In this embodiment, the conjugate zone (1272) appears purplish. The other conjugate zone (1274) contains a high CRP binding partner that is labeled with a black dye and a control binding partner that is labeled with a blue dye. In this embodiment, the conjugate zone (1274) appears bluish.

In operation, a blood sample to be tested is taken from the patient. The sample may be taken by any procedure known in the art. In a preferred embodiment, a sample of 5 μl of blood is added to each of the sample application zones (1273), (1276). Each of the 5 μl samples is preferably collected independently of each other. In preferred embodiments, an arrow (1002) or other indication (shown in FIG. 15A), for example the words "add sample here" shows the user where to place the sample on the test strips (1215), (1225).

The blood is preferably added directly to the device (1200), without any pretreatment. Running buffer is added to the absorbent pad (840), which initiates lateral flow (1285). In preferred embodiments, the running buffer includes one or more lysis agents, for example detergents, to lyse the blood sample and expose the intracellular MxA in the sample. It travels through the conjugate zones (1272), (1274), collecting the MxA binding partners, the low CRP binding partners, the high CRP binding partners, as well as the control conjugate. In some preferred embodiments, the lysis agents NP-40 and sarkosyl are included in a Tris-containing running buffer.

The running buffer, which now contains conjugate, then travels into the transfer pad (1255), which includes the sample application zones (1273), (1276), and to the detection zones (805) on each of the test strips (1215), (1225). If MxA is present in the sample, the MxA test line (802) on the first test strip (1215) will be red. If a threshold low level of C-reactive protein is present in the sample, the low CRP test line (803) on the first test strip (1215) will be black. If a threshold high level of C-reactive protein is present in the sample, the high CRP test line (823) on the second test strip (1225) will be black. In preferred embodiments, the levels of detection are 40 ng/ml for MxA, 10 mg/L for low CRP on the first test strip (1215) and 80 mg/L for high CRP on the second test strip (1225). The results of the test should be visible after approximately 5-20 minutes, preferably within about 10 minutes. If the test was run correctly, the control lines (804) on both the first strip (1215) and the second test strip (1225) will be blue.

In an alternative embodiment, the sample application zones (1273), (1276) are located upstream of the conjugate zones (1272), (1274). In this embodiment, the running buffer travels through the sample application zones (1273), (1276), and then to the conjugate zones (1272), (1274). In still other embodiments, the conjugate zones (1272), (1274) overlap the sample application zones (1273), (1276). In still other embodiments, the conjugate zones (1272), (1274), and/or the sample application zones (1273), (1276) may be located in the receiving pad (845).

In preferred embodiments of the configurations shown in FIGS. 9A through 13C, 15A through 15C and 17, the control is rabbit anti-chicken and the control conjugate is blue latex beads coupled to chicken IgY. In other preferred embodiments, there is at least one lysis agent, preferably a detergent, in the running buffer. In some preferred embodiments, the lysis agents NP-40 and sarkosyl are included in a Tris-containing running buffer.

The bimodal test strips with reagents to detect MxA and C-reactive protein were designed to detect a host immune response (only), not specific viral or bacterial antigens, nucleic acids (including viral DNA shedding) or bacterial cell culture growth. If these test strips are negative, they result in a microbiologically unconfirmed respiratory illness.

The bimodal dual strip test allows for the rapid, visual, qualitative in vitro detection of both MxA and C-reactive protein directly from peripheral whole blood. The test measures a clinically significant immune response to a suspected invasive viral and/or bacterial infection in patients older than 1 year that present within 3 days of an acute onset fever and within 7 days of new onset respiratory symptoms consistent with a suspected community acquired upper respiratory infection (rhinopharyngitis, tonsillopharyngitis, laryngotracheitis) or lower respiratory tract infection (tracheobronchitis, bronchiolitis, or pneumonia). The dual strip bimodal test helps to identify 1) patients with an underlying invasive viral infection from either Influenza A/B, Adenovirus, Respiratory Syncytial Virus, Metapneumovirus, Parainfluenza Virus, or Epstein-Barr Virus; 2) patients with a clinically significant elevated host response consistent with an underlying bacterial infection.

The test is intended for professional use in an outpatient setting and should be used in conjunction with other clinical evidence including laboratory, radiographic, and epidemiological information.

Negative results do not preclude respiratory infection and should not be used as the sole basis for diagnosis, treatment, or other clinical and patient management decisions. In addition to utilizing radiography and clinical presentation to aid in diagnosis, additional laboratory testing (e.g., bacterial and viral culture, immunofluorescence, and viral polymerase chain reaction) must be used to confirm whether a specific respiratory pathogen exists.

In order to clarify the diagnosis, in preferred embodiments, the bimodal test strips described in FIGS. 13-17 (or one or more alternative assay methods and devices able to accurately detect MxA, low CRP, and high CRP levels at certain thresholds, as defined herein), are used in combination with a separate sample analysis device that tests for the presence of procalcitonin. For example, a level of procalcitonin can be determined in the patients with the results shown in FIG. 14A, where the MxA and C-reactive protein results are all negative and the patient's diagnosis is microbiologically unconfirmed. In alternative embodiments, procalcitonin values are taken instead of C-reactive protein values. The diagnostic determination of URIs and LRTIs using procalcitonin and other methods for microbiologically unconfirmed patients shown in FIGS. 3 and 4 would clarify the diagnosis of these patients. As one example, a procalcitonin level equal to or greater than approximately 0.15 ng/ml creates a presumption that the patient has a bacterial infection. In microbiologically unconfirmed patients with lower respiratory infections without an infiltrate, a procalcitonin level less than 0.15 ng/ml creates a presumption that the patient is noninfectious. The combination of results creates a more accurate diagnosis for the patients.

Some examples of assay formats for determining the presence of procalcitonin include, but are not limited to, immunoassays, immunoblotting methods, agglutination reactions, a complement-fixation reaction, a hemolytic reaction, a precipitation reaction, a gold colloid method, a chromatography method, phosphorescence, radioactivity, colorimetry, gravimetry, X-ray diffraction, X-ray absorption, magnetism, fluorescent resonant emissions, or an immunostaining method. Some examples for immunoassays include, but are not limited to, immunoprecipitation, radioimmunoassays (RIA), enzyme immunoassays (EIA or ELISA), a Vidas® immunoassay device (Biomerieux, Hazelwood, Mo.), fluorescent immunoassays (FIA), chemiluminescent immunoassays, physiochemical assays (TIA, LAPIA, or PCIA), lateral flow immunoassays, or flow cytometry. Some preferred immunoassays for these biomarkers include, but are no limited to, ELISAs, fluorescence immunoassays and chemiluminiscent assays. In some preferred embodiments, the assays are automated.

MxA Drives Increased Specificity and Augments Sensitivity of Bacterial Biomarkers Several viral infections such as influenza A/B, adenovirus, Epstein-Barr Virus, cause mild to moderate elevations in the acute phase response, leading to elevations of both C-Reactive Protein (CRP) and procalcitonin (PCT). Historically, C-reactive protein and procalcitonin have been used independently in an effort to distinguish illnesses of viral origin from those of bacterial etiology. At lower concentrations, C-reactive protein has high sensitivity but very low specificity for a bacterial infection and at very high concentrations, the reverse is true and the sensitivity is poor but the specificity is significantly improved. In Scandinavia, point of care C-reactive protein testing is part of the routine evaluation of patients with respiratory infections in general practice, and its use has proved cost-effective, despite the significant overlap in viral and bacterial signs and symptoms at moderate C-reactive protein levels. In general practice, C-reactive protein is found to be valuable aid in reducing unnecessary antibiotics even if it is of modest value at differentiating viral from bacterial disease independently.

Similar to C-reactive protein, at low concentrations, procalcitonin has high sensitivity and low specificity at differentiating a viral from bacterial infection yet at high concentrations, the reverse is true, and sensitivity falls and specificity is increased.

While the host biomarkers of bacterial infection C-reactive protein and procalcitonin are bacterial markers used in the art, they are known for their lack of sensitivity and specificity when used alone. MxA is a biomarker that is specific for viral infection. The Applicant has found that testing for the presence of MxA, a host biomarker of viral infection, combined together with either C-reactive protein or procalcitonin creates an unexpected synergy, greater than an additive phenomenon, and increases both the specificity and sensitivity of both of the bacterial markers. Typically, a bacterial biomarker has an ability to detect bacterial infection with an optimized point that maximizes sensitivity and specificity to identify a bacterial infection. The presence of MxA allows the curve to shift to maximal sensitivity (a lower C-reactive protein or procalcitonin cutoff concentration) without sacrificing the specificity because the MxA identifies the viral patients that have elevated C-reactive protein or procalcitonin (leading to reduced specificity), and correctly recategorizes these patients as viral. Thus, any patient with an elevated C-reactive protein or procalcitonin in the presence of MxA has a viral disease and any elevation of C-reactive protein or procalcitonin (now at a much lower cutoff concentration) in the absence of MxA is bacterial. Furthermore, the lack of elevation of C-reactive protein, procalcitonin, or MxA has an extremely high negative predictive value for the presence of a clinically significant infection. Other host biomarkers of viral infection, for example IFITs (interferon-induced proteins with tetratricopeptide repeats) may alternatively be used to increase sensitivity and specificity of any of the bacterial biomarkers tested alone.

Figure 22:
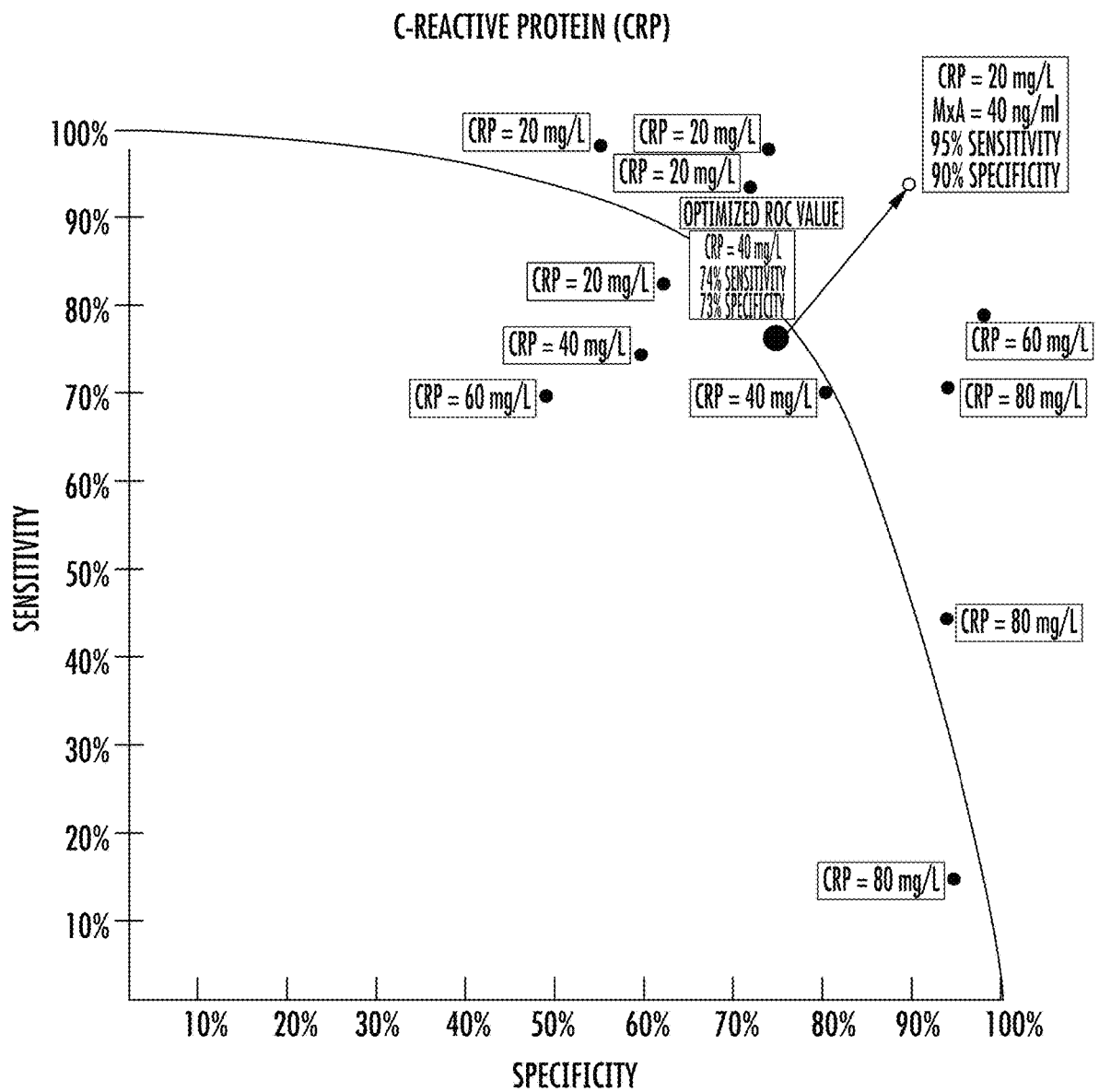
FIG. 22 shows a C-reactive protein receiver-operator curve and its shift upon the addition of MxA.
Figure 23:
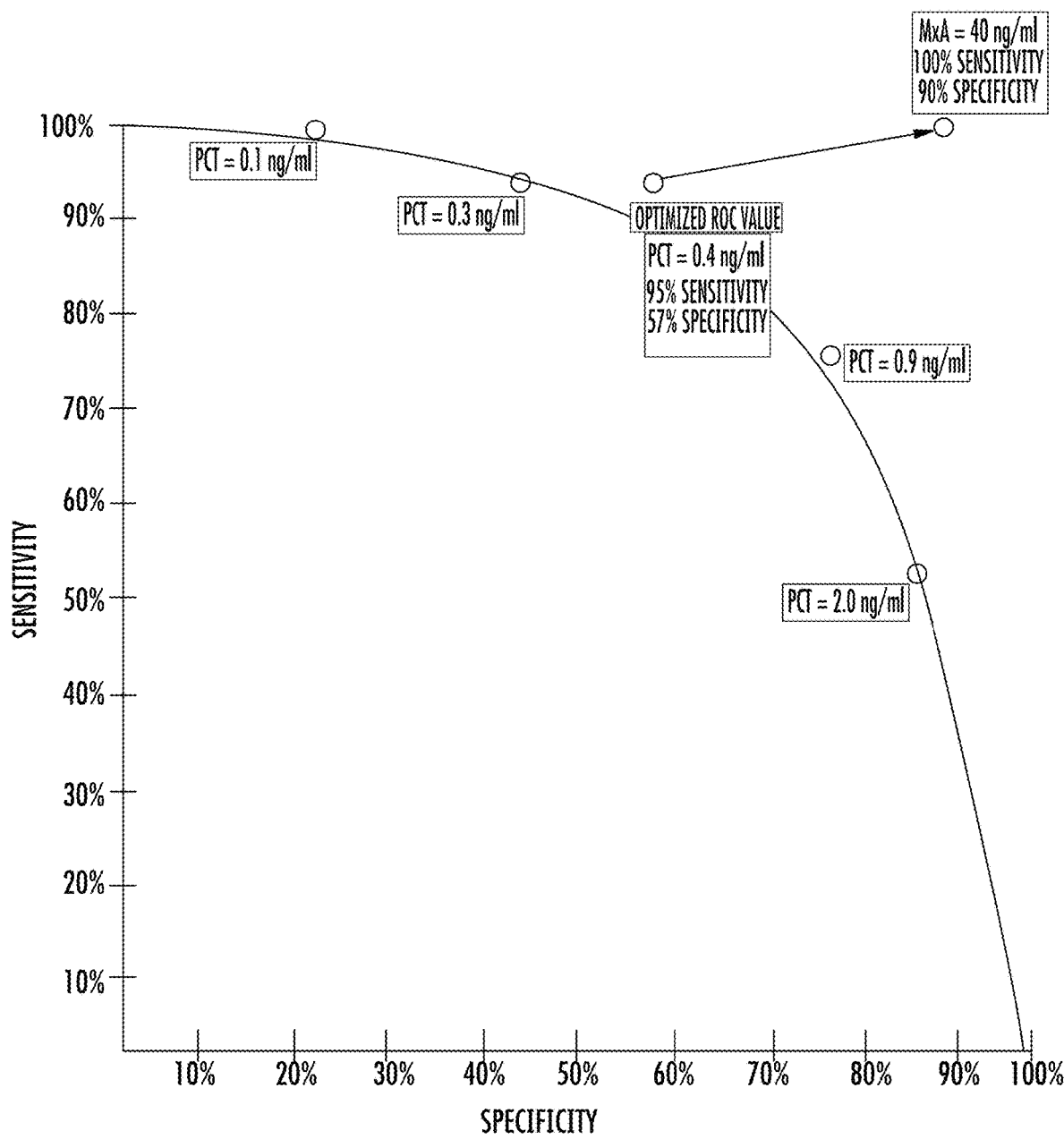
FIG. 23 shows a procalcitonin receiver-operator curve and its shift upon the addition of MxA.

On a receiver-operator curve, there is a point of optimization of specificity and one for sensitivity for detection of each biomarker. Using MxA as a second biomarker in combination, increases the specificity of both procalcitonin and C-reactive protein and also shifts their curves to allow higher optimized sensitivity. A C-reactive protein receiver-operator curve is shown in FIG. 22 and a procalcitonin receiver-operator curve is shown in FIG. 23. The sensitivities and specificities for C-reactive protein from various studies (and the respective references) are shown in Table 9.

Table 9

TABLE 9

| CRP Cut-off | Sensitivity | Specificity | Article |
| --- | --- | --- | --- |
| 20 mg/L | 100% | 75% | Putto A, Ruuskanen O, Meurman O. Arch Dis Child. 1986 Jan: 61(1): 24-9. |
| 20 mg/L | 100% | 54% | Hatherill M, Tibby SM, Sykes K et al. Arch Dis Child 1999: 81: 417-21. |
| 20 mg/L | 83% | 67% | Berger RM, Berger MY, van Steensel-Moll HA, Eur J Pediatr 1996; 155: 468-73. |
| 40 mg/L | 76% | 60% | Lala S, Madhi S, Pettifor J. Ann Trop Pediatr. 2002; 22: 271-279. |
| 40 mg/L | 71% | 81% | Andreola G, Bressan S, Callegaro S. Pediatr Infect Dis J 2007; (8): 672-7. |
| 40 mg/L | 83% | 88% | Liu A, Bui T, Van Nguyen H. Age Ageing 2010: 559-65. |
| 50 mg/L | 94% | 72% | Stolz, D, Christ-Crain M, Gencey MM et al. Swiss Med Wkly. 2006; 136(27-28): 434-440. |
| 60 mg/L | 81% | 96% | Liu A, Bui T, Van Nguyen H. Age Ageing 2010: 559-65. |
| 60 mg/L | 70% | 52% | Moulin F, Raymond J, Lorrot M et al., Arch Dis Child. 2001; 84: 332-336. |
| 80 mg/L | 72% | 97% | Liu A, Bui T, Van Nguyen H. Age Ageing 2010: 559-65. |

TABLE 9-continued

| CRP Cut-off | Sensitivity | Specificity | Article |
| --- | --- | --- | --- |
| 80 mg/L | 15% | 95% | Korppi M, Kroger L. Scand J Infect Dis J 1992; 207-213. |
| 80 mg/L | 46% | 95% | Andreola G, Bressan S, Callegaro S. Pediatr Infect Dis J 2007; (8): 672-7. |

As shown in FIG. 22, the optimized ROC value of C-reactive protein alone is 40 mg/L (74% sensitivity and 73% specificity). Testing for a combination of 20 mg/L C-reactive protein and 40 ng/ml of MxA increases sensitivity and specificity to 95% and 90%, respectively. Testing for a combination of 40 mg/L C-reactive protein and 40 ng/ml of MxA (not shown in the figures) increases sensitivity and specificity to 100% and 90%, respectively. Thus, the use of MxA in combination with C-reactive protein permits a more accurate interpretation with detection of lower levels of C-reactive protein and relying on MxA to provide the specificity.

As shown in FIG. 23, the optimized ROC of procalcitonin alone is 0.4 ng/ml (95% sensitivity and 57% specificity). Testing for a combination of 0.4 ng/ml procalcitonin and 40 ng/ml of MxA increases sensitivity and specificity to 100% and 90%, respectively. Thus, a combination of MxA and procalcitonin allows not only higher sensitivity but also a dramatic increase in specificity.

Interpretation of illness based solely on C-reactive protein or procalcitonin (or other bacterial host biomarkers) obtained by any means, are significantly improved in the context of MxA levels. One can have a C-reactive protein or procalcitonin test result from one test and adding MxA levels (obtained from the same or a different test by any means) improves the clinical characteristics such as sensitivity and specificity.

As defined above, a clinically significant infection is the local microbiological confirmation of a pathogen by cell culture, molecular techniques, and antigen in association with a systemic immune response (C-reactive protein, procalcitonin, MxA, or serological response).

The Applicant also discovered that a positive low C-reactive protein result plus a positive MxA result does not indicate viral-bacterial co-infection. Instead, a patient with that result has a viral infection only. In fact, the Applicant believes that viral-bacterial co-infection only infrequently exists. True infections are either solely bacterial or solely viral. A diagnosis of "co-infection" is the product of the erroneous definitions of infection. The presence of a true infection (versus colonization of a virus or bacteria) requires both the presence of a pathogen and a host response (systemic response) to that infection. In prior art methods, technicians and doctors would culture a sample and ignore whether or not there was a simultaneous presence of a host response. When they saw both a bacterial and viral culture growing together, they would define that as co-infection. In a study of over 300 patients, the Applicant saw no occurrences of co-infection in their patients. Low C-reactive protein and elevated MxA were actually only viral infections.

A rapid lateral flow test aids the primary and urgent care physicians in the outpatient setting to make a rapid assessment of the clinical significance of an acute respiratory infection. Further, the test helps to differentiate infections with a systemic host response from local infections or colonization as well as identify patients as having a viral or bacterial infection versus those with a microbiologically unconfirmed (MU) respiratory illness. The test uses a combination of two biomarkers, including myxovirus resistance protein A (MxA), a novel viral biomarker, and C-reactive protein (CRP). MxA is an intracellular blood protein that is induced by type 1 interferon and is therefore specific for true viral infections (as opposed to viral carriage). The biomarker is normally very low in the blood but has fast induction in case of a viral infection, a long half-life, and stays elevated in the presence of elevated interferon.

The test is preferably a single use disposable test that uses a fingerstick blood (5 µl) sample near the bedside. The time to result is approximately 15 minutes and no additional sample processing is required. The readout of the test is interpreted either as a viral infection when MxA is elevated (MxA positive, C-reactive protein positive or negative) or as a bacterial infection whenever C-reactive protein is elevated in the presence of normal MxA (MxA negative, low or high C-reactive protein positive).

Dual strip formats for a lateral flow test that detects the presence of MxA and C-reactive protein are shown in FIGS. 13A-13C and 15A-15C, and described in U.S. Pat. No. 8,962,260, entitled "Method and Device for Combined Detection of Viral and Bacterial Infections", issued Feb. 24, 2015, and US Patent Publication No. 2013/0196310, entitled "Method and Device for Combined Detection of Viral and Bacterial Infections", published Aug. 1, 2013, both incorporated herein by reference.

In data from a prospective, multicenter clinical trial in the USA using the format shown in FIGS. 13A through 13C, the lateral flow test demonstrated a sensitivity and specificity of 80% and 96%, respectively, to identify a bacterial infection, and a sensitivity and specificity of 86% and 94%, respectively for detecting a viral infection. The patients in this study with positive C-reactive protein (low and/or high CRP) and positive MxA were identified as having a viral infection. For five patients, the test lines for low CRP, high CRP and MxA were all positive, and these patients were all identified as having a viral infection. "Unconfirmed" results are preferably interpreted as "negative".

The test may alternatively be in an even simpler format with only one strip that includes MxA and C-reactive protein (preferably low CRP).

In alternative embodiments, MxA is the viral host biomarker and the bacterial host biomarker is procalcitonin.

IFITs as Viral Host Biomarkers

While MxA has been predominantly discussed herein as the viral host biomarker, alternative viral host biomarkers may be used in combination with procalcitonin and/or C-reactive protein to effectively diagnose infection. As one example, Interferon Induced Proteins with tetratricopeptide repeats (IFITs), which are expressed in response to viral infection, may be used as a marker of viral infection. IFITs could be assayed instead of MxA using lateral flow (for example any of the lateral flow devices described herein) or any other assay device known in the art.

Example 1

One study evaluated the accuracy of a point-of-care immunoassay at identifying an immune response to a viral and/or bacterial infection in patients presenting with suspected pharyngitis or lower respiratory tract infection (LRTI) compared to confirmatory microbiological, radiological, and laboratory testing.

A prospective, single center, blinded clinical feasibility trial was performed at Beth Israel Deaconess Medical Center—a Harvard Medical School teaching tertiary care hospital—from December 2012-August 2013. Sixty subjects were enrolled with acute febrile respiratory infection. Nineteen had pharyngitis and 41 had LRTI. All subjects older than 17 years of age who presented with acute respiratory symptoms consistent with infection that had a fever, or reported having a fever greater than or equal to 100.5 in the last 48 hours, were considered eligible for the study. At enrollment, the 36 case subjects were separated into 12 with presumed pharyngitis and 24 with presumed LRTI. If a patient did not have a fever and was asymptomatic (as described in the inclusion criteria), the patient was considered for inclusion as a control subject. Twenty-four patients were enrolled into the control group.

Qualifying patients with a clinical diagnosis of pharyngitis or LRTI had the following samples collected: a fingerstick blood sample was applied to a rapid, point-of-care immunoassay (testing MxA and C-reactive protein, see assays above described in FIGS. 13-17), followed by the collection of four oropharyngeal samples, one venous blood sample and a urine sample. Two oropharyngeal samples were sent for viral PCR testing and two oropharyngeal samples were sent for routine bacterial cell culture. A venous blood sample measured C-reactive protein and MxA levels with an ELISA and atypical bacteria confirmed with paired serological testing. Patients with suspected LRTI had sputum cultures, chest x-ray, and WBC count measured. A follow-up visit was necessary 4-6 weeks after the first visit to collect a venous blood sample for follow-up serology testing. Personnel performing the immunoassay were blinded to confirmatory test results.

A viral infection was confirmed if oropharyngeal PCR testing was positive for viral pathogens. A bacterial infection was confirmed when throat cultures identified Group A beta hemolytic strep growth or other bacterial growth greater than $1 \times 10^6$ colony forming units (CFU)/mL. If the *Streptococcus pneumoniae* or *Legionella* urine antigen assay was positive, it confirmed a bacterial infection. Bacterial infection was confirmed in positive throat or sputum cultures. Elevated IgM antibodies or two-fold increase in IgG antibodies between acute and convalescent phase indicated atypical bacteria. Positive *Streptococcus* or *Legionella* urine antigen assays also confirmed bacterial infection.

The immunoassay was interpreted by identifying the presence of the control lines or result lines according to Table 10 and FIG. 14A through FIG. 14F.

TABLE 10

| Cont | MxA | CRP | CRP | Test Outcome |
|------|-----|-----|-----|--------------|
| + | + |   |   | Viral Infection |
| + | + | + |   | Viral Infection* |
| + | + | + | + | Bacterial/Co-Infection |
| + |   | + |   | Bacterial/Co-Infection |
| + |   | + | + | Bacterial/Co-Infection |
| + |   |   |   | Negative |
|   |   |   |   | Invalid |

*cannot preclude co-infection

The presence of two control lines (blue) and an MxA line (red) indicates viral infection. The presence of two control lines, an MxA line and a low CRP line (black) indicates a viral infection, but does not preclude co-infection. The presence of only control lines indicates a negative result. The presence of two control lines and a low CRP line indicates a bacterial infection. The presence of two control lines, a low CRP line, and a high CRP line (black) indicates a bacterial infection. The presence of two control lines, an MxA line, a low CRP line and a high CRP line indicates a bacterial or co-infection. No control lines indicate an invalid test.

Two of the oropharyngeal samples were sent for a viral respiratory PCR panel (Luminex xTAG; Austin, Tex.) and other viral PCR testing while the other two oropharyngeal samples were sent for routine bacterial cell culture. A 5 ml peripheral venous blood sample, collected in a purple top tube (ethylenediaminetetraacetic acid [EDTA]), was sent for quantitative MxA enzyme-linked immunosorbent assays (ELISA) testing using the MxA Protein ELISA Test Kit (Kyowa Medex Co., Ltd.; Tokyo, Japan) and WBC measurement. A second sample, collected in a red top tube, was used for C-reactive protein testing with the High Sensitivity C-Reactive Protein Enzyme Immunoassay Test Kit (Biocheck, Inc.; Foster City, Calif.).

Diagnosis of *Chlamydia pneumoniae* and *Mycoplasma pneumoniae* was determined by PCR and performed by means of paired serology at the time of enrollment and at 4-6 weeks thereafter. Commercially available ELISA tests (Ani Labsystems Ltd. Oy.; Vantaa, Finland) were used according to the manufacturer's instructions for the detection of immunoglobulin M (IgM) and IgG antibodies to *M. pneumoniae* and *C. pneumoniae*. Atypical bacterial infection was confirmed if there was identification of *Mycoplasma pneumoniae* and *Chlamydia pneumoniae* by PCR, the presence of *Mycoplasma pneumoniae* and *Chlamydia pneumoniae* IgM antibodies, or a two-fold increase in IgG antibodies between acute and convalescent phase samples.

A definitive typical bacterial infection was considered when a bacterium was cultured from blood, sputum, or if the urine antigen assay for *Legionella* or *Streptococcus* was found to be positive. All subjects suspected of a LRTI had peripheral venous blood collected and sent for plating on routine bacterial blood cultures. Upon reaching the clinical laboratory, the specimens were divided into samples for plating on blood and chocolate agar. All specimens were processed within 24 hours of collection and a single colony-forming unit (CFU)/mL of a single bacterial species indicated an infection and not colonization.

Expectorated sputum was collected from subjects with a productive cough and a presumptive LRTI. Each sputum sample was assessed according to the classification scheme of Miller (Miller, A study of techniques for the examination of sputum in a field survey of chronic bronchitis. Am Rev Respir Dis. 1963; 88:473-483, herein incorporated by reference). In accordance with the criteria of Murray & Washington (Murray et al., Microscopic and bacteriologic analysis of expectorated sputum. Mayo Clin Proc. 1975; 50(6): 339-344, herein incorporated by reference), only samples that had greater than 25 polymorphonuclear leukocytes and less than 25 squamous cells per microscope high-power field were plated for culture. The quality of sputum samples was evaluated by assessing the number of inflammatory and epithelial cells. A definitive bacterial infection was considered when any Group A beta hemolytic strep growth occurred or any other bacterial growth greater than $1 \times 10^5$ CFU/mL from oropharyngeal samples or sputum samples.

Urine samples were collected and assayed for *Streptococcal pneumoniae* and *Legionella pneumophila* antigen Immunochromatographic membrane tests (Alere BinaxNOW *S. pneumoniae* and BinaxNOW *Legionella*; Waltham, Mass.) were performed on urine samples for detection of *Streptococcus pneumoniae* and *Legionella pneumophila* antigens. Identification of *Legionella pneumophila* by PCR also confirmed the diagnosis of *Legionella*.

A definitive viral infection was confirmed if the oropharyngeal PCR respiratory panel (Luminex xTAG; Austin, Tex.) or other viral PCR was positive for viral nucleic acid.

Subjects who did not have definitive microbiological confirmation of disease were characterized according to the methods shown in FIGS. 18 and 19, which were discussed more generally above. High C-reactive protein levels were used to determine bacterial infection in patients initially microbiologically unconfirmed for infection.

Two invalid tests occurred and four subjects were diagnostically indeterminant. Of the remaining 54 patients, the immunoassay correctly identified a combined total of 92% (22/24) of the patients negative for infection, 85% (17/20) of bacterial infections, and 70% (7/10) of viral infections. The percent negative and positive agreement of the test was calculated according to the charts in Tables 11A-11C.

TABLE 11A

| Pharyngitis N = 19 | | Comparator (Microbiological, Radiological, Laboratory Assessment) | | | |
|---|---|---|---|---|---|
| | | Bacterial or Co-infection | Viral | Negative | % Correct |
| Bimodal Dual Strip Immunoassay (for MxA, low CRP and high CRP) | Bacterial or Co-infection | 5 | 1 | 0 | 100% (5/5) |
| | Viral | | 3 | 0 | 75% (3/4) |
| | Negative | 0 | 0 | 7 | 100% (7/7) |
| Total | | 5 | 4 | 7 | |

TABLE 11B

| LRTI N = 27 | | Comparator (Microbiological, Radiological, Laboratory Assessment) | | | |
|---|---|---|---|---|---|
| | | Bacterial/ Co-infection | Viral | Negative | % Correct |
| Bimodal Dual Strip Immunoassay (for | Bacterial/ Co-infection | 12 | 1 | 1 | 80% (12/15) |

TABLE 11B-continued

| LRTI<br>N = 27 | | Comparator<br>(Microbiological, Radiological, Laboratory Assessment) | | | |
|---|---|---|---|---|---|
| | | Bacterial/<br>Co-infection | Viral | Negative | % Correct |
| MxA, low CRP and<br>high CRP) | Viral<br>Negative | 1<br>2 | 4<br>1 | 1<br>15 | 67% (4/6)<br>88% (15/17) |
| Total | | 15 | 6 | | 27 |

TABLE 11C

| Combined<br>N = 54 | | Comparator<br>(Microbiological, Radiological, Laboratory Assessment) | | | |
|---|---|---|---|---|---|
| | | Bacterial/<br>Co-infection | Viral | Negative | % Correct |
| Dual Strip<br>Immunoassay (for MxA,<br>low CRP and high CRP | Bacterial/<br>Co-infection<br>Viral<br>Negative | 17<br>2<br>1 | 2<br>7<br>1 | 1<br>1<br>22 | 85% (17/20)<br>70% (7/10)<br>92% (22/24) |
| Total | | 12 | 6 | 9 | 54 |

Of the 41 enrolled patients with LRTI, 26 were males and 15 were females with an age range from 22-89 and a mean age of 51 years. Of the 19 patients enrolled with pharyngitis, 8 were males and 11 were females with an age range from 18-69 and a mean age of 37 years. Viral pathogens detected by PCR included Influenza A, Influenza B, Parainfluenza 2, Parainfluenza 3, and HSV-1. Three asymptomatic controls had rhinovirus detected but this was deemed likely colonization and was excluded from the microbiological confirmation.

Acute febrile respiratory infections frequently have no confirmed etiology, both for URI such as pharyngitis and LRTI such as community acquired pneumonia (CAP), despite an extensive combination of microbiological and molecular diagnostic techniques, including molecular testing on both bacterial and viral pathogens. A review of the recent scientific literature revealed numerous prospective clinical studies evaluating the etiology of acute respiratory infections and reporting a failure of pathogen detection for 24-44% of the patients (Capelastegui et al. Etiology of community-acquired pneumonia in a population-based study: link between etiology and patients characteristics, process-of-care, clinical evolution and outcomes. BMC Infect Dis. 2012; 12:134; Templeton et al., Improved diagnosis of the etiology of community-acquired pneumonia with real-time polymerase chain reaction. Clin Infect Dis. 2005; 41:345-51; Huijskens et al., The value of signs and symptoms in differentiating between bacterial, viral and mixed aetiology in patients with community-acquired pneumonia. J Med Microbiol. 2014; 63:441-52; Huijskens et al., Viral and bacterial aetiology of community-acquired pneumonia in adults. Influenza Other Respi Viruses. 2013; 7:567-73; Johansson et al., Etiology of community-acquired pneumonia: increased microbiological yield with new diagnostic methods. Clin Infect Dis. 2010; 50:202-9; Endeman et al., Clinical features predicting failure of pathogen identification in patients with community acquired pneumonia. Scand J Infect Dis. 2008:1-6; Ewig et al., Factors associated with unknown aetiology in patients with community-acquired pneumonia. Eur Respir J. 2002; 20:1254-62, all herein incorporated by reference). In the present study, 44% (24/54) of patients had no microbial confirmation of infection. Patients without a microbial confirmation and a limited immune response may represent a potentially less significant clinical case of microbiologically unconfirmed patients.

The results of microbiological testing such as PCR and/or bacterial culture in combination with an accompanying immune response with elevated MxA is suggestive of a true viral infection while C-reactive protein elevates in the presence of bacterial infection.

Although a small sample size, the combined semi-quantitative C-reactive protein and MxA ten-minute fingerstick immunoassay demonstrated encouraging sensitivity and specificity at identifying clinically significant infections and helped differentiate viral and/or bacterial acute febrile infections. The test did not differentiate bacterial infections from bacterial/viral co-infections. Since the presence of a bacterial infection drives antibiotic therapy in cases of co-infection, this was not considered a significant limitation.

While the sample size was small, especially for the viral infection group, and there were no children under the age of 17 enrolled, the interplay between a semi-quantitative value for C-reactive protein and MxA appears to aid in the differentiation of infectious etiology. This study also used a novel method for clinically categorizing patients without definitive microbiological confirmation of disease.

Difficulty in obtaining relevant specimens, the low sensitivity or specificity of the used tests, high costs, and the absence of test results within the critical window for initiating adequate treatment, often result in prescription of antibiotic therapy in the absence of a bacterial infection. In isolation, neither MxA nor C-reactive protein alone is sensitive or specific enough at identifying viral and/or bacterial infection. However, a multiplexed pattern of results consisting of medical decision point reflected cut-off levels of low CRP, high CRP, and MxA together provides a sensitive and specific way to identify an immune response to a viral and/or bacterial infection. Use of a rapid test leads to less unnecessary antibiotic use, reduce antibiotic resistance, and lower healthcare costs.

The immunoassay's interplay between an MxA value and a semi-quantitative C-reactive protein value can aid in the differentiation of infectious etiology. In isolation, neither MxA nor C-reactive protein alone is sensitive or specific at identifying both viral and/or bacterial infection. However, the pattern of results in a 10-minute, point-of-care test provides a sensitive and specific method for differentiating acute febrile respiratory infections. Global use of this type of rapid test may reduce antibiotic overuse, reduce antibiotic resistance, and lower healthcare costs.

This study also permitted the use of C-reactive protein to diagnose infection in microbiologically unconfirmed patients using the methods of FIGS. 18 and 19.

Example 2

The draft NICE clinical guidelines recommend using a point-of-care C-reactive protein (CRP) test with 20 mg/L as a cut-off for identifying clinically significant lower respiratory tract infections requiring antibiotic therapy. The dual strip immunoassay test (testing Myxovirus resistance protein A [MxA] as well as semi-quantitative C-reactive protein, see FIGS. 8-17 and description above) was compared against using C-reactive protein alone to determine potential antibiotic prescription outcomes.

A prospective, multicenter, blinded, clinical feasibility trial was performed at 11 U.S. institutions. One hundred thirty-nine consecutive patients with presumed febrile upper respiratory infection (URI) were enrolled. Two patients were excluded due to incomplete data collection. Qualifying patients with URI symptoms had six samples collected: a fingerstick blood sample for the dual strip immunoassay (testing for MxA, and both a low and high level of C-reactive protein) rapid point-of-care immunoassay, two oropharyngeal samples, one nasopharyngeal sample, and two venous blood samples. One oropharyngeal and the nasopharyngeal sample were combined and sent for testing with the BioFire PCR respiratory panel and additional viral PCR testing for Herpes Simplex Virus, Cytomegalovirus, Epstein-Barr Virus (EBV). The other oropharyngeal sample was sent for routine bacterial cell culture. A venous blood sample measured Procalcitonin (PCT), C-reactive protein, MxA, white blood cell count, and EBV IgM/IgG levels. Personnel performing the immunoassay were blinded to confirmatory test results. The threshold levels for measuring C-reactive protein and MxA in this study were 20 mg/L for low CRP levels, 65 mg/L for high CRP levels, and 25 ng/ml for MxA.

A viral infection was confirmed if oropharyngeal PCR testing was positive for viral pathogens. A bacterial infection was confirmed when throat cultures identified Group A beta hemolytic strep growth or other bacterial growth in association with PCT≥0.1 ng/ml. Subjects who did not have definitive microbiological confirmation of disease were characterized according to the methods shown in FIG. 20. Subjects that were negative for MxA levels greater than 25 ng/ml were negative for viral infection.

More specifically, if microbiological tests, such as PCR, culture, PCT≥0.1 ng/ml or antigen detection (970), are positive (972) for bacteria or virus, the patient is diagnosed with a bacterial or viral infection. If the microbiologic ally confirmatory tests are negative (974), further laboratory confirmation (976) using PCT levels is performed. If the PCT levels in the sample are greater than or equal to 0.15 ng/ml (978), the patient is diagnosed (980) with a bacterial infection. If the PCT levels are less than 0.15 ng/ml (982), the patient is diagnosed (984) as negative for infection.

Figure 21:
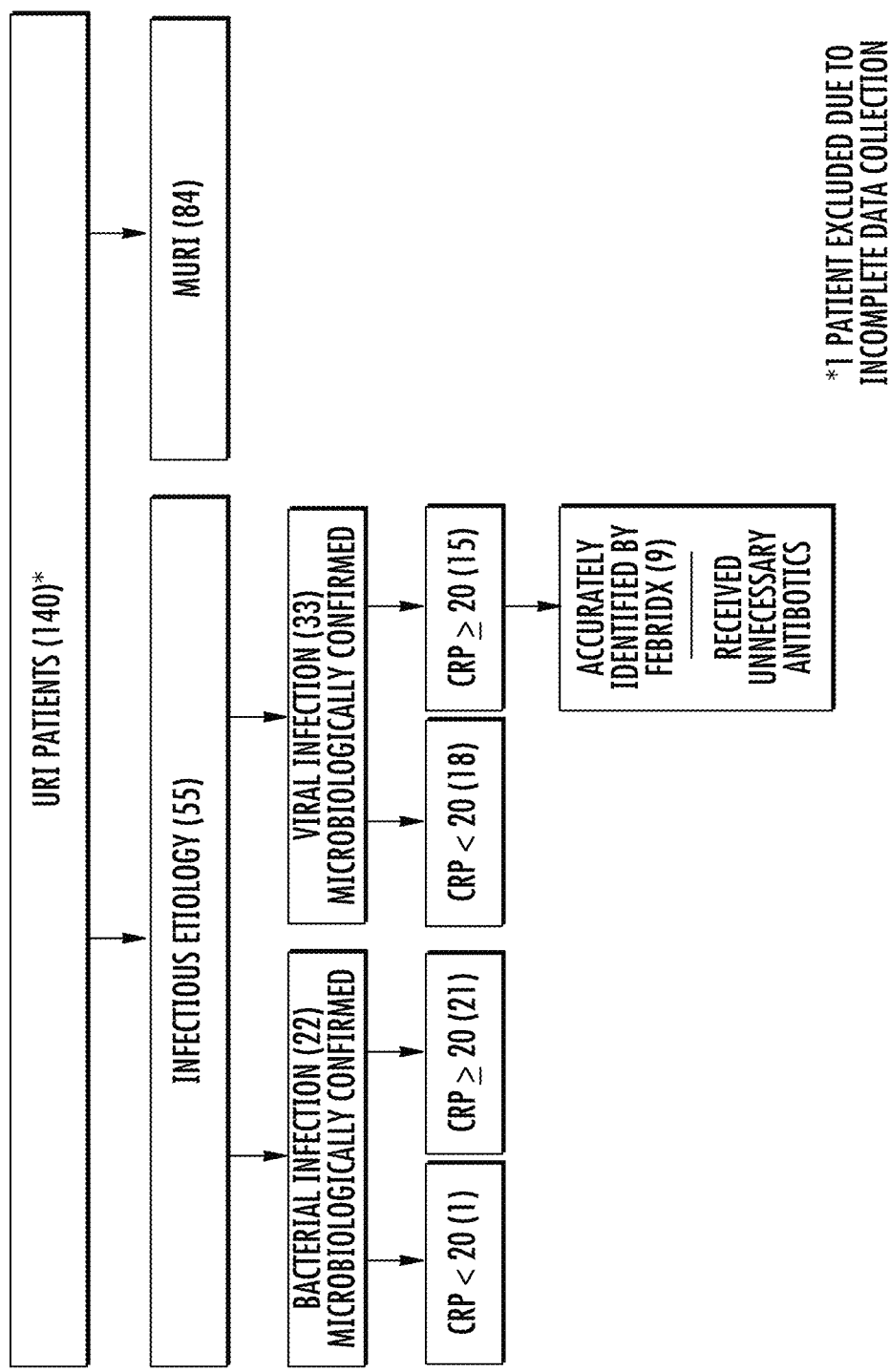
FIG. 21 shows the infectious etiology of patients in a study.

Of the one hundred thirty-seven patients enrolled, 41% (56) were confirmed infectious; 16% (22) bacterial, 25% (34) viral, and 59% (80) microbiologically unconfirmed (MU) respiratory illness. In patients with confirmed bacterial infection, 95% (21/22) had C-reactive protein ≥20 mg/L (see FIG. 21). In patients with confirmed viral infection, 41% (14/34) had C-reactive protein ≥20 mg/L (see FIG. 21, one patient excluded due to incomplete date collection). Using the MxA biomarker, the dual strip immunoassay test correctly identified 64% (9/14) of these viral infection patients who also had an associated C-reactive protein ≥20 mg/L.

The dual strip immunoassay test combines an MxA value with a semi-quantitative C-reactive protein value to help identify clinically significant immune responses and can aid in the differentiation of infectious etiology. Use of the dual strip immunoassay test would reduce the over prescription of antibiotics in 26% (9/34) of confirmed cases of viral infection compared to using C-reactive protein alone. The dual strip immunoassay test can support antibiotic stewardship in the outpatient setting and limit antibiotic resistance, adverse events, and healthcare costs.

The interplay between a semi-quantitative value for C-reactive protein and MxA can help to identify patients with a clinically significant underlying immune response consistent with a suspected respiratory infection from those patients representing a microbiologically unconfirmed (MU) illness. These markers will also simultaneously aid in the differentiation of viral and bacterial acute febrile respiratory infections. Examined together in a 10-minute point-of-care (POC) test, these markers provide a sensitive and specific means to assess clinical significance and differentiate acute febrile respiratory infections.

The use of procalcitonin levels for microbiologically unconfirmed patients adds a valuable diagnostic indicator to the diagnostic testing.

All patent and nonpatent references discussed herein are hereby incorporated by reference in their entireties.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of screening a patient with a suspected respiratory infection for bacterial colonization, comprising the steps of:
   a) performing a first test for a presence of atypical bacteria;
   b) if the first test indicates atypical bacteria is present, performing a second test to quantitatively determine a level of procalcitonin or C-reactive protein and white blood cell count in a patient sample;
   c) indicating a result of the second test as a bacterial colonization if
      a cell culture result of greater than $1\times10^6$ CFU/ml atypical bacteria is present in the first test and a level of procalcitonin is less than 0.15 ng/ml;
      a cell culture result of greater than 1×106 CFU/ml atypical bacteria is present in the first test, a level of procalcitonin is greater than or equal to 0.15 ng/ml and less than 0.25 ng/ml, the white blood cell count is less than 12,000, and no bands are present;
      a cell culture result of greater than 1×106 CFU/ml atypical bacteria is present in the first test and a level of C-reactive protein is less than 20 mg/l; and
      a cell culture result of greater than 1×106 CFU/ml atypical bacteria is present in the first test, a level of C-reactive protein is greater than or equal to 20 mg/l and less than 80 mg/l, the white blood cell count is less than 12,000, and no bands a present; and d) indicating a result of the second test as negative for bacterial infection if the patient sample of the patient tested positive for atypical bacteria using PCR in the first test and a level of procalcitonin in the patient sample from the patient less than 0.1 ng/ml or a level of C-reactive protein in the patient sample from the patient less than 20 mg/l indicates negative for bacterial infection;

e) testing the patient for Strep A or Strep C using a cell culture wherein when the patient tests positive for Strep A or Strep C and a level of procalcitonin is less than 0.1 ng/ml or a level of C-reactive protein is less than 20 mg/l, testing the patient for Streptolysin O antibody and the white blood cell count; wherein a Streptolysin O antibody of less than 80% and a white blood cell count of less than 12,000 indicates colonization; and wherein negative paired serology indicates colonization.

2. A method of screening a patient with a respiratory infection for colonization, comprising the steps of:
a) performing a first test for a presence of a viral infection;
b) if the first test is positive for presence of a virus, performing a second test to determine a level of MxA in a patient sample;
wherein, a level of MxA in the patient sample greater than or equal to 25 ng/ml indicates a viral infection;
wherein a level of MxA in the patient sample less than 25 ng/ml indicates no systemic host response;
c) performing a third test for a presence of atypical bacteria;
d) if the third test indicates atypical bacteria is present, performing a fourth test to determine a level of procalcitonin or C-reactive protein and a white blood cell count in the patient sample;
wherein the second test and the fourth test are performed on the same assay device;
wherein the patient sample testing positive for atypical bacteria using PCR in the third test and a level of procalcitonin in the patient sample less than 0.1 ng/ml or a level of C-reactive protein in the patient sample less than 20 mg/l indicates negative for bacterial infection;
wherein a cell culture result of greater than 1×10$^6$ CFU/ml atypical bacteria in the third test and a level of procalcitonin less than 0.15 ng/ml indicates colonization;
wherein a cell culture result of greater than 1×10$^6$ CFU/ml atypical bacteria in the third test, a level of procalcitonin greater than or equal to 0.15 ng/ml and less than 0.25 ng/ml, the white blood cell count less than 12,000, and no bands indicates colonization;
wherein a cell culture result of greater than 1×10$^6$ CFU/ml atypical bacteria in the third test and a level of C-reactive protein less than 20 mg/l indicates colonization; and
wherein a cell culture result of greater than 1×10$^6$ CFU/ml atypical bacteria in the third test, a level of C-reactive protein greater than or equal to 20 mg/l and less than 80 mg/l, the white blood cell count less than 12,000, and no bands indicates colonization; and
e) testing the patient for Strep A or Strep using a cell culture and when the patient tests positive for Strep A or Strep C and a level of procalcitonin is less than 0.1 ng/ml or a level of C-reactive protein is less than 20 mg/l, testing for Streptolysin O antibody; wherein a Streptolysin O antibody of less than 80% and the white blood cell count of less than 12,000 indicates colonization; and wherein negative paired serology indicates colonization.

3. The method of claim 2, wherein the second test is performed using a membrane and buffer to directly lyse cells, separate blood into serum, and filter cellular debris without any external or pre-processing steps.

4. The method of claim 2, wherein the second test and the fourth test are performed using a membrane and buffer to directly lyse cells, separate blood into serum, and filter cellular debris without any external or pre-processing steps.

5. A method of screening a symptomatic patient for active infection, comprising the steps of:
a) performing a first test to assay for:
i) a host viral biomarker selected from the group consisting of MxA and an interferon induced protein with tetratricopeptide repeats; and
ii) a host bacterial biomarker selected from the group consisting of C-reactive protein, procalcitonin, interleukin-6, serum amyloid A, and human neutrophil lipocalin;
wherein the first test is performed using a membrane and buffer that directly lyses cells, separates blood into plasma/serum, and filters cellular debris to detect the host viral biomarker and the host bacterial biomarker without any pre-processing steps;
wherein a value of the host viral biomarker greater than approximately 2 times the mean in the normal population times the standard deviation indicates a viral infection;
wherein a value of the host bacterial biomarker greater than approximately 2 times the mean in the normal population times the standard deviation indicates a bacterial infection;
wherein a value of the host viral biomarker greater than approximately 2 times the mean in the normal population times the standard deviation and a value of the host bacterial biomarker greater than approximately 2 times the mean in the normal population times the standard deviation indicates a viral infection; and
wherein a value of the host viral biomarker less than approximately 2 times the mean in the normal population times the standard deviation and a value of the host bacterial biomarker less than approximately 2 times the mean in the normal population times the standard deviation indicates a microbiologically unconfirmed state.

6. A method of determining viral infection, comprising the step of assaying a patient sample for MxA and at least one bacterial host biomarker of procalcitonin on the same assay device, wherein, if the patient sample has an MxA level greater than or equal to 25 ng/ml visually indicated on the assay, the patient is diagnosed with a viral infection, regardless of elevated levels of the at least one bacterial host biomarker of procalcitonin in the sample.

7. The method of claim 6, wherein the at least one bacterial host biomarker further comprises C-reactive protein.

8. A method of differentiating between colonization and active infection, comprising the steps of:
a) performing at least one first test for a presence of bacteria or virus in a sample;
b) if the sample is positive for bacteria, performing a second test for a presence of at least approximately 0.10 ng/ml procalcitonin and/or a presence of at least approximately 20 mg/L of C-reactive protein;
  wherein a presence of at least approximately 0.10 ng/ml procalcitonin or at least approximately 20 mg/L of C-reactive protein visually indicates an active bacterial infection;
  wherein an absence of at least approximately 0.10 ng/ml procalcitonin or at least approximately 20 mg/L C-reactive protein visually indicates bacterial colonization;
  c) if the sample is positive for virus, performing a third test for a presence of at least approximately 25 ng/ml MxA;
    wherein the second and third tests are performed on the same assay device wherein a presence of at least approximately 25 ng/ml MxA visually indicates an active viral infection; and
    wherein an absence of at least approximately 25 ng/ml MxA visually indicates viral colonization.

9. The method of claim 8, wherein the first test is selected from the group consisting of: a molecular test, PCR, a radiological test, an antigen test, an immunoassay, a chemoluminescent assay, and a cell culture.

10. A method of differentiating between colonization and active infection comprising the steps of:
  a) performing at least one first test for a presence of bacteria in a sample from a patient;
  b) if the sample is positive for bacteria, performing a second test for a presence of at least approximately 0.10 ng/ml procalcitonin and a presence of at least approximately 20 mg/L of C-reactive protein;
  c) indicating a result of the second test, wherein when a presence of at least approximately 0.10 ng/ml procalcitonin and at least approximately 20 mg/L of C-reactive protein is indicated, an active bacterial infection is present in the patient which provided the sample; and wherein when an absence of at least approximately 0.10 ng/ml procalcitonin and at least approximately 20 mg/L C-reactive protein is indicated, bacterial colonization is present in the sample provided by the patient.

11. The method of claim 10, wherein the first test is selected from the group consisting of: PCR, a radiological test, an antigen test, and a cell culture.

12. A method of differentiating between colonization and active infection, comprising the steps of:
  a) performing at least one first test for a presence of virus in a sample; and
  b) if the sample is positive for virus, performing a second test for a presence of at least approximately 25 ng/ml MxA;
  c) indicating a result of the second test as an active viral infection if there is
    a presence of at least approximately 25 ng/ml MxA and as colonization if there is
    an absence of at least approximately 25 ng/ml MxA.

13. The method of claim 12, wherein the first test is selected from the group consisting of a viral culture, viral antigen testing, viral IFA, and PCR.

14. A method of screening a patient for a bacterial or viral infection, comprising the steps of:
  a) testing for a level of MxA greater than 25 ng/ml in a first sample; and
  b) testing the first sample for a level of a host bacterial biomarker selected from the group consisting of:
    i) a level of C-reactive protein in the first sample greater than 20 mg/L;
    ii) a level of procalcitonin in the first sample greater than 0.10 ng/ml; and
  c) if the levels of MxA and the host bacterial biomarker are undetected in the first sample, taking a second sample approximately 4-48 hours after the first sample has been taken and repeating steps a) and b) on the second sample.

15. The method of claim 14, wherein the second sample in step c) is taken 6-8 hours after the first sample has been taken.

16. The method of claim 14, wherein the first sample and the second sample are both assayed using a quantitative assay.

17. The method of claim 14, wherein the first sample and the second sample are both assayed using a qualitative assay.

18. A kit for diagnosing whether an infection is bacterial and/or viral, comprising at least one antibody for determining a presence of a first threshold concentration of C-reactive protein in a sample, at least one antibody determining a presence of a second threshold concentration of C-reactive protein that is higher than the first threshold concentration of C-reactive protein in the sample, at least one antibody for determining a presence of MxA in the sample, and at least one antibody for determining a presence of procalcitonin in the sample.

19. The kit of claim 18, wherein:
  the antibody that determines the presence of MxA elicits a positive MxA result if at least approximately 25 ng/ml MxA protein is present in the sample;
  the antibody that determines the presence of the first threshold concentration of C-reactive protein elicits a positive low C-reactive protein result if at least approximately 20 mg/L of C-reactive protein is present in the sample;
  the antibody that determines the presence of the second threshold concentration of C-reactive protein elicits a positive high C-reactive protein result if at least approximately 80 mg/L of C-reactive protein is present in the sample; and
  the antibody that determines the presence of procalcitonin elicits a positive procalcitonin result if at least approximately 0.15 ng/ml of procalcitonin is present in the sample.

20. A method for analyzing a sample for a presence of MxA, C-reactive protein and procalcitonin, comprising the steps of:
  a) collecting a sample;
  b) transferring the sample to a first sample analysis device comprising:
    i) a sample compressor comprising:
      A) a first reagent zone for detecting a low level of C-reactive protein comprising at least one first reagent specific to C-reactive protein such that, when the sample contacts the first reagent, a first labeled complex forms if the low level of C-reactive protein is present in the sample and at least one second reagent specific to MxA such that, when the sample contacts the second reagent, a second labeled complex forms if MxA is present in the sample; and
      B) a second reagent zone for detecting a high level of C-reactive protein comprising at least one third reagent C-reactive protein, wherein the third reagent only detects a level of C-reactive protein that is higher than the level of C-reactive protein detected by the first reagent, such that, when the sample contacts the third reagent, a third labeled complex forms if the high level of C-reactive protein is present in the sample;
ii) a first lateral flow chromatographic test strip comprising:
A) a first detection zone comprising a first binding partner, which binds to the first labeled complex, and a second binding partner, which binds to the second labeled complex; and
B) a first diverting zone located upstream of the first detection zone on the lateral flow chromatographic test strip, wherein the first diverting zone interrupts lateral flow on the first lateral flow chromatographic test strip; and
iii) a second lateral flow chromatographic test strip parallel in a lateral flow direction to the first lateral flow chromatographic test strip, comprising:
A) a second detection zone comprising a third binding partner which binds to the third labeled complex; and
B) a second diverting zone located upstream of the second detection zone on the second lateral flow chromatographic test strip, wherein the second diverting zone interrupts lateral flow on the second lateral flow chromatographic test strip;
iv) a first sample application zone wherein sample is placed on the sample analysis device, wherein the first sample application zone is located in a location selected from the group consisting of: i) on the first lateral flow chromatographic test strip upstream of the first detection zone and ii) on the first reagent zone of the sample compressor; and
v) a second sample application zone where sample is placed on the sample analysis device, wherein the second sample application zone is located in a location selected from the group consisting of: i) on the second lateral flow chromatographic test strip upstream of the second detection zone and ii) on the second reagent zone of the sample compressor;
wherein the sample compressor is in a different plane than the first lateral flow chromatographic test strip and the second lateral flow chromatographic test strip;
wherein the first reagent zone of the sample compressor creates a bridge over the first diverting zone and the second reagent zone of the sample compressor creates a bridge over the second diverting zone, diverting flow onto the sample compressor and returning flow to the first chromatographic test strip and the second chromatographic test strips at the end of the first diverting zone and the second diverting zone;
c) transferring the sample to a second sample analysis device comprising at least one reagent for determining a presence of procalcitonin in the sample; and
d) analyzing the sample for a presence of the low level of C-reactive protein, MxA, the high level of C-reactive protein, and procalcitonin.

21. The method of claim 20, wherein the second sample analysis device is selected from the group consisting of a multiparametric assay device, an immunoassay device, a magnetic assay device, a paramagnetic assay device, a device for immunoblotting, a device for performing an agglutination reaction, a device for performing a complement-fixation reaction, a device for performing a hemolytic reaction, a device for performing a precipitation reaction, a device for performing a gold colloid method, a chromatographic device, a device using phosphorescence to detect procalcitonin, a device using radioactivity to detect procalcitonin, a device using colorimetry to detect procalcitonin, a device using gravimetry to detect procalcitonin, an X-ray diffraction device, an X-ray absorption device, a device using magnetism to detect procalcitonin, a device using fluorescent resonant emissions to detect procalcitonin, a device using immunostaining to detect procalcitonin, an ELISA, a flow cytometer, and a Vidas® immunoassay device.

22. The method of claim 20, wherein a threshold concentration to obtain a positive result for the low level of C-reactive protein in the detection zone of the first lateral flow chromatographic test strip is equal to or greater than a serum equivalent of approximately 20 mg/L of C-reactive protein.

23. The method of claim 20, wherein a threshold concentration to obtain a positive result for the high level of C-reactive protein in the detection zone of the second lateral flow chromatographic test strip is equal to or greater than a serum equivalent of approximately 80 mg/L.

24. The method of claim 20, wherein a threshold concentration to obtain a positive result for MxA in the detection zone of the first lateral flow chromatographic test strip is equal to or greater than approximately 25 ng/ml.

25. The method of claim 20, wherein a threshold concentration to obtain a positive result for procalcitonin on the second sample analysis device is equal to or greater than approximately 0.15 ng/ml.

26. The method of claim 20, wherein a first threshold concentration to obtain a positive result for the low level of C-reactive protein in the detection zone of the first lateral flow chromatographic test strip is equal to or greater than a serum equivalent of approximately 20 mg/L of C-reactive protein, a second threshold concentration to obtain a positive result for the high level of C-reactive protein in the detection zone of the second lateral flow chromatographic test strip is equal to or greater than a serum equivalent of approximately 80 mg/L, a third threshold concentration to obtain a positive result for MxA in the detection zone of the first lateral flow chromatographic test strip is equal to or greater than approximately 25 ng/ml; and a fourth threshold concentration to obtain a positive result for procalcitonin on the second sample analysis device is equal to or greater than approximately 0.10 ng/ml.

* * * * *